US011833167B2

(12) United States Patent
Ganapati et al.

(10) Patent No.: US 11,833,167 B2
(45) Date of Patent: Dec. 5, 2023

(54) NICOTINYL RIBOSIDE COMPOUNDS AND THEIR USES

(71) Applicant: MitoPower, LLC, Palo Alto, CA (US)

(72) Inventors: Gangadhara Ganapati, Palo Alto, CA (US); Atignal Shankara Rao Arvind, Bangalore (IN)

(73) Assignee: MitoPower LLC, Palo Alto, CA (US)

( * ) Notice: Subject to any disclaimer, the term of this patent is extended or adjusted under 35 U.S.C. 154(b) by 94 days.

(21) Appl. No.: 17/415,428

(22) PCT Filed: Dec. 12, 2019

(86) PCT No.: PCT/US2019/066064
§ 371 (c)(1),
(2) Date: Jun. 17, 2021

(87) PCT Pub. No.: WO2020/131578
PCT Pub. Date: Jun. 25, 2020

(65) Prior Publication Data
US 2022/0062314 A1 Mar. 3, 2022

Related U.S. Application Data

(60) Provisional application No. 62/780,559, filed on Dec. 17, 2018.

(51) Int. Cl.
*A61K 31/70* (2006.01)
*A01N 43/04* (2006.01)
*A61K 31/706* (2006.01)
*A61P 3/10* (2006.01)
*A61K 31/502* (2006.01)
*A61K 45/06* (2006.01)

(52) U.S. Cl.
CPC .......... *A61K 31/706* (2013.01); *A61K 31/502* (2013.01); *A61K 45/06* (2013.01); *A61P 3/10* (2018.01)

(58) Field of Classification Search
None
See application file for complete search history.

(56) References Cited

U.S. PATENT DOCUMENTS

| | | |
|---|---|---|
| 3,709,786 A | 1/1973 | Nakayama et al. |
| 8,106,184 B2 | 1/2012 | Sauve et al. |
| 8,546,090 B2 | 10/2013 | Haigis et al. |
| 9,321,797 B2 | 4/2016 | Sauve et al. |
| 9,585,876 B2 | 3/2017 | Zemel et al. |
| 9,855,289 B2 | 1/2018 | Normington et al. |
| 10,709,724 B2 | 7/2020 | Alvarez et al. |
| 2007/0117765 A1 | 5/2007 | Sauve et al. |
| 2011/0306597 A1 | 12/2011 | Crawforth et al. |
| 2014/0065099 A1 | 3/2014 | Alvarez et al. |
| 2015/0175645 A1 | 6/2015 | Milburn et al. |
| 2016/0008329 A1 | 1/2016 | Zemel et al. |
| 2016/0168184 A1 | 6/2016 | Migaud et al. |
| 2016/0250241 A1 | 9/2016 | Deren-Lewis et al. |
| 2016/0272668 A1 | 9/2016 | Dellinger et al. |
| 2017/0182076 A1 | 6/2017 | Alvarez et al. |
| 2017/0204131 A1 | 7/2017 | Szczepankiewicz et al. |
| 2017/0210774 A1 | 7/2017 | Carlson et al. |
| 2017/0267709 A1 | 9/2017 | Migaud et al. |
| 2017/0290850 A1 | 10/2017 | Normington et al. |
| 2017/0296564 A1 | 10/2017 | Dellinger et al. |
| 2017/0304338 A1 | 10/2017 | Dellinger et al. |
| 2018/0030079 A1 | 2/2018 | Carlson et al. |
| 2018/0102426 A1 | 4/2018 | Ikoshi et al. |
| 2018/0134742 A1 | 5/2018 | Migaud et al. |
| 2018/0134743 A1 | 5/2018 | Migaud et al. |
| 2018/0147225 A1 | 5/2018 | Brenner et al. |

FOREIGN PATENT DOCUMENTS

| | | | |
|---|---|---|---|
| WO | 2007061798 A2 | 5/2007 | |
| WO | 2012/114204 A2 | 8/2012 | |
| WO | 2014/152016 A1 | 9/2014 | |
| WO | 2015/014722 A1 | 2/2015 | |
| WO | 2015/066382 A1 | 5/2015 | |
| WO | 2015/186068 A1 | 12/2015 | |

(Continued)

OTHER PUBLICATIONS

Diguet, Nicolas, et al. "Nicotinamide riboside preserves cardiac function in a mouse model of dilated cardiomyopathy." Circulation 137.21 (2018): 2256-2273.*
Graziani, Grazia, and Csaba Szabó. "Clinical perspectives of PARP inhibitors." Pharmacological research 52.1 (2005): 109-118.*
Ahmad, Akbar, et al. "The clinically used PARP inhibitor olaparib improves organ function, suppresses inflammatory responses and accelerates wound healing in a murine model of third-degree burn injury." British Journal of Pharmacology 175.2 (2018): 232-245.*
Yoshino et al., "NAD+ Intermediates: The Biology and Therapeutic Potential of NMN and NR", Cell Metabolism, 27, (2017), retrieved from: https://doi.org/10.1016/j.cmet.2017.11.002.
Zhang et al., "Enzymes in the NAD—Salvage Pathway Regulate SIRT1 Activity at Target Gene Promoters", The Journal of Biological Chemistry, vol. 284, No. 30, p. 20408-20417, Jul. 24, 2009.
Zhang et al., "NAD+ repletion improves mitochondrial and stem cell function and enhances life span in mice", Science, vol. 352, Issue 6292, Jun. 17, 2016, p. 1436.

(Continued)

*Primary Examiner* — Patrick T Lewis
(74) *Attorney, Agent, or Firm* — Young Basile Hanlon & MacFarlane, P.C.

(57) ABSTRACT

The disclosure provides nicotinamide riboside (NR), the reduced form of NR (NRH), nicotinic acid riboside (NAR), the reduced form of NAR (NARH), derivatives thereof, compositions thereof and uses thereof. The NR and NAR derivatives have improved stability and bioavailability compared to NR and NAR. NR, NRH, NAR, NARH, and derivatives thereof can increase intracellular NAD$^+$ levels, and can enhance mitochondrial and cellular function and cell viability. Therefore, NR, NRH, NAR, NARH, and derivatives thereof, whether alone or in combination with one or more additional therapeutic agents (e.g., a PARP inhibitor), are useful for treating mitochondrial diseases, mitochondria-related diseases and conditions, and other disorders and conditions.

7 Claims, 12 Drawing Sheets

Specification includes a Sequence Listing.

(56) References Cited

FOREIGN PATENT DOCUMENTS

| WO | 2015186114 A1 | 12/2015 |
|---|---|---|
| WO | 2016/014927 A2 | 1/2016 |
| WO | 2016/016391 A1 | 2/2016 |
| WO | 2016/122832 A1 | 8/2016 |
| WO | 2016/014927 A3 | 9/2016 |
| WO | 2016/144660 A1 | 9/2016 |
| WO | 2016/149395 A1 | 9/2016 |
| WO | 2016/196941 A1 | 12/2016 |
| WO | 2017011788 A1 | 1/2017 |
| WO | 2017024255 A1 | 2/2017 |
| WO | 2017/062311 A1 | 4/2017 |
| WO | 2017079195 A1 | 5/2017 |
| WO | 2017/109195 A1 | 6/2017 |
| WO | 2017/161165 A1 | 9/2017 |
| WO | 2017 /181102 A1 | 10/2017 |
| WO | 2017/184885 A1 | 10/2017 |
| WO | 2017/218580 A1 | 12/2017 |
| WO | 2018/002215 A1 | 1/2018 |
| WO | 2018/033639 A1 | 2/2018 |
| WO | 2018/039207 A1 | 3/2018 |
| WO | 2018/089830 A1 | 5/2018 |
| WO | 2018/102426 A1 | 6/2018 |
| WO | 2018/170389 A1 | 9/2018 |
| WO | 2018/236814 A2 | 12/2018 |

OTHER PUBLICATIONS

Ziegler, "New functions of a long-known molecule Emerging roles of NAD in cellular signaling", Eur. J. Biochem. 267, 1550-1564 (2000).

Croteau, D. L. et al., NAD+ in DNA repair and mitochondrial maintenance. Cell Cycle, Feb. 1, 2017, vol. 16, No. 6, pp. 491-492.

Fang, E. F. et al., NAD+ Replenishment Improves Lifespan and Healthspan in Ataxia Telangiectasia Models via Mitophagy and DNA Repair. Cell Metabolism, Oct. 11, 2016, vol. 24, No. 4, pp. 566-581.

Belenky, Peter, etal. "NAO+ metabolism in health ancl disease." Trends Biocllem. Sci., 32:12-19 (2006).

Diguet, Nicolas, et ai. "Nicotinamide Riboside Preserves Cardiac Function in a Mouse Model of Dilated Cardiomyopatiy." Circulation, 137:2256-2273 (May 22, 20-18).

Frederick, David W., et al. "Loss of NAD Homeostasis Leads To Progressive and Reversible Degeneration of Skeletal Muscle." Cell Metab,, 24:269-282 (2016).

Gariani, Karim, et al. "Inhibiting poly ADP-ribosylation increases fatty acid oxidation and protects against fatty liver disease." J. Hepatology ,66:132-141 (2017).

Gual, Philippe, et al. Therapeutic Potential of Nicotinamide Adenine Di nucleotide for Nonaicoholic Fatty Liver Diseasei Hepatology ,63(4):1074-1077 (2016).

Guan, Yi, et al. "Nicotinamide Mononucleotide, an NAD+ Precursor, Rescues Age-Associated Susceptibility to AKI in a Sirtuin 1-Dependent Manners" J. Am. Soc. Nephrol., 28:2337-2352 (2017).

Li, Qiong, el aL "Dietary nicotinic acid supplementation ameliorates chronic alcohol-Induced Fatty liver in rats." Alcolwl Clin Exp Res. Jul. 2014; 38(7): 1982-1992. doi:10.1111/acer.12396.

Wang, S., et al. "Nicotinamide riboside attenuates alcohol induced liver injuries via activation of SirT1 /PGC-1 al mitochondrial biosynthesis pathway." Redox Biology, '17:89-98 (available online Apr. 5, 2018).

Search Report and Written Opinion for related Singapore Application No. 11201912267S, dated Feb. 22, 2021.

Croteau, Deborah L., et al. "NAO+ in DNA repair and mitochondrial maintenance." Cell Cycle, vol. 16, No. 6, pp. 491-492 (Feb. 1, 2017).

Pradere, Ugo, et al. "Synthesis of Nucleoside Phosphate and Pl10sphonate Prod rugs." Chemical Reviews. vol. 114, No. 18, pp. 9154-9218 (Aug. 21, 2014).

Eldridge, Joshua A. "Synthesis and Stability Studies of Prodrugs and Codrugs of Nal Trexone And 6 -—-—Nal Trexol." Theses and Dissertations—Pharmacy. 16, Dec. 31, 2013.

International Search Report and Written Opinion received in connection with international application AR2 No. PCT/US2018/038201; dated Dec. 20, 2018.

Belenky et al., "*Saccharomyces cerevisiae* YOR071C Encodes the High Affinity Nicotinamide Riboside Transporter Nrt1", J. of Biological Chemistry, vol. 283 (13), Mar. 28, 2008.

Bieganowski et al., Discoveries of Nicotinamide Riboside as a Nutrient and Conserved NRK Genes Establish a Preiss-Handler Independent Route to NAO• in Fungi and Humans-, Cell, vol. 117, oo. 495-502 May 14, 2004.

Bonkowski et al., "Slowing ageing by design: the rise of NAO+ and sirtuin-activating compounds", Nature Reviews, Molecular Cell Biology, vol. 17, Nov. 2016, pp. 679-690.

Brenner, "Boosting NAO to Spare Hearing", Cell Metabolism 20, Dec. 2, 2014, pp. 926-927.

Camacho-Pereira et al., "CD38 Dictates Age-Related NAO Decline and Mitochondrial Dysfunction through an SIRT3-Dependent Mechanism", Cell Metabolism 23, pp. 1127-1139, Jun. 14, 2016.

Canto et al., "The NAO+ Precursor Nicotinamide Riboside Enhances Oxidative Metabolism and Protects against High-Fat Diet-Induced Obesity", Cell Metabolism, vol. 15, pp. 838-847, Jun. 6, 2012.

Chini et al., "NAO and the aging process: Role in life, death and everything in between", Molecular and Cedllular Endocrinology, 455 (2017), pp. 62-74.

Conze et al., "Safety assessment of nicotinamide riboside, a form of vitamin 83", Human and Experimental Toxicology, 2016, vol. 35(11),pp. 1149-1160.

Davies, "Simple Synthesis of the 5-0-Benzoylriboside of 1 .4-Dihydronicotinic Acid; A Cofactor for Ot Diaphorase and Nitroreductase Enzymes", Nucleosides & Nucleotides, 14(3-5), DD. 311-312(19951.

Davila et al., "Nicotinamide adenine dinucleotide is transported into mammalian mitochondria", elife 2018;7:e33246. Retrieved from DOI: https://doi.org/10.7554/elife.33246.

Fletcher et al., "Nicotinamide riboside kinases display redundancy in mediating nicotinamide mononucleotide and nicotinamide riboside metabolism in skeletal muscle cells", Molecular Metabolism vol. 6 (2017) nn. 819-832.

Franchetti et al., "Stereoselective synthesis of nicotinamide 13-riboside and nucleoside analogs", Bioorganic & Medicinal Chemistry Letters, vol. 14 (2004) pp. 4655-4658.

Gomes et al., Declining NAO+ Induces a Pseudohypoxic State Disrupting Nuclear-Mitochondrial Communication during Aging., Cell, 155, pp. 1624-1638, Dec. 19, 2013.

Gross et al., "Digestion and Absorption of NAO by the Small Intestine of the Rat", J. Nutr., vol. 113, pp. 412-420 (1983); Downloaded from https://academic.oup.com/jn/articleabstracV113/2/412/4755226.

Gujar et al., "An NAD+-dependent transcriptional program governs self-renewal and radiation resistance in glioblastoma", PNAS | Published online Dec. 7, 2016, pp. E8247-E8256, retrieved from : www.onas.oJ Q/CQi/doi/10.1073/onas. 1610921114.

Harlan et al., "Enhancing NAO Salvage Pathway Reverts the Toxicity of Primary Astrocytes Expressing Amyotrophic Lateral Sclerosis-linked Mutant Superoxide Dismutase 1 (S0D1)", The Journal of Biological Chemistry, vol. 291, No. 20, pp. 10836-10846, May 13, 2016.

Li et al., A conserved NAD+ binding pocket that regulates protein-protein interactions during aging-, Science, vol. 355, pp. 1312-1317 (2017).

Mei et al., "Calorie Restriction-Mediated Replicative Lifespan Extension in Yeast is Non-Cell Autonomous", (2015) PLoS Biol, 13(1 ):e1002048. doi:10.1371/journal.pbio.1002048.

Mills et al., Long-Term Administration of Nicotinamide Mononucleotide Mitigates Age-Associated Physiological Decline in Mice•. Cell Metabolism, vol. 24, pp. 795-806, Dec. 13, 2016.

Peek et al., "Circadian Clock NAO+ Cycle Drives Mitochondrial Oxidative Metabolism in Mice", Science. (2013, Nov. 1 ); 342(6158): 1243417. doi: 10.1126/science.1243417.

(56) References Cited

OTHER PUBLICATIONS

Pieper et al., "P7C3 and an unbiased approach to drug discovery for neurodegenerative diseases", NIH-Public Access Manuscript. Published in final edited form: Chem Soc Rev. Oct. 7, 2014; 43(19): 6716-6726. doi: 10.1039/c3cs60448a.

Ratajczak et al., "NRK1 controls nicotinamide mononucleotide and nicotinamide riboside metabolism in mammalian cells", Nature Communications 17:131031 (2016) DOI: 10.1038/ncomms 13103.

Ryu et al., "NAO+ repletion improves muscle function in muscular dystrophy and counters global PARylation", Sci. Transl. Med., 8, 361ra139 (2016).

Bato et al., "Circadian Reprogramming in the Liver Identifies Metabolic Pathways of Aging", 2017, Cell, 170, 664.

Sharma et al.,"Pharmacokinetic Evaluation of Nicotinamide Riboside in Rats", MPS 2016, Poster.

Tanimori et al., "An Efficient Chemical Synthesis of Nicotinamide Riboside (NAR) and Analogues", Bioorganic & Medicinal Chemistry Letters, vol. 12, (2002), pp. 1135-1137.

Trammell et al., "Nicotinamide Riboside Opposes Type 2 Diabetes and Neuropathy in Mice", Scientific Reports, vol. 6:26933 (2016) retrieved from: DOI: 10.1038/srep26933.

Trammell et al., Nicotinamide riboside is uniquely and orally bioavailable in mice and humans-, Nature Communications, vol. 7:12948 (2016) retrieved from: DOI: 10.1038/ncomms12948.

Tripathi et al., "Stem Cells and Progenitors in Human Peripheral Blood Get Activated by Extremely Active Resveratrol (XAR™)", Stem Cell Reviews and Reports, Springer; published online Nov. 24, 2017 retrived from: httos://doi.org/10.1007/s12015-017-9784-7.

Van Meter et al., "SIRT6 overexpression induces massive apoptosis in cancer cells but not in normal cells", Cell Cycle, vol. 10:18, pp. 3153-3158; Sep. 15, 2011.

Wang et al., "P7C3 Neuroprotective Chemicals Function by Activating the Rate-Limiting Enzyme in NAO Salvage", Cell, 158, pp. 1324-1334, Sep. 11, 2014.

Yang et al., "Syntheses of Nicotinamide Riboside and Derivatives: Effective Agents for Increasing Nicotinamide Adenine Dinucleotide Concentrations in Mammalian Cells", J. Med. Chem., 2007, 50, DD.6458-6461.

Yang et al., "NAO+ metabolism: Bioenergetics, signaling and manipulation for therapy", Biochimica et Biophysica Acta, 1864, (2016), pp. 1787-1800.

Yin et al., "P7C3 Neuroprotective Chemicals Block Axonal Degeneration and Preserve Function after Traumatic Brain Injury", 2014, Cell Reports, vol. 8, pp. 1731-1740.

Yoshino et al., "Nicotinamide Mononucleotide, a Key NAD+ Intermediate, Treats the Pathophysiology of Diet—and Age-Induced Diabetes in Mice", Cell Metabolism vol. 14, pp. 528-536, Oct. 5, 2011.

\* cited by examiner

Scheme 1:

Scheme 2:

NICOTINYL RIBOSIDE COMPOUNDS AND THEIR USES

CROSS-REFERENCE TO RELATED APPLICATIONS

This application is a 35 USC § 371 of International Application serial No. PCT/US2019/066064, filed Dec. 12, 2019, which claimed the benefit of U.S. Provisional App. No. 62/780,559 filed on Dec. 17, 2018, whose disclosures are incorporated by reference in their entirety.

INCORPORATION BY REFERENCE OF SEQUENCE LISTING

This application incorporates by reference the sequence listing in the ASCII text file entitled "34993-002WO_SL", created on Mar. 4, 2020, file size 929 bytes. This sequence listing has been filed at the U.S. Patent and Trademark Office with the other documents for this application.

FIELD OF THE DISCLOSURE

The disclosure relates to nicotinamide riboside (NR), the reduced form of NR (NRH), nicotinic acid riboside (NAR), the reduced form of NAR (NARH), derivatives thereof, compositions thereof and uses thereof to increase $NAD^+$ levels, to enhance mitochondrial and cellular function and cell viability, and to treat or prevent mitochondrial diseases, mitochondria-related diseases and other diseases.

BACKGROUND OF THE DISCLOSURE

Nicotinamide adenine dinucleotide (NAD) is a coenzyme that is critical for cellular function. It serves two major functions. First, NAD serves as a carrier for redox functions. These are chemical reactions involving the transfer of electrons and form the basis for energy production in every cell [Croteau et al. (2017); Fang et al. (2017); Chini et al. (2016); and Yang et al. (2016)]. The oxidized form of NAD is abbreviated $NAD^+$, and the reduced form of NAD is abbreviated NADH. $NAD^+$ is an oxidizing agent that accepts electrons from other molecules to form NADH, which in turn is a reducing agent that donates electrons to other molecules. Such electron-transfer reactions are the main function of NAD.

Second, NAD is an essential cofactor in several non-redox reactions by providing ADP-ribose to catalyze the enzymatic function of two key protein families—the sirtuins (SIRTs) and the poly(ADP-ribose) polymerases (PARPs). SIRTs are deacetylases involved in the maintenance of nuclear, mitochondrial and cytoplasmic or metabolic homeostasis (Ref. 1-3). PARPs are involved in DNA repair and play a broad role in the maintenance of chromatin structure and function [Croteau et al. (2017); Fang et al. (2017); Chini et al. (2016); and Yang et al. (2016)].

When $NAD^+$ levels are depleted, cellular functioning is impaired due to both reduced level of energy production and disruption of cellular homeostasis. Reduction in $NAD^+$ levels is observed in physiological states such as in aging, and across a wide range of pathological states ranging from acute injury to chronic metabolic and inflammatory conditions [Bonkowski et al. (2016); Frederick et al. (2016); Zang et al. (2016); and Imai et al. (2014)]. In particular, given the central role of the mitochondria in energy production, organs with higher numbers of mitochondria such as the liver, heart, skeletal muscle, brain and kidneys are most susceptible to $NAD^+$ depletion and thus are most amenable to therapies that can enhance $NAD^+$ levels [Bonkowski et al. (2016); Frederick et al. (2016); Zang et al. (2016); and Imai et al. (2014)]. In addition, efficient mitochondrial activity is critical for immune cell function, and mitochondrial dysfunction is associated with poor immune surveillance (impaired antigen recognition and immune exhaustion) and immune cell senescence [Bonkowski et al. (2016); Frederick et al. (2016); Zang et al. (2016); and Imai et al. (2014)].

There are several approaches to enhancing $NAD^+$ levels based on the different ways NAD is synthesized in the body. In each such instance, the starting point is usually a compound obtained from the diet. Such compounds include dietary tryptophan, and derivatives of vitamin $B_3$ that include nicotinic acid (NA), nicotinamide (NAM), nicotinamide riboside (NR) and nicotinamide mononucleotide (NMN). While NAD can also be obtained in the diet, it is rapidly broken down into NAM or NR by extracellular hydrolases such as CD38 and CD73 [Camacho-Pereira et al. (2016)].

Nicotinamide, nicotinic acid and nicotinamide riboside are natural compounds that are currently available as nutritional supplements. NMN is a nucleotide derivative of NAM that is considered to be a biochemical precursor of $NAD^+$. There is in vitro data showing that NR and NMN in particular can elevate $NAD^+$ levels. Further, in animal models NR and NMN elevate $NAD^+$ levels and improve organ function [Fang et al. (2016); Mills et al. (2016); de Picciotto et al. (2016); and Zang et al. (2016)], disease pathology and longevity [Fang et al. (2016); Mills et al. (2016); de Picciotto et al. (2016); and Zang et al. (2016)].

While NR and NMN are useful as precursors of $NAD^+$ and can potentially elevate levels of $NAD^+$ and thus promote cellular health and mitochondrial function, the bioavailability of these molecules is not optimal for their use as pharmacological and nutritional agents [Ratajczak et al. (2016) and Trammell et al. (2016)]. The reasons for their poor bioavailability include pH-dependent stability, degradation due to hydrolysis, and the need for enzymatic conversion within the cell to NAD for biological effects.

SUMMARY OF THE DISCLOSURE

The disclosure relates to nicotinamide riboside (NR), the reduced form of NR (NRH), nicotinic acid riboside (NAR), the reduced form of NAR (NARH), derivatives thereof, compositions thereof and uses thereof, including to increase $NAD^+$ levels, to enhance mitochondrial and cellular function and cell viability, to provide cytoprotection, and to treat or prevent mitochondrial diseases, mitochondria-related disorders and other disorders.

The disclosure provides compounds of Formulas I and II.

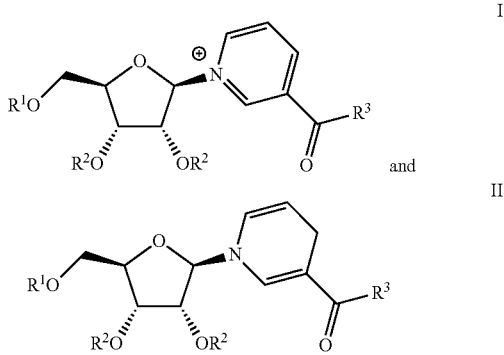

wherein R¹, R² and R³ are defined elsewhere herein.

The disclosure further provides compounds of Formulas III and IV:

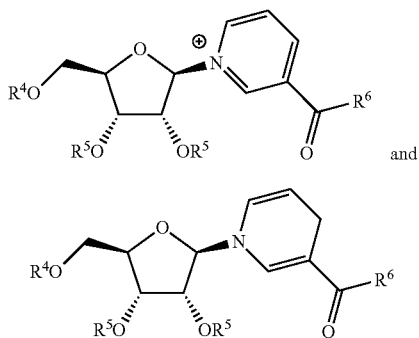

wherein R⁴, R⁵ and R⁶ are defined elsewhere herein.

The compounds of Formulas I, II, III and IV can increase NAD⁺ levels in the mitochondria, the cytoplasm or/and the nucleus of cells (e.g., total cellular NAD⁺ level) and can enhance mitochondrial and cellular function and cell viability, and have suitable bioavailability and stability in intracellular and extracellular environments. Therefore, the compounds are useful for treating mitochondrial diseases, mitochondria-related diseases and conditions, diseases and conditions characterized by acute NAD⁺ depletion due to DNA damage, and other disorders and conditions.

GENERAL STATEMENTS

Figure 1:
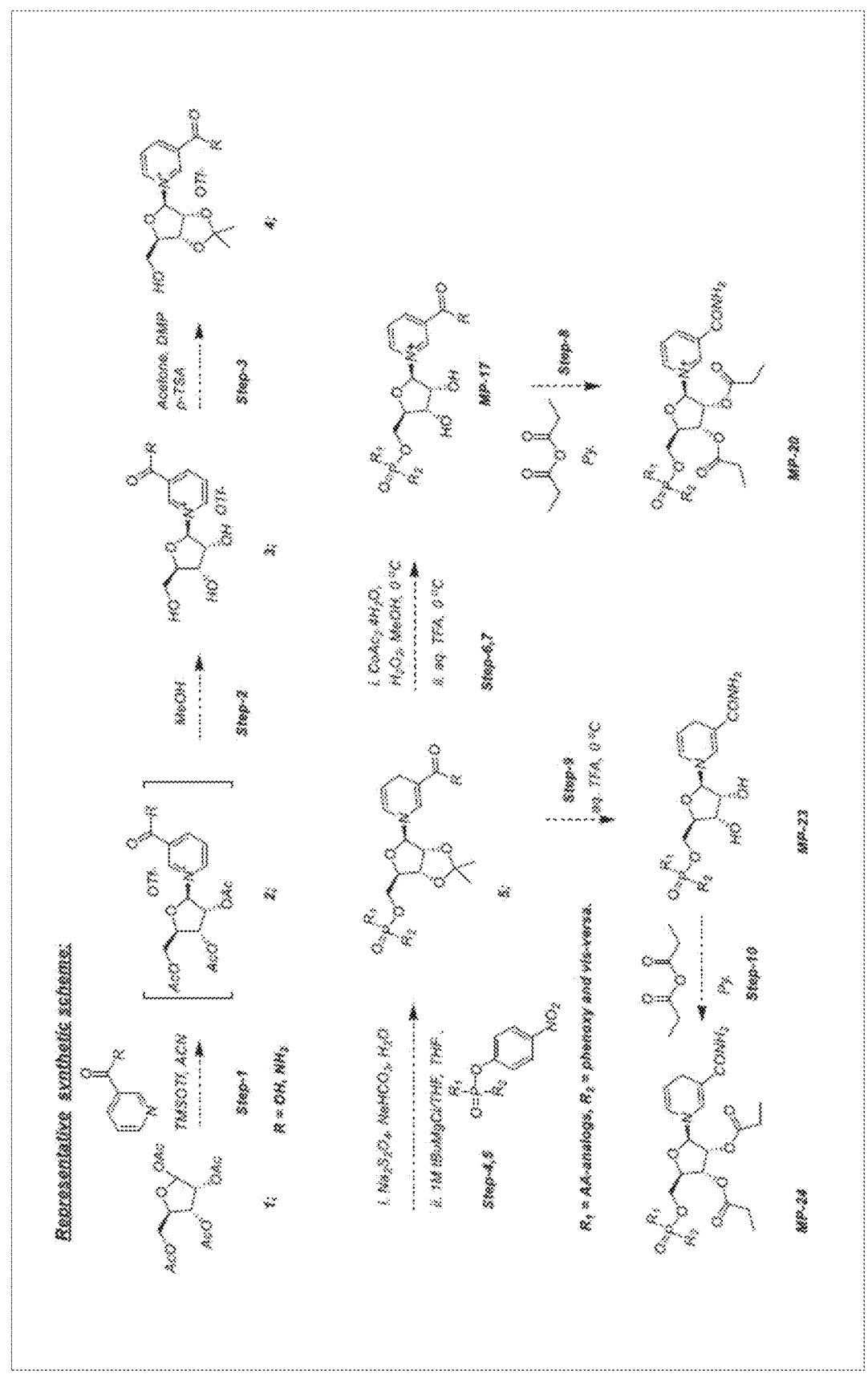
FIG. 1 illustrates an exemplary process for making compounds of Formulas I and II, which can be adapted to make compounds of Formulas III and IV.

While various embodiments of the present disclosure are described herein, it will be obvious to those skilled in the art that such embodiments are provided by way of example only. Numerous modifications and changes to, and variations and substitutions of, the embodiments described herein will be apparent to those skilled in the art without departing from the disclosure. It is understood that various alternatives to the embodiments described herein can be employed in practicing the disclosure. It is also understood that every embodiment of the disclosure can optionally be combined with any one or more of the other embodiments described herein which are consistent with that embodiment.

Where elements are presented in list format (e.g., in a Markush group), it is understood that each possible subgroup of the elements is also disclosed, and any one or more elements can be removed from the list or group.

It is also understood that, unless clearly indicated to the contrary, in any method described or claimed herein that includes more than one act or step, the order of the acts or steps of the method is not necessarily limited to the order in which the acts or steps of the method are recited, but the disclosure encompasses embodiments in which the order is so limited.

It is further understood that, in general, where an embodiment in the description or the claims is referred to as comprising one or more features, the disclosure also encompasses embodiments that consist of, or consist essentially of, such feature(s).

It is also understood that any embodiment of the disclosure, e.g., any embodiment or compound found within the prior art, can be explicitly excluded from the claims, regardless of whether or not the specific exclusion is recited in the specification.

It is further understood that the present disclosure encompasses salts, solvates, hydrates, clathrates and polymorphs of all of the compounds disclosed herein. The specific recitation of "salts", "solvates", "hydrates", "clathrates" or "polymorphs" with respect to a compound or a group of compounds in certain instances of the disclosure shall not be interpreted as an intended omission of any of these forms in other instances of the disclosure where the compound or the group of compounds is mentioned without recitation of any of these forms, unless stated otherwise or the context clearly indicates otherwise.

All patent literature and all non-patent literature cited herein are incorporated herein by reference in their entirety to the same extent as if each patent literature or non-patent literature were specifically and individually indicated to be incorporated herein by reference in its entirety.

Definitions

Unless defined otherwise or clearly indicated otherwise by their use herein, all technical and scientific terms used herein have the same meaning as commonly understood by those of ordinary skill in the art to which this application belongs.

As used in the specification and the appended claims, the indefinite articles "a" and "an" and the definite article "the" can include plural referents as well as singular referents unless specifically stated otherwise or the context clearly indicates otherwise.

The term "exemplary" as used herein means "serving as an example, instance or illustration". Any embodiment or feature characterized herein as "exemplary" is not necessarily to be construed as preferred or advantageous over other embodiments or features.

In some embodiments, the term "about" or "approximately" means within ±10% or 5% of the given value. Whenever the term "about" or "approximately" precedes the first numerical value in a series of two or more numerical values or in a series of two or more ranges of numerical values, the term "about" or "approximately" applies to each one of the numerical values in that series of numerical values or in that series of ranges of numerical values.

Whenever the term "at least" or "greater than" precedes the first numerical value in a series of two or more numerical values, the term "at least" or "greater than" applies to each one of the numerical values in that series of numerical values.

Whenever the term "no more than" or "less than" precedes the first numerical value in a series of two or more numerical values, the term "no more than" or "less than" applies to each one of the numerical values in that series of numerical values.

The term "agent" denotes a chemical compound, a mixture of chemical compounds, a biological macromolecule (such as a nucleic acid, a polypeptide or a portion thereof, or an antibody or a fragment thereof), a mixture of biological macromolecules, or an extract of a biological material such as an animal (particularly a mammalian) cell or tissue, a plant, a bacterium or a fungus. The term "polypeptides" includes peptides (e.g., polypeptides containing no more than about 50 amino acid residues) and proteins (which are larger polypeptides).

A "modulator" of, e.g., a receptor or enzyme can be an activator or inhibitor of that receptor or enzyme, and can increase or reduce the activity or/and the level of that receptor or enzyme. For example, a "sirtuin-modulating compound" can be an activator or inhibitor of a sirtuin, and can increase or reduce the activity or/and the level of a sirtuin.

The term "therapeutic agent" refers to any biologically, physiologically or pharmacologically active substance that acts locally or systemically in a subject and is administered to a subject for purposes of diagnosis, treatment, mitigation, cure or prevention of a medical condition or enhancement of a desired physical or mental development or condition.

The term "therapeutically effective amount" refers to an amount of an agent that, when administered to a subject, is sufficient to prevent, reduce the risk of developing, delay the onset of, slow the progression of or cause regression of the medical condition being treated, or to alleviate to some extent the medical condition or one or more symptoms or complications of that condition, at least in some fraction of the subjects taking that agent. The term "therapeutically effective amount" also refers to an amount of an agent that is sufficient to elicit the biological or medical response of a cell, tissue, organ, system, animal or human which is sought by a researcher, veterinarian, medical doctor or clinician.

The terms "treat", "treating" and "treatment" include alleviating, ameliorating, inhibiting the progress of, reversing or abrogating a medical condition or one or more symptoms or complications associated with the condition, and alleviating, ameliorating or eradicating one or more causes of the condition. Reference to "treatment" of a medical condition includes prevention of the condition. The terms "prevent", "preventing" and "prevention" include precluding, reducing the risk of developing and delaying the onset of a medical condition or one or more symptoms or complications associated with the condition.

The term "medical conditions" (or "conditions" for short) includes diseases and disorders. The terms "diseases" and "disorders" are used interchangeably herein.

"Diabetes mellitus" (or "diabetes" for short) is a metabolic disorder characterized by high blood sugar level over a prolonged period, and can include complications such as ketoacidosis. Diabetes is characterized by chronic, general metabolic abnormalities resulting from prolonged high blood sugar level or/and a decrease in glucose tolerance. The main types of diabetes include type 1 diabetes (T1D), type 2 diabetes (T2D) and gestational diabetes.

"Mitochondrial diseases" are disorders caused by dysfunctional mitochondria, and occur when the mitochondria of the cell, e.g., fail to produce enough energy for cell or organ function, or produce excessive amounts of reactive oxygen species (ROS) that cause oxidative damage to the cell or components thereof or lead to other pathological effects. A mitochondrial disease can be due to, e.g., a congenital genetic deficiency or defect (e.g., a mutation or deletion in mitochondrial DNA resulting in defective mitochondria), or an acquired deficiency or defect. A mitochondrial disease can be caused by, e.g., oxidative damage during aging, excessive mitochondrial calcium level, excessive exposure of affected cells to nitric oxide, ischemia, hypoxia, microtubule-associated deficit in axonal transport of mitochondria, or excessive expression of mitochondrial uncoupling proteins. Congenital mitochondrial diseases result from, e.g., hereditary mutations, deletions or other defects in mitochondrial DNA or in nuclear genes encoding proteins (e.g., those regulating mitochondrial DNA function or integrity). Acquired mitochondrial defects can be caused by, e.g., damage to mitochondrial DNA due to oxidative processes or aging, mitochondrial dysfunction, inhibition of respiratory chain complexes, mitochondrial respiration deficiencies and defects, oxygen deficiency, impaired nuclear-mitochondrial interactions, and excessive expression of mitochondrial uncoupling proteins in response to, e.g., lipids, oxidative damage or inflammation.

The term "subject" refers to an animal, including but not limited to a mammal, such as a primate (e.g., a human, a chimpanzee or a monkey), a rodent (e.g., a rat, a mouse, a guinea pig, a gerbil or a hamster), a lagomorph (e.g., a rabbit), a bovine (e.g., a cattle), a suid (e.g., a pig), a caprine (e.g., a sheep), an equine (e.g., a horse), a canine (e.g., a dog) or a feline (e.g., a cat). The terms "subject" and "patient" are used interchangeably herein in reference, e.g., to a mammalian subject, such as a human subject.

The term "bioavailable", when referring to an agent, refers to the extent to which the agent is taken up by a cell, tissue or organ, or otherwise physiologically available to the subject after administration.

The term "parenteral" refers to a route of administration other than through the alimentary canal, such as by injection, infusion or inhalation. Parenteral administration includes without limitation subcuticular, intradermal, subcutaneous, intravascular, intravenous, intra-arterial, intramuscular, intracardiac, intraperitoneal, intracavitary, intra-articular, intracapsular, subcapsular, intra-orbital, transtracheal, intrasternal, intrathecal, intramedullary, intraspinal, subarachnoid and topical administrations. Topical administration includes without limitation dermal/epicutaneous, transdermal, mucosal, transmucosal, intranasal (e.g., by nasal spray or drop), ocular (e.g., by eye drop), pulmonary (e.g., by oral or nasal inhalation), buccal, sublingual, rectal (e.g., by suppository), and vaginal (e.g., by suppository).

The term "pharmaceutically acceptable" refers to a substance (e.g., an active ingredient or an excipient) that is suitable for use in contact with the tissues and organs of a subject without excessive irritation, allergic response, immunogenicity and toxicity, is commensurate with a reasonable benefit/risk ratio, and is effective for its intended use. A "pharmaceutically acceptable" excipient or carrier of a pharmaceutical composition is also compatible with the other ingredients of the composition.

The term "nicotinyl (or nicotinoyl or nicotinic) riboside compounds" as used herein includes nicotinamide riboside (NR), the reduced form of NR (NRH), nicotinic acid riboside (NAR), the reduced form of NAR (NARH), and derivatives thereof. As used herein, the term "nicotinamide riboside (NR) derivatives" includes derivatives of both the oxidized form and the reduced form of NR, and the term "nicotinic acid riboside (NAR) derivatives" includes derivatives of both the oxidized form and the reduced form of NAR.

The disclosure encompasses salts, solvates, hydrates, clathrates and polymorphs of the compounds described herein. A "solvate" of a compound includes a stoichiometric or non-stoichiometric amount of a solvent (e.g., water, acetone or an alcohol [e.g., ethanol]) bound non-covalently to the compound. A "hydrate" of a compound includes a stoichiometric or non-stoichiometric amount of water bound non-covalently to the compound. A "clathrate" of a compound contains molecules of a substance (e.g., a solvent) enclosed in the crystal structure of the compound. A "polymorph" of a compound is a crystalline form of the compound.

The term "alkyl" refers to a linear (straight chain) or branched, saturated monovalent hydrocarbon radical. The term "lower alkyl" refers to a linear $C_1$-$C_6$ or branched $C_3$-$C_6$ alkyl group. Lower alkyl groups include without limitation methyl, ethyl, propyl (including n-propyl and isopropyl), butyl (including all isomeric forms, such as n-butyl, isobutyl, sec-butyl and tert-butyl), pentyl (including all isomeric forms, such as n-pentyl), and hexyl (including all isomeric forms, such as n-hexyl).

The term "cycloalkyl" refers to a cyclic saturated monovalent hydrocarbon radical. $C_3$-$C_6$ cycloalkyl groups include cyclopropyl, cyclobutyl, cyclopentyl and cyclohexyl.

Examples of 3- to 6-membered, nitrogen-containing heterocyclic rings include without limitation aziridinyl, azetidinyl, pyrrolidinyl, piperidinyl, piperazinyl and morpholinyl.

DETAILED DESCRIPTION OF THE DISCLOSURE

The disclosure provides nicotinamide riboside (NR), the reduced form of NR (NRH), nicotinic acid riboside (NAR), the reduced form of NAR (NARH), derivatives thereof, pharmaceutical compositions thereof and uses thereof. The NR and NAR derivatives described herein can act as precursors or prodrugs of NR/NRH and NAR/NARH and thereby serve as sources of NR/NRH and NAR/NARH with improved stability and bioavailability.

Both the oxidized form and the reduced form of both NR and NAR can be converted within the body to NMN and then to $NAD^+$. Alternatively, without intending to be bound by theory, NRH and NARH may be converted to a reduced form of NMN and NAMN (NMNH and NAMNH), which may then be converted to NADH, which functions as a reducing agent in redox reactions and becomes oxidized to $NAD^+$ in the process. By increasing $NAD^+$ levels, the NR and NAR derivatives can enhance mitochondrial and cellular function and provide cytoprotection, and thus are useful for treating mitochondrial diseases, mitochondria-related diseases and conditions, diseases and conditions associated with acute $NAD^+$ depletion induced by DNA damage, and other disorders.

NR and NAR Derivatives

In some embodiments, NR and NAR derivatives have Formulas I and II.

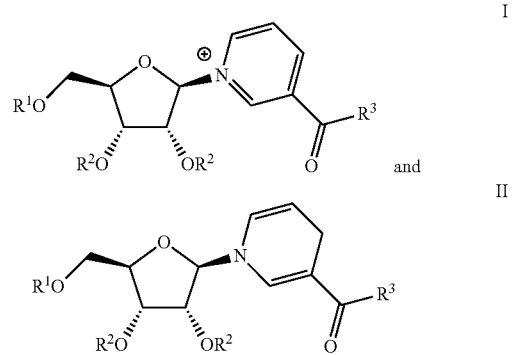

wherein:
$R^1$ is hydrogen,

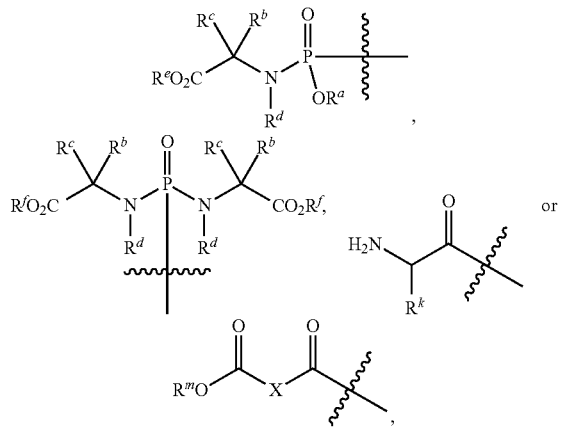

wherein:
$R^a$ is hydrogen, a counterion, linear or branched $C_1$-$C_6$ alkyl, $C_3$-$C_6$ cycloalkyl, phenyl, 1-naphthyl or 2-naphthyl, wherein the phenyl is optionally substituted with F, Cl, —$NO_2$, linear or branched $C_1$-$C_4$ alkyl, —$CF_3$ or —O-(linear or branched $C_1$-$C_4$ alkyl);
$R^b$ and $R^c$ at each occurrence independently are hydrogen, linear or branched $C_1$-$C_5$ alkyl, —$CH_2$-phenyl, —$CH_2$-3-indole or —$CH_2$-5-imidazole, wherein the alkyl is optionally substituted with —OH, —$OR^j$, —SH, —SR$^j$, —NH$_2$, —NHR$^j$, —N(R$^j$)$_2$, —NHC(=O)R$^j$, —NHC(=NH)NH$_2$, —C(=O)NH$_2$, —CO$_2$H or —C(=O)OR$^j$, and the phenyl is optionally substituted with —OH or —OR$^j$, wherein R$^j$ at each occurrence independently is linear or branched C$_1$-C$_4$ alkyl;

R$^d$ at each occurrence independently is hydrogen, methyl or linear or branched C$_2$-C$_4$ alkyl;

R$^e$ and R$^f$ at each occurrence independently are hydrogen, a counterion, linear or branched C$_1$-C$_8$ alkyl, C$_3$-C$_6$ cycloalkyl, —CH$_2$—(C$_3$-C$_6$ cycloalkyl), phenyl or —CH$_2$-phenyl, wherein the phenyl is optionally substituted with F, Cl, —NO$_2$, linear or branched C$_1$-C$_4$ alkyl, —CF$_3$ or —O-(linear or branched C$_1$-C$_4$ alkyl);

R$^k$ is hydrogen, linear or branched C$_1$-C$_6$ alkyl, —CH$_2$-phenyl, —CH$_2$-3-indole or —CH$_2$-5-imidazole, wherein the alkyl is optionally substituted with —OH, —OR$^j$, —SH, —SR$^j$, —NH$_2$, —NHR$^j$, —N(R$^j$)$_2$, —NHC(=O)R$^j$, —NHC(=NH)NH$_2$, —C(=O)NH$_2$, —CO$_2$H or —C(=O)OR$^j$, and the phenyl is optionally substituted with —OH or —OR$^j$, wherein R$^j$ at each occurrence independently is linear or branched C$_1$-C$_4$ alkyl;

R$^m$ is hydrogen, a counterion, linear or branched C$_1$-C$_6$ alkyl, C$_3$-C$_6$ cycloalkyl, phenyl, —CH$_2$-phenyl or

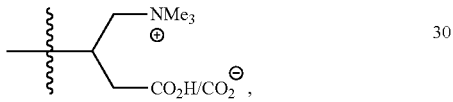

wherein the phenyl is optionally substituted with F, Cl, —NO$_2$, linear or branched C$_1$-C$_4$ alkyl, —CF$_3$ or —O-(linear or branched C$_1$-C$_4$ alkyl); and X is cis or trans —HC=CH— or —(CH$_2$)$_n$— optionally substituted with —OH, —OR$^j$ or —OC(=O)R$^j$, wherein R$^j$ is linear or branched C$_1$-C$_4$ alkyl and n is 1, 2, 3, 4, 5 or 6;

R$^2$ at each occurrence independently is hydrogen,

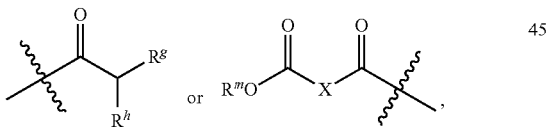

wherein:

R$^9$ is hydrogen, linear or branched C$_1$-C$_5$ alkyl, —CH$_2$-phenyl, —CH$_2$-3-indole or —CH$_2$-5-imidazole, wherein the alkyl is optionally substituted with —OH, —OR$^j$, —SH, —SR$^j$, —NH$_2$, —NHR$^j$, —N(R$^j$)$_2$, —NHC(=O)R$^j$, —NHC(=NH)NH$_2$, —C(=O)NH$_2$, —CO$_2$H or —C(=O)OR$^j$, and the phenyl is optionally substituted with —OH or —OR$^j$, wherein R$^j$ at each occurrence independently is linear or branched C$_1$-C$_4$ alkyl;

R$^h$ is hydrogen, methyl or —NH$_2$;

or R$^g$ and R$^h$ together with the carbon atom to which they are connected form a C$_3$-C$_6$ cycloalkyl or phenyl ring, wherein the phenyl ring is optionally substituted with F, Cl, —NO$_2$, linear or branched C$_1$-C$_4$ alkyl, —CF$_3$ or —O-(linear or branched C$_1$-C$_4$ alkyl); and R$^m$ and X are as defined above; and R$^3$ is —NH$_2$, —NHR$''$, —N(R$''$)$_2$, —OH, —OR$^o$ or

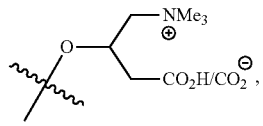

wherein:

R$''$ at each occurrence independently is linear or branched C$_1$-C$_6$ alkyl or allyl, wherein the alkyl is optionally substituted with —OH or —O-(linear or branched C$_1$-C$_3$ alkyl), or both occurrences of R$''$ and the nitrogen atom to which they are connected form a 3- to 6-membered heterocyclic ring; and R$^o$ is a counterion, linear or branched C$_1$-C$_6$ alkyl, C$_3$-C$_6$ cycloalkyl, phenyl or —CH$_2$-phenyl, wherein the phenyl is optionally substituted with F, Cl, —NO$_2$, linear or branched C$_1$-C$_4$ alkyl, —CF$_3$ or —O-(linear or branched C$_1$-C$_4$ alkyl);

or pharmaceutically acceptable salts, solvates, hydrates, clathrates, polymorphs or stereoisomers thereof;

with the proviso that:

1) R$^1$ and both occurrences of R$^2$ all are not hydrogen except when R$^3$ is

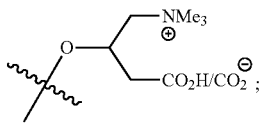

and 2) the compounds of Formulas I and II are not:

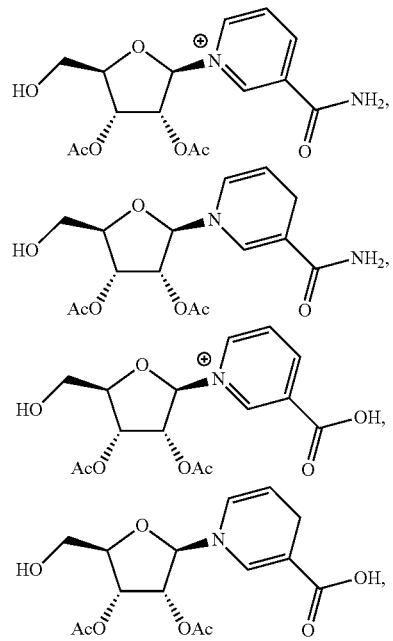

11
-continued
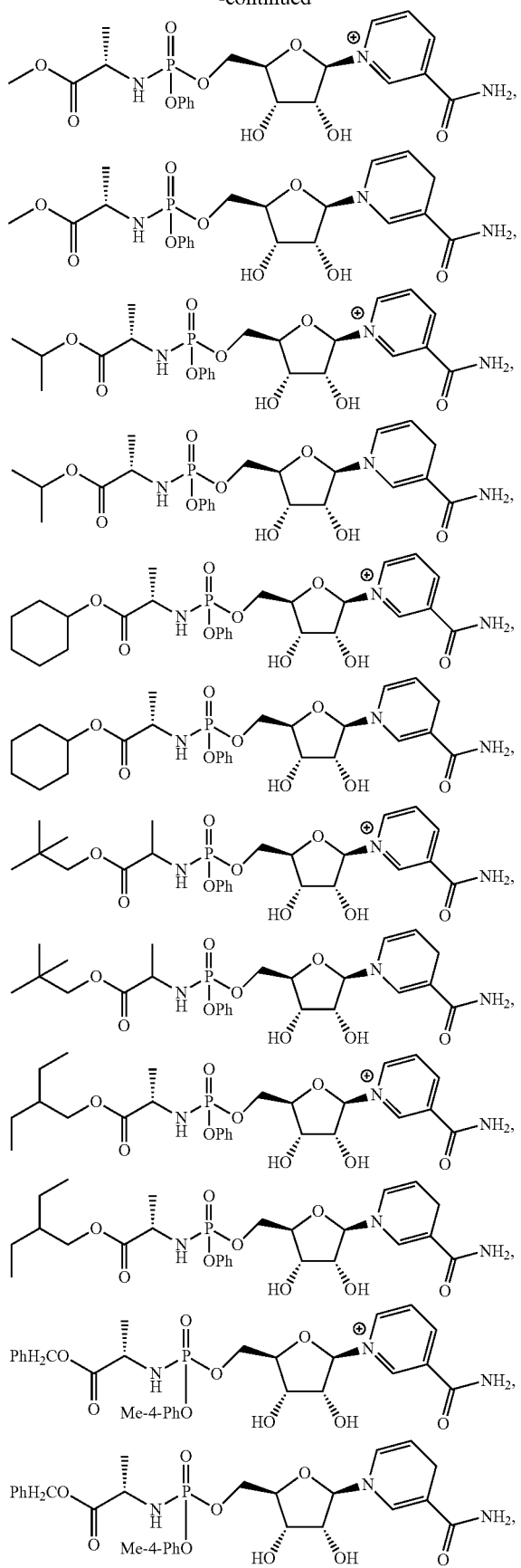
12
-continued
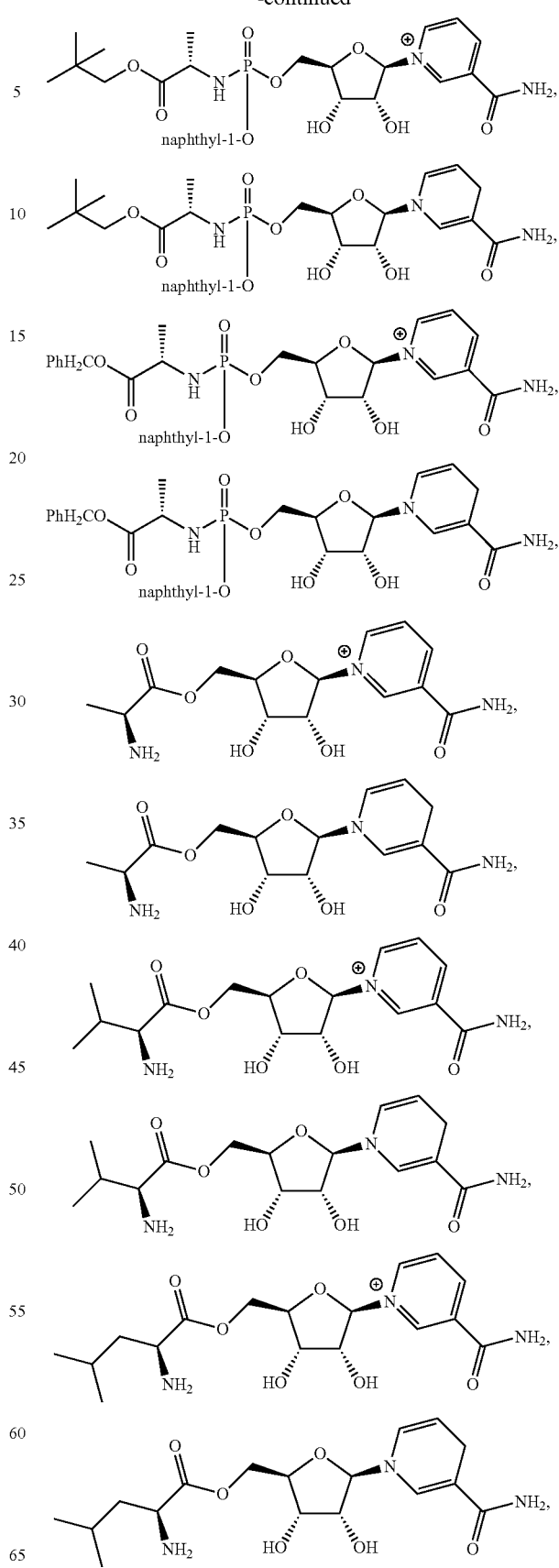

-continued

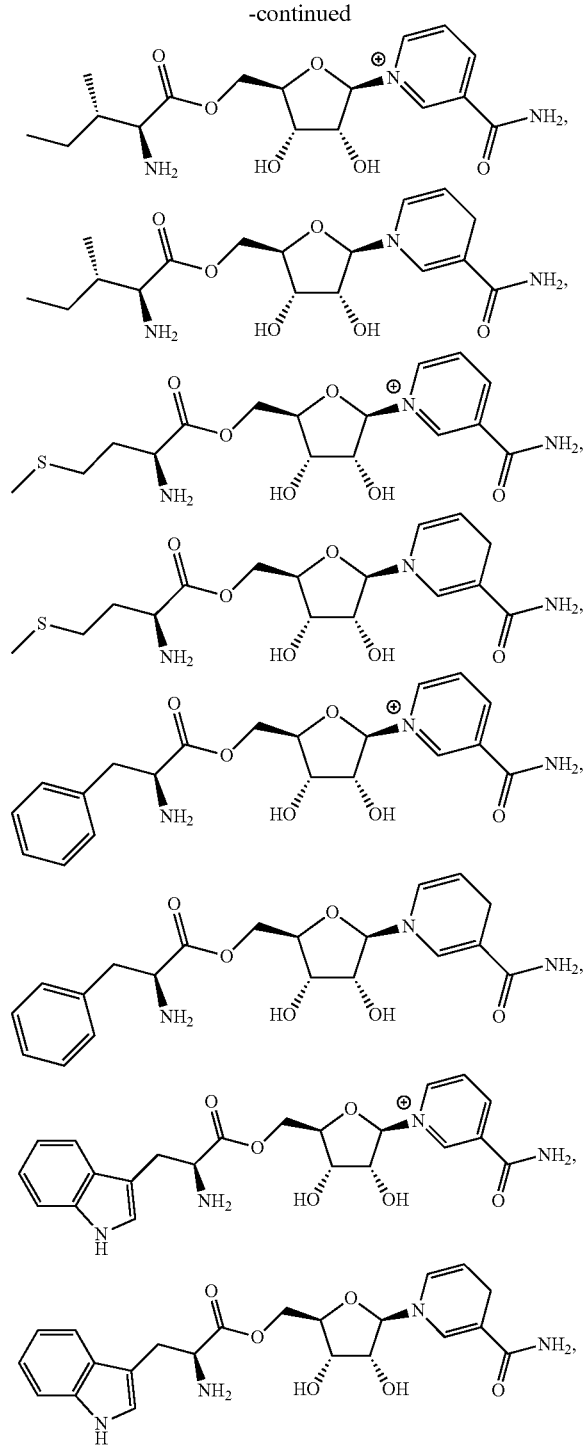

or salts or stereoisomers thereof.

However, the compounds excluded from Formulas I and II above can be included within the scope of NR/NAR derivatives generally, or within the scope of Formulas I and II more specifically, in some embodiments of pharmaceutical compositions and therapeutic or medical uses.

In some embodiments, when both occurrences of $R^2$ are acetyl:
1) $R^1$ is not hydrogen; or
2) $R^3$ is not —$NH_2$ or —OH or a salt thereof; or
3) $R^1$ is not hydrogen and $R^3$ is not —$NH_2$ or —OH or a salt thereof.

In certain embodiments, when $R^1$ is

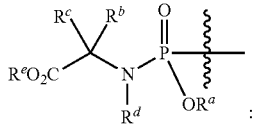

1) both occurrences of $R^2$ are not hydrogen; or
2) $R^3$ is not —$NH_2$ or —OH or a salt thereof; or
3) both occurrences of $R^2$ are not hydrogen and $R^3$ is not —$NH_2$ or —OH or a salt thereof.

In some embodiments, when $R^1$ is

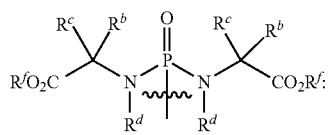

1) both occurrences of $R^2$ are not hydrogen; or
2) $R^3$ is not —$NH_2$ or —OH or a salt thereof; or
3) both occurrences of $R^2$ are not hydrogen and $R^3$ is not —$NH_2$ or —OH or a salt thereof.

In certain embodiments, when $R^1$ is

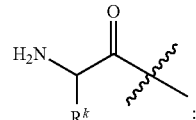

1) both occurrences of $R^2$ are not hydrogen; or
2) $R^3$ is not —$NH_2$ or —OH or a salt thereof; or
3) both occurrences of $R^2$ are not hydrogen and $R^3$ is not —$NH_2$ or —OH or a salt thereof.

In some embodiments, $R^1$ is

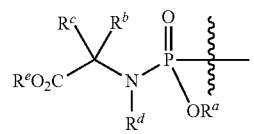

(phosphoramidate). In certain embodiments, $R^1$ is

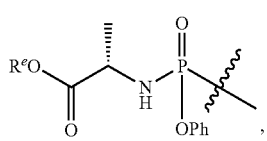

and $R^e$ is linear or branched $C_1$-$C_6$ alkyl. In certain embodiments, $R^e$ is methyl, ethyl or isopropyl.

In further embodiments, R¹ is

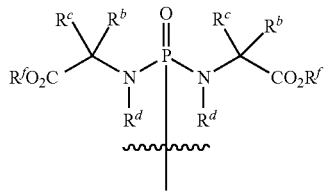

(phosphorodiamidate/bisphosphoramidate). In certain embodiments, R¹ is

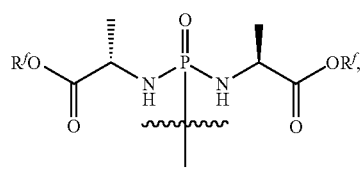

and both occurrences of $R^f$ are linear or branched $C_1$-$C_6$ alkyl. In certain embodiments, both occurrences of $R^f$ are methyl, ethyl or isopropyl.

In other embodiments, R¹ is

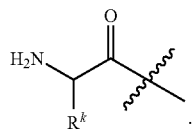

In certain embodiments, R¹ is

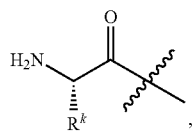

and $R^k$ is linear or branched $C_1$-$C_6$ alkyl. In certain embodiments, $R^k$ is methyl, ethyl or isopropyl. An amino acid group can facilitate penetration of an NR/NAR derivative through membrane barriers via peptide transporters, such as peptide transporter 1 in the intestinal epithelium.

In additional embodiments, R¹, or/and R² at either occurrence or at both occurrences, is/are

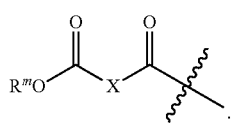

In some embodiments, X is trans —HC═CH—, —CH₂CH₂— or —CH(OH)CH₂—, and $R^m$ is hydrogen, a counterion, linear or branched $C_1$-$C_6$ alkyl (e.g., methyl, ethyl or isopropyl) or

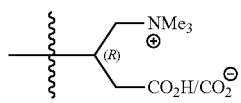

(an L-carnitine group). The —CH(OH)CH₂— portion can have the S-stereochemistry or a mixture (e.g., an approximately 1:1 ratio) of S/R-stereochemistry. In certain embodiments, R¹, or/and R² at either occurrence or at both occurrences, is/are selected from:

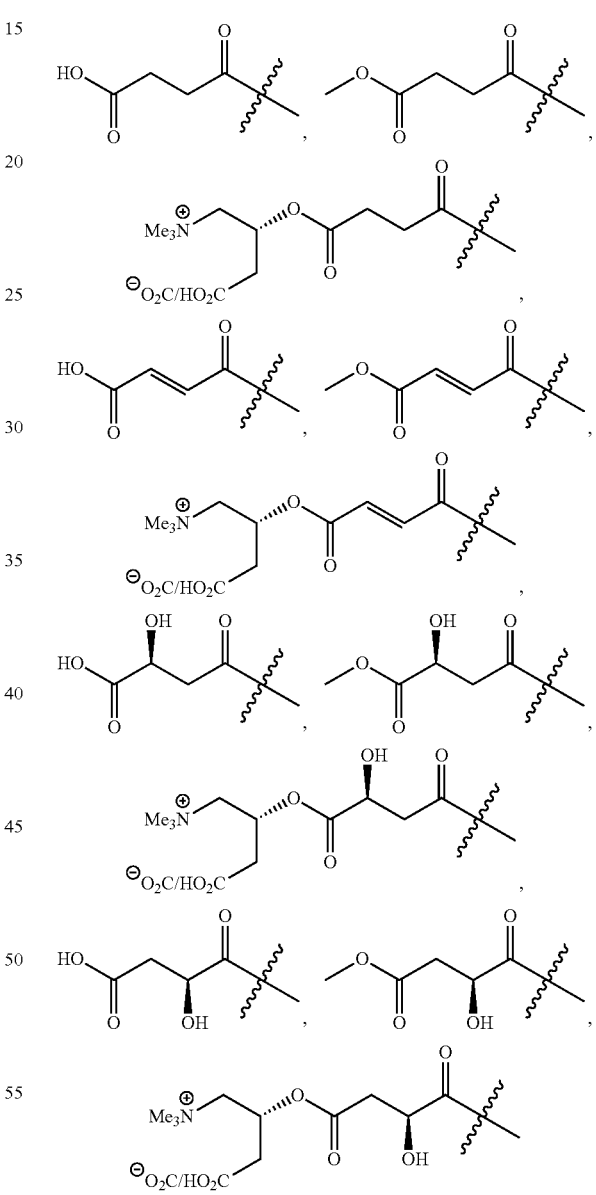

and salts thereof. A carnitine group can facilitate transport of an NR/NAR derivative into the mitochondria.

In some embodiments, R² at each occurrence independently, or at both occurrences, is hydrogen, —C(═O)- (linear or branched $C_1$-$C_6$ alkyl),

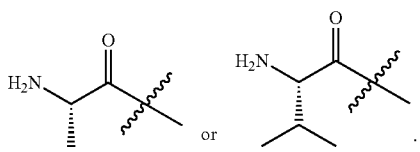

In certain embodiments, $R^2$ at each occurrence independently, or at both occurrences, is hydrogen, acetyl or propanoyl.

If a compound of Formula I or II comprises an amino acid group at $R^1$ or/and at either occurrence or both occurrences of $R^2$, including an amino acid group in a phosphoramidate moiety at $R^1$ or two amino acid groups in a phosphorodiamidate/bisphosphoramidate moiety at $R^1$, the amino acid group can independently be a natural amino acid or an unnatural amino acid. In some embodiments, an amino acid group is glycine, alanine, valine, leucine, isoleucine, methionine, proline, tryptophan, phenylalanine, tyrosine, serine, threonine, cysteine, asparagine, glutamine, aspartic acid, glutamic acid, lysine, arginine or histidine, or a derivative thereof. In other embodiments, an amino acid group is an unnatural or non-proteinogenic amino acid, such as ornithine, citrulline or homoarginine. In certain embodiments, an amino acid group is glycine, alanine or valine. An amino acid group can be the L-isomer or the D-isomer, or can be a D/L (e.g., racemic) mixture. In certain embodiments, an amino acid group is the L-isomer.

In some embodiments, $R^3$ is —$NH_2$, —OH or a salt thereof, or

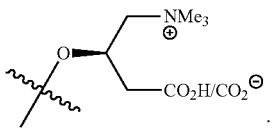

In certain embodiments, $R^3$ is

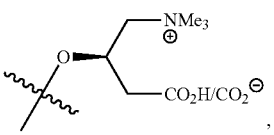, an L-carnitine moiety. The carnitine moiety can exist as a zwitterion.

In some embodiments of compounds of Formulas I and II:
1) $R^1$ is

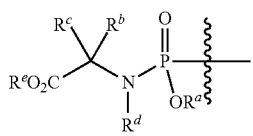

and both occurrences of $R^2$ are acetyl or propanoyl; or

2) $R^1$ is

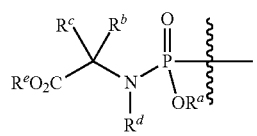

and $R^3$ is —OH or a salt thereof; or

3) $R^1$ is

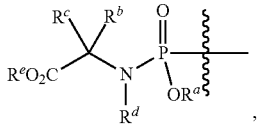, both occurrences of $R^2$ are acetyl or propanoyl, and $R^3$ is —OH or a salt thereof.

In certain embodiments, $R^1$ is

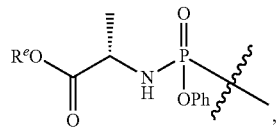, and $R^e$ is linear or branched $C_1$-$C_6$ alkyl. In certain embodiments, $R^e$ is methyl, ethyl or isopropyl.

In further embodiments of compounds of Formulas I and II:

$R^1$ is

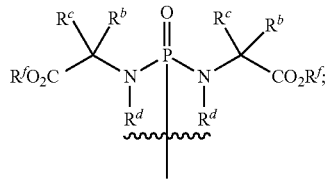, wherein $R^e$ is linear or branched $C_1$-$C_6$ alkyl;
$R^2$ at both occurrences is —C(=O)-(linear or branched $C_1$-$C_6$ alkyl); and
$R^3$ is —$NH_2$ or —OH or a salt thereof.

In certain embodiments, $R^e$ of the $R^1$ moiety is methyl, ethyl or isopropyl, and both occurrences of $R^2$ are acetyl or propanoyl.

In other embodiments of compounds of Formulas I and II:
$R^1$ is

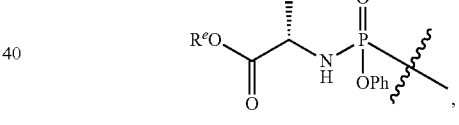

$R^2$ at each occurrence independently, or at both occurrences, is hydrogen, acetyl or propanoyl; and
$R^3$ is —$NH_2$ or —OH or a salt thereof.

In some embodiments:
$R^b$ and $R^c$ at each occurrence independently are hydrogen or linear or branched $C_1$-$C_5$ alkyl, or each pair of $R^b$ and $R^c$ is hydrogen and linear or branched $C_1$-$C_5$ alkyl;

$R^d$ at both occurrences is hydrogen; and
$R^f$ at both occurrences is linear or branched $C_1$-$C_6$ alkyl.

In certain embodiments, $R^1$ is

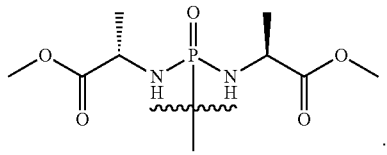

In further embodiments of compounds of Formulas I and II:
$R^1$ is

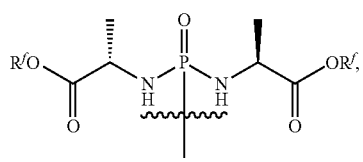

wherein both occurrences of $R^f$ are linear or branched $C_1$-$C_6$ alkyl;
$R^2$ at each occurrence independently, or at both occurrences, is hydrogen or —C(=O)-(linear or branched $C_1$-$C_6$ alkyl); and
$R^3$ is —$NH_2$ or —OH or a salt thereof.

In certain embodiments, both occurrences of $R^f$ of the $R^1$ moiety are methyl, ethyl or isopropyl, and $R^2$ at each occurrence independently, or at both occurrences, is hydrogen, acetyl or propanoyl.

In additional embodiments of compounds of Formulas I and II:
$R^1$ is

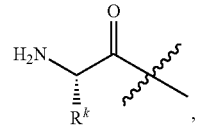

wherein $R^k$ is linear or branched $C_1$-$C_6$ alkyl;
$R^2$ at each occurrence independently, or at both occurrences, is hydrogen or —C(=O)-(linear or branched $C_1$-$C_6$ alkyl); and
$R^3$ is —$NH_2$ or —OH or a salt thereof.

In certain embodiments, $R^k$ of the $R^1$ moiety is methyl, ethyl or isopropyl, and $R^2$ at each occurrence independently, or at both occurrences, is hydrogen, acetyl or propanoyl.

In other embodiments of compounds of Formulas I and II:
$R^1$ is

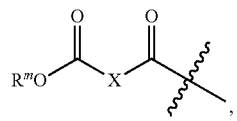

wherein:
X is cis or trans —HC=CH— or —$(CH_2)_n$— optionally substituted with —OH, —$OR^j$ or —OC(=O)$R^j$, wherein $R^j$ is linear or branched $C_1$-$C_4$ alkyl and n is 1, 2, 3, 4, 5 or 6; and $R^m$ is hydrogen, a counterion, linear or branched $C_1$-$C_6$ alkyl or

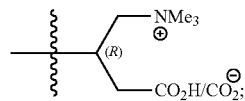

$R^2$ at each occurrence independently, or at both occurrences, is hydrogen or —C(=O)-(linear or branched $C_1$-$C_6$ alkyl); and
$R^3$ is —$NH_2$ or —OH or a salt thereof.

In certain embodiments:
for the $R^1$ moiety, X is trans —HC=CH—, —$CH_2CH_2$— or —CH(OH)$CH_2$—, and $R^m$ is hydrogen, a counterion, methyl, ethyl, isopropyl or

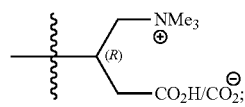

$R^2$ at each occurrence independently, or at both occurrences, is hydrogen, acetyl or propanoyl; and
$R^3$ is —$NH_2$.

In some embodiments, the compounds of Formulas I and II are selected from:

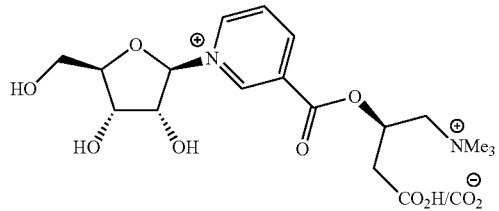

MP-09

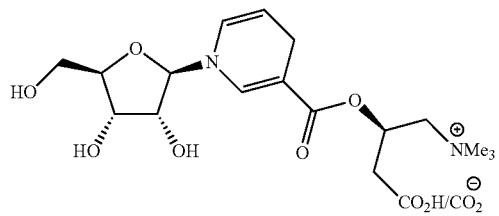

MP-10

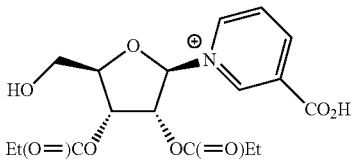

MP-07

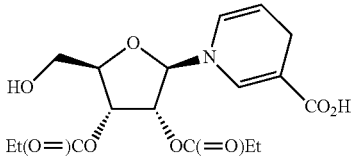

MP-08

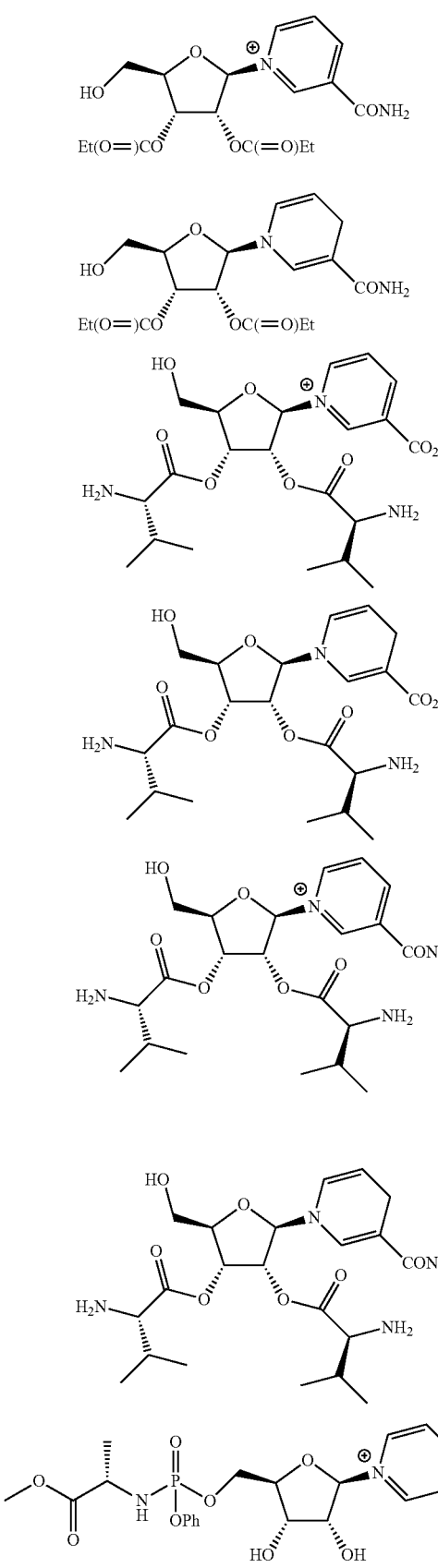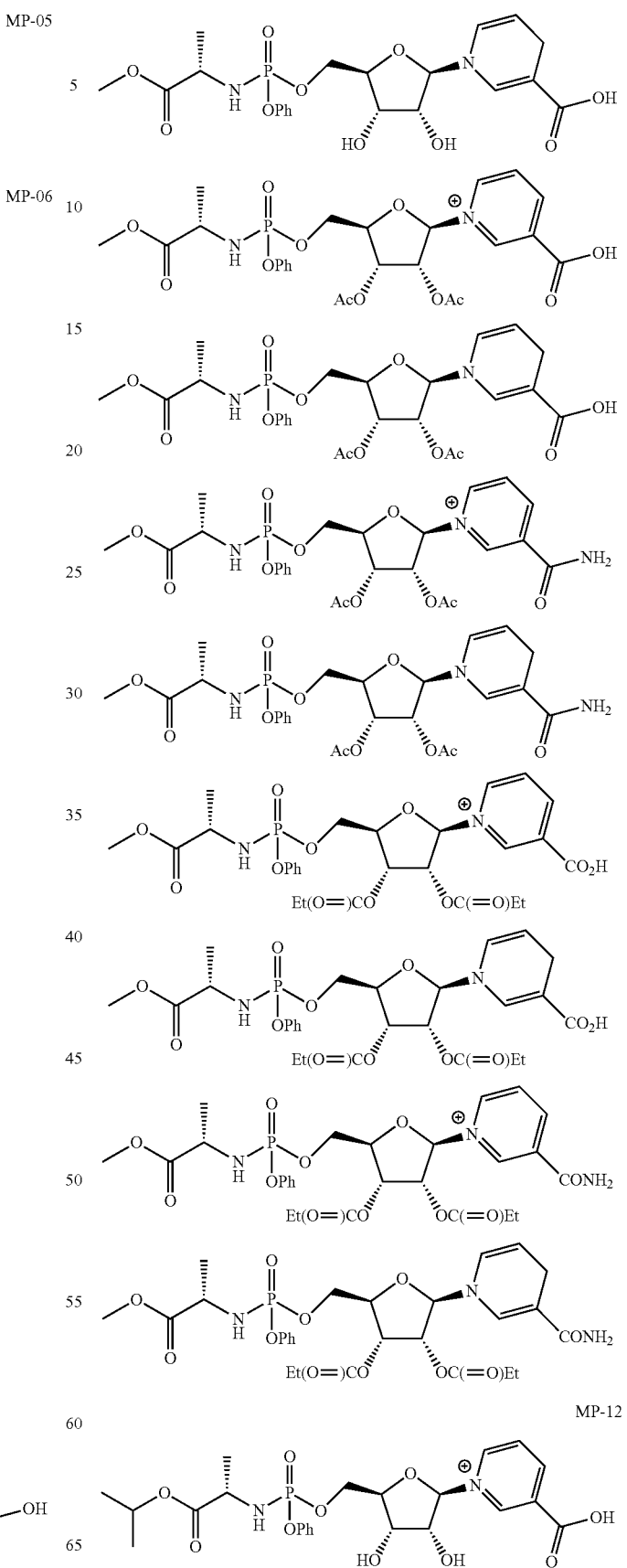

-continued
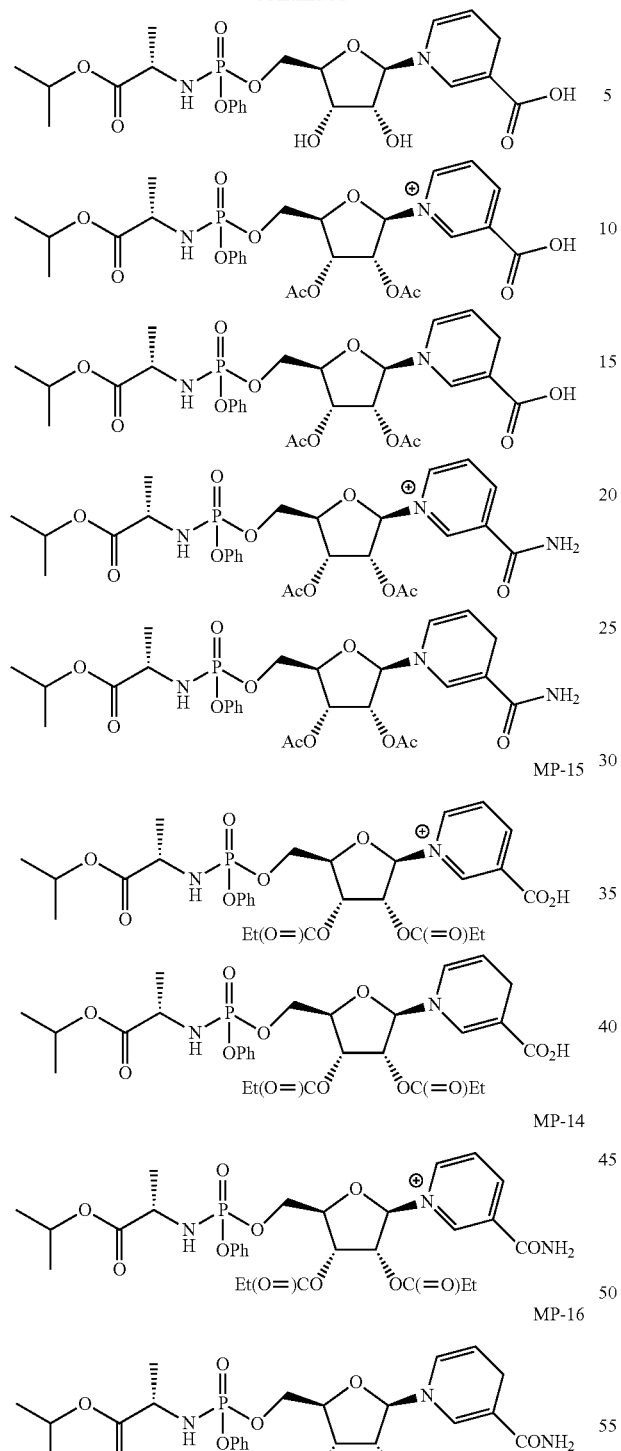
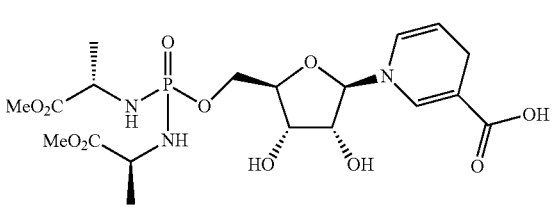
MP-19
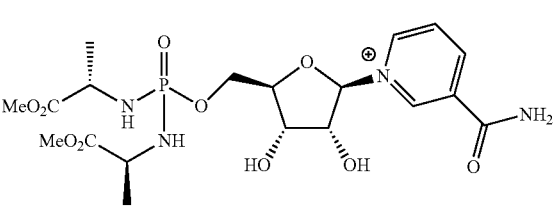
MP-17
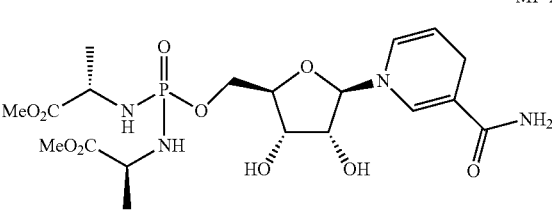
MP-23
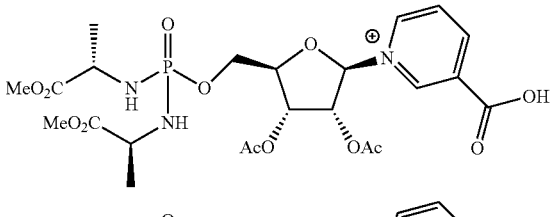
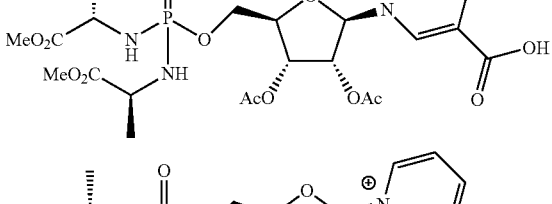
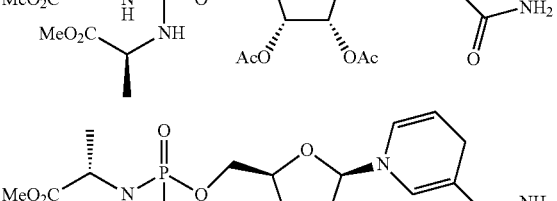
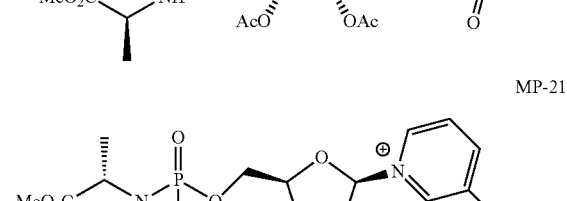
MP-21
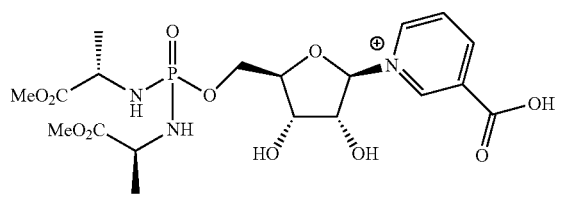

-continued
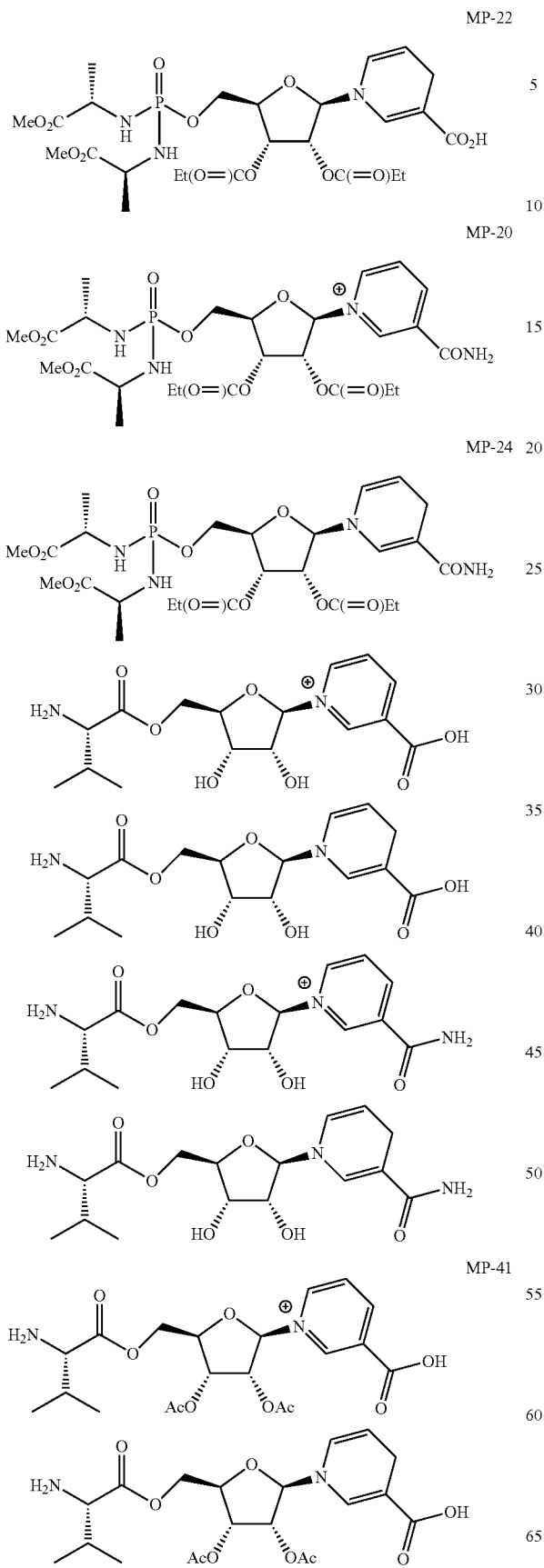
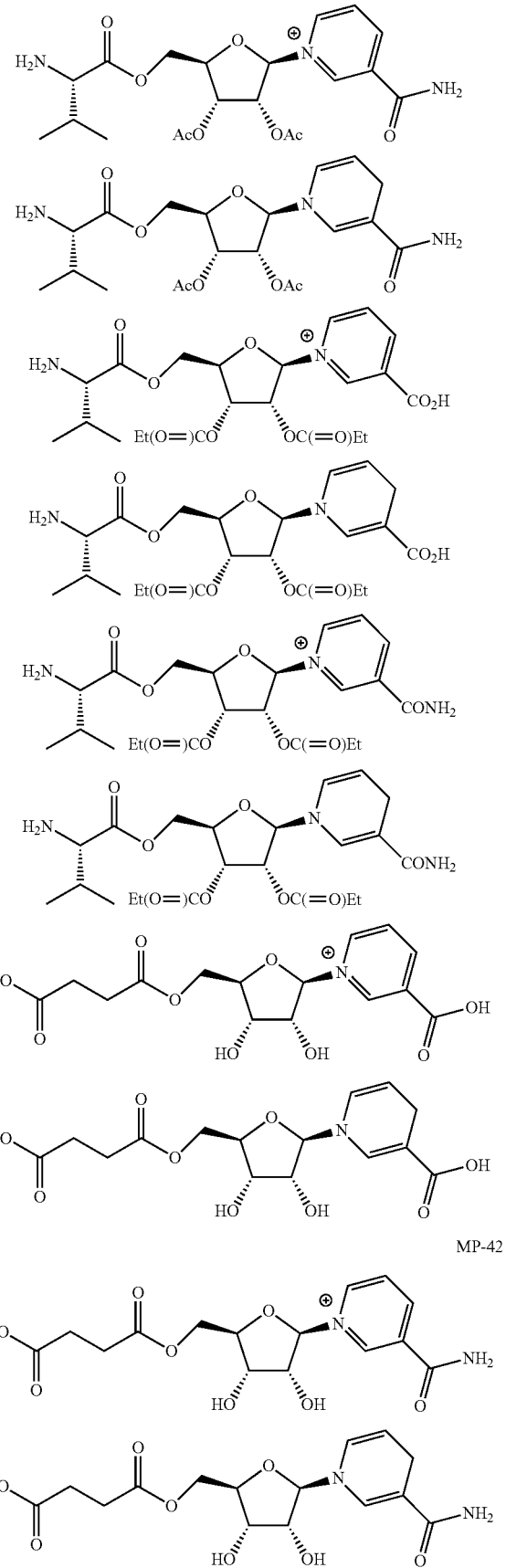

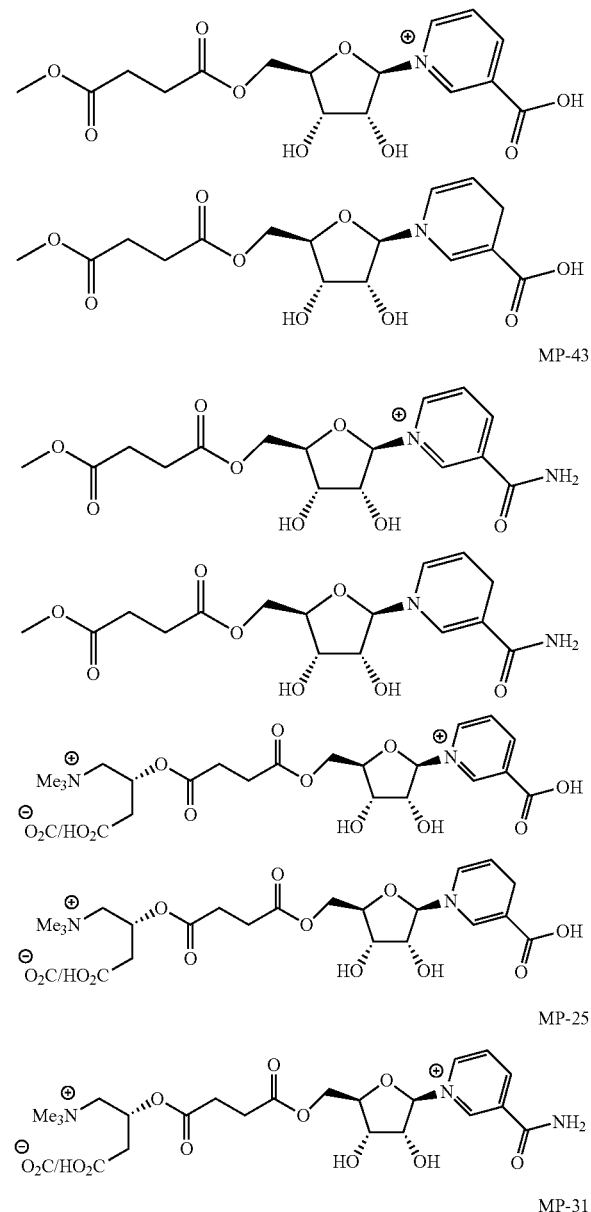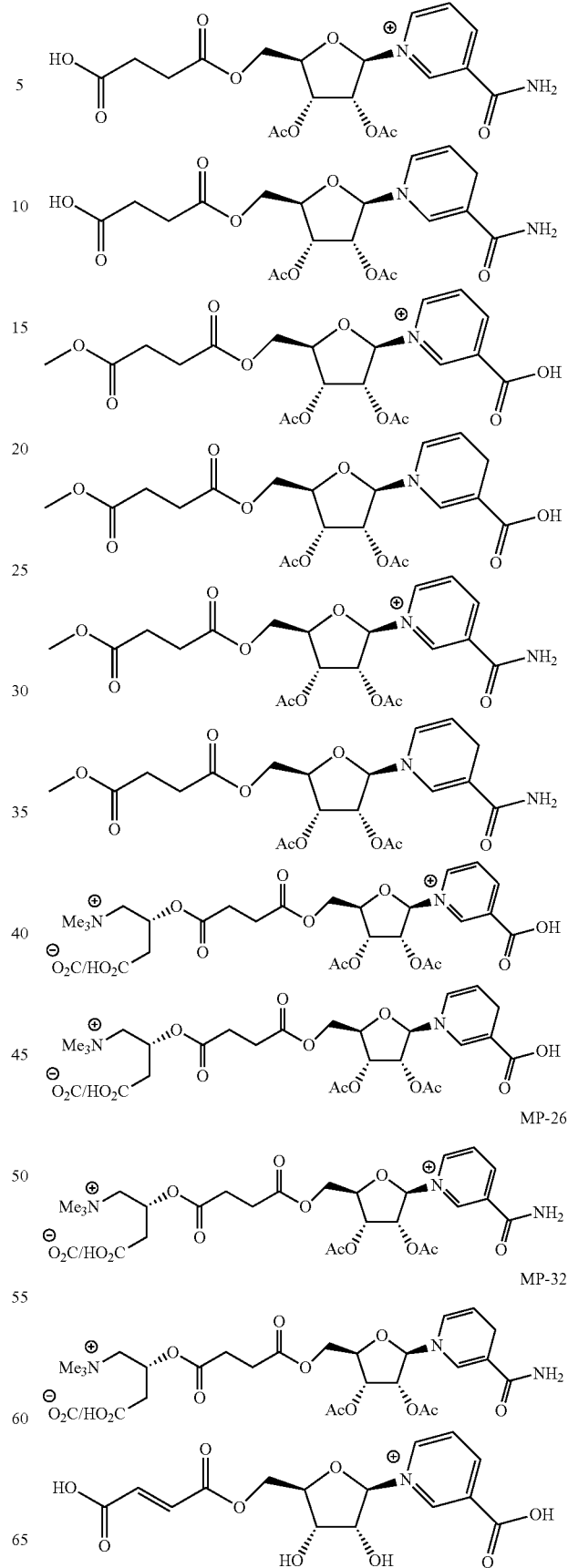

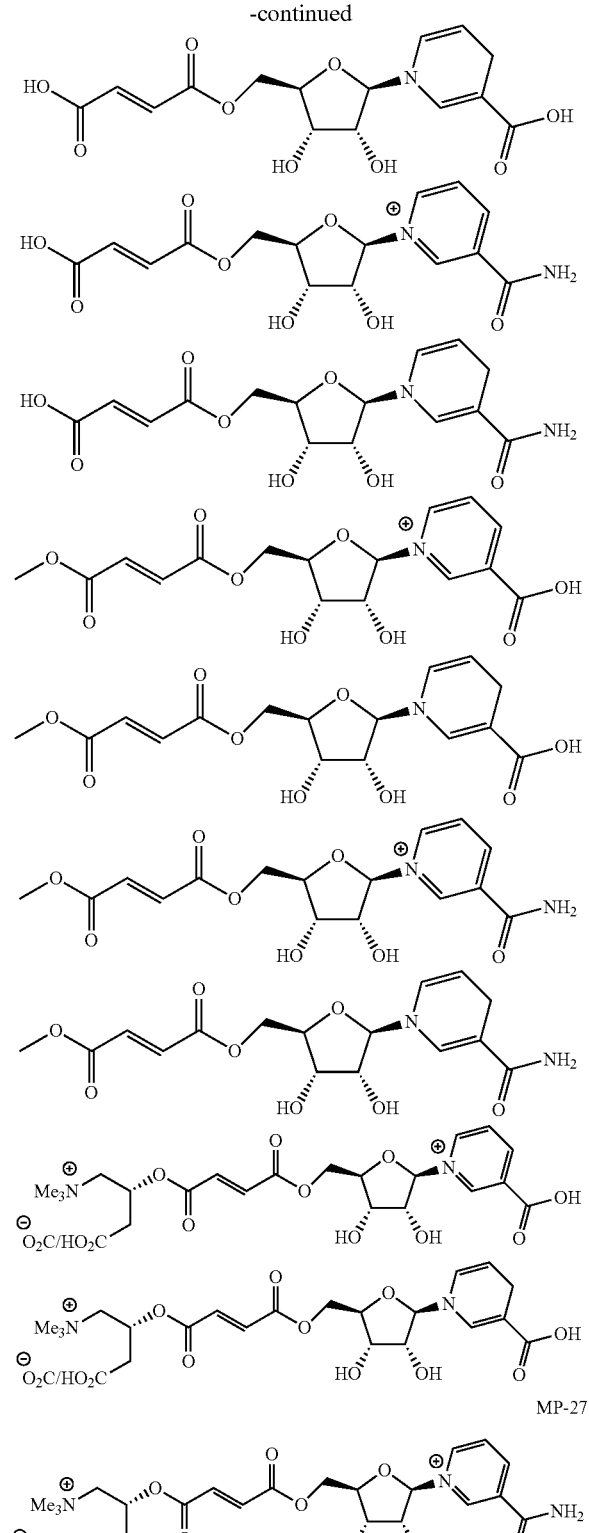
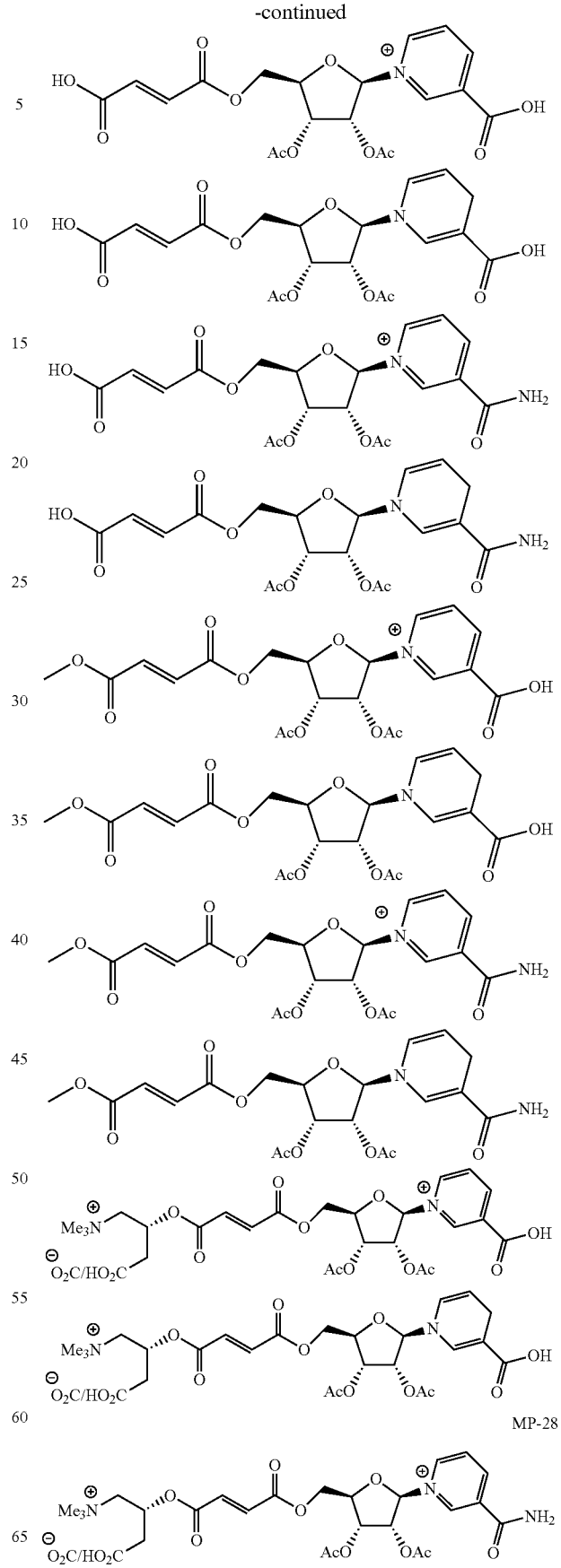

31
-continued
MP-34
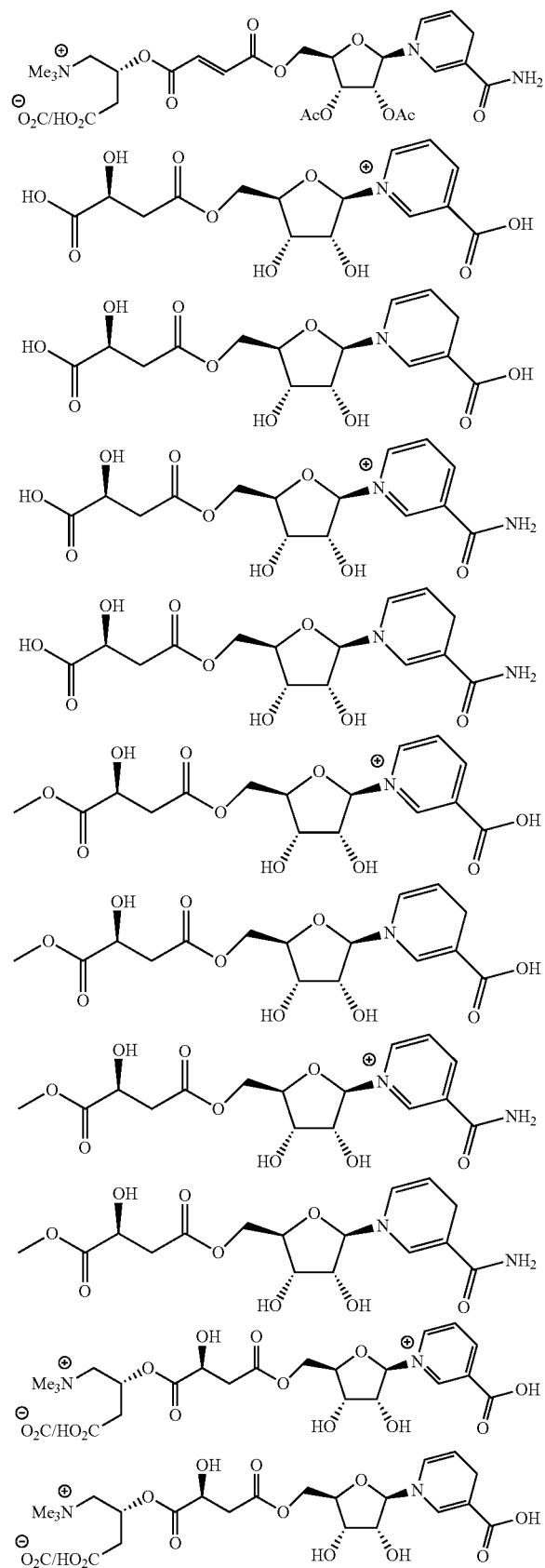
32
-continued
MP-29
MP-35
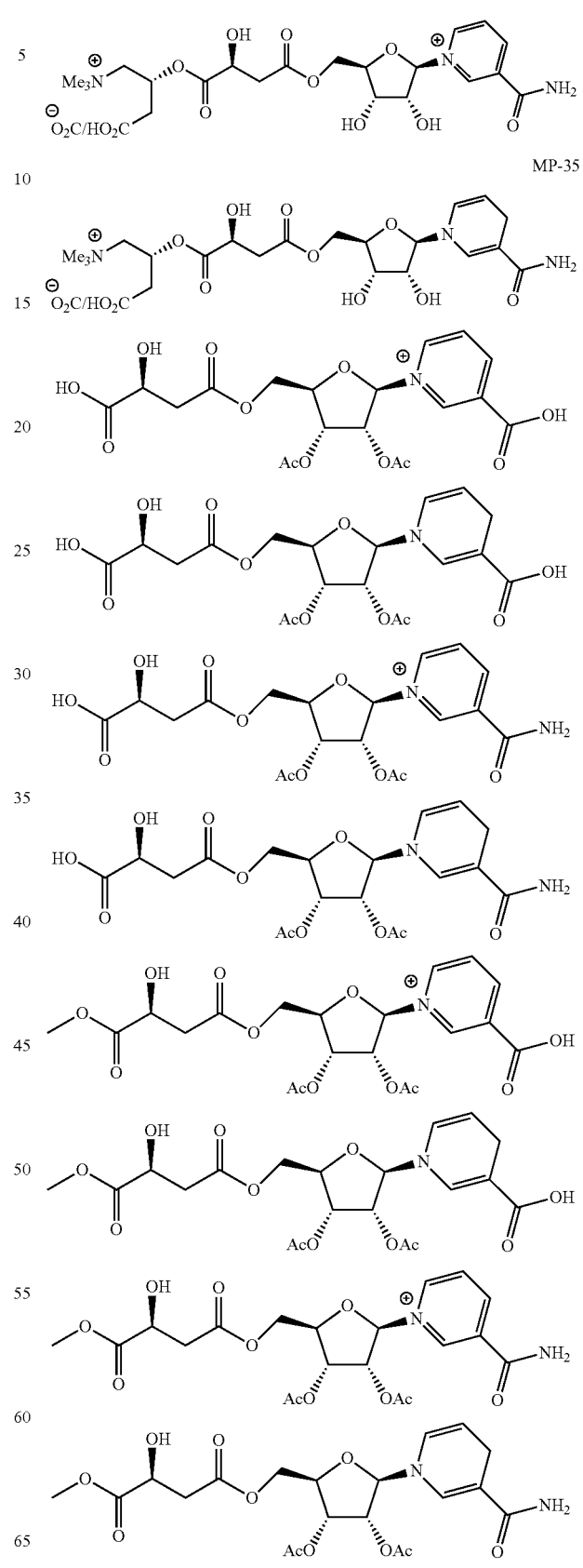

-continued
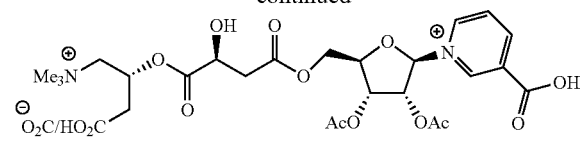
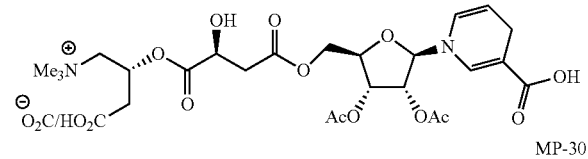
MP-30
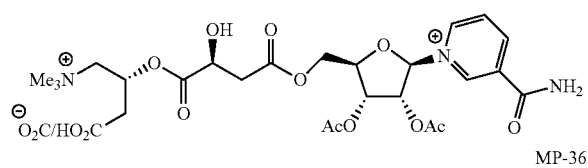
MP-36
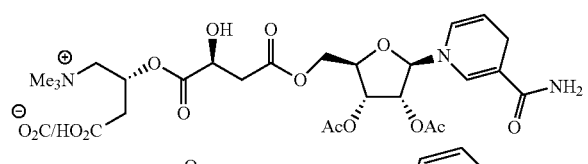
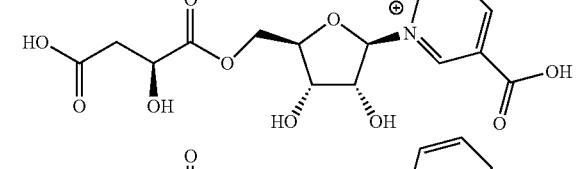
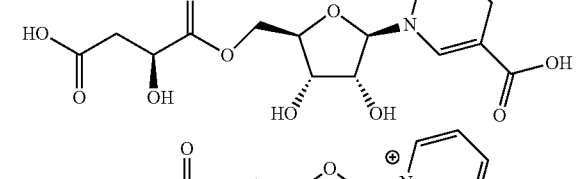
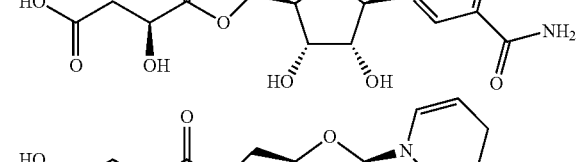
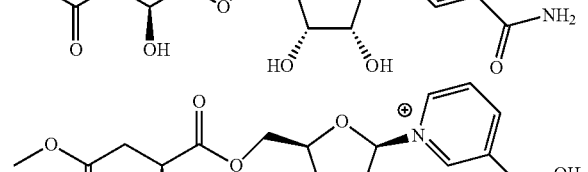
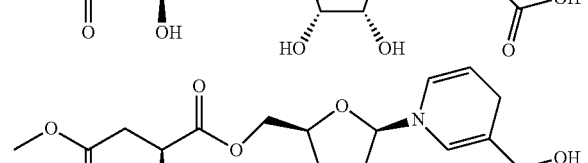
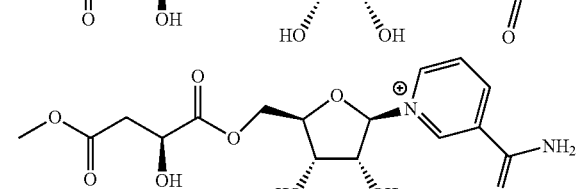
-continued
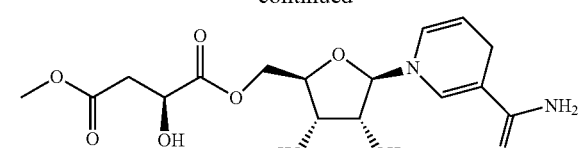
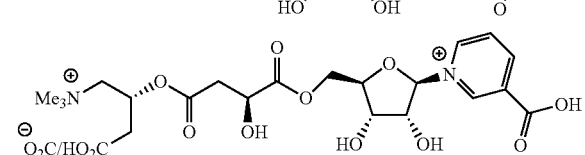
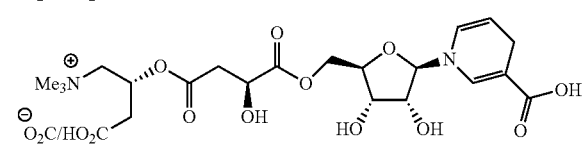
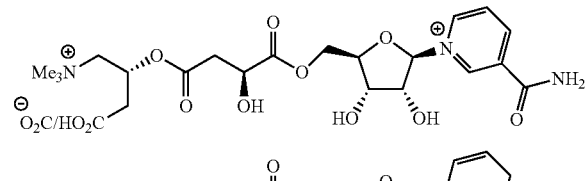
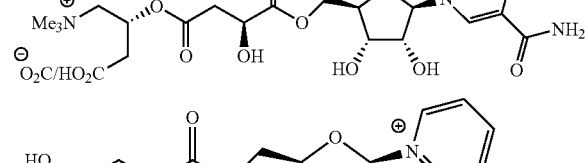
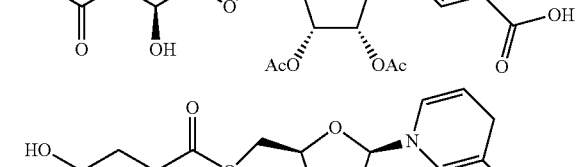
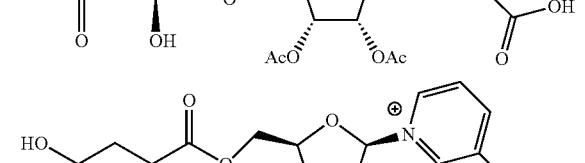
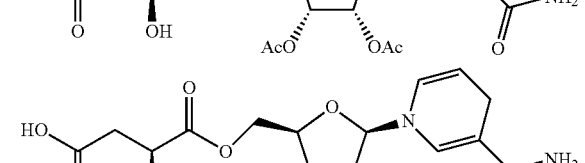
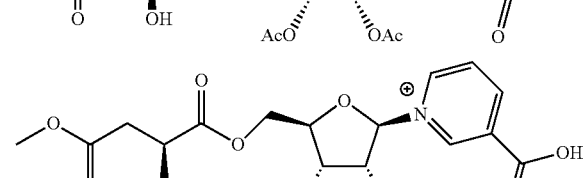
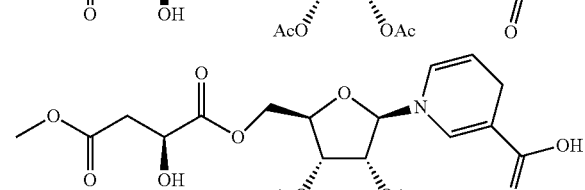

-continued

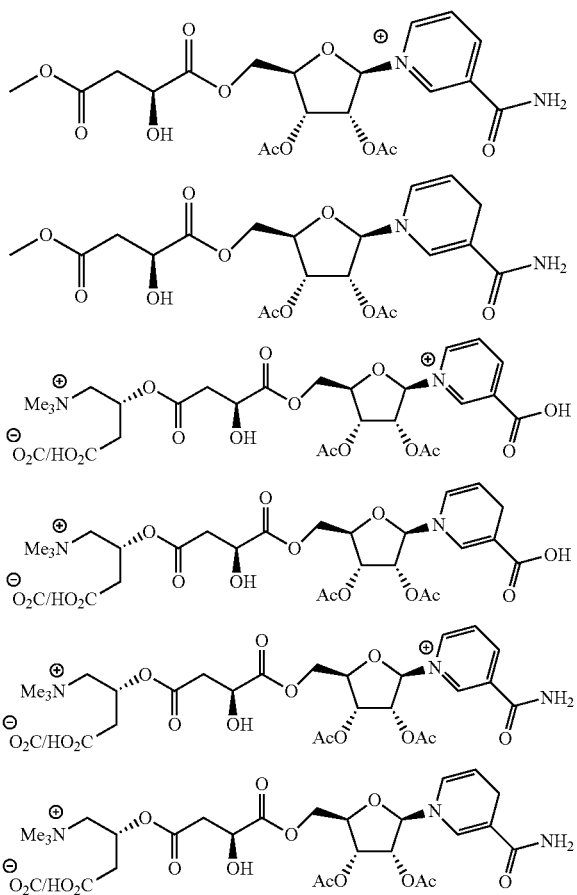

and pharmaceutically acceptable salts, solvates, hydrates, clathrates, polymorphs and stereoisomers thereof.

Other embodiments of the disclosure relate to NAR derivatives of Formulas III and IV:

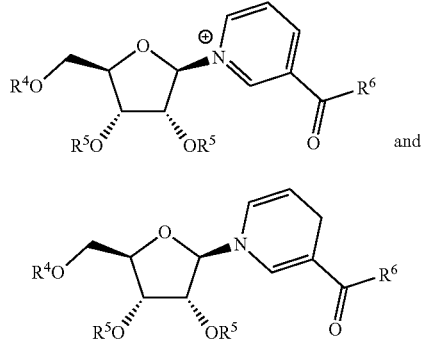

wherein:

$R^4$ is hydrogen or —C(=O)$R^7$, wherein $R^7$ is linear or branched $C_1$-$C_6$ alkyl, $C_3$-$C_6$ cycloalkyl, or phenyl optionally substituted with F, Cl, —NO$_2$, linear or branched $C_1$-$C_4$ alkyl, —CF$_3$ or —O-(linear or branched $C_1$-$C_4$ alkyl);

$R^5$ at each occurrence independently is hydrogen or —C(=O)$R^8$, wherein $R^8$ has the same definition as $R^7$; and $R^6$ is

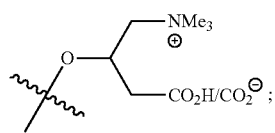

and pharmaceutically acceptable salts, solvates, hydrate, clathrates, polymorphs and stereoisomers thereof.

In some embodiments of compounds of Formulas III and IV:

$R^4$ is hydrogen or —C(=O)$R^7$, wherein $R^7$ is linear or branched $C_1$-$C_6$ alkyl; and $R^5$ at each occurrence independently, or at both occurrences, is hydrogen or —C(=O)$R^8$, wherein $R^8$ is linear or branched $C_1$-$C_6$ alkyl.

In certain embodiments, $R^4$ is hydrogen, acetyl or propanoyl, and $R^5$ at each occurrence independently, or at both occurrences, is hydrogen, acetyl or propanoyl. In preferred embodiments, the carnitine moiety of $R^6$ is the L-isomer

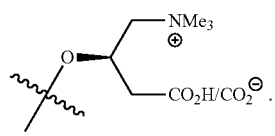

In certain embodiments, the compounds of Formulas III and IV are selected from:

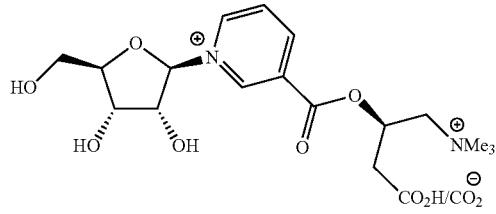

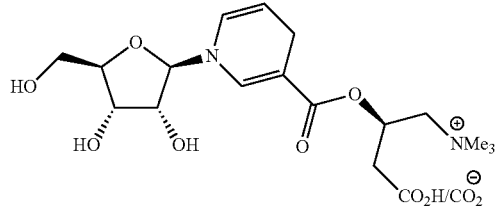

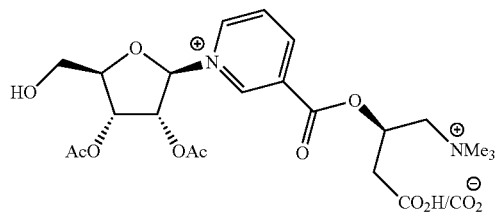

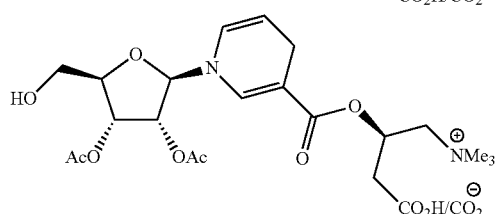

-continued

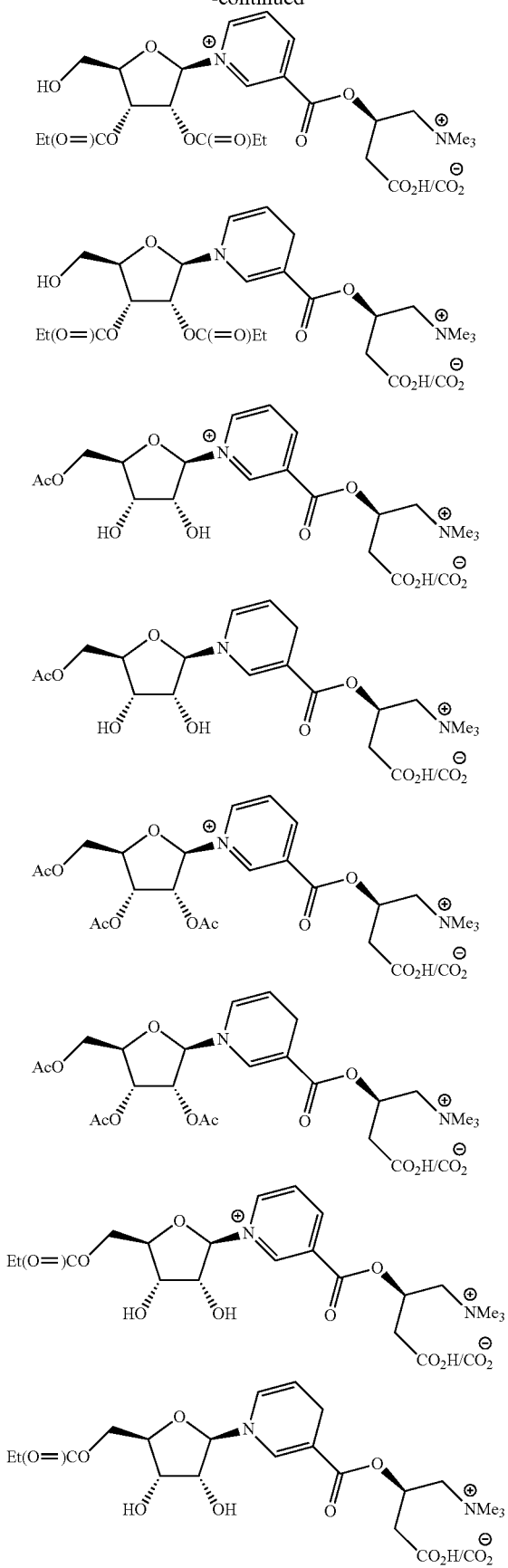

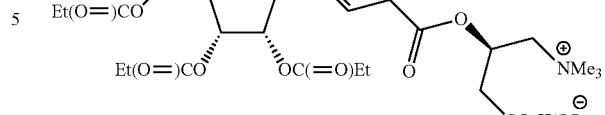

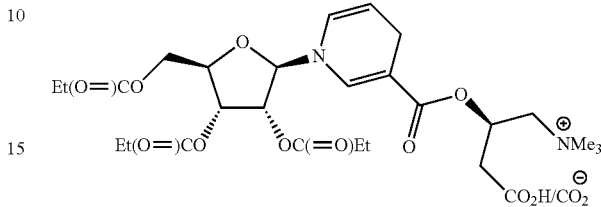

and pharmaceutically acceptable salts, solvates, hydrates, clathrates, polymorphs and stereoisomers thereof.

The compounds of Formulas I, II, III and IV can comprise a hydrophobic/lipophilic group at $R^1/R^4$, at either occurrence or both occurrences of $R^2/R^5$, or at $R^3$, or any combination thereof. One or more hydrophobic groups can facilitate permeation of an NR/NAR derivative through membrane barriers, including the cell membrane. In certain embodiments, a hydrophobic group contains 6-20 or 8-20 carbon atoms. In some embodiments, for the compounds of Formulas I and II:

$R^a$ can be linear or branched $C_1$-$C_{20}$ alkyl;

$R^b$ or $R^c$ can be linear or branched $C_1$-$C_{20}$ alkyl for a phosphoramidate moiety;

$R^b$ or $R^c$ at either occurrence or both occurrences can be linear or branched $C_1$-$C_{20}$ alkyl for a phosphorodiamidate/bisphosphoramidate moiety;

$R^e$ can be linear or branched $C_1$-$C_{20}$ alkyl;

$R^f$ at either occurrence or both occurrences can be linear or branched $C_1$-$C_{20}$ alkyl;

$R^g$ can be linear or branched $C_1$-$C_{20}$ alkyl;

$R^k$ can be linear or branched $C_1$-$C_{20}$ alkyl;

$R^m$ at any occurrence can be linear or branched $C_1$-$C_{20}$ alkyl;

$R^n$ at any occurrence can be linear or branched $C_1$-$C_{20}$ alkyl;

$R^o$ can be linear or branched $C_1$-$C_{20}$ alkyl; or n for —$(CH_2)_n$— for X at any occurrence can be an integer from 1 to 20; or any combination or all of the above.

In some embodiments, for the compounds of Formulas III and IV:

$R^7$ can be linear or branched $C_1$-$C_{20}$ alkyl; or/and $R^8$ at either occurrence or both occurrences can be linear or branched $C_1$-$C_{20}$ alkyl.

In some embodiments, the NR and NAR derivatives are the reduced form—i.e., have Formula II or IV.

The disclosure also encompasses isotopologues of the compounds of Formulas I, II, III and IV. Isotopically enriched forms of the NR and NAR derivatives described herein include without limitation those enriched in the content of $^2H$ (deuterium), $^{13}C$, $^{15}N$, $^{17}O$ or $^{18}O$, or any combination thereof, at one or more, or all, positions of the corresponding atom(s).

Isomers of Compounds

The present disclosure encompasses all possible stereoisomers, including both enantiomers and all possible diastereomers in substantially pure form and mixtures of both enantiomers in any ratio (including a racemic mixture of enantiomers) and mixtures of two or more diastereomers in any ratio, of the compounds described herein, and not only the specific stereoisomers as indicated by drawn structure or nomenclature. In preferred embodiments, the disclosure relates to the specific stereoisomers indicated by drawn structure or nomenclature, including the beta-anomer of nicotinamide and nicotinic acid D-riboside derivatives. The specific recitation of the phrase "or stereoisomers thereof" or the like with respect to a compound in certain instances of the disclosure shall not be interpreted as an intended omission of any of the other possible stereoisomers of the compound in other instances of the disclosure where the compound is mentioned without recitation of the phrase "or stereoisomers thereof" or the like, unless stated otherwise or the context clearly indicates otherwise.

In some embodiments, the NR and NAR derivatives are stereoisomerically pure. In some embodiments, at least about 90%, 95%, 98% or 99% of the compounds of Formulas I, II, III and IV have the stereochemistry indicated by drawn structure or nomenclature, including the beta-D-riboside configuration. In similar embodiments, the compounds of Formulas I, II, III and IV have the beta-D-riboside configuration and an enantiomeric excess of at least about 80%, 90% or 95%.

In other embodiments, the compounds of Formulas I, II, III and IV are mixtures of enantiomers or mixtures of two or more diastereomers. In certain embodiments, the compounds of Formulas I, II, III and IV are racemic mixtures. In other embodiments, the compounds of Formulas I, II, III and IV have the D-riboside configuration and a mixture of beta-/alpha-anomers. In certain embodiments, the compounds of Formulas I, II, III and IV have the D-riboside configuration and an approximately 1:1 ratio of beta-alpha-anomers.

The description and all of the embodiments relating to isomers of the NR and NAR derivatives disclosed herein also apply to isomers of other NR and NAR derivatives (e.g., nicotinamide riboside triacetate [NRTA, i.e., NR having an acetate group at each of the C-2, C-3 and C-5 positions of riboside], the reduced form of NRTA [NRHTA], nicotinic acid riboside triacetate [NARTA], and the reduced form of NARTA [NARHTA]) and to isomers of NR, NRH, NAR and NARH.

Salt Forms of Compounds

The NR and NAR derivatives described herein can exist as salts, in particular their oxidized form—i.e., NR and NAR derivatives of Formulas I and III. The disclosure encompasses all pharmaceutically acceptable salts of NR and NAR derivatives. Examples of counteranions of salts of NR and NAR derivatives, including those of Formulas I and III, include without limitation internal salt, fluoride, chloride, bromide, iodide, nitrate, sulfate, sulfite, phosphate, bicarbonate, carbonate, thiocyanate, formate, acetate, trifluoroacetate, glycolate, lactate, gluconate, ascorbate, benzoate, oxalate, malonate, succinate, citrate, methanesulfonate (mesylate), ethanesulfonate, propanesulfonate, benzenesulfonate (bezylate), p-toluenesulfonate (tosylate) and trifluoromethanesulfonate (triflate). In certain embodiments, the NR and NAR derivatives, including those of Formulas I and III, are chloride, formate, acetate, trifluoroacetate or triflate salts.

If an NR or NAR derivative has an acidic group, such as a carboxylic acid group, it may form a salt with the acidic group. The countercation can be, e.g., $Li^+$, $Na^+$, $K^+$, $Ca^{+2}$, $Mg^{+2}$, ammonium, a protonated organic amine (e.g., diethanolamine) or a quaternary ammonium compound (e.g., choline).

The description and all of the embodiments relating to salt forms of the NR and NAR derivatives disclosed herein also apply to salt forms of other NR and NAR derivatives (e.g., NRTA, NRHTA, NARTA and NARHTA) and to salt forms of NR, NRH, NAR and NARH.

Pharmaceutical Compositions

The disclosure provides pharmaceutical compositions comprising one or more NR/NAR derivatives described herein, or a pharmaceutically acceptable salt, solvate, hydrate, clathrate, polymorph or stereoisomer thereof, and one or more pharmaceutically acceptable excipients or carriers. The compositions can optionally contain an additional therapeutic agent. In some embodiments, a pharmaceutical composition comprises a compound of Formula II or a compound of Formula IV. In further embodiments, a pharmaceutical composition comprises a compound of Formula I and a compound of Formula II, or a compound of Formula III and a compound of Formula IV. A pharmaceutical composition generally contains a therapeutically effective amount of the active ingredient, but can contain an appropriate fraction thereof. For purposes of the content of a pharmaceutical composition, the term "active ingredient", "active agent", "therapeutic agent" or "drug" encompasses a prodrug. For brevity, the term "pharmaceutical composition" encompasses a cosmetic composition.

A pharmaceutical composition contains an NR or NAR derivative in substantially pure form. In some embodiments, the purity of the NR or NAR derivative is at least about 95%, 96%, 97%, 98% or 99%. In certain embodiments, the purity of the NR or NAR derivative is at least about 98% or 99%. In addition, a pharmaceutical composition is substantially free of contaminants or impurities. In some embodiments, the level of contaminants or impurities other than residual solvent in a pharmaceutical composition is no more than about 5%, 4%, 3%, 2% or 1% relative to the combined weight of the intended active and inactive ingredients. In certain embodiments, the level of contaminants or impurities other than residual solvent in a pharmaceutical composition is no more than about 2% or 1% relative to the combined weight of the intended active and inactive ingredients.

Pharmaceutical compositions/formulations can be prepared in sterile form. For example, pharmaceutical compositions/formulations for parenteral administration by injection or infusion generally are sterile. Sterile pharmaceutical compositions/formulations are compounded or manufactured according to pharmaceutical-grade sterilization standards known to those of skill in the art, such as those disclosed in or required by the United States Pharmacopeia Chapters 797, 1072 and 1211, and 21 Code of Federal Regulations 211.

Pharmaceutically acceptable excipients and carriers include pharmaceutically acceptable substances, materials and vehicles. Non-limiting examples of types of excipients include liquid and solid fillers, diluents, binders, lubricants, glidants, surfactants, dispersing agents, disintegration agents, emulsifying agents, wetting agents, suspending agents, thickeners, solvents, isotonic agents, buffers, pH adjusters, absorption-delaying agents, stabilizers, antioxidants, preservatives, antimicrobial agents, antibacterial agents, antifungal agents, chelating agents, adjuvants, sweetening agents, flavoring agents, coloring agents, encapsulating materials and coating materials. The use of such excipients in pharmaceutical formulations is known in the art. For example, conventional vehicles and carriers include without limitation oils (e.g., vegetable oils such as olive oil and sesame oil), aqueous solvents {e.g., saline, buffered saline (e.g., phosphate-buffered saline [PBS]) and isotonic solutions (e.g., Ringer's solution)}, and organic solvents (e.g., dimethyl sulfoxide [DMSO] and alcohols [e.g., ethanol, glycerol and propylene glycol]). Except insofar as any conventional excipient or carrier is incompatible with the active ingredient, the disclosure encompasses the use of conventional excipients and carriers in formulations containing one or more NR/NAR derivatives. See, e.g., Remington: The Science and Practice of Pharmacy, 21st Ed., Lippincott Williams & Wilkins (Philadelphia, Pa.) (2005); Handbook of Pharmaceutical Excipients, 5th Ed., Rowe et al., Eds., The Pharmaceutical Press and the American Pharmaceutical Association (2005); Handbook of Pharmaceutical Additives, 3rd Ed., Ash and Ash, Eds., Gower Publishing Co. (2007); and Pharmaceutical Pre-formulation and Formulation, Gibson, Ed., CRC Press (Boca Raton, Fla.) (2004).

Appropriate formulation can depend on various factors, such as the route of administration chosen. Potential routes of administration of pharmaceutical compositions containing one or more NR/NAR derivatives include without limitation oral, parenteral (including intradermal, subcutaneous, intramuscular, intravascular, intravenous, intra-arterial, intraperitoneal, intracavitary, intramedullary, intrathecal and topical), and topical (including dermal/epicutaneous, transdermal, mucosal, transmucosal, intranasal [e.g., by nasal spray or drop], ocular [e.g., by eye drop], pulmonary [e.g., by oral or nasal inhalation], buccal, sublingual, rectal [e.g., by suppository], and vaginal [e.g., by suppository]). Topical formulations can be designed to produce a local or systemic therapeutic effect.

As an example, formulations of NR/NAR derivatives suitable for oral administration can be presented as, e.g., boluses; capsules (including push-fit capsules and soft capsules), tablets, pills, cachets or lozenges; as powders or granules; as semisolids, electuaries, pastes or gels; as solutions or suspensions in an aqueous liquid or/and a non-aqueous liquid; or as oil-in-water liquid emulsions or water-in-oil liquid emulsions.

Push-fit capsules or two-piece hard gelatin capsules can contain one or more NR/NAR derivatives in admixture with, e.g., a filler or inert solid diluent (e.g., calcium carbonate, calcium phosphate, kaolin or lactose), a binder (e.g., a starch), a glidant or lubricant (e.g., talc or magnesium stearate), and a disintegrant (e.g., crospovidone), and optionally a stabilizer or/and a preservative. For soft capsules or single-piece gelatin capsules, one or more NR/NAR derivatives can be dissolved or suspended in a suitable liquid (e.g., liquid polyethylene glycol or an oil medium, such as a fatty oil, peanut oil, olive oil or liquid paraffin), and the liquid-filled capsules can contain one or more other liquid excipients or/and semi-solid excipients, such as a stabilizer or/and an amphiphilic agent (e.g., a fatty acid ester of glycerol, propylene glycol or sorbitol).

Tablets can contain one or more NR/NAR derivatives in admixture with, e.g., a filler or inert diluent (e.g., calcium carbonate, calcium phosphate, lactose, mannitol or microcrystalline cellulose), a binding agent (e.g., a starch, gelatin, acacia, alginic acid or a salt thereof, or microcrystalline cellulose), a lubricating agent (e.g., stearic acid, magnesium stearate, talc or silicon dioxide), and a disintegrating agent (e.g., crospovidone, croscarmellose sodium or colloidal silica), and optionally a surfactant (e.g., sodium lauryl sulfate). The tablets can be uncoated or can be coated with, e.g., an enteric coating that protects the active ingredient from the acidic environment of the stomach, or with a material that delays disintegration and absorption of the active ingredient in the gastrointestinal (GI) tract and thereby provides a sustained action over a longer time period.

Compositions for oral administration can also be formulated as solutions or suspensions in an aqueous liquid and/or a non-aqueous liquid, or as oil-in-water liquid emulsions or water-in-oil liquid emulsions. Dispersible powder or granules of one or more NR/NAR derivatives can be mixed with any suitable combination of an aqueous liquid, an organic solvent or/and an oil and any suitable excipients (e.g., any combination of a dispersing agent, a wetting agent, a suspending agent, an emulsifying agent or/and a preservative) to form a solution, suspension or emulsion.

NR and NAR derivatives can also be formulated for parenteral administration by, e.g., injection or infusion to circumvent GI absorption and first-pass metabolism. An exemplary parenteral route is intravenous. Additional advantages of intravenous administration include direct administration of a therapeutic agent into systemic circulation to achieve a rapid systemic effect, and the ability to administer the agent continuously or/and in a large volume if desired. Formulations for injection or infusion can be in the form of, e.g., solutions, suspensions or emulsions in oily or aqueous vehicles, and can contain excipients such as suspending agents, dispersing agents or/and stabilizing agents. For example, aqueous (e.g., saline) or non-aqueous (e.g., oily) sterile injection solutions can contain one or more NR/NAR derivatives along with excipients such as an antioxidant, a buffer, a bacteriostat and solutes that render the formulation isotonic with the blood of the subject. Aqueous or non-aqueous sterile suspensions can contain one or more NR/NAR derivatives along with excipients such as a suspending agent and a thickening agent, and optionally a stabilizer and an agent that increases the solubility of the NR/NAR derivative(s) to allow for the preparation of a more concentrated solution or suspension. As another example, a sterile aqueous solution for injection or infusion (e.g., subcutaneously or intravenously) can contain one or more NR/NAR derivatives, sodium chloride, a buffering agent (e.g., sodium citrate), a preservative (e.g., meta-cresol), and optionally a base (e.g., NaOH) or/and an acid (e.g., HCl) to adjust pH.

In some embodiments, a composition for parenteral (e.g. intravenous) administration comprises a complex of an NR or NAR derivative with a dendrimer [e.g., a poly(amidoamine) (PAMAM) dendrimer], which can be, e.g., in an aqueous solution or a colloidal liposomal formulation. As an illustrative example, an NR or NAR derivative can be combined with a dendrimer (e.g., a PAMAM dendrimer) by encapsulation (e.g., the dendrimer forms a micelle encapsulating the NR or NAR derivative), electrostatic or ionic interaction, or covalent conjugation using, e.g., an enzyme-cleavable linker (e.g., Gly-Phe-Leu-Gly). The dendrimer can optionally have one or more moieties that target the dendrimer-NR/NAR derivative complex to specific organ(s), tissue(s), cell type(s) or organelle(s), such as the liver, tumor/cancer cells or mitochondria. For example, the dendrimer can optionally have one or more N-acetylgalactosamine (GalNAc) moieties, which can target the dendrimer-containing composition to the liver by binding to asialoglycoprotein receptors on hepatocytes for treatment of, e.g., a liver or metabolic disorder. Such a dendrimer-containing composition can also be formulated for oral administration or other modes of parenteral administration (e.g., subcutaneous, intramuscular, intrathecal or topical).

For topical administration, one or more NR/NAR derivatives can be formulated as, e.g., a buccal or sublingual tablet or pill. Advantages of a buccal or sublingual tablet or pill include avoidance of GI absorption and first-pass metabolism, and rapid absorption into systemic circulation. A buccal or sublingual tablet or pill can be designed to provide faster release of the NR/NAR derivative(s) for more rapid uptake into systemic circulation. A buccal or sublingual tablet or pill can contain suitable excipients, including without limitation any combination of fillers and diluents (e.g., mannitol and sorbitol), binding agents (e.g., sodium carbonate), wetting agents (e.g., sodium carbonate), disintegrants (e.g., crospovidone and croscarmellose sodium), lubricants (e.g., silicon dioxide [including colloidal silicon dioxide] and sodium stearyl fumarate), stabilizers (e.g., sodium bicarbonate), flavoring agents (e.g., spearmint flavor), sweetening agents (e.g., sucralose), and coloring agents (e.g., yellow iron oxide).

For topical administration, NR and NAR derivatives can also be formulated for intranasal administration. The nasal mucosa provides a big surface area, a porous endothelium, a highly vascular subepithelial layer and a high absorption rate, and hence allows for high bioavailability. Moreover, intranasal administration avoids first-pass metabolism and can introduce a significant concentration of the active ingredient to the central nervous system (CNS). An intranasal formulation can comprise one or more NR/NAR derivatives along with excipients, such as a solubility enhancer (e.g., propylene glycol), a humectant (e.g., mannitol or sorbitol), a buffer and water, and optionally a preservative (e.g., benzalkonium chloride), a mucoadhesive agent (e.g., hydroxyethylcellulose) or/and a penetration enhancer. An intranasal solution or suspension formulation can be administered to the nasal cavity by any suitable means, including but not limited to a dropper, a pipette, or spray using, e.g., a metering atomizing spray pump.

An additional mode of topical administration of NR and NAR derivatives is pulmonary, including by oral inhalation and nasal inhalation. The lungs serve as a portal to the systemic circulation. Advantages of pulmonary drug delivery include, for example: 1) avoidance of first-pass hepatic metabolism; 2) fast drug action; 3) large surface area of the alveolar region for absorption, high permeability of the lungs (thin air-blood barrier), and profuse vasculature of the airways; 4) reduced extracellular enzyme levels compared to the GI tract due to the large alveolar surface area; and 5) smaller doses to achieve equivalent therapeutic effect compared to other oral routes, and hence reduced systemic side effects. Oral inhalation can also enable more rapid action of a drug in the CNS. An advantage of oral inhalation over nasal inhalation includes deeper penetration/deposition of the drug into the lungs. Oral or nasal inhalation can be achieved by means of, e.g., a metered-dose inhaler, a dry powder inhaler or a nebulizer, as is known in the art. In certain embodiments, a sterile aqueous solution for oral inhalation contains one or more NR/NAR derivatives, sodium chloride, a buffering agent (e.g., sodium citrate), optionally a preservative (e.g., meta-cresol), and optionally a base (e.g., NaOH) or/and an acid (e.g., HCl) to adjust pH.

Topical formulations for application to the skin or mucosa can be useful for transdermal or transmucosal administration of a drug into the underlying tissue or/and the blood for systemic distribution. Advantages of topical administration can include circumvention of GI absorption and first-pass metabolism, delivery of a drug with a short half-life and low oral bioavailability, more controlled and sustained release of the drug, a more uniform plasma dosing or delivery profile of the drug, less frequent dosing of the drug, less side effects, minimal or no invasiveness, ease of self-administration, and increased patient compliance.

In general, compositions suitable for topical administration include without limitation liquid or semi-liquid preparations such as sprays, gels, liniments and lotions, oil-in-water or water-in-oil emulsions such as creams, foams, ointments and pastes, and solutions or suspensions such as drops (e.g., eye drops, nose drops and ear drops). In some embodiments, a topical composition comprises a drug dissolved, dispersed or suspended in a carrier. The carrier can be in the form of, e.g., a solution, a suspension, an emulsion, an ointment or a gel base, and can contain, e.g., petrolatum, lanolin, a wax (e.g., bee wax), mineral oil, a long-chain alcohol, polyethylene glycol or polypropylene glycol, or a diluent (e.g., water or/and an alcohol [e.g., ethanol or propylene glycol]), or any combination thereof. A solvent such as an alcohol can be used to solubilize the drug. A topical composition can contain any of a variety of excipients, such as a gelling agent, an emulsifier, a thickening agent, a buffer, a stabilizer, an antioxidant, a preservative, a chemical permeation enhancer (CPE) or an irritation-mitigating agent, or any combination thereof. A topical composition can include, or a topical formulation can be administered by means of, e.g., a transdermal or transmucosal delivery device, such as a transdermal patch, a microneedle patch or an iontophoresis device. A topical composition can deliver a drug transdermally or transmucosally via a concentration gradient (with or without the use of a CPE) or an active mechanism (e.g., iontophoresis or microneedles).

For transdermal or transmucosal administration, in some embodiments a topical composition comprises a chemical penetration enhancer (CPE) that increases permeation of a drug across the skin or mucosa into the underlying tissue or/and systemic circulation. Examples of CPEs include without limitation alcohols and fatty alcohols (e.g., methanol, ethanol, isopropyl alcohol, pentanol, lauryl alcohol, oleyl alcohol, benzyl alcohol, diethylene glycol mono-ethyl ether, propylene glycol, dipropylene glycol, polyethylene glycol and glycerol); fatty acids (e.g., capric acid, lauric acid, myristic acid, oleic acid, linoleic acid and linolenic acid); esters, fatty alcohol esters and fatty acid esters (e.g., ethyl acetate, methyl laurate, isopropyl myristate, isopropyl palmitate, methyl oleate, ethyl oleate, propylene glycol mono-oleate, glycerol mono-oleate, triacetin and pentadecalactone); hydroxyl-containing esters, fatty alcohol esters and fatty acid esters (e.g., lauryl lactate, glyceryl/glycerol monolaurate, glycerol monoleate [mono-olein], sorbitan oleate and octyl salicylate); amides, fatty amine amides and fatty acid amides (e.g., urea, dimethylformamide, dimethylacetamide, diethylacetamide, diethyltoluamide, N-lauroyl sarcosine, 1-dodecylazacycloheptane-2-one [laurocapram or Azone®], Azone-related compounds, and pyrrolidone compounds [e.g., 2-pyrrolidone and N-methyl-2-pyrrolidone]); and ionic and non-ionic surfactants (e.g., cetyltrimethylammonium bromide, sodium laurate, sodium laureth sulfate [sodium lauryl ether sulfate], sodium cholate, sodium lauroyl sarcosinate, N-lauroyl sarcosine, sorbitan monolaurate, Brij® surfactants, Pluronic® surfactants, Tween® surfactants, saponins, alkyl glycosides, and fatty ether and fatty ester saccharides). US 2007/0269379 provides an extensive list of CPEs.

In some embodiments, the CPE includes a surfactant. In certain embodiments, the CPE includes two or more surfactants, such as a non-ionic surfactant (e.g., sorbitan monolaurate or N-auroyl sarcosine) and an ionic surfactant (e.g., an anionic surfactant such as sodium lauroyl sarcosinate). In other embodiments, the CPE includes a surfactant (e.g., an anionic surfactant such as sodium laureth sulfate) and an aromatic compound (e.g., 1-phenylpiperazine). Such combinations of CPEs can greatly enhance permeation of a drug through the skin with a low potential for skin irritation.

For transmucosal administration, in certain embodiments the CPE is or includes an alkyl glycoside (e.g., a 1-O or S—$C_8$-$C_{20}$ alkyl glycoside such as the corresponding glucoside, galactoside, mannoside, lactoside, maltoside [e.g., dodecyl, tridecyl or tetradecyl maltoside], melibioside or sucroside [e.g., dodecyl sucrose]), or a fatty ether or fatty ester saccharide (e.g., a $C_8$-$C_{20}$ alkyl ether or ester saccharide such as the corresponding glucoside, galactoside, mannoside, lactoside, maltoside, melibioside, sucroside [e.g., sucrose monododecanoate] or trehaloside).

In some embodiments, one or more NR/NAR derivatives are administered via a transdermal patch. In certain embodiments, a transdermal patch is a reservoir-type patch comprising an impermeable backing layer/film, a liquid- or gel-based drug reservoir, a semi-permeable membrane that controls drug release, and a skin-contacting adhesive layer. The semi-permeable membrane can be composed of, e.g., a suitable polymeric material such as cellulose nitrate or acetate, polyisobutene, polypropylene, polyvinyl acetate or a polycarbonate. In other embodiments, a transdermal patch is a drug-in-adhesive patch comprising an impermeable backing layer/film and a skin-contacting adhesive layer incorporating the drug in a polymeric or viscous adhesive. The adhesive of the drug-loaded, skin-contacting adhesive layer can be, e.g., a pressure-sensitive adhesive (PSA), such as a PSA composed of an acrylic polymer (e.g., polyacrylate), a polyalkylene (e.g., polyisobutylene) or a silicone-based polymer (e.g., silicone-2675 or silicone-2920). Transdermal drug-delivery systems, including patches, can be designed to provide controlled and prolonged release of a drug over a period of about 1 week, 2 weeks, 3 weeks, 1 month or longer.

In some embodiments, one or more NR/NAR derivatives are delivered from a sustained-release composition. As used herein, the term "sustained-release composition" encompasses sustained-release, prolonged-release, extended-release, delayed-release and slow-release compositions, systems and devices. A sustained-release composition can also be designed to be controlled-release. Advantages of a sustained-release composition include without limitation a more uniform blood level of the drug (e.g., avoidance of wide peak-to-trough fluctuations), delivery of a therapeutically effective amount of the drug over a prolonged time period, reduced frequency of administration, and reduced side effects (e.g., avoidance of a drug overdose). In certain embodiments, a sustained-release composition delivers one or more NR/NAR derivatives over a period of at least about 2 days, 3 days, 1 week, 2 weeks, 3 weeks, 1 month, 2 months, 3 months or longer. In some embodiments, a sustained-release composition is a drug-encapsulation system, such as nanoparticles, microparticles or a capsule made of, e.g., a biodegradable polymer or/and a hydrogel. In certain embodiments, a sustained-release composition comprises a hydrogel. Non-limiting examples of polymers of which a hydrogel can be composed include polyvinyl alcohol, acrylate polymers (e.g., sodium polyacrylate), and other homopolymers and copolymers having a relatively large number of hydrophilic groups (e.g., hydroxyl or/and carboxylate groups). In other embodiments, a sustained-release drug-encapsulation system comprises a membrane-enclosed reservoir, wherein the reservoir contains a drug and the membrane is permeable to the drug. Such a drug-delivery system can be in the form of, e.g., a transdermal patch.

In certain embodiments, a sustained-release composition is an oral dosage form, such as a tablet or capsule. For example, a drug can be embedded in an insoluble porous matrix such that the dissolving drug must make its way out of the matrix before it can be absorbed through the GI tract. Alternatively, a drug can be embedded in a matrix that swells to form a gel through which the drug exits. Sustained release can also be achieved by way of a single-layer or multi-layer osmotic controlled-release oral delivery system (OROS). An OROS is a tablet with a semi-permeable outer membrane and one or more small laser-drilled holes in it. As the tablet passes through the body, water is absorbed through the semi-permeable membrane via osmosis, and the resulting osmotic pressure pushes the drug out through the hole(s) in the tablet and into the GI tract where it can be absorbed.

In further embodiments, a sustained-release composition is formulated as polymeric nanoparticles or microparticles, which can be delivered, e.g., by injection or inhalation or as an implant (e.g., a depot). In some embodiments, the polymeric implant or polymeric nanoparticles or microparticles are composed of a biodegradable polymer. In certain embodiments, the biodegradable polymer comprises lactic acid or/and glycolic acid [e.g., an L-lactic acid-based copolymer, such as poly(L-lactide-co-glycolide) or poly(L-lactic acid-co-D,L-2-hydroxyoctanoic acid)]. For instance, biodegradable polymeric microspheres composed of polylactic acid or/and polyglycolic acid can serve as sustained-release pulmonary drug-delivery systems. The biodegradable polymer of the polymeric implant or polymeric nanoparticles or microparticles can be selected so that the polymer substantially completely degrades around the time the period of treatment is expected to end, and so that the byproducts of the polymer's degradation, like the polymer, are biocompatible.

In some embodiments, a sustained-release composition comprises a water-soluble polymer [e.g., poly(DL-lactide)] encapsulating an NR or NAR derivative complexed with or conjugated to a dendrimer (e.g., PAMAM). The dendrimer can optionally have one or more moieties for targeting to specific organ(s), tissue(s), cell type(s) or organelle(s), such as one or more N-acetylgalactosamine moieties for targeting to the liver for treatment of, e.g., a liver or metabolic disorder.

For a delayed or sustained release of one or more NR/NAR derivatives, a composition can also be formulated as a depot that can be implanted in or injected into a subject, e.g., intramuscularly or subcutaneously. A depot formulation can be designed to deliver an NR or NAR derivative over a longer period of time, e.g., over a period of at least about 1 week, 2 weeks, 3 weeks, 1 month, 6 weeks, 2 months, 3 months or longer. For example, an NR or NAR derivative can be formulated with a polymeric material (e.g., polyethylene glycol [PEG], polylactic acid [PLA] or polyglycolic acid [PGA], or a copolymer thereof [e.g., PLGA]), a hydrophobic material (e.g., as an emulsion in an oil) or/and an ion-exchange resin, or as a sparingly soluble derivative (e.g., a sparingly soluble salt). As an illustrative example, an NR or NAR derivative can be incorporated or embedded in sustained-release microparticles composed of PLGA and formulated as a monthly depot.

In some embodiments, a pharmaceutical composition containing one or more NR/NAR derivatives is a controlled-release composition. A controlled-release composition can deliver a drug in a controlled time-dependent manner, and can be designed to deliver the drug, e.g., with delay after administration or/and for a prolonged time period. A controlled-release composition can also be designed to achieve particular profiles of dissolution of the drug in particular environments (e.g., in the GI tract) and to improve pharmacokinetics (e.g., bioavailability) of the drug. In certain embodiments, a controlled-release composition is administered once daily, once every two or three days, twice weekly or once weekly. In certain embodiments, a controlled-release composition is enterically coated for oral administration.

In some embodiments, a capsule for oral administration contains a plurality of pellets, each pellet comprising a pellet core containing one or more NR/NAR derivatives and a controlled-release coating surrounding the pellet core. The one or more NR/NAR derivatives can be, e.g., dispersed in a solid or semi-solid pellet core or in a drug layer coating the pellet core. In certain embodiment, the controlled-release coating comprises ethyl cellulose; povidone or/and hydroxypropyl methyl cellulose; and a plasticizer.

In addition, pharmaceutical compositions comprising one or more NR/NAR derivatives can be formulated as, e.g., liposomes, micelles (e.g., those composed of biodegradable natural or/and synthetic polymers, such as lactosomes), nanoparticles, microparticles or microspheres, whether or not designed for sustained release. For example, liposomes can be used as a sustained-release pulmonary drug-delivery system that delivers a drug to the alveolar surface for treatment of a lung disorder or a systemic disorder.

In some embodiments, liposomes or micelles are composed of one or more phospholipids. Phospholipids include without limitation phosphatidic acids (e.g., DEPA, DLPA, DMPA, DOPA, DPPA and DSPA), phosphatidylcholines (e.g., DDPC, DEPC, DLPC, DLOPC, DMPC, DOPC, DPPC, DSPC, MPPC, MSPC, PLPC, PMPC, POPC, PSPC, SMPC, SOPC and SPPC), phosphatidylethanolamines (e.g., DEPE, DLPE, DMPE, DOPE, DPPE, DSPE and POPE), phosphatidylglycerols (e.g., DEPG, DLPG, DMPG, DOPG, DPPG, DSPG and POPG), phosphatidylserines (e.g., DLPS, DMPS, DOPS, DPPS and DSPS), and salts (e.g., sodium and ammonium salts) thereof. In certain embodiments, liposomes or micelles are composed of one or more phosphatidylcholines. Liposomes have a hydrophilic core, so liposomes are particularly suited for delivery of more hydrophilic drugs, whereas micelles have a hydrophobic core, so micelles are particularly suited for delivery of more hydrophobic drugs. Liposomes and micelles can permeate across biological membranes. Liposomes and micelles composed of a fusogenic lipid (e.g., DPPG) can fuse with the plasma membrane of cells and thereby deliver a drug into those cells. Liposomes and micelles can provide sustained release of a drug based in part on the rate of degradation of the liposomes and micelles.

Pharmaceutical compositions can be manufactured in any suitable manner known in the art, e.g., by means of conventional mixing, dissolving, suspending, granulating, dragee-making, levigating, emulsifying, encapsulating, entrapping or compressing processes.

A pharmaceutical composition can be presented in unit dosage form as a single dose wherein all active and inactive ingredients are combined in a suitable system, and components do not need to be mixed to form the composition to be administered. A unit dosage form generally contains a therapeutically effective dose of the drug, but can contain an appropriate fraction thereof so that taking multiple unit dosage forms achieves the therapeutically effective dose. Representative examples of a unit dosage form include a tablet, capsule or pill for oral uptake; a solution in a pre-filled syringe of a single-use pen or a pen with a dose counter for parenteral (e.g., intravenous, subcutaneous or intramuscular) injection; a capsule, cartridge or blister pre-loaded in or manually loaded into an inhaler; and a reservoir-type transdermal patch or a drug-in-adhesive patch.

Alternatively, a pharmaceutical composition can be presented as a kit in which the drug, excipients and carriers (e.g., solvents) are provided in two or more separate containers (e.g., ampules, vials, tubes, bottles or syringes) and need to be combined to form the composition to be administered. The kit can contain instructions for storing, preparing and administering the composition (e.g., a solution to be injected parenterally).

A kit can contain all active and inactive ingredients in unit dosage form or the active ingredient and inactive ingredients in two or more separate containers, and can contain instructions for administering or using the pharmaceutical composition to treat a medical condition. A kit can further contain a device for delivering the composition, such as an injection pen, an inhaler or a transdermal patch.

In some embodiments, a kit contains one or more NR/NAR derivatives or a pharmaceutical composition comprising the same, and instructions for administering or using the one or more NR/NAR derivatives or the pharmaceutical composition comprising the same to treat a disease, disorder or condition described herein. In certain embodiments, a kit contains a compound of Formula II or a compound of Formula IV. In further embodiments, a kit contains a compound of Formula I and a compound of Formula II, or a compound of Formula III and a compound of Formula IV.

The description and all of the embodiments relating to pharmaceutical compositions and kits comprising the NR and NAR derivatives described herein also apply to pharmaceutical compositions and kits comprising other NR and NAR derivatives (e.g., NRTA, NRHTA, NARTA and NARHTA) and to pharmaceutical compositions and kits comprising NR, NRH, NAR or/and NARH.

Uses of NR and NAR Derivatives

The NR and NAR derivatives described herein can increase $NAD^+$ levels in a subject, including in cells, tissues and organs and potentially in the blood. By increasing $NAD^+$ levels, the NR and NAR derivatives can improve mitochondrial and cellular function (e.g., DNA repair) in target cells, tissues and organs and can improve cell viability. Benefits of improved mitochondrial function include without limitation enhanced mitochondrial oxidative metabolism, mitochondrial respiration, ATP production, mitochondrial membrane potential, mitophagy (autophagy of defective mitochondria) and mitochondrial biogenesis, and reduced levels of reactive oxygen species (ROS). For example, higher $NAD^+$ levels increase the activity of the mitochondrial NAD-dependent deacetylases sirtuin-1 (SIRT1) and sirtuin-3 (SIRT3). SIRT1 promotes autophagy of defective mitochondria, stimulates mitochondrial biogenesis, inhibits the pro-inflammatory transcription factor NF-κB, increases insulin sensitivity, and mimics the effects of calorie restriction. Stimulation of SIRT3 activity increases mitochodrial biogenesis, increases cellular respiration and energy production, reduces ROS levels (e.g., by stimulating mitochondrial superoxide dismutase 2 [SOD2]), promotes cell survival during genotoxic stress, functions as a mitochondrial tumor suppressor, increases insulin sensitivity and sensitizes cells to glucose uptake, and mimics calorie restriction and exercise. Improved DNA repair reduces cell damage and enhances cell function, health and lifespan. In addition, prevention of $NAD^+$ depletion protects neurons in excitotoxic or ischemic conditions.

Therefore, the NR and NAR derivatives are useful for treating pellagra, mitochondrial diseases, mitochondria-related diseases and conditions, diseases and conditions associated with acute NAD$^+$ depletion resulting from DNA damage, aging-related disorders and conditions, skin disorders and conditions, and other types of disorders and conditions. In some embodiments, a single NR or NAR derivative (e.g., a compound of Formula II or IV) is used to treat a disease/disorder or condition disclosed herein or to bring about a biological effect disclosed herein (e.g., increase NAD$^+$ level, enhance mitochondrial or cellular function, improve metabolic health or cell viability, or provide cytoprotection). In other embodiments, a compound of Formula I and a compound of Formula II, or a compound of Formula III and a compound of Formula IV, are used to treat a disease/disorder or condition disclosed herein or to bring about a biological effect disclosed herein. The use of both an oxidized form of an NR or NAR derivative (Formula I or III) and a reduced form of an NR or NAR derivative (Formula II or IV) can have an additive effect or potentially a synergistic effect. In further embodiments, one or more NR/NAR derivatives disclosed herein are used in conjunction with NR, NRH, NAR or NARH, or any combination thereof, to treat a disease/disorder or condition disclosed herein or to bring about a biological effect disclosed herein. The use of an NR or NAR derivative plus NR, NRH, NAR or NARH can have an additive effect or potentially a synergistic effect. A single NR or NAR derivative can be administered in the form of, e.g., a pharmaceutical or cosmetic composition. If, e.g., two NR/NAR derivatives are utilized, they can be administered in the same composition or in different compositions.

The NR and NAR derivatives have other beneficial effects. For example, they can enhance immune function in peripheral blood mononuclear cells (e.g., T-cells, B-cells, macrophages and natural killer [NK] cells) based on improved antigen recognition and proliferation as a function of immune surveillance. For such an application, one or more NR/NAR derivatives can be employed alone, as a component of a vaccine, as a component of an ex vivo therapy (e.g., a CAR-T cell therapy), or as a component of some other therapy.

Mitochondrial diseases include without limitation mitochondrial myopathies; limb-girdle distribution weakness; Kearns-Sayre syndrome (KSS); Pearson syndrome; Leigh syndrome; Barth syndrome; Friedreich's ataxia; neuropathy, ataxia, retinitis pigmentosa and ptosis (NARP); mitochondrial DNA depletion syndrome (Alper's disease); mitochondrial neurogastrointestinal encephalopathy (MNGIE) syndrome; mitochondrial encephalopathy, lactic acidosis and stroke-like episodes (MELAS) syndrome; myoclonic epilepsy with ragged red fibers (MERRF or Fukubara syndrome); chronic progressive external ophthalmoplegia (CPEO); Leber's hereditary optic neuropathy (LHON); inherited forms of blindness and deafness (e.g., diabetes mellitus and deafness); and acquired forms of reversible or permanent hearing loss {e.g., type 2 diabetes-associated hearing loss and hearing loss induced by ototoxic chemicals (e.g., heavy metals [e.g., lead], solvents [e.g., styrene and toluene] and asphyxiants [e.g., carbon monoxide]) and medications (e.g., loop diuretics [e.g., bumetanide and furosemide], NSAIDs [e.g., aspirin, celecoxib, diclofenac, ibuprofen and naproxen], PDE5 inhibitors, macrolide antibiotics, aminoglycosides [e.g., gentamicin], platinum-based chemotherapeutics [e.g., carboplatin and cisplatin], paracetamol and quinine)}.

Mitochondria-related diseases and conditions include, but are not limited to, neurodegenerative disorders, neuronal activation disorders, muscle disorders (including eye muscle disorders), fatty acid/beta oxidation disorders, metabolic disorders, inflammatory disorders, vascular disorders (including ocular vascular disorders), renal disorders, liver disorders, tumors, cancers, male and female infertility, and aging-related disorders.

Neurodegenerative disorders include without limitation dementias (e.g., Alzheimer's disease [AD], vascular dementia, dementia with Lewy bodies and frontotemporal dementia [Pick's disease]), motor neuron disorders (e.g., Parkinson's disease, amyotrophic lateral sclerosis [ALS or Lou Gehrig's disease], primary lateral sclerosis [PLS] and spinal muscular atrophy [SMA]), ataxia (e.g., spinocerebellar ataxia/degeneration, Friedreich's ataxia, ataxia-telangiectasia [Louis-Bar syndrome] and fragile X-associated tremor/ataxia syndrome [FXTAS]), dyskinesias (e.g., cerebral palsy, chorea, dystonia and essential tremor), cognitive-motor disorders (e.g., corticobasal degeneration, Huntington's disease [HD] and Parkinson-plus syndromes), chorea-acanthocytosis, retinal neuronal degeneration, Batten disease, DNA-repair syndromes (e.g., Cockayne syndrome), and prion diseases (e.g., Creutzfeldt-Jakob disease).

Neuronal activation disorders include without limitation neurodegenerative disorders (e.g., ALS), neuronal injuries (including traumatic and mechanical injuries to the brain, the spinal cord and the peripheral nervous system [PNS], and excitotoxic neuronal injuries such as those associated with seizures and ischemia), nerve lesions, neuropathies (e.g., peripheral neuropathies [e.g., Charcot-Marie-Tooth disease], mononeuropathies [e.g., those caused by compression, traumatic injury, cumulative trauma, ischemia, inflammation, connective tissue disorders and neoplasms], polyneuropathies [e.g., chronic inflammatory demyelinating polyneuropathy], brachial plexus neuropathies, diabetic neuropathies [e.g. third nerve palsy, mononeuropathy, mononeuropathy multiplex, autonomic neuropathy, thoracoabdominal neuropathy and diabetic amyotrophy], and chemotherapy-induced neuropathies), autoimmune nerve disorders (e.g., multiple sclerosis, Guillain-Barré syndrome, Lambert-Eaton myasthenic syndrome and myasthenia gravis), neuroinflammation, tardy ulnar nerve palsy, and toxic myoneural disorder.

Muscle disorders include, but are not limited to, muscle structure disorders, muscle mass disorders and muscle fatigue disorders. Muscle structure disorders include without limitation myopathies (e.g., cardiomyopathy), neuromuscular degeneration, muscular dystrophy (MD), congenital MD, distal MD, Duchenne MD, Becker MD, Emery-Dreifuss MD, limb-girdle MD, myotonic MD, facioscapulohumeral MD, oculopharyngeal MD, Bethlem myopathy, central core disease, congenital fiber type disproportion, hyaline body myopathy, muscle sodium channel disorders, myotonic dystrophy, myotonic chondrodystrophy, myotubular myopathy, nemaline body disease, myositis, sarcopenia, rhabdomyolysis, and stress urinary incontinence. Muscle mass disorders include without limitation muscle atrophy, cachexia, cartilage degeneration, cerebral palsy, compartment syndrome, critical illness myopathy, inclusion body myositis, sarcopenia, steroid myopathy, and systemic lupus erythematosus (SLE). Muscle fatigue disorders include without limitation chronic fatigue syndrome, fibromyalgia, thyrotoxic myopathy, lipid-storage myopathy, Friedreich's ataxia, glycogen storage diseases (e.g., Pompe disease), intermittent claudication, MELAS, and mucopolysaccharidosis.

Eye muscle disorders include, but are not limited to, disorders of refraction, disorders of accommodation, disorders of refraction and accommodation, strabismus, progressive external ophthalmoplegia, internal ophthalmoplegia, esotropia, exotropia, hypermetropia, myopia, astigmatism, anisometropia, and presbyopia.

Fatty acid/beta oxidation disorders include without limitation systemic carnitine transporter deficiency, carnitine palmitoyl transferase (CPT) II deficiency, very long-chain acyl-CoA dehydrogenase (LCHAD or VLCAD) deficiency, medium-chain acyl-CoA dehydrogenase (MCAD) deficiency, short-chain acyl-CoA dehydrogenase (SCAD) deficiency, trifunctional enzyme deficiency, and riboflavin-responsive disorders of β-oxidation (RR-MADD).

Metabolic disorders include without limitation lipodystrophy (genetic and acquired), metabolic syndrome, hyperglycemia, impaired glucose tolerance (including prediabetes and diabetes), insulin resistance, hyperinsulinism, diabetes mellitus (including types 1 and 2), diabetic complications (e.g., diabetic neuropathy and diabetic retinopathy), obesity, dyslipidemia, hyperlipidemia, hyperchlolesterolemia, non-high-density lipoprotein (HDL) hypercholesterolemia, low-density lipoprotein (LDL) hypercholesterolemia, HDL hypocholesterolemia, hypertriglyceridemia, dyslipoproteinemia, very low-density lipoprotein (VLDL) hyperproteinemia, apolipoprotein A-I hypoproteinemia, hypertension, cardiovascular diseases (e.g., cardiomyopathy [e.g., metabolic cardiomyopathy], cardiac insufficiency, myocardial infarction, atherosclerosis, thrombotic disorders and peripheral vascular diseases), inflammatory disorders (e.g., arthritis, asthma and pancreatitis), liver disorders (e.g., non-alcoholic fatty liver disease [NAFLD] and non-alcoholic steatohepatitis [NASH]), kidney disorders (e.g., chronic kidney disease), gastrointestinal (GI) disorders (e.g., Crohn's disease, hypersensitive intestine syndrome, ulcerative colitis and dyspepsia), neurodegenerative disorders (e.g., Alzheimer disease), demyelinating disorders (e.g., multiple sclerosis), skin disorders (e.g., acne, dermatitis, psoriasis and skin aging), trichosis, adrenal leukodystrophy, edema, ketoacidosis, sexual (e.g., erectile) dysfunction, and tumors and cancers.

In some embodiments, the NR and NAR derivatives are used to treat hyperglycemia, impaired glucose tolerance and insulin resistance and disorders and conditions related thereto, including prediabetes, types 1 and 2 diabetes, and obesity-related disorders and conditions. The NR and NAR derivatives stimulate SIRT1 and SIRT3 activity, either of which increases insulin sensitivity, sensitizes cells to glucose uptake and mimics calorie restriction. Increased insulin sensitivity can reduce insulin production. Hyperinsulinemia promotes differentiation of preadipocytes into adipocytes. Therefore, reduction of blood insulin level can inhibit fat cell differentiation and adipogenesis and thus can have therapeutic effects on obesity-related disorders and conditions, including but not limited to dyslipogenesis, hyperlipidemia, hypercholesterolemia, atherosclerosis, metabolic syndrome, lipodystrophy and hypertension.

ROS incite inflammation, in part by activating transcriptions factors such as NF-κB that increase the expression of pro-inflammatory cytokines. The NR and NAR derivatives disclosed herein can reduce ROS levels by, e.g., stimulating SIRT3 activity. Moreover, the NR and NAR derivatives can increase the activity of NAD-dependent deacetylase sirtuin-1 (SIRT1), which inhibits NF-κB. NF-κB is the main promoter of the transcription of genes encoding pro-inflammatory cytokines. Thus, the NR and NAR derivatives are useful for treating inflammatory disorders. Inflammatory disorders include without limitation neuroinflammation (e.g., neuritis [e.g., ocular neuritis and peripheral neuritis], Alzheimer's disease and multiple sclerosis), GI disorders (e.g., gastritis, necrotizing enterocolitis, mucous colitis, ulcerative colitis, inflammatory bowel disease, irritable bowel syndrome, Crohn's disease and celiac disease), peritonitis, pancreatitis (acute and chronic), glomerulonephritis, liver disorders (e.g., hepatitis, non-alcoholic and alcoholic steatohepatitis, cirrhosis and chronic liver disease), multiple organ dysfunction syndrome (e.g., secondary to septicemia or trauma), metabolic disorders (e.g., diabetes [e.g., types 1 and 2 diabetes and juvenile-onset diabetes] and metabolic syndrome), cardiac disorders (e.g., myocarditis and myocardial infarction), vascular disorders (e.g., vasculitis, atherosclerosis, stroke, peripheral artery disease and shock), reperfusion injury (e.g., due to myocardial ischemia, cerebral ischemia, cardiopulmonary bypass or kidney dialysis), airway disorders (e.g., rhinitis [e.g., allergic rhinitis], esophagitis, asthma, acute respiratory distress syndrome, bronchitis [e.g., chronic bronchitis], pneumonitis and chronic obstructive pulmonary disease [COPD]), arthritis (e.g., osteoarthritis [degenerative joint disease], rheumatoid arthritis, psoriatic arthritis, gouty arthritis, axial spondyloarthritis, ankylosing spondylitis and juvenile arthritis), skin disorders (e.g., dermatitis/eczema, psoriasis, urticaria, dermatosis with acute inflammatory components, and sunburn), Sjögren syndrome, eye disorders (e.g., conjunctivitis, retinitis and AMD), SLE, hypertension and dysmenorrhea (menstrual cramps).

Inflammation is a major stimulant of fibrosis. In part by reducing inflammation, the NR and NAR derivatives disclosed herein are useful for treating fibrotic disorders. Fibrotic disorders include without limitation cardiomyopathy (e.g., diabetic cardiomyopathy and uremic cardiomyopathy), cardiac fibrosis, myocardial fibrosis, collagen-vascular diseases (e.g., arterial stiffness and vascular fibrosis), atherosclerosis, chronic heart failure, diabetic nephropathy, renal fibrosis, chronic kidney disease (e.g., chronic renal failure), liver fibrosis, cirrhosis, NASH, chronic liver disease, liver failure (e.g., chronic liver failure), pulmonary fibrosis (e.g., idiopathic pulmonary fibrosis and radiation-induced pulmonary fibrosis), cystic fibrosis, and scleroderma (e.g., localized scleroderma and systemic scleroderma/systemic sclerosis)

Vascular disorders include, but are not limited to, cardiovascular diseases (e.g., myocardial ischemia, ischemia-reperfusion injury [IRI], arteriosclerosis and atherosclerosis), cerebrovascular diseases (e.g., cerebral ischemia and IRI), peripheral vascular diseases (e.g., peripheral vascular insufficiency, peripheral artery disease, intermittent/vascular claudication, critical limb ischemia, peripheral artery occlusive disease, and peripheral obliterative arteriopathy), thrombotic/blood clotting/hemostatic disorders (e.g., disseminated intravascular coagulation, deep vein thrombosis, thrombophilia [e.g., due to anti-thrombin III deficiency, protein S deficiency, protein C deficiency or resistance to activated protein C], thrombotic thrombocytopenic purpura, heparin-induced thrombocytopenia, dysfibrinogenemia, atherosclerosis, arteriosclerosis, myocardial ischemia/infarction, angina [e.g., unstable angina], ischemic stroke, sickle cell disease, myeloproliferative neoplasms, cancer metastasis, homocystinuria, and miscarriage), and embolism (e.g., thromboembolism, fat embolism, arterial embolism [e.g., myocardial ischemia, ischemic stroke and acute limb ischemia], and venous embolism [e.g., pulmonary embolism]). As an illustrative example, one or more NR/NAR derivatives can be used to treat or prevent thrombosis or a thrombotic disorder, including to reduce or prevent thrombotic events or re-occlusion during or/and after a clot-clearing intervention (e.g., a surgery such as angioplasty).

Ocular vascular disorders include without limitation retinopathy (e.g., hypertensive retinopathy and diabetic retinopathy), macular degeneration (e.g., age-related macular degeneration [AMD]), Stargardt disease, retinal hemorrhage and glaucoma.

Renal disorders include without limitation acute nephritis, chronic nephritis, rapidly progressive nephritis, glomerulonephritis, glomerulosclerosis, hypertensive nephrosclerosis, renal ischemia, IRI, Bartter syndrome, diabetic nephropathy, acute renal failure (acute kidney injury), chronic renal failure, nephrotic syndrome, recurrent hematuria and persistent hematuria.

Liver disorders include without limitation NAFLD, NASH, alcoholic liver disease, hepatitis (e.g., autoimmune hepatitis, hepatitis B and hepatitis C), cholestatic disorders (e.g., cholestasis, primary biliary cholangitis/cirrhosis and primary sclerosing cholangitis), liver injury, chronic liver disease, liver failure (acute and chronic), cirrhosis, and liver cancer.

Tumors (benign and malignant) and cancers include without limitation brain tumors, spinal cord tumors, germ cell tumors, neuroendocrine tumors, carcinoid tumors, tumors and cancers associated with viral infections (e.g., HIV and HTLV-1), carcinomas, sarcomas, and cancers of the digestive/gastrointestinal system, gynecological organs (e.g., the breast), genitourinary system, musculoskeletal system, respiratory system, head and neck, eye, skin (e.g., melanomas), blood (e.g., leukemias, multiple myeloma, Hodgkin's lymphomas and non-Hodgkin's lymphomas), endocrine system (e.g., hormone-dependent cancers such as breast, ovarian, prostate and testicular cancers), neuroendocrine system, neurological system, and germ cells. In some embodiments, one or more NR/NAR derivatives are used to treat a cancer of the breast, ovary, colon/large intestine, rectum, pancreas, liver, kidney, lung, prostate, brain or skin. In further embodiments, one or more NR/NAR derivatives are used to treat a hematological malignancy, such as acute lymphoblastic leukemia (ALL), acute myeloid leukemia (AML), chronic lymphocytic leukemia (CLL), chronic myelogenous leukemia (CML), non-Hodgkin lymphoma or multiple myeloma.

Disorders relating to female infertility include without limitation polycystic ovarian syndrome (PCOS), diminished ovarian reserve, endometriosis, and infertility caused by radiation or chemotherapy. Disorders relating to male infertility include without limitation oligospermia and spermatogenesis caused by medications.

Somatic mutations in mitochondrial DNA increase significantly with age, which can result in defective mitochondria. Moreover, respiratory chain activity diminishes with age. Non-limiting examples of aging-related disorders are described below.

In some embodiments, one or more NR/NAR derivatives are used to treat a mitochondria-related disease or condition selected from genetic lipodystrophy, metabolic syndrome, obesity, types 1 and 2 diabetes, NAFLD, NASH, alcoholic liver disease, autoimmune hepatitis, cholestatic liver disease, hemochromatosis, alpha-1 antitrypsin deficiency, other hereditary inborn errors of metabolism, and renal ischemia and IRI.

Diseases and conditions characterized by acute $NAD^+$ depletion due to DNA damage include without limitation exposure to radiation (e.g., UV and ionizing radiation such as X-ray), radiation or chemotherapy-induced disorders (e.g., dermatitis, myositis, myocarditis, colitis, prostatitis, hepatitis, pneumonitis, neuropathies and bone marrow failure), burn injuries (including first-degree burns, second-degree burns and third-degree burns), chemical exposure with manifestation of exfoliative dermatitis, exposure to chemical warfare agents, Stevens-Johnson syndrome, acute respiratory distress syndrome, inhalational lung injury due to smoke or chemical toxins, trauma-related crush injuries (including those with bone fractures), peripheral nerve injuries, spinal cord injuries, and contusion to internal organs (such as the heart, lung, liver and kidney). Such diseases and conditions can generate a large amount of ROS such as superoxide, peroxides and hydroxyl radical, which cause DNA damage and hence cell damage or cell death. In other words, DNA damage induced by, e.g., radiation, chemotherapy or oxidative stress can cause acute $NAD^+$ depletion that results in systemic toxicity and systemic disorders (e.g., dermatitis, pneumonitis, bone marrow failure and neuropathies), as well as local toxicity and local disorders. Exemplary chemical warfare agents include blister agents (e.g., vesicants, nitrogen mustards, sulfur mustards, arsenicals and urticants [e.g., phosgene]), blood agents (e.g., cyanide), pulmonary agents (e.g., phosgene), and nerve agents (e.g., G-series agents [e.g., sarin and soman], GV-series agents and V-series agents).

Reduced $NAD^+$ levels are associated with aging, which leads to aging-related metabolic dysfunction and disorders (e.g., inflammatory disorders). For example, the expression and activity of CD38, which rapidly degrades $NAD^+$ and its precursor NMN, increase during the aging process. Therefore, the NR and NAR derivatives described herein are useful for treating aging-related disorders and conditions. Furthermore, the NR and NAR derivatives described herein can extend the lifespan of cells by, e.g., slowing or delaying the aging/senescence of cells, promoting the survival of cells, preventing apoptosis of cells, extending the proliferative capacity of cells, increasing cellular resistance to stress (e.g., oxidative stress), mimicking the effects of calorie restriction or promoting wound healing, or any combination thereof. In addition, NAD repletion improves stem cell function. Aging-related disorders and conditions include, but are not limited to, aging/senescence, hypertension, eye disorders (e.g., AMD, cataracts and keratoconjunctivitis sicca [dry eye syndrome]), hearing loss, osteoporosis, sarcopenia, dementias (e.g., Alzheimer's disease), metabolic disorders (e.g., metabolic decline, diabetes [including T1D and T2D] and obesity), cardiovascular disorders (e.g., arteriosclerosis), inflammatory disorders (e.g., arthritis and COPD), DNA-repair syndromes (e.g., Cockayne syndrome), and tumors and cancers. Because of their cytoprotective and antioxidant properties, for example, the NR and NAR derivatives can be used to prevent or mitigate hearing loss, including noise-induced hearing loss, trauma-induced hearing loss and progressive hearing loss syndromes.

By enhancing cell viability, providing cytoprotection or/and increasing cell lifespan, the NR and NAR derivatives of the disclosure can be used to treat disorders characterized by cell degeneration or death. For example, retinal disorders characterized by cell degeneration or death include, but are not limited to, AMD, retinitis pigmentosa, cone-rod dystrophy/degeneration, diabetic retinopathy, Leber's congenital amaurosis, and vision loss.

The cytoprotective NR and NAR derivatives can be used to treat other disorders and conditions characterized by cell degeneration or/and cell death, including without limitation neuronal disorders (e.g., Alzheimer's disease, Creutzfeld-Jakob disease, Parkinson's disease, ALS and multiple sclerosis), degeneration of the brain (e.g., cerebellar degeneration and traumatic brain injury), muscle disorders (e.g., muscular dystrophies such as Duchenne MD, facioscapulohumeral MD and myotonic dystrophy), ischemic disorders (e.g., myocardial ischemia/infarction and cerebral ischemia [stroke]/infarction), atherosclerosis, myelodysplastic syndromes (e.g., aplastic anemia), hepatitis (e.g., alcoholic hepatitis, fulminant hepatitis, hepatitis A, hepatitis B, hepatitis C, hepatitis D and hepatitis E), joint disorders (e.g., osteoarthritis), skin atrophy, lichen planus, skin damage caused by UV light, graft rejections, alopecia, AIDS, and cell damage or/and cell death caused by trauma (e.g., to the brain or the spinal cord), surgery, medications, chemicals, biological and chemical toxins, and radiation (e.g., ionizing radiation such as X-ray). To prevent cell damage or/and cell death that may result from, e.g., a medical intervention such as surgery or radiation therapy, one or more NR/NAR derivatives can be administered to the subject prior to or/and shortly after the intervention.

In part because of their ability to protect cells from the effects of DNA damage and to enhance cell viability and lifespan, the NR and NAR derivatives described herein are useful for treating skin disorders and conditions. The skin disorders and conditions can be associated with or caused by, e.g., natural aging, inflammation, oxidative stress or sun damage. Such skin disorders and conditions include without limitation skin wrinkles, dermatitis/eczema (e.g., atopic dermatitis, contact dermatitis [allergic and irritant], exfoliative dermatitis and seborrheic dermatitis), psoriasis (e.g., plaque psoriasis), skin damage caused by sunlight or other light sources (e.g., sunburn, actinic keratosis and xeroderma pigmentosum), keratinization disorders, erythemas (e.g., erythema multiforme and erythema nodosum), dermatomyositis, discoid lupus erythematosus, pemphigoid (e.g., bullous pemphigoid), pemphigus (e.g., pemphigus vulgaris), epidermolysis bullosa, burns (e.g., first-degree burns, second-degree burns and third-degree burns, and thermal burns, radiation burns, chemical burns and electrical burns), wounds, and skin cancers.

Partly because of their cytoprotective properties, the NR and NAR derivatives disclosed herein can promote donor graft preservation in organ transplantation. Therefore, the NR and NAR derivatives can be applied to cells, tissue or organ employed in transplantation and cell therapies, such as solid-tissue grafts, organ transplants, cell suspensions, stem cells and bone marrow cells. The cells, tissue or organ may be an autograft, an allograft, a syngraft or a xenograft. The cells, tissue or organ can be treated with one or more NR/NAR derivatives prior to, concurrently with or/and post administration/implantation of the cells, tissue or organ into a recipient. The cells, tissue or organ can be treated with one or more NR/NAR derivatives prior to removal of the cells, tissue or organ from the donor, ex vivo after removal of the cells, tissue or organ from the donor, or post administration/implantation into the recipient. For example, the donor or/and the recipient can be treated systemically with one or more NR/NAR derivatives, or can have a subset of cells, tissue or organ treated locally with one or more NR/NAR derivatives. In certain embodiments, the cells, tissue or organ (or the donor or/and the recipient) are treated with an additional therapeutic agent that prolongs graft survival, such as an immunosuppressant, a cytokine or an angiogenic factor, or any combination thereof.

As an example, since enhancement of $NAD^+$ levels promotes differentiation of transplanted cells, the use of one or more NR/NAR derivatives can improve engraftment of a bone marrow transplant, which can minimize cytopenia (including neutropenia, lymphopenia, anemia and thrombocytopenia), the need for growth factors and complications of infection. As another example, the use of one or more NR/NAR derivatives can prevent graft versus host disease (GVHD) in an allogeneic transplant.

In some embodiments, one or more NR/NAR derivatives are used in culture medium as a component of an ex vivo therapy, such as a chimeric antigen receptor (CAR) T-cell therapy. A CAR-T cell therapy can be autologous or allogeneic. In certain embodiments, the ex vivo therapy utilizes hematopoietic stem cells (HSC), embryonic stem cells (ESC) or pluripotent stem cells (PSC). One or more NR/NAR derivatives can be used to improve the yield of pancreatic endocrine cells during the final stages of in vitro ESC and PSC differentiation into pancreatic islet-like, insulin-secreting cells.

In further embodiments, the NR and NAR derivatives are used to enhance mitochondrial or cellular function or/and cellular energy production in oocytes, postnatal female germline stem cells or/and pre-implantation embryos prior to or/and following in vitro fertilization, or following exposure of ovaries, oocytes, postnatal female germline cells or/and preimplantation embryos in vivo. In some embodiments, one or more NR/NAR derivatives are used with a solution selected from cell culture medium, oocyte retrieval solution, oocyte washing solution, oocyte in vitro maturation medium, ovarian follicle in vitro maturation medium, oocyte in vitro fertilization medium, vitrification solution and cryopreservation solution in assisted reproduction techniques such as in vitro fertilization. The disclosure encompasses compositions comprising an isolated oocyte, oogonial stem cell (OSC) or OSC progeny, and one or more NR/NAR derivatives.

The therapeutically effective amount and the frequency of administration of, and the length of treatment with, an NR or NAR derivative to treat a disease/disorder or condition disclosed herein may depend on various factors, including the nature and severity of the disease/disorder or condition, the potency of the compound, the route of administration, the age, body weight, general health, gender and diet of the subject, and the response of the subject to the treatment, and can be determined by the treating physician. In some embodiments, the therapeutically effective amount of an NR or NAR derivative to treat a disease/disorder or condition disclosed herein, or to bring about a biological effect (e.g., increase $NAD^+$ level, enhance mitochondrial or cellular function, improve metabolic health or cell viability, or provide cytoprotection), is about 1-1000 mg, 1-100 mg, 100-500 mg or 500-1000 mg (e.g., per day or per dose), or as deemed appropriate by the treating physician, which can be administered in a single dose or in divided doses. In further embodiments, the therapeutically effective amount of an NR or NAR derivative is about 1-50 mg, 50-100 mg, 100-200 mg, 200-300 mg, 300-400 mg, 400-500 mg, 500-600 mg, 600-700 mg, 700-800 mg, 800-900 mg or 900-1000 mg (e.g., per day or per dose). In additional embodiments, the therapeutically effective amount of an NR or NAR derivative is about 50 mg, 100 mg, 150 mg, 200 mg, 250 mg, 300 mg, 400 mg, 500 mg, 600 mg, 700 mg, 800 mg, 900 mg or 1000 mg (e.g., per day or per dose).

In some embodiments, the therapeutically effective amount of an NR or NAR derivative is about 100-500 mg, 100-200 mg, 200-300 mg, 300-400 mg or 400-500 mg per day, which can be administered in a single dose (e.g., N mg once daily) or in divided doses (e.g., N/2 mg twice daily). In further embodiments, the therapeutically effective amount of an NR or NAR derivative is about 100 mg, 150 mg, 200 mg, 250 mg, 300 mg, 400 mg or 500 mg per day. In certain embodiments, the therapeutically effective amount of an NR or NAR derivative is about 200-300 mg per day, or about 200 mg, 250 mg or 300 mg per day.

The therapeutically effective dose of an NR or NAR derivative can be administered one, two or more times a day, once every two days, once every three days, twice a week or once a week, or as deemed appropriate by the treating physician. In certain embodiments, the therapeutically effective dose of an NR or NAR derivative is administered once or twice daily. As an illustrative example, if the therapeutically effective dose of an NR or NAR derivative is about 300 mg per day, 300 mg of the compound can be taken once daily, or 150 mg of the compound can be taken twice daily.

Where a more rapid establishment of a therapeutic level of an NR or NAR derivative is desired, such as in the treatment of an ischemia-reperfusion injury, the compound can be administered under a dosing schedule in which a loading dose is administered, followed by (i) one or more additional loading doses and then one or more therapeutically effective maintenance doses, or (ii) one or more therapeutically effective maintenance doses without an additional loading dose, as deemed appropriate by the treating physician. In such a case, a loading dose of a drug is larger (e.g., about 1.5, 2, 3, 4 or 5 times larger) than a subsequent maintenance dose and is designed to establish a therapeutic level of the drug more quickly. The one or more therapeutically effective maintenance doses can be any therapeutically effective amount/dose described herein. In certain embodiments, the loading dose is about three times larger than the maintenance dose. In some embodiments, a loading dose of an NR or NAR derivative is administered on day 1 and a maintenance dose is administered on day 2 and thereafter for the duration of therapy. In other embodiments, a first loading dose of an NR or NAR derivative is administered on day 1, a second loading dose is administered on day 2, and a maintenance dose is administered on day 3 and thereafter for the duration of therapy. In certain embodiments, the first loading dose is about three times larger than the maintenance dose, and the second loading dose is about two times larger than the maintenance dose.

The length of treatment with an NR or NAR derivative can be based on, e.g., the nature and severity of the disease/disorder or condition and the response of the subject to the treatment. In certain embodiments, a therapeutically effective amount of an NR or NAR derivative is administered over a period of about 1, 2, 3, 4, 5 or 6 days, or about 1, 2, 3, 4, 5 or 6 weeks, to treat an acute disease/disorder or condition. Acute disorders and conditions include without limitation damage and injury to tissues and organs (e.g., the brain, spinal cord, kidney and liver) and ischemic disorders (e.g., myocardial ischemia/infarction and cerebral ischemia/infarction). In other embodiments, a therapeutically effective amount of an NR or NAR derivative is administered over a period of at least about 6 weeks, 8 weeks (2 months), 3 months, 6 months, 1 year, 2 years, 3 years, 4 years, 5 years, 10 years or longer to treat a chronic disease/disorder or condition. It is understood that the delineation between acute and chronic may vary based on, e.g., the particular disease/disorder or condition.

An NR or NAR derivative can also be taken pro re nata (as needed) until clinical manifestations of the condition disappear or clinical targets are achieved. For example, an NR or NAR derivative can be taken until attainment of a target blood glucose level, blood pressure, blood levels of lipids, body weight or body mass index, or any combination thereof. If clinical manifestations of the condition re-appear or the clinical targets are not maintained, administration of the NR or NAR derivative can resume.

An NR or NAR derivative can be administered via any suitable route. Potential routes of administration of an NR or NAR derivative include without limitation oral, parenteral (including intradermal, subcutaneous, intravascular, intravenous, intra-arterial, intramuscular, intraperitoneal, intracavitary, intramedullary, intrathecal and topical), and topical (including dermal/epicutaneous, transdermal, mucosal, transmucosal, intranasal [e.g., by nasal spray or drop], pulmonary [e.g., by oral or nasal inhalation], ocular [e.g., by eye drop], buccal, sublingual, rectal [e.g., by suppository] and vaginal [e.g., by suppository]). In some embodiments, an NR or NAR derivative is administered orally (e.g., as a tablet or capsule, optionally with an enteric coating). In other embodiments, an NR or NAR derivative is administered parenterally (e.g., intravenously, subcutaneously or intramuscularly).

The mode of administration can depend on, e.g., the particular disease/disorder or condition being treated. As an example, for treatment of an ocular or retinal disorder, an NR or NAR derivative can be administered, e.g., by eye drop. As another example, for treatment of a skin disorder or condition, a topical composition containing an NR or NAR derivative can be applied to the affected area(s) of the skin. As an additional example, for treatment of an airway disorder, an NR or NAR derivative can be administered by oral inhalation.

An NR or NAR derivative can be administered at any time convenient to the patient, such as in the morning or/and at nighttime (e.g., bedtime). Moreover, an NR or NAR derivative can be taken substantially with food (e.g., with a meal or within about 1 hour or 30 minutes before or after a meal) or substantially without food (e.g., at least about 1 or 2 hours before or after a meal).

The disclosure provides a method of treating a disease/disorder or condition described herein, or bringing about a biological effect described herein, comprising administering to a subject in need of treatment a therapeutically effective amount of one or more NR/NAR derivatives or a pharmaceutical composition comprising the same. The disclosure further provides one or more NR/NAR derivatives, or a composition comprising one or more NR/NAR derivatives, for use as a medicament. In addition, the disclosure provides for the use of one or more NR/NAR derivatives in the preparation of a medicament. The medicament containing the one or more NR/NAR derivatives can be used to treat any disease/disorder or condition described herein or to bring about any biological effect described herein. In certain embodiments, the one or more NR/NAR derivatives are or include a compound of Formula II or IV. In further embodiments, the one or more NR/NAR derivatives are or include a compound of Formula I and a compound of Formula II, or a compound of Formula III and a compound of Formula IV. The one or more NR/NAR derivatives can optionally be used with one or more additional therapeutic agents.

The description and all of the embodiments relating to therapeutic use of the NR and NAR derivatives described herein, including without limitation the diseases/disorders and conditions that can be treated, the biological effects that can be achieved, the therapeutically effective amount, loading dose/maintenance dose, the frequency and route of administration, the length of treatment and combination therapies, also apply to therapeutic use of other NR and NAR derivatives (e.g., NRTA, NRHTA, NARTA and NARHTA), and to therapeutic use of NR, NRH, NAR and NARH, alone or in combination with one or more other therapeutic agents described herein (e.g., a PARP inhibitor).

Combination Therapies with Other Therapeutic Agents:

One or more NR/NAR derivatives disclosed herein can be used alone or in combination with one or more additional therapeutic agents to treat a disease/disorder or condition disclosed herein, or to bring about a biological effect disclosed herein. The additional therapeutic agent(s) can be administered prior to, concurrently with or subsequent to administration of the NR/NAR derivative(s). Furthermore, the additional therapeutic agent(s) and the NR/NAR derivative(s) can be administered in the same pharmaceutical composition or in separate compositions.

Other types of therapeutic agents that can be used in combination with the NR and NAR derivatives of the disclosure include without limitation sirtuin-activating agents, AMPK-activating agents, CD38 inhibitors, PARP inhibitors, stimulators of cellular oxygen consumption, NMDA receptor antagonists, acetylcholinesterase inhibitors, antidiabetics, anti-obesity agents, antiplatelet agents, anticoagulants, antihypertensive agents, antioxidants, anti-inflammatory agents, analgesics, anesthetics, anticancer agents, antivirals, antibiotics, antifungals, natural compounds, vitamins and vaccines. The additional therapeutic agents can also include, e.g., farnesoid X receptor agonists and sunblocks.

Combination therapies with PARP inhibitors are described in detail in a separate section below. The disclosure in this section can also apply to combination therapies with PARP inhibitors.

Sirtuin-activating agents include agents that increase the activity, level (e.g., expression) or signaling of a sirtuin such as SIRT1 or SIRT3. SIRT1 and SIRT3's beneficial properties are described above. Sirtuin-activating agents mimic calorie restriction, enhance mitochondrial and cellular function, enhance cell viability, increase cell lifespan, increase mitochondrial biogenesis, protect against fatty liver and muscle wasting, and have anti-inflammatory, antidiabetic, cardioprotective and anti-aging effects, among other therapeutic effects. SIRT1-activating agents include without limitation lamin A, methylene blue, resveratrol, SRT-1460, SRT-1720, SRT-2104, SRT-2183, and analogs, derivatives, fragments and salts thereof. In addition to resveratrol, other polyphenols that activate sirtuins such as SIRT1 include, but are not limited to, butein, fisetin, isoliquiritigenin, piceatannol, quercetin, and analogs, derivatives and salts thereof. Metformin increases the activity of sirtuins such as SIRT1 by increasing $NAD^+$ levels via activation of the $NAD^+$ salvage pathway enzyme nicotinamide phosphoribosyltransferase (NAMPT) and by increasing the $NAD^+/NADH$ ratio. Other sirtuin-activating agents include amino acids with a branched side chain and metabolites thereof, including without limitation leucine and its metabolites such as hydroxymethylbutyrate and keto-isocaproic acid/isocaproate. Such amino acids increase the levels and stimulate the signaling of sirtuins such as SIRT1 and SIRT3.

AMPK-activating agents include agents that increase the activity, level (e.g., expression) or signaling of 5'-AMP-activated protein kinase (AMPK). AMPK plays an important role in cellular energy homeostasis, largely through stimulation of glucose and fatty acid uptake and oxidation when cellular energy is low. Activation of AMPK stimulates lipolysis, hepatic and skeletal muscle fatty acid oxidation, ketogenesis and glucose uptake, inhibits cholesterol and triglyceride synthesis and lipogenesis (including adipocyte lipogenesis), and modulates insulin secretion by pancreatic β-cells. Activation of AMPK can also increase $NAD^+$ levels. AMPK-activating agents include without limitation sirtuin-activating agents (e.g., resveratrol, quercetin, metformin, and amino acids with a branched side chain and metabolites thereof), Lhiazolidinedione PPAR-γ agonists (infra, such as pioglitazone and rosiglitazone), cannabinoids, 5-aminoimidazole-4-caroxamide-1-β-D-riboside, berberine, curcumine, dinitrophenol (DNP), epigallocatechin-3-galate, α-lipoic acid, A-769662, PT-1, adiponectin, ghrelin, leptin, interleukin-6 (IL-6), and analogs, derivatives, fragments and salts thereof.

$NAD^+$ and its precursor NMN are rapidly degraded by the extracellular glycohydrolase CD38. CD38 expression and activity increase during the aging process, which reduces $NAD^+$ levels and leads to aging-related metabolic dysfunction and disorders (e.g., inflammatory disorders). Inhibition of CD38 increases $NAD^+$ levels and thereby improves mitochondrial and cellular function and increases the activity of sirtuins such as SIRT1 and SIRT3. CD38 inhibitors include, but are not limited to, flavonoids (e.g., apigenin and quercetin), thiazoloquin(az)olin(on)es disclosed in C. Haffner et al., *J. Med. Chem.*, 58:3548-3571 (2015) (e.g., compounds 76a, 76c, 77a, 77c, 77d, 78a, 78c, 78d, 78e, 79a, 79c and 79d), and analogs, derivatives and salts thereof.

Cellular oxygen consumption is a reliable indicator of mitochondrial activity since mitochondrial activity is responsible for nearly all oxygen use by cells. Mitochondria play critical roles in various cellular processes including energy production and biosynthesis. Agents that increase mitochondrial activity can be used, e.g., to treat mitochondrial diseases (e.g., Leigh syndrome and LHON), mitochondria-related diseases and conditions (e.g., metabolic disorders and neurodegenerative disorders [e.g., Alzheimer's disease, Parkinson's disease, ALS, Friedreich's ataxia and FXTAS]), to aid recovery from injury (e.g., traumatic brain injury) or illness, and to delay aging. Stimulators of cellular oxygen consumption increase mitochondrial activity through increased mitochondrial function or/and number.

Stimulators of cellular oxygen consumption include without limitation acarbose, chlormadinone (e.g., chlormadinone acetate), desoxymetasone, dichlorophene, enilconazole, flumazenil, quinidine (e.g., quinidine gluconate), succinylsulfathiazole, toltrazuril, and analogs, derivatives and salts thereof.

In some embodiments, one or more NR/NAR derivatives described herein are used in combination with an N-methyl-D-aspartate receptor (NMDAR) antagonist to treat a disorder characterized by neurodegeneration or neurotoxicity, such as a dementia (e.g., Alzheimer's disease) or a motor neuron disorder (e.g., Parkinson's disease). In certain embodiments, the NMDAR antagonist is an uncompetitive antagonist (or channel blocker) that has a moderate affinity (e.g., a $K_i$ or $IC_{50}$ from about 200 nM to about 10 μM) for the dizocilpine (MK-801)/phencyclidine-binding site at or near the $Mg^{2+}$-binding site in the opened ion channel of activated NMDAR, which allows the antagonist to inhibit NMDAR-mediated excitotoxicity while preserving physiological NMDAR activity. Such NMDAR uncompetitive antagonists include without limitation alaproclate, amantadine, atomoxetine, budipine, delucemine, dextrallorphan, dextromethorphan, dextrorphan, dexanabinol, eliprodid ketamine, lanicemine, minocycline, memantine, nitromemantine, NEFA (a tricyclic small molecule), neramexane, orphenadrine, procyclidine, ARL/FPL 12495/12495AA (desglycine metabolite of remacemide), and analogs, derivatives and salts thereof. In some embodiments, the NMDAR antagonist is memantine, nitromemantine, amantadine, lanicemine, neramexane, dextrall orphan, dextromethorphan, dextrorphan (metabolite of dextromethorphan) or procyclidine. In certain embodiments, the NMDAR antagonist is memantine, nitromemantine, dextrallorphan, dextromethorphan or dextrorphan.

In further embodiments, one or more NR/NAR derivatives disclosed herein are used in combination with an acetylcholinesterase inhibitor (AChEI) to treat a cognitive disorder (e.g., a dementia such as Alzheimer's disease, Lewy body dementia or Parkinson-associated dementia) or a neuromuscular disorder (e.g., myasthenia gravis). Reversible AChEIs include, but are not limited to, neostigmine, physostigmine, pyridostigmine, rivastigmine, ambenonium, demecarium, donepezil, edrophonium, ladostigil, and analogs, derivatives and salts thereof.

Other therapeutic agents that can be used in conjunction with one or more NR/NAR derivatives to treat Parkinson's disease include without limitation levodopa, dopamine agonists (e.g., apomorphine, bromocriptine, cabergoline, lisuride, pergolide, piribedil, pramipexole, ropinirole and rotigotine), catechol-O-methyltransferase (COMT) inhibitors (e.g., entacapone, opicapone and tolcapone), monoamine oxidase B (MAO-B) inhibitors (e.g., ladostigil, safinamide, selegiline and rasagiline), peripheral aromatic L-amino acid decarboxylase inhibitors (e.g., carbidopa), and analogs, derivatives and salts thereof.

In additional embodiments, one or more NR/NAR derivatives disclosed herein are used in combination with one or more antidiabetic agents to treat hyperglycemia, insulin resistance or diabetes (e.g., type 1 or type 2), or a disorder associated therewith (e.g., NAFLD or NASH). In certain embodiments, the one or more antidiabetic agents are or include a biguanide (e.g., metformin), a thiazolidinedione (e.g., pioglitazone or rosiglitazone), a GLP-1 agonist (e.g., dulaglutide or semaglutide) or a SGLT2 inhibitor (e.g., empagliflozin or tofogliflozin), or any combination thereof.

Antidiabetic agents include without limitation:
AMP-activated protein kinase (AMPK) agonists, including biguanides (e.g., buformin, metformin and phenformin);
peroxisome proliferator-activated receptor gamma (PPAR-γ) agonists, including thiazolidinediones (e.g., balaglitazone, ciglitazone, darglitazone, englitazone, lobeglitazone, netoglitazone, pioglitazone, rivoglitazone, rosiglitazone and troglitazone) and saroglitazar (dual PPAR-α/γ agonist);
glucagon-like peptide-1 (GLP-1) receptor agonists, including exendin-4, albiglutide, dulaglutide, exenatide, liraglutide, lixisenatide, semaglutide, taspoglutide, CNTO736, CNT03649, HM11260C (LAPS-Exendin), NN9926 (OG9S7GT), TT401 and ZYOG1;
dual GLP-1 receptor (GLP-1R)/glucagon receptor (GCGR) agonists, including longer-acting oxyntomodulin analogs {e.g., lipid-conjugated OXM analogs (e.g., DualAG disclosed in A. Pocai et al., *Diabetes*, 58:2258-2266 [2009]), PEGylated OXM analogs, cross-linked OXM analogs disclosed in A. Muppidi et al., *ACS Chem. Biol.*, 11:324-328 (2016) and OX-SR disclosed in R. Scott et al., *Peptides*, 104:70-77 (2018) }, HM12525A, JNJ-54728518, LY2944876 (TT-401), MED10382, MK-8521, MOD-6031, NN9277, SAR425899, SP-1373 and ZP2929;
dual GLP-1R/gastric inhibitory peptide receptor (GIPR) agonists, including Cpd86, LY3298176, NN9709 (MAR709), SAR438335, ZP-DI-70 and ZP-I-98;
triple GLP-1R/GIPR/GCGR agonists, including HM15211 and MAR423;
dipeptidyl peptidase 4 (DPP-4) inhibitors, including alogliptin, anagliptin, dutogliptin, evogliptin, gemigliptin, gosogliptin, linagliptin, omarigliptin, saxagliptin, septagliptin, sitagliptin, des-fluoro-sitagliptin, teneligliptin, trelagliptin and vildagliptin;
inhibitors of α-glucosidases, including acarbose, miglitol and voglibose;
ketohexokinase (KHK) inhibitors, including PF-06835919;
sodium-glucose transport protein 2 (SGLT2) inhibitors, including canagliflozin (also inhibits SGLT1), dapagliflozin, empagliflozin, ertugliflozin, ipragliflozin, remogliflozin etabonate, sotagliflozin (also inhibits SGLT1) and tofogliflozin;
blockers of ATP-dependent $K^+$ ($K_{ATP}$) channels on pancreatic beta cells, including meglitinides (e.g., mitiglinide, nateglinide and repaglinide) and sulfonylureas (including first generation (e.g., acetohexamide, carbutamide, chlorpropamide, glycyclamide [tolhexamide], metahexamide, tolazamide and tolbutamide) and second generation (e.g., glibenclamide [glyburide], glibornuride, gliclazide, glimepiride, glipizide, gliquidone, glisoxepide and glyclopyramide)};
insulin and analogs thereof, including fast-acting insulin (e.g., insulin aspart, insulin glulisine and insulin lispro), intermediate-acting insulin (e.g., NPH insulin), and long-acting insulin (e.g., insulin degiudec, insulin detemir and insulin glargine); and
analogs, derivatives and salts thereof.

In further embodiments, one or more NR/NAR derivatives described herein are used in combination with one or more anti-obesity agents to treat obesity or hyperlipidemia or a disorder associated therewith, such as a metabolic disorder (e.g., T2D, metabolic syndrome or NAFLD) or a cardiovascular disorder (e.g., atherosclerosis or coronary artery disease). Obesity also promotes inflammatory processes. In certain embodiments, the one or more anti-obesity agents are or include a lipase inhibitor (e.g., orlistat) or/and an antihyperlipidemic agent (e.g., a statin such as atorvastatin, or/and a fibrate such as fenofibrate).

Anti-obesity agents include, but are not limited to:
appetite suppressants (anorectics), including amphetamine, dexamphetamine, amfepramone, clobenzorex, mazindol, phentermine (with or without topiramate) and lorcaserin;
pro-satiety agents, including ciliary neurotrophic factor (e.g., axokine) and longer-acting analogs of amylin, calcitonin, cholecystokinin (CCK), glucagon (GCG), GLP-1, gastric inhibitory peptide (GIP, also called glucose-dependent insulinotropic polypeptide), leptin, oxyntomodulin (OXM), pancreatic polypeptide (PP), peptide YY (PYY) and neuropeptide Y (NPY);
lipase inhibitors, including caulerpenyne, cetilistat, ebelactone A and B, esterastin, lipstatin, orlistat, percyquinin, panclicin A-E, valilactone and vibralactone;
agents that increase energy expenditure or/and fat burning, including longer-acting glucagon analogs, glucagon receptor agonists (e.g., NN9030) and dual GLP-1 receptor/glucagon receptor agonists (supra); triiodothyronine ($T_3$) and thyroid hormone receptor-beta (THR-β) agonists (e.g., MB07344, MB07811, MGL-3196, MGL-3745, VK0214 and VK2809); and fibroblast growth factor 21 (FGF21) and analogs and derivatives thereof (e.g., BMS-986036 [PEGylated FGF21]);

antihyperlipidemic agents;

other agents that reduce body weight or/and fat mass, including dual GLP-1R/GIPR agonists (supra) and triple GLP-1R/GIPR/GCGR agonists (supra); and analogs, derivatives and salts thereof.

Antihyperlipidemic agents include without limitation:

HMG-CoA reductase inhibitors, including statins {e.g., atorvastatin, cerivastatin, fluvastatin, mevastatin, monacolins (e.g., monacolin K [lovastatin]), pitavastatin, pravastatin, rosuvastatin and simvastatin} and flavanones (e.g., naringenin);

squalene synthase inhibitors, including lapaquistat, zaragozic acid and RPR-107393;

acetyl-CoA carboxylase (ACC) inhibitors, including anthocyanins, avenaciolides, chloroacetylated biotin, cyclodim, diclofop, haloxyfop, soraphens (e.g., soraphen $A_{1\alpha}$), 5-(tetradecyloxy)-2-furancarboxylic acid (TOFA), CP-640186, GS-0976, NDI-010976; 7-(4-propyloxy-phenylethynyl)-3,3-dimethyl-3,4 dihydro-2H-benzo[b][1,4]dioxepine; N-ethyl-N'-(3-{[4-(3,3-dimethyl-1-oxo-2-oxa-7-azaspiro[4.5]dec-7-yl)piperidin-1-yl]-carbonyl}-1-benzothien-2-yl)urea; 5-(3-acetamidobut-1-ynyl)-2-(4-propyloxyphenoxy) thiazole; and 1-(3-{[4-(3,3-dimethyl-1-oxo-2-oxa-7-azaspiro[4.5]dec-7-yl)piperidin-1-yl]-carbonyl}-5-(pyridin-2-yl)-2-thienyl)-3-ethylurea;

ATP citrate lyase (ACL) inhibitors, including bempedoic acid (ETC-1002), 2-furoic acid, (-)-hydroxycitric acid, BMS-303141, MEDICA-16 and SB-204990;

PPAR-α agonists, including fibrates (e.g., bezafibrate, ciprofibrate, clinofibrate, clofibric acid, clofibrate, aluminum clofibrate [alfibrate], clofibride, etofibrate, fenofibric acid, fenofibrate, gemfibrozil, ronifibrate and simfibrate), isoflavones (e.g., daidzein and genistein), and perfluoroalkanoic acids (e.g., perfluorooctanoic acid and perfluorononanoic acid);

PPAR-δ agonists, including elafibranor (dual PPAR-α/δ agonist), lanifibranor (triple PPAR-α/δ/γ agonist), GFT505 (dual PPAR-α/δ agonist), GW0742, GW501516 (dual PPAR-β/δ agonist), sodelglitazar (GW677954), MBX-8025, and isoflavones (e.g., daidzein and genistein);

PPAR-γ agonists, including thiazolidinediones (supra), saroglitazar (dual PPAR-α/γ agonist), 4-oxo-2-thioxothiazolines (e.g., rhodanine), berberine, honokiol, perfluorononanoic acid, cyclopentenone prostaglandins (e.g., cyclopentenone 15-deoxy-Δ-prostaglandin $J_2$ [15d-PGJ$_2$]), and isoflavones (e.g., daidzein and genistein);

liver X receptor (LXR) agonists, including endogenous ligands (e.g., oxysterols such as 22(R)-hydroxycholesterol, 24(S)-hydroxycholesterol, 27-hydroxycholesterol and cholestenoic acid) and synthetic agonists (e.g., acetyl-podocarpic dimer, hypocholamide, N,N-dimethyl-3β-hydroxy-cholenamide [DMHCA], GW3965 and T0901317);

retinoid X receptor (RXR) agonists, including endogenous ligands (e.g., 9-cis-retinoic acid) and synthetic agonists (e.g., bexarotene, AGN 191659, AGN 191701, AGN 192849, BMS649, LG100268, LG100754 and LGD346);

triiodothyronine and thyroid hormone receptor-beta agonists (supra);

ketohexokinase inhibitors (supra);

inhibitors of acyl-CoA cholesterol acyltransferase (ACAT, also called sterol O-acyltransferase [SOAT], including ACAT1 [SOAT1] and ACAT2 [SOAT2]), including avasimibe, pactimibe, pellitorine, terpendole C and flavanones (e.g., naringenin);

inhibitors of stearoyl-CoA desaturase-1 (SCD-1, also called stearoyl-CoA delta-9 desaturase) activity or expression, including aramchol, CAY-10566, CVT-11127, SAR-224, SAR-707, XEN-103; 3-(2-hydroxyethoxy)-4-methoxy-N-[5-(3-trifluoromethylbenzyl)thiazol-2-yl]benzamide and 4-ethylamino-3-(2-hydroxyethoxy)-N-[5-(3-trifluoromethylbenzyl) thiazol-2-yl]benzamide; 1'-{6-[5-(pyridin-3-ylmethyl)-1,3,4-oxadiazol-2-yl]pyridazin-3-yl}-5-(trifluoromethyl)-3,4-dihydrospiro[chromene-2,4'-piperidine]; 5-fluoro-1'-{6-[5-(pyridin-3-ylmethyl)-1,3,4-oxadiazol-2-yl]pyridazin-3-yl}-3,4-dihydrospiro [chromene-2,4'-piperidine]; 6-[5-(cyclopropylmethyl)-4,5-dihydro-1'H,3H-spiro[1,5-benzoxazepine-2,4'-piperidin]-1'-yl]-N-(2-hydroxy-2-pyridin-3-ylethyl) pyridazine-3-carboxamide; 6-[4-(2-methylbenzoyl) piperidin-1-yl]pyridazine-3-carboxylic acid (2-hydroxy-2-pyridin-3-ylethyl)amide; 4-(2-chlorophenoxy)-N-[3-(methyl carbamoyl)phenyl]piperidine-1-carboxamide; the cis-9,trans-11 isomer and the trans-10,cis-12 isomer of conjugated linoleic acid, substituted heteroaromatic compounds disclosed in WO 2009/129625 A1, anti-sense polynucleotides and peptide-nucleic acids (PNAs) that target mRNA for SCD-1, and SCD-1-targeting siRNAs;

cholesterylester transfer protein (CETP) inhibitors, including anacetrapib, dalcetrapib, evacetrapib, torcetrapib and AMG 899 (TA-8995);

inhibitors of microsomal triglyceride transfer protein (MTTP) activity or expression, including implitapide, lomitapide, dirlotapide, mitratapide, CP-346086, JTT-130, SLx-4090, anti-sense polynucleotides and PNAs that target mRNA for MTTP, MTTP-targeting microRNAs (e.g., miRNA-30c), and MTTP-targeting siRNAs;

GLP-1 receptor agonists (supra), glucagon receptor agonists (supra) and dual GLP-1 receptor/glucagon receptor agonists (supra);

fibroblast growth factor 21 (FGF21) and analogs and derivatives thereof, including BMS-986036 (pegylated FGF21);

inhibitors of pro-protein convertase subtilisin/kexin type 9 (PCSK9) activity or expression, including berberine (reduces PCSK9 level), annexin A2 (inhibits PCSK9 activity), anti-PCSK9 antibodies (e.g., alirocumab, bococizumab, evolocumab, LGT-209, LY3015014 and RG7652), peptides that mimic the epidermal growth factor-A (EGF-A) domain of the LDL receptor which binds to PCSK9, PCSK9-binding adnectins (e.g., BMS-962476), anti-sense polynucleotides and PNAs that target mRNA for PCSK9, and IPCSK9-targeting siRNAs (e.g., inclisiran [ALN-PCS] and ALN-PCS02);

FGF21 and analogs and derivatives thereof (supra);

apolipoprotein mimetic peptides, including apoA-I mimetics (e.g., 2F, 3F, 3F-1, 3F-2, 3F-14, 4F, 4F-P-4F, 4F-IHS-4F, 4F2, 5F, 6F, 7F, 18F, 5A, 5A-C1, 5A-CH1, 5A-CH2, 5A-H1, 18A, 37 pA [18A-P-18A], ELK [name], ELK-1A, ELK-1F, ELK-1K1A1E, ELK-1L1K, ELK-1W, ELK-2A, ELK-2A2K2E, ELK-2E2K, ELK-2F, ELK-3E3EK, ELK-3E3K3A, ELK-3E3LK, ELK-PA, ELK-P2A, ELKA [name], ELKA-CH2, ATI-5261, CS-6253, ETC-642, FAMP [name], FREL [name] and KRES [name]) and apoE mimetics (e.g., Ac-hE18A-NH$_2$ [AEM-28], Ac-[R]hE18A-NH$_2$, AEM-28-14, EpK, hEp, mR18L, COG-112, COG-133 and COG-1410);

omega-3 fatty acids, including docosahexaenoic acid (DHA), docosapentaenoic acid (DPA), eicosapentaenoic acid (EPA), α-linolenic acid (ALA), fish oils (which contain, e.g., DHA and EPA), and esters (e.g., glyceryl and ethyl esters) thereof; and analogs, derivatives and salts thereof.

In other embodiments, one or more NR/NAR derivatives of the disclosure are used in combination with an antiplatelet agent or/and an anticoagulant to treat a thrombotic or hemostatic disorder, such as a cardiovascular disorder (e.g., myocardial ischemia/infarction) or a cerebrovascular disorder (e.g., ischemic stroke). In certain embodiments, the antiplatelet agent is or includes a COX-1 inhibitor (e.g., aspirin) or/and a P2Y$_{12}$ inhibitor (e.g., clopidogrel), and the anticoagulant is or includes a direct factor Xa inhibitor (e.g., apixaban or rivaroxaban) or/and a direct thrombin inhibitor (e.g., dabigatran).

Antiplatelet agents include without limitation:

cyclooxygenase (e.g., COX-1) inhibitors, including baspirin, naproxen, triflusal and 2-hydroxy-4-trifluoromethylbenzoic acid (the main metabolite of triflusal);

thromboxane (e.g., A$_2$) synthase inhibitors, including isbogrel, ozagrel, picotamide, ridogrel, samixogrel, terbogrel and EV-077;

thromboxane (e.g., A$_2$) receptor antagonists, including dipyridamole, ifetroban, isbogrel, picotamide, ramatroban, ridogrel, samixogrel, terbogrel, terutroban, EV-077 and TRA-418;

adenosine diphosphate (ADP) receptor/P2Y$_{12}$ inhibitors, including cangrelor, clopidogrel, prasugrel, ticagrelor and ticlopidine;

adenosine reuptake inhibitors, including cilostazol and dipyridamole;

glycoprotein IIb/IIIa inhibitors, including abciximab, eptifibatide, tirofiban, TRA-418, and prostacyclin and analogs thereof;

phosphodiesterase (e.g., PDE3 or/and PDE5) inhibitors, including cilostazol and dipyridamole;

protease-activated receptor 1 (PAR1) antagonists, including vorapaxar;

prostacyclin and analogs thereof, including ataprost, beraprost (e.g., esuberaprost), 5,6,7-trinor-4,8-inter-m-phenylene-9-fluoro-PGI$_2$, carbacyclin, isocarbacyclin, clinprost (isocarbacyclin methyl ester), ciprostene, eptaloprost, cicaprost (metabolite of eptaloprost), iloprost, pimilprost, SM-10906 (des-methyl pimilprost), naxaprostene, taprostene, treprostinil, CS-570, OP-2507 and TY-11223; and analogs, derivatives and salts thereof.

Anticoagulants include, but are not limited to:

vitamin K antagonists, including 4-hydroxycoumarins (e.g., acenocoumarol, brodifacoum, coumatetralyl, dicoumarol, phenprocoumon, tioclomarol and warfarin) and 1,3-indandiones (e.g., clorindione, diphenadione, fluindione and phenindione);

indirect factor Xa inhibitors, including heparin (unfractionated), low molecular weight (MW) heparin (e.g., Fraxiparine®), low MW heparin derivatives (e.g., bemiparin, certoparin, dalteparin, enoxaparin, nadroparin, parnaparin, reviparin and tinzaparin), heparin analogs (e.g., fondaparinux and idraparinux), and heparinoids (e.g., danaparoid, sulodexide and dermatan sulfate);

direct factor Xa inhibitors, including apixaban, betrixaban, darexaban, edoxaban, eribaxaban, letaxaban, otamixaban, razaxaban, rivaroxaban, LY-517717 and YM-466;

direct thrombin (factor IIa) inhibitors (DTIs), including univalent DTIs (e.g., argatroban, dabigatran, inogatran, melagatran and ximelagatran) and bivalent DTIs (e.g., hirudin and hirudin analogs [e.g., bivalirudin, desirudin and lepirudin]); and analogs, derivatives and salts thereof.

In additional embodiments, one or more NR/NAR derivatives disclosed herein are used in combination with one or more antihypertensive agents. Hypertension is a clinical feature of or is a major risk factor for a wide range of disorders. Hypertension-associated disorders include without limitation cardiovascular disorders (e.g., cardiomyopathy, heart failure, atherosclerosis, arteriosclerosis, coronary artery diseases [e.g., myocardial ischemia/infarction], and peripheral vascular diseases [e.g., peripheral artery disease]), cerebrovascular disorders (e.g., stroke and cerebral infarction), metabolic disorders (e.g., metabolic syndrome and T2D), kidney disorders (e.g., diabetic nephropathy, glomerulonephritis, renal ischemia, nephrotic syndrome, and kidney failure [e.g., acute kidney injury and chronic kidney disease]), liver failure (e.g., cirrhosis), and eye disorders (e.g., retinopathy, damage to blood vessels in the eye, and vision loss).

Antihypertensive agents include without limitation:

antagonists of the renin-angiotensin-aldosterone system (RAAS), including renin inhibitors (e.g., aliskiren), angiotensin-converting enzyme (ACE) inhibitors (e.g., benazepril, captopril, enalapril, fosinopril, lisinopril, moexipril, perindopril, quinapril, ramipril and trandolapril), angiotensin II receptor type 1 (AT$_1$) antagonists (e.g., azilsartan, candesartan, eprosartan, fimasartan, irbesartan, losartan, olmesartan medoxomil, olmesartan, telmisartan and valsartan), and aldosterone receptor antagonists (e.g., eplerenone and spironolactone);

diuretics, including loop diuretics (e.g., bumetanide, ethacrynic acid, furosemide and torsemide), thiazide diuretics (e.g., bendroflumethiazide, chlorothiazide, hydrochlorothiazide, epitizide, methyclothiazide and polythiazide), thiazide-like diuretics (e.g., chlorthalidone, indapamide and metolazone), cicletanine (an early distal tubular diuretic), potassium-sparing diuretics (e.g., amiloride, eplerenone, spironolactone and triamterene), and theobromine;

calcium channel blockers, including dihydropyridines (e.g., amlodipine, levamlodipine, cilnidipine, clevidipine, felodipine, isradipine, lercanidipine, nicardipine, nifedipine, nimodipine, nisoldipine and nitrendipine) and non-dihydropyridines (e.g., diltiazem and verapamil);

α$_2$-adrenoreceptor agonists, including clonidine, guanabenz, guanfacine, methyldopa and moxonidine;

α$_1$-adrenoreceptor antagonists (alpha blockers), including doxazosin, indoramin, nicergoline, phenoxybenzamine, phentolamine, prazosin, terazosin and tolazoline;

β-adrenoreceptor (β$_1$ or/and β$_2$) antagonists (beta blockers), including atenolol, betaxolol, bisoprolol, carteolol, carvedilol, labetalol, metoprolol, nadolol, nebivolol, oxprenolol, penbutolol, pindolol, propranolol and timolol;

mixed alpha/beta blockers, including bucindolol, carvedilol and labetalol;

endothelin receptor antagonists, including selective ET$_A$ receptor antagonists (e.g., ambrisentan, atrasentan, edonentan, sitaxentan, zibotentan and BQ-123) and dual ET$_A$/ET$_B$ antagonists (e.g., bosentan, macitentan and tezosentan);

other vasodilators, including hydralazine, minoxidil, theobromine, sodium nitroprusside, organic nitrates (e.g., isosorbide mononitrate, isosorbide dinitrate and nitroglycerin, which are converted to nitric oxide in the body), endothelial nitric oxide synthase (eNOS) stimulators (e.g., cicletanine), activators of soluble guanylate cyclase (e.g., cinaciguat and riociguat), phosphodiesterase type 5 (PDE5) inhibitors (e.g., avanafil, benzamidenafil, dasantafil, dynafil, lodenafil, mirodenafil, sildenafil, tadalafil, udenafil, vardenafil, dipyridamole, papaverine, propentofylline, zaprinast and T-1032), prostaglandin E$_1$ (alprostadil) and analogs thereof (e.g., limaprost amd misoprostol), prostacyclin and analogs thereof (supra), non-prostanoid prostacyclin receptor agonists (e.g., 1-phthalazinol, ralinepag, selexipag, ACT-333679 [MRE-269, active metabolite of selexipag], and TRA-418), phospholipase C (PLC) inhibitors, and protein kinase C (PKC) inhibitors (e.g., BIM-1, BIM-2, BIM-3, BIM-8, chelerythrine, cicletanine, gossypol, miyabenol C, myricitrin, ruboxistaurin and verbascoside);

minerals, including magnesium and magnesium sulfate; and analogs, derivatives and salts thereof.

In certain embodiments, the one or more antihypertensive agents are or include a thiazide or thiazide-like diuretic (e.g., hydrochlorothiazide or chlorthalidone), a calcium channel blocker (e.g., amlodipine or nifedipine), an ACE inhibitor (e.g., benazepril, captopril or perindopril) or an angiotensin II receptor antagonist (e.g., olmesartan medoxomil, olmesartan, telmisartan or valsartan), or any combination thereof.

In further embodiments, one or more NR/NAR derivatives described herein are used in combination with one or more antioxidants to treat a disorder whose pathogenesis or pathophysiology involves oxidative stress or/and oxidative damage/injury. Such oxidative disorders include without limitation neurodegenerative disorders (e.g., Alzheimer's, Huntington's and Parkinson's diseases, ALS and multiple sclerosis), metabolic disorders (e.g., types 1 and 2 diabetes and metabolic syndrome), cardiovascular disorders (e.g., atherosclerosis, heart failure, myocardial ischemia/infarction and IRI), cerebrovascular disorders (e.g., stroke and IRI), kidney disorders (e.g., diabetic nephropathy), liver disorders (e.g., cirrhosis), and eye disorders (e.g., AMD). Furthermore, oxidants (e.g., ROS) and oxidized molecules (e.g., oxidized lipids) can be highly inflammatory.

Antioxidants include without limitation:

vitamins and analogs thereof, including vitamin A, vitamin B$_3$ (e.g., niacin [nicotinic acid] and nicotinamide), vitamin C (ascorbic acid), vitamin E (including tocopherols [e.g., α-tocopherol] and tocotrienols), and vitamin E analogs (e.g., trolox [water-soluble]);

carotenoids, including carotenes (e.g., β-carotene), xanthophylls (e.g., lutein, zeaxanthin and meso-zeaxanthin), and carotenoids in saffron (e.g., crocin and crocetin);

sulfur-containing antioxidants, including glutathione (GSH), N-acetyl-L-cysteine (NAC), bucillamine, S-nitroso-N-acetyl-L-cysteine (SNAC), S-allyl-L-cysteine (SAC), S-adenosyl-L-methionine (SAM), α-lipoic acid and taurine;

scavengers of ROS and radicals, including carnosine, N-acetylcarnosine, curcuminoids (e.g., curcumin, demethoxycurcumin and tetrahydrocurcumin), cysteamine, ebselen, glutathione, hydroxycinnamic acids and derivatives (e.g., esters and amides) thereof (e.g., caffeic acid, rosmarinic acid and tranilast), melatonin and metabolites thereof, nitrones (e.g., disufenton sodium [NXY-059]), nitroxides (e.g., XJB-5-131), polyphenols (e.g., flavonoids [e.g., apigenin, genistein, luteolin, naringenin and quercetin]), superoxide dismutase mimetics (infra), tirilazad, vitamin C, vitamin E and analogs thereof (e.g., α-tocopherol and trolox), and xanthine derivatives (e.g., pentoxifylline);

inhibitors of enzymes that produce ROS, including NADPH oxidase (NOX) inhibitors (e.g., apocynin, decursin and decursinol angelate [both inhibit NOX-1, -2 and -4 activity and expression], diphenylene iodonium, and GKT-831 [formerly GKT-137831, a dual NOX1/4 inhibitor]), NADH:ubiquinone oxidoreductase (complex I) inhibitors (e.g., metformin and rotenone), and myeloperoxidase inhibitors (e.g., azide and 4-aminobenzoic acid hydrazide, and apoE mimetics such as AEM-28 and AEM-28-14);

substances that mimic or increase the activity or production of antioxidant enzymes, including superoxide dismutase (SOD) {e.g., SOD mimetics such as manganese (III)- and zinc (III)-porphyrin complexes (e.g., MnT-BAP, MnTMPyP and ZnTBAP), manganese (II) pentaazamacrocyclic complexes (e.g., M40401 and M40403), manganese (III)-salen complexes (e.g., those disclosed in U.S. Pat. No. 7,122,537) and OT-551 (a cyclopropyl ester prodrug of tempol hydroxylamine), and resveratrol and apoA-I mimetics such as 4F (both increase expression)}, catalase (e.g., catalase mimetics such as manganese (III)-salen complexes [e.g., those disclosed in U.S. Pat. No. 7,122,537], and zinc [increases activity]), glutathione peroxidase (GPx) (e.g., apomorphine and zinc [both increase activity], and beta-catenin, etoposide and resveratrol [all three increase expression]), glutathione reductase (e.g., 4-tert-butylcatechol and redox cofactors such as flavin adenine dinucleotide [FAD] and NADPH [all three enhance activity]), glutathione S-transferase (GST) (e.g., phenylalkyl isothiocyanate-cysteine conjugates {e.g., S—[N-benzyl(thiocarbamoyl)]-L-cysteine}, phenobarbital, rosemary extract and carnosol [all enhance activity]), thioredoxin (Trx) (e.g., geranylgeranylacetone, prostaglandin E$_i$ and sulforaphane [all increase expression]), NADPH-quinone oxidoreductase 1 (NQO1) {e.g., flavones [e.g., β-naphthoflavone (5,6-benzoflavone)] and triterpenoids [e.g., oleanolic acid analogs such as TP-151 (CDDO), TP-155 (CDDO methyl ester), TP-190, TP-218, TP-222, TP-223 (CDDO carboxamide), TP-224 (CDDO monomethylamide), TP-225, TP-226 (CDDO dimethylamide), TP-230, TP-235 (CDDO imidazolide), TP-241, CDDO monoethylamide, CDDO mono(trifluoroethyl)amide, and (+)-TBE-B], all of which increase expression by activating Nrf2}, heme oxygenase 1 (HO-1) {e.g., curcuminoids (e.g., curcumin), triterpenoids (e.g., oleanolic acid analogs [supra, such as TP-225]), and apoA-I mimetics (supra, such as 4F), all of which increase expression}, and paraoxonase 1 (PON-1) (e.g., apoE mimetics [supra, such as AEM-28 and AEM-28-14] and apoA-I mimetics [supra, such as 4F], both types increasing activity);

activators of transcription factors that upregulate expression of antioxidant enzymes, including activators of nuclear factor (erythroid-derived 2)-like 2 (NFE2L2 or Nrf2) {e.g., bardoxolone methyl, OT-551, fumarates (e.g., dimethyl and monomethyl fumarate), dithiolethiones (e.g., oltipraz), flavones (e.g., p-naphthoflavone), isoflavones (e.g., genistein), sulforaphane, trichostatin A, triterpenoids (e.g., oleanolic acid analogs [supra, such as TP-225]), and melatonin (increases Nrf2 expression)};

mitochondria-targeted antioxidants, including MitoE and MitoQ;

other kinds of antioxidants, including anthocyanins, benzenediol abietane diterpenes (e.g., carnosic acid), cyclopentenone prostaglandins (e.g., 15d-PGJ$_2$), flavonoids {e.g., flavonoids in *Ginkgo biloba* (e.g., myricetin and quercetin [increases levels of GSH, SOD, catalase, GPx and GST]), prenylflavonoids (e.g., isoxanthohumol), flavones (e.g., apigenin), isoflavones (e.g., genistein), flavanones (e.g., naringenin) and flavanols (e.g., catechin and epigallocatechin-3-gallate)}, omega-3 fatty acids and esters thereof (supra), phenylethanoids (e.g., tyrosol and hydroxytyrosol), retinoids (e.g., all-trans retinol [vitamin A]), stilbenoids (e.g., resveratrol), uric acid, apoA-I mimetics (e.g., 4F), apoE mimetics (e.g., AEM-28 and AEM-28-14), and minerals (e.g., selenium and zinc [e.g., zinc monocysteine]); and analogs, derivatives and salts thereof.

In certain embodiments, the one or more antioxidants are or include a vitamin or an analog thereof (e.g., vitamin E or an analog thereof such as α-tocopherol or trolox) or/and an ROS or radical scavenger (e.g., melatonin or/and glutathione). In other embodiments, the antioxidant or/and the natural compound are selected from resveratrol, pterostilbene, ellagic acid, urolithin A, quercetin, coenzyme Q, glutathione, N-acetyl-L-cysteine, α-lipoic acid, melatonin, creatine, S-adenosyl methionine, leucine, pyruvic acid/pyruvate and combinations thereof.

In some embodiments, one or more NR/NAR derivatives are used in conjunction with one or more B vitamins selected from thiamine ($B_1$), riboflavin ($B_2$), niacin ($B_3$), pantothenic acid ($B_5$), pyridoxine ($B_6$), biotin ($B_7$), folic acid ($B_9$) and cobalamin ($B_{12}$). In certain embodiments, one or more NR/NAR derivatives are used in conjunction with vitamin $B_1$, $B_2$, $B_3$ or $B_6$, or any combination thereof.

In additional embodiments, one or more NR/NAR derivatives disclosed herein are used in combination with one or more anti-inflammatory agents to treat an inflammatory disorder. Inflammation contributes to the pathogenesis or pathophysiology of a wide range of disorders. Furthermore, inflammation is a major stimulant of fibrosis. In certain embodiments, the one or more anti-inflammatory agents are or include and NSAID or/and an inhibitor of a pro-inflammatory cytokine or a receptor therefor or the production thereof (e.g., TNF-α, IL-4, IL-6 or IL-23, or any combination thereof).

Anti-inflammatory agents include without limitation:

non-steroidal anti-inflammatory drugs (NSAIDs), including those listed below;

immunomodulators, including imides (e.g., thalidomide, lenalidomide, pomalidomide and apremilast) and xanthine derivatives (e.g., lisofylline, pentoxifylline and propentofylline);

immunosuppressants, including interferon-beta (IFN-β) glucocorticoids (infra), antimetabolites (e.g., hydroxyurea [hydroxycarbamide], antifolates [e.g., methotrexate], and purine analogs [e.g., azathioprine, mercaptopurine and thioguanine]), pyrimidine synthesis inhibitors (e.g., leflunomide and teriflunomide), calcineurin inhibitors (e.g., ciclosporin [cyclosporine A], pimecrolimus and tacrolimus), inosine-5'-monophosphate dehydrogenase (IMPDH) inhibitors (e.g., mycophenolic acid and derivatives thereof [e.g., mycophenolate sodium and mycophenolate mofetil]), mechanistic/mammalian target of rapamycin (mTOR) inhibitors (e.g., rapamycin [sirolimus], deforolimus [ridaforolimus], everolimus, temsirolimus, umirolimus [biolimus A9], zotarolimus and RTP-801), modulators of sphingosine-1-phosphate receptors (e.g., S1PR1) (e.g., fingolimod), and serine C-palmitoyltransferase inhibitors (e.g., myriocin);

anti-inflammatory cytokines and compounds that increase their production, including IL-10 and compounds that increase IL-10 production {e.g., S-adenosyl-L-methionine, melatonin, metformin, rotenone, curcuminoids (e.g., curcumin), prostacyclin and analogs thereof (supra) triterpenoids (e.g., oleanolic acid analogs [supra, such as TP-225]), and apoA-I mimetics (supra, such as 4F)};

inhibitors of pro-inflammatory cytokines or receptors therefor, including inhibitors of (e.g., antibodies or fragments thereof targeting) tumor necrosis factor-alpha (TNF-α) (e.g., adalimumab, certolizumab pegol, golimumab, infliximab, etanercept, bupropion, curcumin, catechins and ART-621) or the receptor therefor (TNFR1), inhibitors of thymic stromal lymphopoietin (e.g., anti-TSLP antibodies and fragments thereof [e.g., tezepelumab and M702] and immunoconjugates comprising the extracellular domain of TSLPR) or the receptor therefor (TSLPR), inhibitors of (e.g., antibodies or fragments thereof targeting) pro-inflammatory interferons (e.g., interferon-alpha [IFN-α]) or receptors therefor, inhibitors of (e.g., antibodies or fragments thereof targeting) pro-inflammatory interleukins or receptors therefor {e.g., IL-1 (e.g., IL-1α and IL-1β [e.g., canakinumab and rilonacept]) or IL-1R (e.g., anakinra and isunakinra [EBI-005]), IL-2 or IL-2R (e.g., basiliximab and daclizumab), IL-4 or IL-4R (e.g., dupilumab), IL-5 (e.g., mepolizumab and reslizumab) or IL-5R, IL-6 (e.g., clazakizumab, elsilimomab, olokizumab, siltuximab and sirukumab) or IL-6R (e.g., sarilumab and tocilizumab), IL-8 or IL-8R, IL-12 (e.g., briakinumab and ustekinumab) or IL-12R, IL-13 or IL-13R, IL-15 or IL-15R, IL-17 (e.g., ixekizumab and secukinumab) or IL-17R (e.g., brodalumab), IL-18 (e.g., GSK1070806) or IL-18R, IL-20 (e.g., the antibody 7E) or IL-20R, IL-22 (e.g., fezakinumab) or IL-22R, IL-23 (e.g., briakinumab, guselkumab, risankizumab, tildrakizumab [SCH-900222], ustekinumab and BI-655066) or IL-23R, IL-31 (e.g., anti-IL-31 antibodies disclosed in U.S. Pat. No. 9,822,177) or IL-31R (e.g., anti-IL-31 receptor A antibodies such as nemolizumab), IL-33 or IL-33R, and IL-36 or IL-36R}, and inhibitors of monocyte chemoattractant protein 1 (MCP-1) {e.g., bindarit, anti-MCP1 antibodies (e.g., 5D3-F7 and 10F7), MCP1-binding peptides (e.g., HSWRHFHTLGGG), and MCP1-binding RNA aptamers (e.g., ADR22 and mNOX-E36 [a spiegelmer])} or receptors therefor (e.g., CCR2 antagonists such as spiropiperidines [e.g., RS-29634, RS-102895 and RS-504393]);

inhibitors of the production of pro-inflammatory cytokines or receptors therefor, including inhibitors of the production of TNF-α {e.g., N-acetyl-L-cysteine, S-adenosyl-L-methionine, L-carnitine, hydroxychloroquine, melatonin, parthenolide, pirfenidone, sulfasalazine, mesalazine (5-aminosalicylic acid), taurine, flavonoids (e.g., epigallocatechin-3-gallate [EGCG], naringenin and quercetin), omega-3 fatty acids and esters thereof, glucocorticoids, immunomodulatory imides and xanthine derivatives, PDE4 inhibitors, serine protease inhibitors (e.g., gabexate and nafamostat), prostacyclin and analogs thereof, SOCS1 mimetics (infra), myxoma virus M013 protein, Yersinia YopM protein, apoA-I mimetics (e.g., 4F), and apoE mimetics (e.g., AEM-28 and hEp)}, IFN-α (e.g., alefacept), IL-1 (e.g., IL-1α and IL-1β)(e.g., chloroquine, hydroxychloroquine, nafamostat, pirfenidone, sulfasalazine, mesalazine, prostacyclin and analogs thereof, glucocorticoids, TNF-α inhibitors, PAR1 antagonists [e.g., vorapaxar], M013 protein, YopM protein and apoA-I mimetics [e.g., 4F]), IL-1β (e.g. melatonin, metformin, rotenone, flavonoids [e.g., EGCG and naringenin], annexin A1 mimetics, and caspase-1 inhibitors [e.g., belnacasan, pralnacasan and parthenolide]), IL-2 (e.g., glucocorticoids, calcineurin inhibitors and PDE4 inhibitors), IL-4 (e.g., glucocorticoids and serine protease inhibitors [e.g., gabexate and nafamostat]), IL-5 (e.g., glucocorticoids), IL-6 (e.g., nafamostat, parthenolide, prostacyclin and analogs thereof, tranilast, L-carnitine, taurine, flavonoids [e.g., EGCG, naringenin and quercetin], omega-3 fatty acids and esters thereof, glucocorticoids, immunomodulatory imides, TNF-α inhibitors, M013 protein and apoE mimetics [e.g., AEM-28 and hEp]), IL-8 (e.g., alefacept and glucocorticoids), IL-12 (e.g., apilimod, PDE4 inhibitors and YopM protein), IL-15 (e.g., YopM protein), IL-17 (e.g., protein kinase C inhibitors such as sotrastaurin), IL-18 (e.g., M013 protein, YopM protein and caspase-1 inhibitors), and IL-23 (e.g., apilimod, alefacept and PDE4 inhibitors), and MCP-1 (e.g., EGCG, melatonin and tranilast);

inhibitors of pro-inflammatory transcription factors or their activation or expression, including inhibitors of NF-κB or its activation or expression {e.g., aliskiren, melatonin, minocycline and parthenolide (both inhibit NF-κB nuclear translocation), nafamostat, niclosamide, (−)-DIMEQ, IT-603, IT-901, PBS-1086, flavonoids (e.g., EGCG and quercetin), hydroxycinnamic acids and esters thereof (e.g., ethyl caffeate), lipoxins (e.g., 15-epi-LXA4 and LXB4), omega-3 fatty acids and esters thereof, stilbenoids (e.g., resveratrol), statins (e.g., rosuvastatin), triterpenoids (e.g., oleanolic acid analogs such as TP-225), TNF-α inhibitors, apoE mimetics (e.g., AEM-28), M013 protein, penetratin, and activators of sirtuin 1 (SIRT1, which inhibits NF-κB) (e.g., flavones [e.g., luteolin], phenylethanoids [e.g., tyrosol, which induces SIRT1 expression], stilbenoids [e.g., resveratrol, which increases SIRT1 activity and expression] and lamin A)}, and inhibitors of STAT (signal transducer and activator of transcription) proteins or their activation or expression {e.g., Janus kinase 1 (JAK1) inhibitors (e.g., itacitinib, upadacitinib, GLPG0634 and GSK2586184), JAK2 inhibitors (e.g., lestaurtinib, pacritinib, CYT387, TG101348, SOCS1 mimetics and SOCS3 mimnetics), JAK3 inhibitors (e.g., ASP-015K, R348 and VX-509), dual JAK1/JAK2 inhibitors (e.g., baricitinib and ruxolitinib), dual JAK1/JAK3 inhibitors (e.g., tofacitinib), suppressor of cytokine signaling (SOCS) mimetic peptides (e.g., SOCS1 mimetics [e.g., SOCS1-KIR, NewSOCS1-KIR, PS-5 and Tkip] and SOCS3 mimetics), niclosamide, hydroxycinnamic acids and esters thereof (e.g., rosmarinic acid), and lipoxins (e.g., 15-epi-LXA4 and LXB4)}; inhibitors of pro-inflammatory prostaglandins (e.g., prostaglandin $E_2$ [$PGE_2$]) or receptors therefor (e.g., $EP_3$) or the production thereof, including cyclooxygenase inhibitors (e.g., NSAIDs [including non-selective COX-1/COX-2 inhibitors such as aspirin and selective COX-2 inhibitors such as coxibs], glucocorticoids [which inhibit COX activity and expression], omega-3 fatty acids and esters thereof, curcuminoids [e.g., curcumin], stilbenoids [e.g., resveratrol, which inhibits COX-1 and -2 activity and expression], and vitamin E and analogs thereof [e.g., α-tocopherol and trolox]), cyclopentenone prostaglandins (e.g., prostaglandin $J_2$ [$PGJ_2$], $\Delta12$-$PGJ_2$ and 15-deoxy-$\Delta12,14$-$PGJ_2$), hydroxycinnamic acids and esters thereof (e.g., ethyl caffeate, which suppresses COX-2 expression), and triterpenoids (e.g., oleanolic acid analogs such as TP-225, which suppress COX-2 expression);

inhibitors of leukotrienes or receptors therefor or the production thereof, including cysteinyl leukotriene receptor 1 (cysLTR1) antagonists (e.g., cinalukast, gemilukast [dual cysLTR1/cysLTR2 antagonist], iralukast, montelukast, pranlukast, tomelukast, verlukast, zafirlukast, CP-195494, CP-199330, ICI-198615, MK-571 and lipoxins [e.g., LXA4 and 15-epi-LXA4]), cysLTR2 antagonists (e.g., HAMI-3379), 5-lipoxygenase (5-LOX) inhibitors (e.g., baicalein, caffeic acid, curcumin, hyperforin, γ-linolenic acid [GLA], meclofenamic acid, meclofenamate sodium, minocycline, zileuton, MK-886, and omega-3 fatty acids and esters thereof), and immunomodulatory xanthine derivatives;

inhibitors of phospholipase A2 (e.g., secreted and cytosolic PLA2), including glucocorticoids, arachidonyl trifluoromethyl ketone, bromoenol lactone, chloroquine, cytidine 5-diphosphoamines, darapladib, quinacrine, vitamin E, RO-061606, ZPL-521, lipocortins (annexins, such as annexin A1), and annexin mimetic peptides (e.g., annexin A1 mimetics [e.g., Ac2-26 and CGEN-855A]);

suppressors of C-reactive protein (CRP) activity or level, including statins (e.g., rosuvastatin), thiazolidinediones (supra), DPP-4 inhibitors (supra), stilbenoids (e.g., resveratrol), epigallocatechin-3-gallate and CRP-i2;

mast cell stabilizers, including cromoglicic acid (cromolyn), ketotifen, methylxanthines, nedocromil, nicotinamide, olopatadine, omalizumab, pemirolast, quercetin and zinc sulfate;

phosphodiesterase inhibitors, including PDE4 inhibitors (e.g., apremilast, cilomilast, ibudilast, piclamilast, roflumilast, crisaborole, diazepam, luteolin, mesembrenone, rolipram, AN2728 and E6005);

specialized pro-resolving mediators (SPMs), including metabolites of polyunsaturated fatty acids (PUFAs) such as lipoxins (e.g., LXA4, 15-epi-LXA4, LXB4 and 15-epi-LXB4), resolvins (e.g., resolvins derived from 5Z,8Z,11Z,14Z,17Z-eicosapentaenoic acid [EPA], resolvins derived from 4Z,7Z,10Z,13Z,16Z,19Z-docosahexaenoic acid [DHA], and resolvins derived from 7Z,10Z,13Z,16Z,19Z-docosahexaenoic acid [n-3 DPA]), protectins/neuroprotectins (e.g., DHA-derived protectins/neuroprotectins and n-3 DPA-derived protectins/neuroprotectins), maresins (e.g., DHA-derived maresins and n-3 DPA-derived maresins), n-3 DPA metabolites, n-6 DPA (4Z,7Z,10Z,13Z,16Z-docosapentaenoic acid) metabolites, oxo-DHA metabolites, oxo-DPA metabolites, docosahexaenoyl ethanolamide metabolites, cyclopentenone prostaglandins (e.g., Δ12-$PGJ_2$ and 15-deoxy-Δ12,14-$PGJ_2$), and cyclopentenone isoprostanes (e.g., 5,6-epoxyisoprostane $A_2$ and 5,6-epoxyisoprostane $E_2$);

other kinds of anti-inflammatory agents, including pirfenidone, nintedanib, vitamin A, omega-3 fatty acids and esters thereof, apoA-I mimetics (e.g., 4F), apoE mimetics (e.g., AEM-28 and AEM-28-14), and antioxidants (e.g., sulfur-containing antioxidants); and analogs, derivatives, fragments and salts thereof.

Non-steroidal anti-inflammatory drugs (NSAIDs) include without limitation:

acetic acid derivatives, such as aceclofenac, bromfenac, diclofenac, etodolac, indomethacin, ketorolac, nabumetone, sulindac, sulindac sulfide, sulindac sulfone and tolmetin;

anthranilic acid derivatives (fenamates), such as flufenamic acid, meclofenamic acid, mefenamic acid and tolfenamic acid;

enolic acid derivatives (oxicams), such as droxicam, isoxicam, lornoxicam, meloxicam, piroxicam and tenoxicam;

propionic acid derivatives, such as fenoprofen, flurbiprofen, ibuprofen, dexibuprofen, ketoprofen, dexketoprofen, loxoprofen, naproxen and oxaprozin;

salicylates, such as diflunisal, salicylic acid, acetylsalicylic acid (aspirin), choline magnesium trisalicylate, salsalate and mesalazine;

COX-2-selective inhibitors, such as apricoxib, celecoxib, etoricoxib, firocoxib, fluorocoxibs (e.g., fluorocoxibs A-C), lumiracoxib, mavacoxib, parecoxib, rofecoxib, tilmacoxib (JTE-522), valdecoxib, 4-O-methylhonokiol, niflumic acid, DuP-697, CG100649, GW406381, NS-398, SC-236, SC-58125, benzothieno[3,2-d]pyrimidin-4-one sulfonamide thio-derivatives, and COX-2 inhibitors derived from *Tribulus terrestris;* other kinds of NSAIDs, such as monoterpenoids (e.g., eucalyptol and phenols [e.g., carvacrol]), anilinopyridinecarboxylic acids (e.g., clonixin), sulfonanilides (e.g., nimesulide), and dual inhibitors of lipooxygenase (e.g., 5-LOX) and cyclooxygenase (e.g., COX-2) {e.g., chebulagic acid, licofelone, 2-(3,4,5-trimethoxyphenyl)-4-(N-methylindol-3-yl)thiophene, and di-tert-butylphenol-based compounds (e.g., DTPBHZ, DTPINH, DTPNHZ and DTPSAL)}; and analogs, derivatives and salts thereof.

The glucocorticoid class of corticosteroids has anti-inflammatory and immunosuppressive properties. Glucocorticoids include without limitation hydrocortisone types (e.g., cortisone and derivatives thereof [e.g., cortisone acetate], hydrocortisone and derivatives thereof [e.g., hydrocortisone acetate, hydrocortisone-17-aceponate, hydrocortisone-17-buteprate, hydrocortisone-17-butyrate and hydrocortisone-17-valerate], prednisolone, methylprednisolone and derivatives thereof [e.g., methylprednisolone aceponate], prednisone, and tixocortol and derivatives thereof [e.g., tixocortol pivalate]), betamethasone types (e.g., betamethasone and derivatives thereof [e.g., betamethasone dipropionate, betamethasone sodium phosphate and betamethasone valerate], dexamethasone and derivatives thereof [e.g., dexamethasone sodium phosphate], and fluocortolone and derivatives thereof [e.g., fluocortolone caproate and fluocortolone pivalate]), halogenated steroids (e.g., alclometasone and derivatives thereof [e.g., alclometasone dipropionate], beclometasone and derivatives thereof [e.g., beclometasone dipropionate], clobetasol and derivatives thereof [e.g., clobetasol-17-propionate], clobetasone and derivatives thereof [e.g., clobetasone-17-butyrate], desoximetasone and derivatives thereof [e.g., desoximetasone acetate], diflorasone and derivatives thereof [e.g., diflorasone diacetate], diflucortolone and derivatives thereof [e.g., diflucortolone valerate], fluprednidene and derivatives thereof [e.g., fluprednidene acetate], fluticasone and derivatives thereof [e.g., fluticasone propionate], halobetasol [ulobetasol] and derivatives thereof [e.g., halobetasol proprionate], halometasone and derivatives thereof [e.g., halometasone acetate], and mometasone and derivatives thereof [e.g., mometasone furoate]), acetonides and related substances (e.g., amcinonide, budesonide, ciclesonide, desonide, fluocinonide, fluocinolone acetonide, flurandrenolide [flurandrenolone or fludroxycortide], halcinonide, triamcinolone acetonide and triamcinolone alcohol), carbonates (e.g., prednicarbate), and analogs, derivatives and salts thereof.

In additional embodiments, one or more NR/NAR derivatives of the disclosure are used in conjunction with one or more antifibrotic agents to treat a fibrotic disorder. In some embodiments, the one or more antifibrotic agents are or include an anti-inflammatory agent or/and an antioxidant (e.g., vitamin E or an analog thereof [e.g., α-tocopherol or trolox], a sulfur-containing antioxidant or an ROS or radical scavenger [e.g., melatonin], or any combination thereof). In certain embodiments, the one or more antifibrotic agents are or include pirfenidone (which among its various antifibrotic and anti-inflammatory properties described herein also reduces fibroblast proliferation) or/and nintedanib (which blocks signaling of fibroblast growth factor receptors [FG-FRs], platelet-derived growth factor receptors [PDGFRs] and vascular endothelial growth factor receptors [VEGFRs] involved in fibroblast proliferation, migration and transformation).

In further embodiments, the one or more antifibrotic agents are or include one or more agents that have anti-hyperglycemic or/and insulin-sensitizing activity for treatment of a fibrotic disorder in which hyperglycemia, diabetes or insulin resistance contributes to development of fibrosis. Examples of such a disorder include diabetic nephropathy, which is characterized by renal fibrosis, and NASH and cirrhosis, both of which are characterized by hepatic fibrosis. Use of anti-hyperglycemic or/and insulin-sensitizing agent(s) can curtail or prevent, e.g., renal inflammation and fibrosis or hepatic inflammation and fibrosis. In certain embodiments, the one or more antifibrotic agents are or include a PPAR-γ agonist (e.g., a thiazolidinedione [supra], such as pioglitazone or rosiglitazone). PPARγ-activating thiazolidinediones have both anti-hyperglycemic and insulin-sensitizing properties.

Antifibrotic agents include without limitation:

inhibitors of collagen accumulation, including protein kinase C (PKC) inhibitors (supra, inhibit collagen production), colchicine and its metabolite colchiceine (both inhibit collagen synthesis and deposition), dilinoleoyl-phosphatidylcholine (inhibits collagen production induced by transforming growth factor-beta1 [TGF-β1]), luteolin (reduces fibrosis in part by increasing expression of matrix metalloproteinase 9 [MMP-9] and metallothionein, which degrade the extracellular matrix [ECM]), malotilate (reduces procollagen I α2 [Col1a2] expression), melatonin (inhibits expression of procollagens I and III), S-nitroso-N-acetyl-L-cysteine (reduces collagen I amount in part by activating MMP- 13 and suppressing tissue inhibitor of metalloproteinases 2 [TIMP-2]), oxymatrine {reduces procollagen I α1 (Col1a1) (and α-smooth muscle actin [α-SMA] expression)}, pioglitazone (reduces collagen I [and α-SMA] production), pirfenidone (reduces production of procollagens I and II and inhibits TGF-β-stimulated collagen production), quercetin (reduces Col1a1 and procollagen III α1 [Col3a1] expression), resveratrol (reduces collagen I [and α-SMA] production), RGD mimetics and analogs (infra, reduce collagen I accumulation in part by increasing secretion of collagenases), safironil (reduces collagen I [and α-SMA] production), statins (e.g., atorvastatin, lovastatin and simvastatin [all three reduce collagen production]), tranilast (inhibits procollagen expression and fibroblast proliferation), valproic acid (reduces collagen deposition), inhibitors of collagen cross-linking {e.g., D-penicillamine and lysyl oxidase-like 2 (LOXL2, which promotes collagen cross-linking) inhibitors (e.g., β-aminopropionitrile and anti-LOXL2 antibodies [e.g., simtuzumab and AB-0023])}, procollagen-proline dioxygenase (or prolyl 4-hydroxylase, which forms more stable hydroxylated collagen) inhibitors (e.g., malotilate, HOE-077, S-0885 and S-4682), and procollagen glucosyltransferase (or galactosylhydroxylysine glucosyltransferase, which is important for collagen fibril formation) inhibitors (e.g., malotilate);

inhibitors of pro-fibrotic growth factors (e.g., transforming growth factor-beta [including TGF-β1], connective tissue growth factor [CTGF] and platelet-derived growth factor [including PDGF-B, PDGF-C and PDGF-D]) or their production, activation or signaling, including TGF-β inhibitors {e.g., anti-TGF-β antibodies (e.g., fresolimumab [GC1008] and CAT-192) and soluble TGF-β receptors (e.g., sTGFβR1, sTGFβR2 and sTGFβR3)}, TGFβR antagonists {e.g., TGFβR1 (ALK5) antagonists (e.g., galunisertib [LY-2157299], EW-7197, GW-788388, LY-2109761, SB-431542, SB-525334, SKI-2162, SM-16, and inhibitory Smads [e.g., Smad6 and Smad7])}, anti-CTGF antibodies (e.g., FG-3019), PDGF inhibitors (e.g., squalamine, PP1, anti-PDGF aptamers [e.g., E10030], anti-PDGF antibodies [e.g., those targeting PDGF-B, PDGF-C and PDGF-D], and soluble PDGF receptors [e.g., sPDGFRα and sPDGFRβ]), PDGFR (e.g., PDGFRα or/and PDGFRβ) antagonists (e.g., anti-PDGFR antibodies [e.g., REGN2176-3]), bone morphogenic protein-7 (BMP-7) (directly antagonizes TGF-β1 signaling and Smad3 activation, and promotes mesenchymal-to-epithelial transition), N-acetyl-L-cysteine (inhibits TGF-β expression and activation by monomerization of the biologically active TGF-β dimer), S-nitroso-N-acetyl-L-cysteine (suppresses TGF-β1), L-carnitine (reduces PDGF-B expression), epigallocatechin-3-gallate (suppresses activation of Smad2 and Smad3 [and Akt]), galectin-7 (binds to and inhibits phosphorylated Smad2 and Smad3), Leu-Ser-Lys-Leu (inhibits TGF-β1 activation), α-lipoic acid (inhibits TGF-β signaling via inhibition of Smad3 and AP-1), luteolin (inhibits TGF-β and PDGF signaling), melatonin (inhibits TGF-β and CTGF expression and Smad3 activation), naringenin (suppresses Smad3 expression and activation), niacin (reduces TGF-β expression), pirfenidone (reduces TGF-β production), quercetin (reduces expression of TGF-β1, CTGF, PDGF-B and Smad3), resveratrol (suppresses TGF-β expression), simvastatin (reduces TGF-β1 [and α-SMA] expression), taurine (reduces TGF-β1 [and α-SMA] expression), tranilast (inhibits TGF-β1 expression), vitamin E and analogs thereof (e.g., α-tocopherol and trolox, both of which suppress TGF-β expression), and $\alpha_v\beta_6$ integrin (which activates TGF-β1) inhibitors (e.g., anti-$\alpha_v\beta_6$ antibodies such as STX-100);

receptor tyrosine kinase (TK) inhibitors, including epidermal growth factor receptor (EGFR) TK inhibitors (e.g., afatinib, brigatinib, erlotinib, gefitinib, icotinib, lapatinib, osimertinib and isoflavones [e.g., genistein]), PDGFR TK inhibitors (e.g., crenolanib, imatinib and AG-1295), dual FGFR/VEGFR TK inhibitors (e.g., brivanib and brivanib alaninate), dual PDGFR/VEGFR TK inhibitors (e.g., axitinib, sorafenib, sunitinib, vatalanib and X-82), and triple FGFR/PDGFR/VEGFR TK inhibitors (e.g., nintedanib and pazopanib);

anti-EGFR antibodies, such as cetuximab, matuzumab, nimotuzumab, panitumumab and zalutumumab;

anti-inflammatory agents, including those listed above, such as anti-inflammatory cytokines (e.g., IL-10), inhibitors of pro-inflammatory cytokines or their receptors or their production (e.g., TNF-α [e.g., an anti-TNF-α antibody such as infliximab or an immunomodulator such as pentoxifylline], IL-10, IL-6 and MCP-1), colchicine, curcuminoids (e.g., curcumin), malotilate, nintedanib, pirfenidone and tranilast; anti-oxidants, including those listed above, such as vitamins and analogs thereof (e.g., vitamin E and analogs thereof such as α-tocopherol and trolox), sulfur-containing antioxidants (e.g., glutathione, NAC, SNAC, SAC [also suppresses α-SMA expression] and SAM), ROS and radical scavengers (e.g., melatonin and glutathione), Nrf2 activators {e.g., fumarates (e.g., dimethyl and monomethyl fumarate), trichostatin A, and triterpenoids (e.g., oleanolic acid analogs [supra, such as TP-225])}, and omega-3 fatty acids and esters thereof (e.g., Lovaza fish oil);

antagonists of the renin-angiotensin-aldosterone system (RAAS), including those listed above, such as renin inhibitors (e.g., aliskiren [reduces hepatic steatosis, oxidative stress, inflammation and fibrosis]), ACE inhibitors (e.g., captopril [inhibits fibroblast proliferation and reduces fibrotic lung response] and perindopril [inhibits liver fibrosis]), and angiotensin II receptor type 1 ($AT_1$) antagonists (e.g., candesartan [inhibits liver fibrosis], irbesartan and losartan) (activation of $AT_1$ by angiotensin II activates PLC, leading to increased cytosolic $Ca^{2+}$ concentration and hence PKC stimulation, also activates tyrosine kinases and promotes ECM formation);

inhibitors of the accumulation or effects of advanced glycation end-products (AGEs, which inter alia increase arterial stiffness and stimulate mesangial matrix expansion), including inhibitors of AGE formation (e.g., aminoguanidine, aspirin, benfotiamine, carnosine, α-lipoic acid, metformin, pentoxifylline, pimagedine, pioglitazone, pyridoxamine, taurine and vitamin C), cleavers of AGE crosslinks (e.g., aminoguanidine, N-phenacylthiazolium bromide, rosmarinic acid, alagebrium [ALT-711], ALT-462, ALT-486 and ALT-946), and inhibitors of AGE effects (e.g., natural phenols such as curcumin and resveratrol);

other kinds of antifibrotic agents, including RGD mimetics and analogs (inhibit adhesion of fibroblasts and immune cells to ECM glycoproteins) (e.g., NS-11, SF-6,5 and GRGDS), galectin-3 (which is critical for liver fibrosis) inhibitors (e.g., GM-CT-01 and GR-MD- 02), marinobufagenin inhibitors (e.g., resibufogenin, spironolactone and canrenone), trichostatin A (inhibits TGFβ1-induced epithelial-to-mesenchymal transition), and PPAR-γ agonists (e.g., thiazolidinediones [supra]); and analogs, derivatives, fragments and salts thereof.

Non-alcoholic fatty liver disease (NAFLD), the most common liver disorder in developed countries, is characterized by fatty liver that occurs when fat, in particular free fatty acids and triglycerides, accumulates in the liver cells (hepatic steatosis) due to causes other than excessive alcohol consumption, such as nutrient overload, high caloric intake and metabolic dysfunction (e.g., hyperlipidemia and impaired glucose control). A liver can remain fatty without disturbing liver function, but a fatty liver can progress to become non-alcoholic steatohepatitis (NASH), a condition in which steatosis is accompanied by inflammation, hepatocyte ballooning and cell injury with or without fibrosis of the liver. Fibrosis is the strongest predictor of mortality from NASH. NASH is the most extreme form of NAFLD. NASH is a progressive disease, with about 20% of patients developing cirrhosis of the liver and about 10% dying from a liver disease, such as cirrhosis or a liver cancer (e.g., hepatocellular carcinoma).

NAFLD, including NASH, is associated with obesity, metabolic syndrome and insulin resistance. For instance, insulin resistance contributes to progression of fatty liver to hepatic inflammation and fibrosis and thus NASH. Furthermore, obesity drives and exacerbates NASH, and weight loss can alleviate NASH.

In some embodiments, one or more NR/NAR derivatives described herein are used in combination with one or more additional therapeutic agents to treat NAFLD, such as NASH. In some embodiments, the one or more additional therapeutic agents are selected from antidiabetic agents, anti-obesity agents, anti-inflammatory agents, antifibrotic agents, antioxidants, and combinations thereof.

Therapeutic agents that can be used to treat NAFLD (e.g., NASH) include without limitation:

PPAR agonists, including PPAR-δ agonists (e.g., MBX-8025, elafibranor [dual PPAR-α/δ agonist], lanifibranor [triple PPAR-α/δ/γ agonist] and GW501516 [dual PPAR-β/δ agonist]) and PPAR-γ agonists (e.g., thiazolidinediones such as pioglitazone and rosiglitazone, and saroglitazar [dual PPAR-α/γ agonist])—PPAR-δ and -γ agonism increases insulin sensitivity, PPAR-α agonism reduces liver steatosis and PPAR-δ agonism inhibits activation of macrophages and Kupffer cells;

GLP-1R agonists (e.g., exenatide, liraglutide and semaglutide), dual GLP-1R/GCGR agonists (e.g., MEDI0382 and SP-1373) and dual GLP-1R/GIPR agonists—such agonists reduce liver steatosis, inflammation and fibrosis;

farnesoid X receptor (FXR) agonists, such as obeticholic acid, EDP-305, GS-9674, LJN452 and TERN-101—FXR agonists reduce liver gluconeogenesis, lipogenesis, steatosis and fibrosis;

thyroid hormone receptor-beta agonists, such as MGL-3196 and VK2809—THR-β agonists reduce liver steatosis;

fibroblast growth factor 19 (FGF19) and analogs and derivatives thereof, such as NGM-282-FGF19 analogs reduce liver gluconeogenesis and steatosis;

fibroblast growth factor 21 (FGF21) and analogs and derivatives thereof, such as BMS-986036 and PF-05231023-FGF21 analogs reduce liver steatosis, cell injury and fibrosis;

HMG-CoA reductase inhibitors, including statins (e.g., atorvastatin, pitavastatin and rosuvastatin)—statins reduce steatohepatitis and fibrosis;

ACC inhibitors, such as NDI-010976 (liver-targeted) and GS-0976-ACC inhibitors reduce de novo lipogenesis and liver steatosis;

SCD-1 inhibitors, such as aramchol—SCD-1 inhibitors reduce liver steatosis and increase insulin sensitivity;

ATP citrate lyase inhibitors, such as bempedoic acid—ACL inhibitors reduce reduce liver steatosis;

ketohexokinase inhibitors, such as PF-06835919—KHK inhibitors reduce liver lipogenesis and inflammation;

SGLT2 inhibitors, such as canagliflozin, dapagliflozin, empagliflozin, ipragliflozin and luseogliflozin—SGLT2 inhibitors reduce body weight, liver ALT level and fibrosis;

vascular adhesion protein-1 (VAP-1) inhibitors, such as N-[4-(2-{4-[(2-amino-1H-imidazol-4-yl)methyl]phenyl}ethyl)thiazol-2-yl]acetamide hydrochloride, 2-bromoethylamine, semicarbazide, ASP8232, BI-1467335 (PXS-4728A), PXS-4681A, PRX-167700 and TERN-201—VAP-1 inhibitors increase insulin sensitivity and reduce liver inflammation and fibrosis;

antagonists of CCR2 or/and CCR5, such as cenicriviroc—antagonists of CCR2 (binds to CCL2 [MCP1]) and CCR5 (binds to CCL5 [RANTES]) inhibit activation and migration of inflammatory cells (e.g., macrophages) to the liver and reduce liver fibrosis;

apoptosis inhibitors, including apoptosis signal-regulating kinase 1 (ASK1) inhibitors (e.g., selonsertib) and caspase inhibitors (e.g., emricasan [pan-caspase inhibitor])—apoptosis inhibitors reduce liver steatosis and fibrosis;

TGF-β inhibitors (e.g., fresolimumab) and TGF-βR antagonists (e.g., galunisertib)—they reduce liver fibrosis;

lysyl oxidase-like 2 (LOXL2) inhibitors, such as simtuzumab—LOXL2 is a key matrix enzyme in collagen formation and is highly expressed in the liver;

galectin-3 inhibitors, such as GR-MD-02 and TD139—galectin-3 is critical for development of liver fibrosis;

inhibitors of lysophosphatidic acid (LPA) or receptors therefor (e.g., LPAR1) or the production thereof, such as autotaxin inhibitors (e.g., GLPG1690, HA-130, ONO-8430506, PF-8380, S-32826) and anti-autotaxin DNA aptamers (e.g., RB011 and RB014)—such inhibitors inhibit myofibroblast proliferation and hence liver fibrosis;

antioxidants, including vitamin E (e.g., α-tocopherol) and scavengers of ROS and free radicals (e.g., cysteamine, glutathione, melatonin and pentoxifylline [also anti-inflammatory via inhibition of TNF-α and phosphodiesterases])—vitamin E reduces liver steatosis, hepatocyte ballooning and lobular inflammation; and analogs, derivatives and salts thereof.

In some embodiments, the one or more additional therapeutic agents for treatment of NAFLD (e.g., NASH) are or include a PPAR agonist (e.g., a PPAR-δ agonist such as elafibranor or/and a PPAR-γ agonist such as pioglitazone), a HMG-CoA reductase inhibitor (e.g., a statin such as rosuvastatin), an FXR agonist (e.g., obeticholic acid) or an antioxidant (e.g., vitamin E), or any combination thereof. In certain embodiments, the one or more additional therapeutic agents for treatment of NAFLD (e.g., NASH) are or include vitamin E or/and pioglitazone.

In other embodiments, one or more NR/NAR derivatives of the disclosure are used in combination with one or more anticancer agents to treat a tumor (benign or malignant) or a cancer. For brevity, the term "anticancer agents" as used herein encompasses antitumor agents. In some embodiments, the one or more anticancer agents are or include radiation therapy, chemotherapy or cancer immunotherapy, or any combination or all thereof.

In some embodiments, the chemotherapeutic agent is or includes a PARP inhibitor, a TGF-β inhibitor or a cytotoxic agent, or any combination or all thereof. Examples of PARP inhibitors are described above. In certain embodiments, the PARP inhibitor is olaparib.

Transforming growth factor-beta (TGF-β) is a cytokine that promotes the growth of pre-cancer and cancer cells, angiogenesis and invasion of cancer cells. TGF-β also converts effector T-cells, which normally attack cancer cells with an inflammatory (immune) reaction, into regulatory T-cells that suppress the immune reaction. An increase in TGF-β expression often correlates with the malignancy of many cancers. Therefore, inhibitors of TGF-β or the production, activation or signaling thereof can be used to treat tumors and cancers. Since TGF-β (including TGF-β1) is also a major driver of collagen production and fibrosis, inhibitors of TGF-β or the production, activation or signaling thereof are listed among antifibrotic agents above.

Anticancer cytotoxic agents include without limitation:

alkylating agents, including aziridines (e.g., diaziquone, mytomycin and thiotepa), nitrogen mustards (e.g., mannomustine, mustine [mechlorethamine or chlormethine], aniline mustard, bendamustine, benzoic acid mustard, chlorambucil, C6-galactose mustard, melphalan, ossichlorin [nitromin], prednimustine, uramustine, nitrogen mustard carbamates [e.g., estramustine], and oxazaphosphorines [e.g., cyclophosphamide, ifosfamide, mafosfamide, and trofosfamide]), nitrosoureas (e.g., carmustine, fotemustine, lomustine, nimustine, N-nitroso-N-methylurea, ranimustine, semustine and streptozotocin), platinum-containing compounds (e.g., cisplatin, carboplatin and oxaliplatin), alkylsulfonates (e.g., busulfan, mannosulfan and treosulfan), hydrazines (e.g., dacarbazine and procarbazine), imidazotetrazines (e.g., mitozolomide and temozolomide), and triazines (e.g., hexamethylmelamine [altretamine]);

cytotoxic antibiotics, including anthracyclines (e.g., aclarubicin, daunorubicin, doxorubicin, epirubicin, idarubicin, mitoxantrone, pirarubicin and valrubicin), actinomycins (e.g., actinomycin D), bleomycins (e.g., bleomycins $A_2$ and $B_2$), mitomycins (e.g., mitomycin C), and plicamycins;

antimetabolites, including antifolates (e.g., aminopterin, methotrexate, pemetrexed and pralatrexate), deoxynucleoside analogs (e.g., 5-azacytidine [azacitidine], 5-aza-2'-deoxycytidine [decitabine], cladribine, clofarabine, cytarabine, decitabine, fludarabine, gemcitabine, nelarabine and pentostatin), fluoropyrimidines (e.g., 5-fluorouracil, capecitabine, 5-fluoro-5'-deoxyuridine [doxifluridine] and trifluridine), and thiopurines (e.g., thioguanine, azathioprine and mercaptopurine);

antimicrotubule agents, including dolastatins (e.g., dolastatin 15), epothilones (e.g., epothilones A-F), halichondrins (e.g., halichondrin B) and analogs thereof (e.g., eribulin), maytansine, maytansinoids (e.g., ansamitocin, emtansine, mertansine, ravtansine and soravtansine), taxanes (e.g., paclitaxel, docetaxel and cabazitaxel), *vinca* alkaloids (e.g., vinblastine, vincristine, vindesine, vinflunine and vinorelbine), colchicine, nocodazole, podophyllotoxin and rhizoxin;

histone deacetylase inhibitors, including trichostatins (e.g., trichostatin A), romidepsin, panobinostat and vorinostat;

kinase inhibitors, including bortezomib, erlotinib, gefitinib, imatinib, vemurafenib, vismodegib, curcumin, cyclocreatine, deguelin, fostriecin, hispidin, staurosporine and derivatives thereof (e.g., midostaurin), and tyrphostins (e.g., tyrphostins AG 34 and AG 879);

topoisomerase I inhibitors, including camptothecin, irinotecan and topotecan;

topoisomerase II-targeting agents, including topoisomerase II poisons (e.g., etoposide, tafluposide, teniposide, doxorubicin and mitoxantrone) and topoisomerase II inhibitors (e.g., novobiocin, merbarone and aclarubicin);

DNA or RNA synthesis inhibitors, including 3-amino-1,2,4-benzotriazine 1,4-dioxide, cytosine β-D-arabinofuranoside, 5,6-dichlorobenzimidazole 1-β-D-ribofuranoside, ganciclovir and hydroxyurea;

protein synthesis inhibitors, including homoharringtonine;

cell growth and differentiation regulators, including retinoids (e.g., all-trans retinol [vitamin A], 11-cis retinol, all-trans retinal [vitamin A aldehyde], 11-cis retinal, all-trans retinoic acid [tretinoin], 9-cis-retinoic acid [alitretinoin], 11-cis retinoic acid, 13-cis-retinoic acid [isotretinoin], all-trans retinyl esters, etretinate, acitretin, adapalene, bexarotene and tazarotene);

cell proliferation inhibitors, including mTOR inhibitors (e.g., everolimus, novolimus, ridaforolimus, sirolimus [rapamycin], temsirolimus, umirolimus [biolimus A9] and zotarolimus), apigenin, cholecalciferol (vitamin $D_3$) and sex hormone-binding globulin;

apoptosis inducers, including 17-allylamino-17-demethoxygeldanamycin, melatonin, mevinolin, psoralen, thapsigargin, troglitazone, inhibitors of histone deacetylases (e.g., romidepsin), and RXR agonists (supra, such as retinoids [e.g., bexarotene]); and analogs, derivatives and salts thereof.

Cancer immunotherapeutic agents include agents that block immune checkpoints and agents that stimulate the immune system. In certain embodiments, the cancer immunotherapeutic agent is or includes an anti-PD-1 antibody or an anti-PD-L1 antibody, or/and an anti-CTLA-4 antibody.

Anticancer agents that block immune checkpoints include without limitation:

inhibitors of programmed cell death 1 (PD-1) receptor or ligands thereof (e.g., PD-L1 and PD-L2), including anti-PD-1 antibodies (e.g., cemiplimab, nivolumab, pembrolizumab, pidilizumab and MEDI-0680 [AMP-514]), anti-PD-1 fusion proteins (e.g., AMP-224 [containing an $F_c$ Ab domain and PD-L2]), anti-PD-L1 antibodies (e.g., avelumab, atezolizumab, durvalumab, and BMS-936559 [MDX-1105]), and small-molecule inhibitors of PD-L1 (e.g., BMS-1001 and BMS-1166);

inhibitors of cytotoxic T lymphocyte-associated protein 4 (CTLA-4) receptor or ligands thereof, including anti-CTLA-4 antibodies (e.g., ipilimumab and tremelimumab);

inhibitors of killer cell immunoglobulin-like receptors (KIRs) or ligands thereof, including anti-KIR antibodies (e.g., lirilumab);

inhibitors of lymphocyte activation gene 3 (LAG-3) receptor or ligands thereof, including anti-LAG-3 antibodies (e.g., BMS-986016 and GSK2831781);

inhibitors of T-cell immunoglobulin and mucin domain-containing 3 (TIM-3, also called hepatitis A virus cellular receptor 2 [HAVCR2]), including anti-TIM3 antibodies (e.g., LY3321367, MBG453 and TSR-022);

inhibitors of indoleamine 2,3-dioxygenase (IDO or IDO1), including indoximod (1-methyl-D-tryptophan), navoximod, α-methyl-tryptophan, β-carboline (9H-pyrido[3,4-b]indole or norharmane), epacadostat (INCB024360), BMS-986205, NLG-919, and COX-2 inhibitors (e.g., coxibs [supra], which down-regulate the expression of IDO); and analogs, derivatives, fragments and salts thereof.

Anticancer agents that stimulate the immune system include, but are not limited to:

agonists of tumor necrosis factor receptor superfamily member 4 (TNFRSF4, OX40 or CD134), including OX40-targeting antibodies (e.g., MEDI-6469 and 9B12) and ligands for OX40 (e.g., OX40L);

agonists of TNFRSF member 5 (TNFRSF5 or CD40), including CD40-targeting antibodies (e.g., dacetuzumab and CP-870,893) and ligands for CD40 (e.g., CD40L [CD154]);

agonists of TNFRSF member 9 (TNFRSF9, 4-1BB or CD137), including 4-1BB-targeting antibodies (e.g., urelumab and PF-05082566) and ligands for 4-1BB (e.g., 4-1BBL);

agonists of TNFRSF member 18 (TNFRSF18, glucocorticoid-induced TNFR-related protein [GITR] or CD357), including GITR-targeting antibodies (e.g., DTA-1 and TRX518) and ligands for GITR (e.g., GITRL);

agonists of toll-like receptors (TLRs), including ligands for TLR9 (e.g., unmethylated CpG oligodeoxynucleotides [CpG ODNs], such as agatolimod);

cytokines and hormones that stimulate immune cells, including IL-6 and epinephrine (stimulator of, e.g., natural killer cells); and analogs, derivatives, fragments and salts thereof.

Angiogenesis is important for the transition of a benign tumor to a malignant tumor (i.e., a cancer), and for metastasis of a cancer. Thus, anticancer agents include angiogenesis inhibitors. Angiogenesis inhibitors include without limitation inhibitors of vascular endothelial growth factors (VEGFs) {e.g., squalamine, ACU-6151, LHA-510, PAN-90806, decorin, anti-VEGF antibodies and fragments thereof (e.g., bevacizumab, ranibizumab, brolucizumab, ENV1305, ESBA903 and ESBA1008), anti-VEGF immunoconjugates (e.g., KSI-301), anti-VEGF aptamers (e.g., pegaptanib), anti-VEGF designed ankyrin repeat proteins (DARPins) (e.g., abicipar pegol), soluble VEGFRs (e.g., sVEGFR1), and soluble fusion proteins containing one or more extracellular domains of one or more VEGFRs (e.g., VEGFR1, VEGFR2 and VEGFR3) (e.g., aflibercept, conbercept and OPT-302)}, inhibitors of receptors for VEGFs (e.g., VEGFR1 and VEGFR2) (e.g., axitinib, fruquintinib, pazopanib, regorafenib, sorafenib, sunitinib, tivozanib, isoxanthohumol, pristimerin, KPI-285, PF-337210, PP1, TG100572, X-82, D-(LPR), decorin, and anti-VEGFR antibodies and fragments thereof [e.g., ramucirumab]), inhibitors of platelet-derived growth factors (PDGFs) {e.g., squalamine, PP1, decorin, anti-PDGF aptamers (e.g., E10030 and pegpleranib), anti-PDGF antibodies and fragments thereof (e.g., rinucumab), and soluble PDGFRs} or receptors therefor (PDGFRs) (e.g., axitinib, imatinib, nilotinib, pazopanib, sorafenib, sunitinib, X-82, and anti-PDGFR antibodies and fragments thereof [e.g., REGN2176-3]), inhibitors of fibroblast growth factors (FGFs) (e.g., squalamine, decorin, anti-FGF antibodies and fragments thereof, anti-FGF aptamers and soluble FGFRs) or receptors therefor (FGFRs) (e.g., erdafitinib, pazopanib and anti-FGFR antibodies and fragments thereof), inhibitors of angiopoietins (e.g., decorin, anti-angiopoietin antibodies and fragments thereof such as nesvacumab and REGN910-3, and soluble angiopoietin receptors) or receptors therefor (e.g, antibodies and fragments thereof against angiopoietin receptors), bispecific anti-VEGF/anti-angiopoietin antibodies and fragments thereof (e.g., anti-VEGF/anti-angiopoietin-2 antibodies such as ABP-201 and RG7716), inhibitors of integrins (e.g., ALG-1001, JSM-6427, SF0166, and anti-integrin antibodies and fragments thereof), tissue factor (TF) inhibitors (e.g., anti-TF antibodies and fragments thereof and fusion proteins thereof [e.g., ICON-1]), kallikrein inhibitors (e.g., avoralstat, ecallantide, BCX7353, KVD001, and anti-kallikrein antibodies and fragments thereof [e.g., DX-2930]), serine/arginine-protein kinase 1 (SRPK1) inhibitors (e.g., SPHINX31), Src kinase inhibitors (e.g., SKI-606 and TG100572), anecortave (anecortave acetate), angiostatin (e.g., angiostatin K1-3), $α_νβ_3$ inhibitors (e.g., etaracizumab), apoA-I mimetics (e.g., L-4F and L-5F), apoE mimetics (e.g., apoEdp), azurin(50-77) (p28), berberine, bleomycins, borrelidin, carboxyamidotriazole, cartilage-derived angiogenesis inhibitors (e.g., chondromodulin I and troponin I), castanospermine, CM101, corticosteroids (including glucocorticoids), cyclopropene fatty acids (e.g., sterculic acid), α-difluoromethylornithine, endostatin, everolimus, fumagillin, genistein, heparin, interferon-α, interleukin-12, interleukin-18, itraconazole, KV11, linomide, 2-methoxyestradiol, pigment epithelium-derived factor (PEDF), platelet factor-4, PPAR-α agonists (e.g., fibrates), PPAR-γ agonists (e.g., thiazolidinediones), prolactin, rapamycin (sirolimus), sphingosine-1-phosphate inhibitors (e.g., sonepcizumab), squalene, staurosporine, angiostatic steroids (e.g., tetrahydrocortisol) plus heparin, stilbenoids, suramin, SU5416, tasquinimod, tecogalan, tetrathiomolybdate, thalidomide and derivatives thereof (e.g., lenalidomide and pomalidomide), thiabendazole, thrombospondins (e.g., thrombospondin 1), TNP-470, tranilast, triterpenoids (e.g., oleanolic acid analogs [supra] such as TP-225), (+)-TBE-B, tumstatin and fusion proteins thereof (e.g., OCU200), vasostatin, vasostatin 48, Withaferin A, and analogs, derivatives, fragments and salts thereof.

Other kinds of anticancer agents include, but are not limited to:

drug-efflux pump inhibitors, including β-glycoprotein inhibitors (e.g., mifepristone and verapamil);

cell adhesion inhibitors, such as cimetidine;

Golgi apparatus disruptors, such as brefeldins (e.g., brefeldin A);

ionizing radiation, such as X-ray;

radiopharmaceuticals, such as $^{131}$I-iodide, $^{131}$I-MIBG (m-iodobenzylguanidine), $^{223}$Ra-dichloride, $^{153}$Sm-EDTMP (ethylenediaminotetramethylenephosphoric acid), and $^{89}$Sr-chloride;

sensitizers of cancer cells to radiation, including PARP inhibitors (infra), berberine and indomethacin;

enhancers of cell survival after treatment with cytotoxic drugs or radiation, such as pifithrin-α;

vaccines, including those that stimulate the immune system to recognize proteins produced by tumor/cancer cells and thereby to attack tumor/cancer cells; and analogs, derivatives and salts thereof.

An NR or NAR derivative can enhance the immune response to an acute or chronic viral, bacterial or fungal infection when used in conjunction with an antiviral, antibacterial or antifungal agent. In certain embodiments, the antibiotic is ethionamide and optionally SMARt-420 for treatment of, e.g., tuberculosis. Ethionamide has antibiotic properties against mycobacteria such as M. tuberculosis. SMARt-420 reverses resistance of, e.g., M. tuberculosis to ethionamide and increases the bacteria's sensitivity to ethionamide.

An NR or NAR derivative can also enhance and direct the adaptive immune response to a vaccine antigen, thereby improving the effectiveness of the vaccine. An NR or NAR derivative can be utilized as a component of a vaccine adjuvant. In certain embodiments, an NR or NAR derivative is administered in combination with a vaccine to a subject in order to enhance the effectiveness of the vaccine.

The optional additional therapeutic agent(s) independently can be administered in any suitable mode, including without limitation oral, parenteral (including intramuscular, intradermal, subcutaneous, intravascular, intravenous, intraarterial, intraperitoneal, intracavitary, intramedullary, intrathecal and topical), and topical (including dermal/epicutaneous, transdermal, mucosal, transmucosal, intranasal [e.g., by nasal spray or drop], pulmonary [e.g., by oral or nasal inhalation], ocular [e.g., by eye drop], buccal, sublingual, rectal [e.g., by suppository] and vaginal [e.g., by suppository]). In certain embodiments, an additional therapeutic agent is administered orally. In other embodiments, an additional therapeutic agent is administered parenterally (e.g., intravenously, subcutaneously or intramuscularly).

The optional additional therapeutic agent(s) independently can be administered in any suitable frequency, including without limitation daily (one, two or more times per day), once every two or three days, twice weekly or once weekly, or on a pro re nata (as-needed) basis, which can be determined by the treating physician. The dosing frequency can depend on, e.g., the mode of administration chosen. The length of treatment with the optional additional therapeutic agent(s) can be determined by the treating physician and can independently be, e.g., at least about 1 day, 2 days, 3 days, 1 week, 2 weeks, 3 weeks, 4 weeks (1 month), 6 weeks, 2 months, 3 months, 6 months, 1 year, 2 years, 3 years, 4 years, 5 years or longer.

The therapeutically effective amount of, the frequency and route of administration of, and the length of treatment with, an optional additional therapeutic agent can be based in part on recommendations for that therapeutic agent and can be determined by the treating physician.

In some embodiments, an NR or NAR derivative and an additional therapeutic agent are administered in separate pharmaceutical compositions. In other embodiments, an NR or NAR derivative and an additional therapeutic agent are administered in the same pharmaceutical composition, such as in a fixed-dose combination dosage form. In some embodiments, the fixed-dose combination dosage form is formulated for controlled-release, slow-release or sustained-release of the NR or NAR derivative or/and the additional therapeutic agent. In certain embodiments, the fixed-dose combination dosage form is formulated for oral administration, such as once or twice daily and such as in the form of a tablet, capsule or pill. In other embodiments, the fixed-dose combination dosage form is formulated for parenteral administration, such as intravenously, subcutaneously or intramuscularly.

Combination Therapies with PARP Inhibitors

When activated by DNA damage, poly(ADP-ribose) polymerase (PARP) recruits other proteins that repair single-stranded DNA breaks ("nicks"). PARP activity is necessary for repair of DNA nicks. PARP expression and activity are upregulated under diverse conditions that lead to DNA damage and ultimately cell injury or cell death, including hypoxia. However, PARP is a major consumer of $NAD^+$ in the cell, and markedly increased PARP activity can deplete NAD and cause profound mitochondrial and cellular dysfunction. Therefore, PARP inhibition can increase $NAD^+$ level (e.g., in mitochondria, the cytosol or/and the nucleus, such as total cellular $NAD^+$ level) and thereby can enhance mitochondrial function (e.g., oxidative metabolism), mitochondrial biogenesis and cellular function (e.g., increase the activity of sirtuins such as SIRT1 and SIRT3).

PARP inhibitors are currently approved as antitumor/anticancer agents. DNA damage occurs countless times during each cell cycle, and failure to repair damaged DNA leads to the death of tumor/cancer cells. Some PARP inhibitors mainly block PARP enzyme activity and do not trap PARP on DNA, while other PARP inhibitors both block PARP enzyme activity and act as PARP poison. In the latter case, PARP bound to a PARP inhibitor becomes trapped at the site of a DNA nick, and such a trapped PARP-DNA complex (PARP poison) is more toxic to cells than the unrepaired single-strand DNA breaks that accumulate in the absence of PARP activity because it blocks DNA replication. PARP inhibitors include without limitation niraparib, olaparib, pamiparib (BGB290), rucaparib, talazoparib, veliparib, 4-amino-1,8-naphthalimide, CEP9722, E7016, PJ34, and analogs, derivatives and salts thereof.

The inventors have surprisingly discovered that the combination of nicotinamide riboside plus olaparib at a dose much lower than its chemotherapeutic dose synergistically increases $NAD^+$ level (e.g., in mitochondria, the cytosol or/and the nucleus, such as total cellular $NAD^+$ level) and provides cytoprotection (reduces cytotoxicity) under DNA damage-inducing conditions (see Example 6 below). Without intending to be bound by theory, low-level PARP inhibition by a PARP inhibitor (e.g., olaparib) at a low dose can reduce the rate of $NAD^+$ consumption by PARP, increase $NAD^+$ level and hence enhance mitochondrial and cellular function and provide cytoprotection. Moreover, low-level PARP inhibition can avoid the trapping of PARP at the site of a DNA nick, thereby allowing the cellular DNA-repair machinery to repair damaged DNA.

In some embodiments, one or more nicotinyl riboside compounds in combination with a PARP inhibitor increase $NAD^+$ level (e.g., total cellular $NAD^+$ level, such as that in target cells) by at least about 20%, 30%, 50%, 100% (2-fold), 150%, 200% (3-fold), 4-fold, 5-fold, 6-fold, 7-fold, 8-fold, 9-fold or 10-fold in vitro, ex vivo or in vivo. In certain embodiments, one or more nicotinyl riboside compounds in combination with a PARP inhibitor increase $NAD^+$ level (e.g., total cellular $NAD^+$ level, such as that in target cells) by at least about 50%, 100% (2-fold), 3-fold or 5-fold in vitro, ex vivo or in vivo.

In further embodiments, one or more nicotinyl riboside compounds in combination with a PARP inhibitor increase the number of viable cells (e.g., target cells) by at least about 10%, 20%, 30%, 50%, 100% (2-fold), 150%, 200% (3-fold), 4-fold or 5-fold in vitro, ex vivo or in vivo. In certain embodiments, one or more nicotinyl riboside compounds in combination with a PARP inhibitor increase the number of viable cells (e.g., target cells) by at least about 20%, 50%, 100% or 200% in vitro, ex vivo or in vivo.

In some embodiments, one or more nicotinyl riboside compounds are used in combination with a PARP inhibitor at a dose significantly lower than its recommended dose as an antitumor/anticancer agent to treat a non-tumor/non-cancer disease/disorder or condition disclosed herein, or to bring about a biological effect disclosed herein (e.g., increase $NAD^+$ level or/and provide cytoprotection). The PARP inhibitor can inhibit one or more members of the PARP family, such as PARP-1 or/and PARP-2. In certain embodiments, the PARP inhibitor is a selective or non-selective inhibitor of PARP-1. The non-tumor/non-cancer disease or condition can be, e.g., any mitochondrial disease, mitochondria-related disease or condition, or disease or condition characterized by acute $NAD^+$ depletion due to DNA damage described herein. In certain embodiments, the disease or condition is a metabolic disorder (e.g., obesity or type 2 diabetes). One or more other therapeutic agents described herein can optionally be used in combination with one or more nicotinyl riboside compounds and a PARP inhibitor. In some embodiments, the one or more nicotinyl riboside compounds are or comprise one or more of NR, NRH, NAR and NARH, or/and one or more NR/NAR derivatives (such as one or more NR/NAR derivatives disclosed herein). In certain embodiments, the one or more nicotinyl riboside compounds are or comprise NR or/and NRH. In other embodiments, the one or more nicotinyl riboside compounds are or comprise nicotinamide riboside triacetate (NRTA, i.e., NR having an acetate group at each of the C-2, C-3 and C-5 positions of riboside), the reduced form of NRTA (NRHTA), nicotinic acid riboside triacetate (NARTA), or the reduced form of NARTA (NARHTA), or any combination thereof. The use of one or more nicotinyl riboside compounds in combination with a PARP inhibitor (e.g., olaparib) at a significantly sub-chemotherapeutic dose can synergistically increase $NAD^+$ level (e.g., in mitochondria, the cytosol or/and the nucleus, such as total cellular $NAD^+$ level) or/and provide cytoprotection (e.g., reduce cell injury, damage or death), or can have a synergistic therapeutic effect.

A PARP inhibitor at a significantly sub-chemotherapeutic dose can be used in combination with one or more nicotinyl riboside compounds to treat any non-tumor/non-cancer disease/disorder or condition associated with DNA damage. The DNA damage can be due to any cause, such as radiation (e.g., UV or an ionizing radiation such as X-ray), a chemical, a chemotherapeutic agent, oxidative stress or hypoxia. The disease/disorder or condition can be acute or chronic, and can be associated with $NAD^+$ depletion or/and cell injury, damage, degeneration or death. Such diseases/disorders and conditions include without limitation diseases and conditions characterized by acute $NAD^+$ depletion due to DNA damage and described above. In certain embodiments, the disease/disorder or condition is an acute life-threatening cardiovascular (e.g., myocardial ischemia/infarction/IRI) or cerebrovascular (e.g., cerebral ischemia/infarction/IRI) disorder, or a neurodegenerative disorder.

In some embodiments, the dose of a PARP inhibitor to treat a non-tumor/non-cancer disease/disorder or condition disclosed herein, or to bring about a biological effect disclosed herein, in combination with one or more nicotinyl riboside compounds is no more than about 10%, 5%, 1%, 0.5% or 0.1% of the recommended dose of the PARP inhibitor as an antitumor/anticancer agent. In certain embodiments, the dose of a PARP inhibitor for such a use is no more than about 1% of the recommended dose of the PARP inhibitor as an antitumor/anticancer agent. In some embodiments, the PARP inhibitor is olaparib, and the dose (e.g., per day or per dose) of olaparib to treat a non-tumor/non-cancer disease/disorder or condition disclosed herein, or to bring about a biological effect disclosed herein, in combination with one or more nicotinyl riboside compounds is no more than about 10 mg, 5 mg, 1 mg, 0.5 mg or 0.1 mg; or is from about 0.01 or 0.1 mg to about 10 mg, from about 0.01 or 0.1 mg to about 1 mg, or from about 1 mg to about 10 mg; or is about 0.01-0.1 mg, 0.1-0.5 mg, 0.5-1 mg, 1-5 mg or 5-10 mg; or is about 10 µg, 50 µg, 0.1 mg, 0.5 mg, 1 mg, 5 mg or 10 mg. In certain embodiments, the dose (e.g., per day or per dose) of olaparib for such a use is no more than about 1 mg.

A PARP inhibitor can be administered in any suitable frequency. In certain embodiments, the PARP inhibitor is administered once or twice daily.

The dose or therapeutically effective amount, the frequency of administration and the route of administration of a nicotinyl riboside compound used in conjunction with a low dose of a PARP inhibitor can be, e.g., any dose or therapeutically effective amount, any frequency of administration and any route of administration of the NR/NAR derivatives of the disclosure described herein. In some embodiments, the dose of a nicotinyl riboside compound (e.g., NR, NRH, NRTA, NRHTA or an NR/NAR derivative disclosed herein) is from about 1, 50 or 100 mg to about 500 or 1000 mg per day, which can be administered (e.g., orally) in a single dose (e.g., N mg once daily) or in divided doses (e.g., N/2 mg twice daily). In certain embodiments, the dose of a nicotinyl riboside compound is about 1-100 mg, 100-500 mg or 500-1000 mg per day, or about 50 mg, 100 mg, 150 mg, 200 mg, 250 mg, 300 mg, 400 mg, 500 mg, 600 mg, 700 mg, 800 mg, 900 mg or 1000 mg per day. In further embodiments, the dose of a nicotinyl riboside compound is about 1-50 mg, 50-100 mg, 100-200 mg, 200-300 mg, 300-400 mg or 400-500 mg per day. In certain embodiments, the dose of a nicotinyl riboside compound is from about 10, 50 or 100 mg to about 200 or 300 mg per day. In some embodiments, a lower dose of a nicotinyl riboside compound is used to treat a less severe non-tumor/non-cancer disease/disorder or condition, while a higher dose of a nicotinyl riboside compound is used to treat a more severe non-tumor/non-cancer disease/disorder or condition.

A nicotinyl riboside compound can be administered in any suitable frequency. In certain embodiments, a nicotinyl riboside compound is administered once or twice daily.

The length of treatment with a PARP inhibitor and one or more nicotinyl riboside compounds to treat a non-tumor/non-cancer disease/disorder or condition disclosed herein, or to bring about a biological effect disclosed herein, can be determined by the treating physician. For example, the length of treatment with the PARP inhibitor and the one or more nicotinyl riboside compounds can independently be at least about 1 day, 2 days, 3 days, 1 week, 2 weeks, 3 weeks, 4 weeks (1 month), 6 weeks, 2 months, 3 months, 6 months, 1 year, 2 years, 3 years, 4 years, 5 years or longer. The PARP inhibitor and the one or more nicotinyl riboside compounds can also be taken pro re nata (as needed).

The synergistic effects of a combination of one or more nicotinyl riboside compounds and a low dose of a PARP inhibitor, such as in elevating $NAD^+$ level and enhancing cytoprotection, can be exploited prophylactically to prevent a non-tumor/non-cancer disease/disorder or condition, or potentially to prevent a tumor or cancer. As an example, one or more nicotinyl riboside compounds and a low dose of a PARP inhibitor can be given prior to a surgery to reduce morbidity caused by general anesthesia or hypoxia- or hypotension-induced cytotoxicity. For instance, one or more nicotinyl riboside compounds and a low dose of a PARP inhibitor can be given prior to a cardiac procedure (e.g., angioplasty or valvular surgery) to reduce morbidity and mortality due to hypotensive or bleeding episodes. As another example, one or more nicotinyl riboside compounds and a low dose of a PARP inhibitor can be applied to the skin to prevent sunlight-induced skin injury.

One or more nicotinyl riboside compounds and a PARP inhibitor can be administered to a subject via any suitable route. In certain embodiments, the one or more nicotinyl riboside compounds or/and the PARP inhibitor are administered orally. In other embodiments, the one or more nicotinyl riboside compounds or/and the PARP inhibitor are administered parenterally (e.g., intravenously, subcutaneously or intramuscularly). The route of administration of the one or more nicotinyl riboside compounds and the PARP inhibitor can depend in part on the disorder or condition being treated. For example, the one or more nicotinyl riboside compounds or/and the PARP inhibitor can be administered dermally or transdermally to treat a skin disorder or condition.

One or more nicotinyl riboside compounds and a PARP inhibitor can be administered in the same pharmaceutical composition or in separate compositions. In some embodiments, the one or more nicotinyl riboside compounds (e.g., NR or/and NRH, NRTA or/and NRHTA, or one or more NR/NAR derivatives disclosed herein) and the PARP inhibitor (e.g., olaparib) are administered in a fixed-dose combination dosage form, where the dose of the PARP inhibitor is significantly lower than its recommended dose as an anti-tumor/anticancer agent. In some embodiments, the fixed-dose combination dosage form is a controlled-release, slow-release or sustained-release form. In certain embodiments, the fixed-dose combination dosage form is formulated for oral administration, such as once or twice daily and such as in the form of a tablet, capsule or pill. In other embodiments, the fixed-dose combination dosage form is formulated for parenteral administration, such as intravenously, subcutaneously or intramuscularly. In further embodiments, the one or more nicotinyl riboside compounds or/and the PARP inhibitor are administered as a complex with a dendrimer (e.g., PAMAM) or via a dendrimer-containing composition. The dendrimer can optionally have one or more moieties for targeting to specific organ(s), tissue(s), cell type(s) or organelle(s), such as one or more N-acetylgalactosamine moieties for targeting to the liver for treatment of, e.g., a liver or metabolic disorder.

In other embodiments, one or more nicotinyl riboside compounds or/and a PARP inhibitor are utilized in ex vivo therapy, including in any ex vivo therapy described herein. In yet other embodiments, one or more nicotinyl riboside compounds and a PARP inhibitor are employed to enhance DNA editing, such as in the use of a CRISPR, transcription activator-like effector nuclease (TALEN) or Arcus nuclease to promote non-homologous end joining (NHEJ) or homology-directed repair (HDR). Low-level PARP inhibition by a low dose of a PARP inhibitor permits repair of single-stranded DNA breaks.

REPRESENTATIVE EMBODIMENTS

The following embodiments of the disclosure are provided to illustrate the disclosure:
1. A compound of Formula I or II:

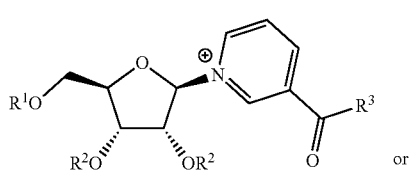

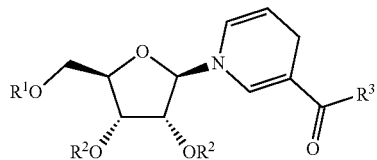

wherein:
R$^1$ is hydrogen,

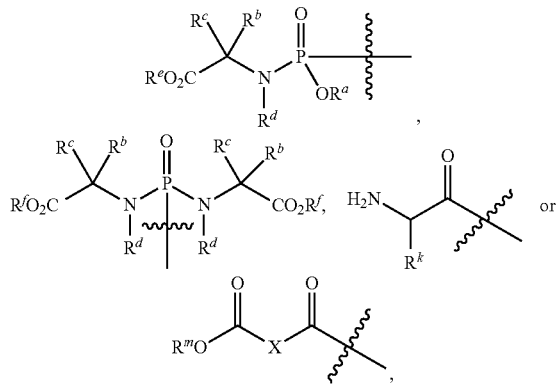

wherein:
R$^a$ is hydrogen, a counterion, linear or branched C$_1$-C$_6$ alkyl, C$_3$-C$_6$ cycloalkyl, phenyl, 1-naphthyl or 2-naphthyl, wherein the phenyl is optionally substituted with F, Cl, —NO$_2$, linear or branched C$_1$-C$_4$ alkyl, —CF$_3$ or —O-(linear or branched C$_1$-C$_4$ alkyl);

R$^b$ and R$^c$ at each occurrence independently are hydrogen, linear or branched C$_1$-C$_5$ alkyl, —CH$_2$-phenyl, —CH$_2$-3-indole or —CH$_2$-5-imidazole, wherein the alkyl is optionally substituted with —OH, —OR$^j$, —SH, —SR$^j$, —NH$_2$, —NHR$^j$, —N(R$^j$)$_2$, —NHC(=O)R$^j$, —NHC(=NH)NH$_2$, —C(=O)NH$_2$, —CO$_2$H or —C(=O)OR$^j$, and the phenyl is optionally substituted with —OH or —OR$^j$, wherein R$^j$ at each occurrence independently is linear or branched C$_1$-C$_4$ alkyl;

R$^d$ at each occurrence independently is hydrogen, methyl or linear or branched C$_2$-C$_4$ alkyl;

R$^e$ and R$^f$ at each occurrence independently are hydrogen, a counterion, linear or branched C$_1$-C$_8$ alkyl, C$_3$-C$_6$ cycloalkyl, —CH$_2$—(C$_3$-C$_6$ cycloalkyl), phenyl or —CH$_2$-phenyl, wherein the phenyl is optionally substituted with F, Cl, —NO$_2$, linear or branched C$_1$-C$_4$ alkyl, —CF$_3$ or —O-(linear or branched C$_1$-C$_4$ alkyl);

R$^k$ is hydrogen, linear or branched C$_1$-C$_6$ alkyl, —CH$_2$-phenyl, —CH$_2$-3-indole or —CH$_2$-5-imidazole, wherein the alkyl is optionally substituted with —OH, —OR$^j$, —SH, —SR$^j$, —NH$_2$, —NHR$^j$, —N(R$^j$)$_2$, —NHC(=O)R$^j$, —NHC(=NH)NH$_2$, —C(=O)NH$_2$, —CO$_2$H or —C(=O)OR$^j$, and the phenyl is optionally substituted with —OH or —OR$^j$, wherein R$^j$ at each occurrence independently is linear or branched C$_1$-C$_4$ alkyl;

R$^m$ is hydrogen, a counterion, linear or branched C$_1$-C$_6$ alkyl, C$_3$-C$_6$ cycloalkyl, phenyl, —CH$_2$-phenyl or

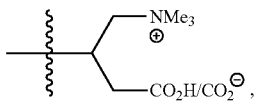

wherein the phenyl is optionally substituted with F, Cl, —$NO_2$, linear or branched $C_1$-$C_4$ alkyl, —$CF_3$ or —O-(linear or branched $C_1$-$C_4$ alkyl); and X is cis or trans —HC=CH— or —$(CH_2)_n$— optionally substituted with —OH, —$OR^j$ or —OC(=O)$R^j$, wherein $R^j$ is linear or branched $C_1$-$C_4$ alkyl and n is 1, 2, 3, 4, 5 or 6;

$R^2$ at each occurrence independently is hydrogen,

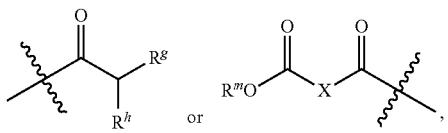

wherein:

$R^g$ is hydrogen, linear or branched $C_1$-$C_5$ alkyl, —$CH_2$-phenyl, —$CH_2$-3-indole or —$CH_2$-5-imidazole, wherein the alkyl is optionally substituted with —OH, —$OR^j$, —SH, —$SR^j$, —$NH_2$, —$NHR^j$, —$N(R^j)_2$, —NHC(=O)$R^j$, —NHC(=NH)$NH_2$, —C(=O)$NH_2$, —$CO_2H$ or —C(=O)$OR^j$, and the phenyl is optionally substituted with —OH or —$OR^j$, wherein $R^j$ at each occurrence independently is linear or branched $C_1$-$C_4$ alkyl;

$R^h$ is hydrogen, methyl or —$NH_2$;

or $R^g$ and $R^h$ together with the carbon atom to which they are connected form a $C_3$-$C_6$ cycloalkyl or phenyl ring, wherein the phenyl ring is optionally substituted with F, Cl, —$NO_2$, linear or branched $C_1$-$C_4$ alkyl, —$CF_3$ or —O-(linear or branched $C_1$-$C_4$ alkyl); and $R^m$ and X are as defined above; and $R^3$ is —$NH_2$, —$NHR''$, —$N(R'')_2$, —OH, —$OR^o$ or

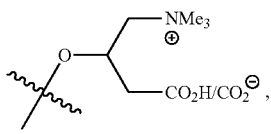

wherein:

$R''$ at each occurrence independently is linear or branched $C_1$-$C_6$ alkyl or allyl, wherein the alkyl is optionally substituted with —OH or —O-(linear or branched $C_1$-$C_3$ alkyl), or both occurrences of $R''$ and the nitrogen atom to which they are connected form a 3- to 6-membered heterocyclic ring; and $R^o$ is a counterion, linear or branched $C_1$-$C_6$ alkyl, $C_3$-$C_6$ cycloalkyl, phenyl or —$CH_2$-phenyl, wherein the phenyl is optionally substituted with F, Cl, —$NO_2$, linear or branched $C_1$-$C_4$ alkyl, —$CF_3$ or —O-(linear or branched $C_1$-$C_4$ alkyl);

or a pharmaceutically acceptable salt, solvate, hydrate, clathrate, polymorph or stereoisomer thereof, with the proviso that:

1) $R^1$ and both occurrences of $R^2$ all are not hydrogen except when $R^3$ is and 2) the compound of Formula I or II is not:

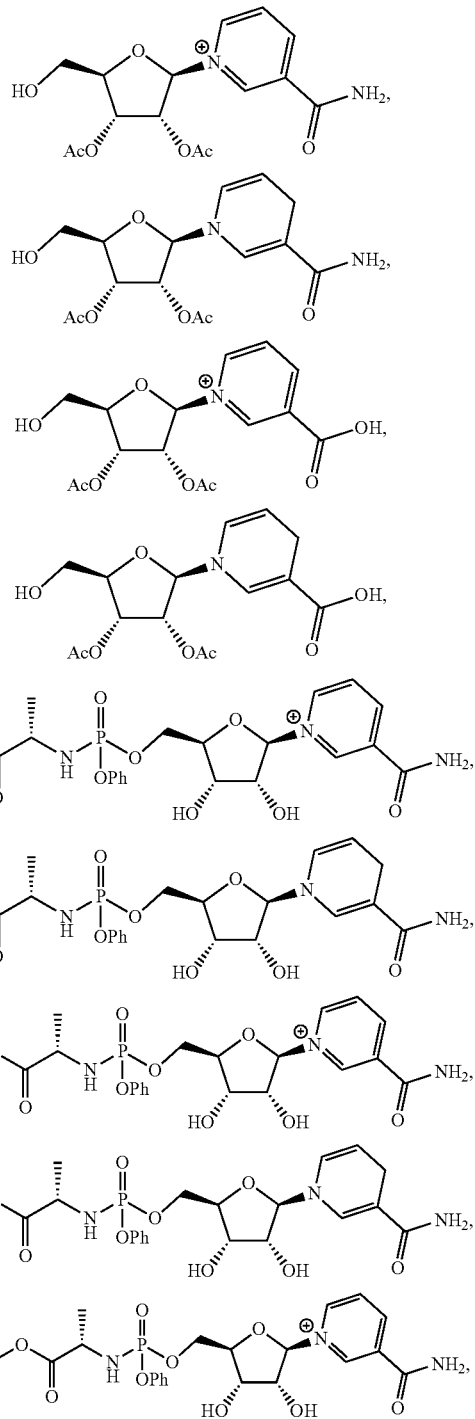

91
-continued
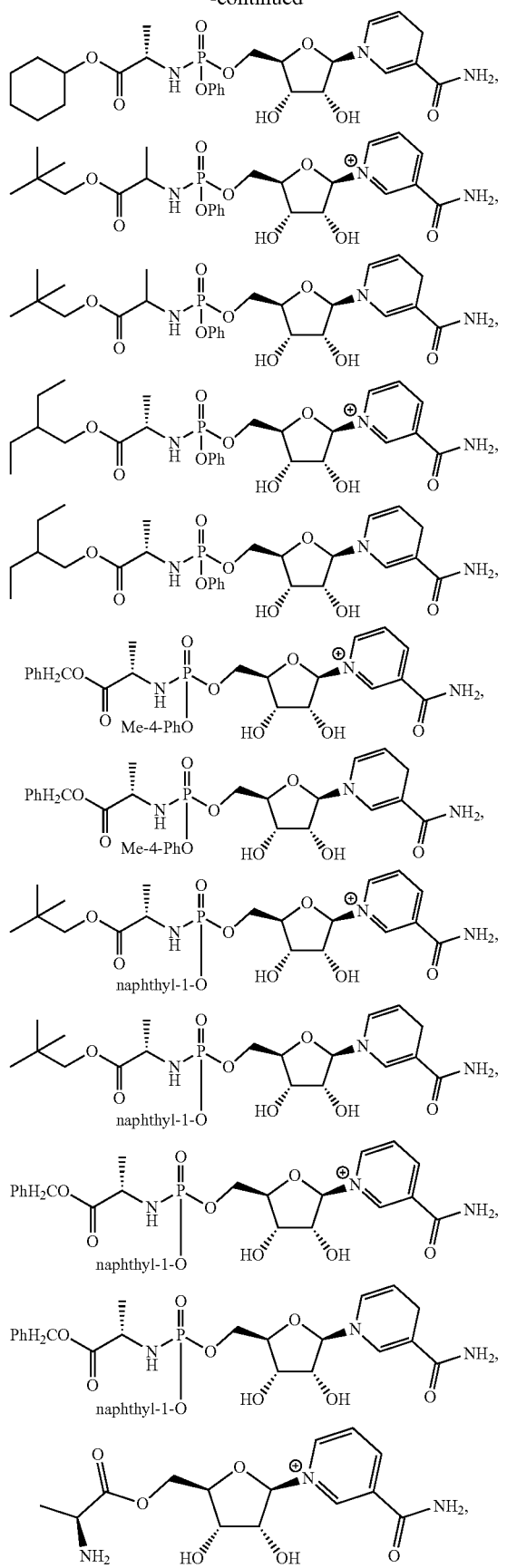
92
-continued
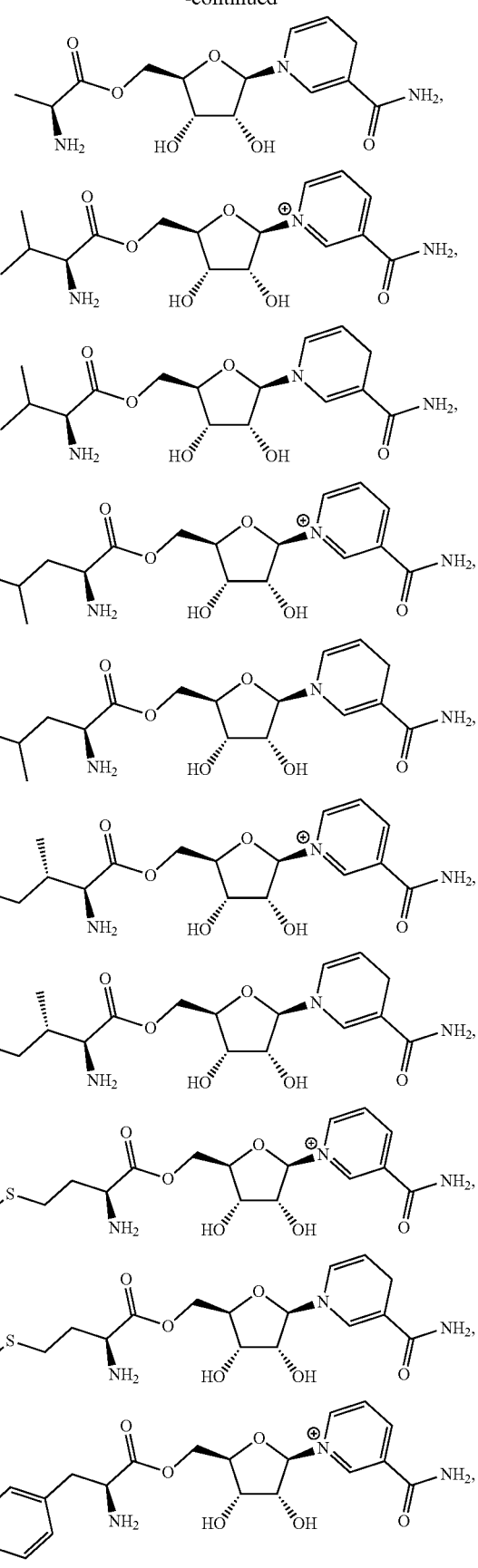

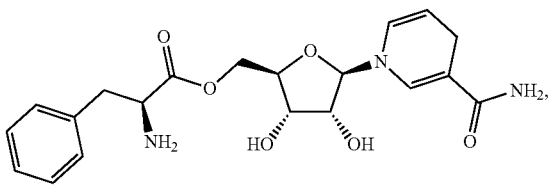

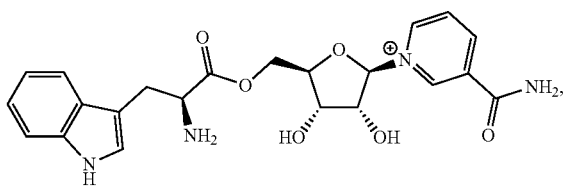

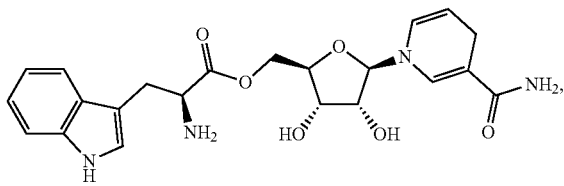

or a salt or stereoisomer thereof.

2. The compound of Formula I or II of embodiment 1, wherein when both occurrences of $R^2$ are acetyl:
 1) $R^1$ is not hydrogen; or
 2) $R^3$ is not —$NH_2$ or —OH or a salt thereof; or
 3) $R^1$ is not hydrogen and $R^3$ is not —$NH_2$ or —OH or a salt thereof.

3. The compound of Formula I or II of embodiment 1, wherein when $R^1$ is

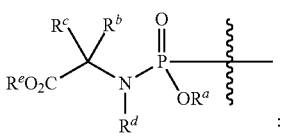

1) both occurrences of $R^2$ are not hydrogen; or
 2) $R^3$ is not —$NH_2$ or —OH or a salt thereof; or
 3) both occurrences of $R^2$ are not hydrogen and $R^3$ is not —$NH_2$ or —OH or a salt thereof.

4. The compound of Formula I or II of embodiment 1, wherein when $R^1$ is

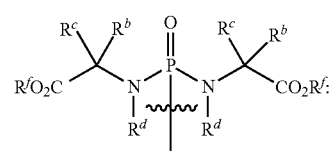

1) both occurrences of $R^2$ are not hydrogen; or
 2) $R^3$ is not —$NH_2$ or —OH or a salt thereof; or
 3) both occurrences of $R^2$ are not hydrogen and $R^3$ is not —$NH_2$ or —OH or a salt thereof.

5. The compound of Formula I or II of embodiment 1, wherein when $R^1$ is

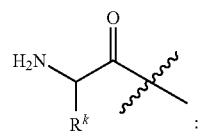

1) both occurrences of $R^2$ are not hydrogen; or
 2) $R^3$ is not —$NH_2$ or —OH or a salt thereof; or
 3) both occurrences of $R^2$ are not hydrogen and $R^3$ is not —$NH_2$ or —OH or a salt thereof.

6. The compound of Formula I or II of embodiment 1, wherein $R^1$ is hydrogen.

7. The compound of Formula I or II of embodiment 1 or 3, wherein $R^1$ is

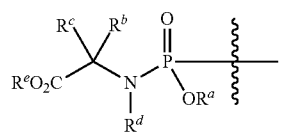

8. The compound of Formula I or II of embodiment 7, wherein $R^1$ is

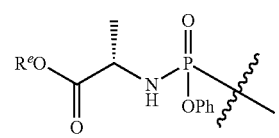

and $R^e$ is linear or branched $C_1$-$C_6$ alkyl, such as methyl, ethyl or isopropyl.

9. The compound of Formula I or II of embodiment 1 or 4, wherein $R^1$ is

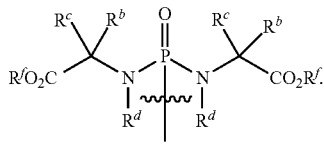

10. The compound of Formula I or II of embodiment 9, wherein $R^1$ is

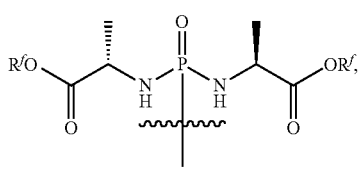

and both occurrences of $R^f$ are linear or branched $C_1$-$C_6$ alkyl, such as methyl, ethyl or isopropyl.

11. The compound of Formula I or II of embodiment 1, wherein $R^1$ is

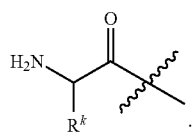

12. The compound of Formula I or II of embodiment 11, wherein $R^1$ is

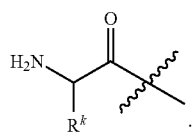

and $R^k$ is linear or branched $C_1$-$C_6$ alkyl, such as methyl, ethyl or isopropyl.

13. The compound of Formula I or II of embodiment 1, wherein $R^1$, or/and $R^2$ at either occurrence or at both occurrences, is/are

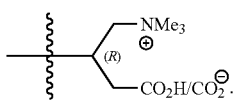

14. The compound of Formula I or II of embodiment 13, wherein:

X is trans —HC=CH—, —CH$_2$CH$_2$— or —CH(OH)CH$_2$—; and $R^m$ is hydrogen, a counterion, linear or branched $C_1$-$C_6$ alkyl (e.g., methyl, ethyl or isopropyl) or

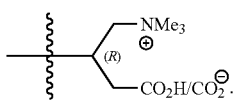

15. The compound of Formula I or II of embodiment 14, wherein $R^1$, or/and $R^2$ at either occurrence or at both occurrences, is/are selected from:

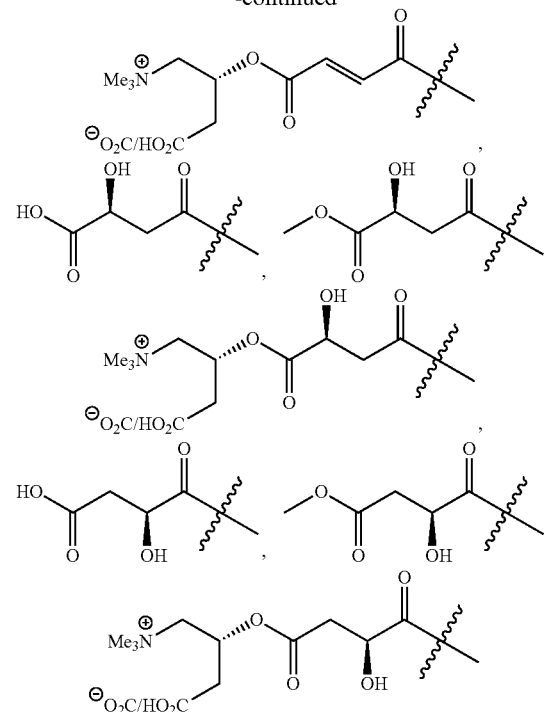

and salts thereof.

16. The compound of Formula I or II of any one of the preceding embodiments, wherein $R^2$ at each occurrence independently, or at both occurrences, is hydrogen, —C(=O)-(linear or branched $C_1$-$C_6$ alkyl),

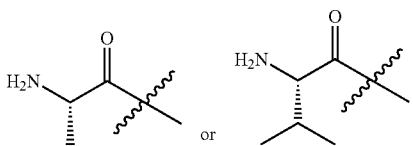

17. The compound of Formula I or II of embodiment 16, wherein $R^2$ at each occurrence independently, or at both occurrences, is hydrogen, acetyl or propanoyl.

18. The compound of Formula I or II of any one of the preceding embodiments, wherein $R^3$ is —NH$_2$, —OH or a salt thereof, or

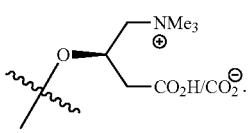

19. The compound of Formula I or II of embodiment 18, wherein $R^3$ is

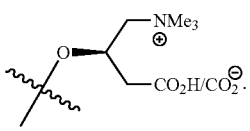

20. The compound of Formula I or II of embodiment 1 or 3, wherein:
1) $R^1$ is

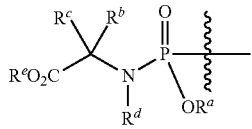

and both occurrences of $R^2$ are acetyl or propanoyl; or
2) $R^1$ is

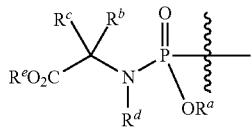

and $R^3$ is —OH or a salt thereof; or
3) $R^1$ is

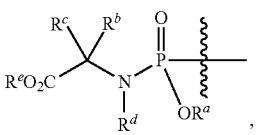

both occurrences of $R^2$ are acetyl or propanoyl, and $R^3$ is —OH or a salt thereof.

21. The compound of Formula I or II of embodiment 20, wherein $R^1$ is

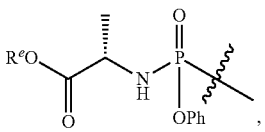

and $R^e$ is linear or branched $C_1$-$C_6$ alkyl, such as methyl, ethyl or isopropyl.

22. The compound of Formula I or II of embodiment 1 or 3, wherein:
$R^1$ is

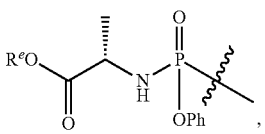

wherein $R^e$ is linear or branched $C_1$-$C_6$ alkyl;
$R^2$ at both occurrences is —C(=O)-(linear or branched $C_1$-$C_6$ alkyl); and
$R^3$ is —NH$_2$ or —OH or a salt thereof.

23. The compound of Formula I or II of embodiment 22, wherein:
$R^e$ of the $R^1$ moiety is methyl, ethyl or isopropyl; and
$R^2$ at both occurrences is acetyl or propanoyl.

24. The compound of Formula I or II of embodiment 1 or 4, wherein:

$R^1$ is

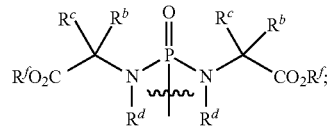

$R^2$ at each occurrence independently, or at both occurrences, is hydrogen, acetyl or propanoyl; and
$R^3$ is —NH$_2$ or —OH or a salt thereof.

25. The compound of Formula I or II of embodiment 24, wherein for the $R^1$ moiety:
$R^b$ and $R^c$ at each occurrence independently are hydrogen or linear or branched $C_1$-$C_5$ alkyl, or each pair of $R^b$ and $R^c$ is hydrogen and linear or branched $C_1$-$C_5$ alkyl;
$R^d$ at both occurrences is hydrogen; and
$R^f$ at both occurrences is linear or branched $C_1$-$C_6$ alkyl.

26. The compound of Formula I or II of embodiment 25, wherein $R^1$ is

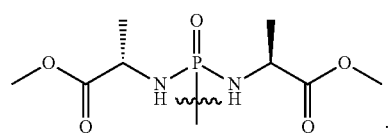

27. The compound of Formula I or II of embodiment 1 or 4, wherein:
$R^1$ is

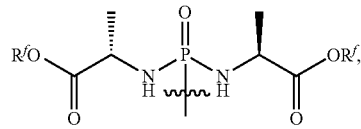

wherein $R^f$ at both occurrences is linear or branched $C_1$-$C_6$ alkyl;
$R^2$ at each occurrence independently, or at both occurrences, is hydrogen or —C(=O)-(linear or branched $C_1$-$C_6$ alkyl); and
$R^3$ is —NH$_2$ or —OH or a salt thereof.

28. The compound of Formula I or II of embodiment 27, wherein:
$R^f$ of the $R^1$ moiety at both occurrences is methyl, ethyl or isopropyl; and
$R^2$ at each occurrence independently, or at both occurrences, is hydrogen, acetyl or propanoyl.

29. The compound of Formula I or II of embodiment 1, wherein:
$R^1$ is

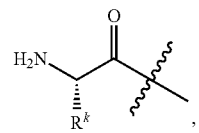

wherein $R^k$ is linear or branched $C_1$-$C_6$ alkyl;
$R^2$ at each occurrence independently, or at both occurrences, is hydrogen or —C(=O)-(linear or branched $C_1$-$C_6$ alkyl); and $R^3$ is —$NH_2$ or —OH or a salt thereof.

30. The compound of Formula I or II of embodiment 29, wherein:
    $R^k$ of the $R^1$ moiety is methyl, ethyl or isopropyl; and
    $R^2$ at each occurrence independently, or at both occurrences, is hydrogen, acetyl or propanoyl.

31. The compound of Formula I or II of embodiment 1, wherein:
    $R^1$ is

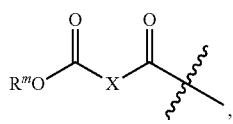

wherein:
X is cis or trans —HC=CH— or —$(CH_2)_n$— optionally substituted with —OH, —$OR^j$ or —$OC(=O)R^j$, wherein $R^j$ is linear or branched $C_1$-$C_4$ alkyl and n is 1, 2, 3, 4, 5 or 6; and
$R^m$ is hydrogen, a counterion, linear or branched $C_1$-$C_6$ alkyl or

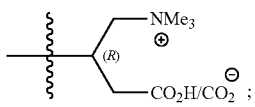

$R^2$ at each occurrence independently, or at both occurrences, is hydrogen or —C(=O)-(linear or branched $C_1$-$C_6$ alkyl); and
$R^3$ is —$NH_2$ or —OH or a salt thereof.

32. The compound of Formula I or II of embodiment 31, wherein:
    for the $R^1$ moiety, X is trans —HC=CH—, —$CH_2CH_2$— or —CH(OH)$CH_2$—, and $R^m$ is hydrogen, a counterion, methyl, ethyl, isopropyl or

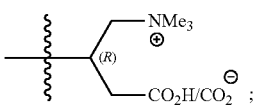

$R^2$ at each occurrence independently, or at both occurrences, is hydrogen, acetyl or propanoyl; and
$R^3$ is —$NH_2$.

33. The compound of Formula I or II of embodiment 1, which is selected from:

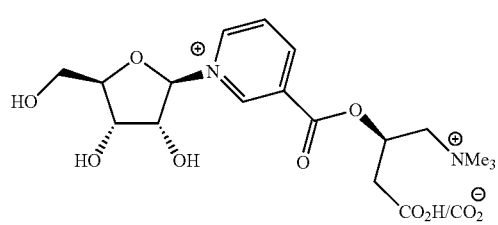

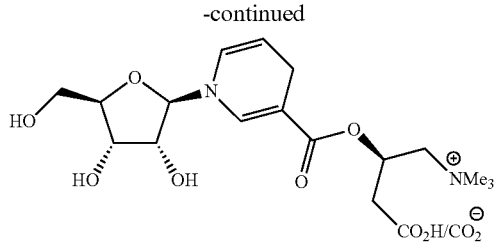

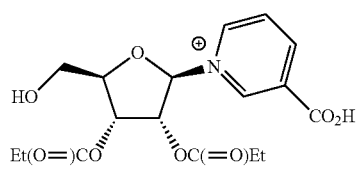

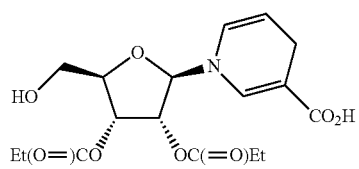

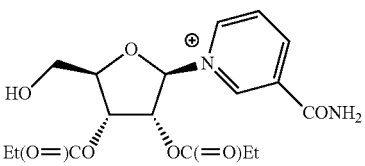

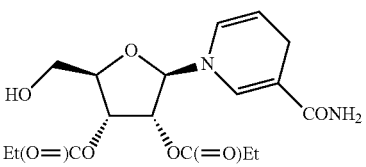

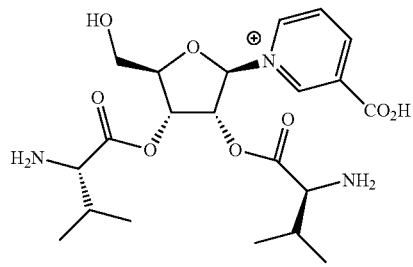

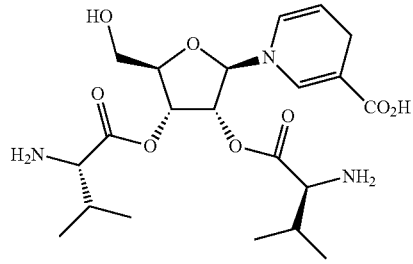

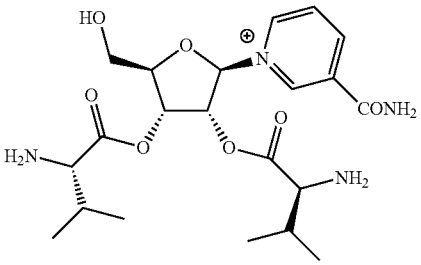

101
-continued
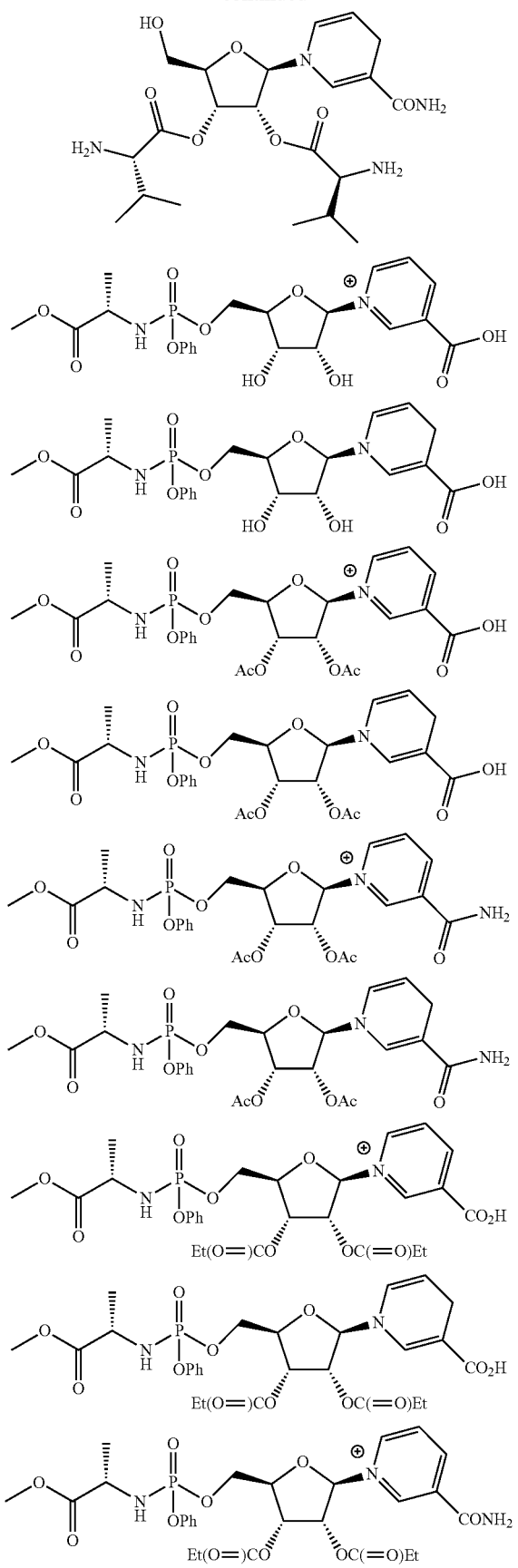
102
-continued
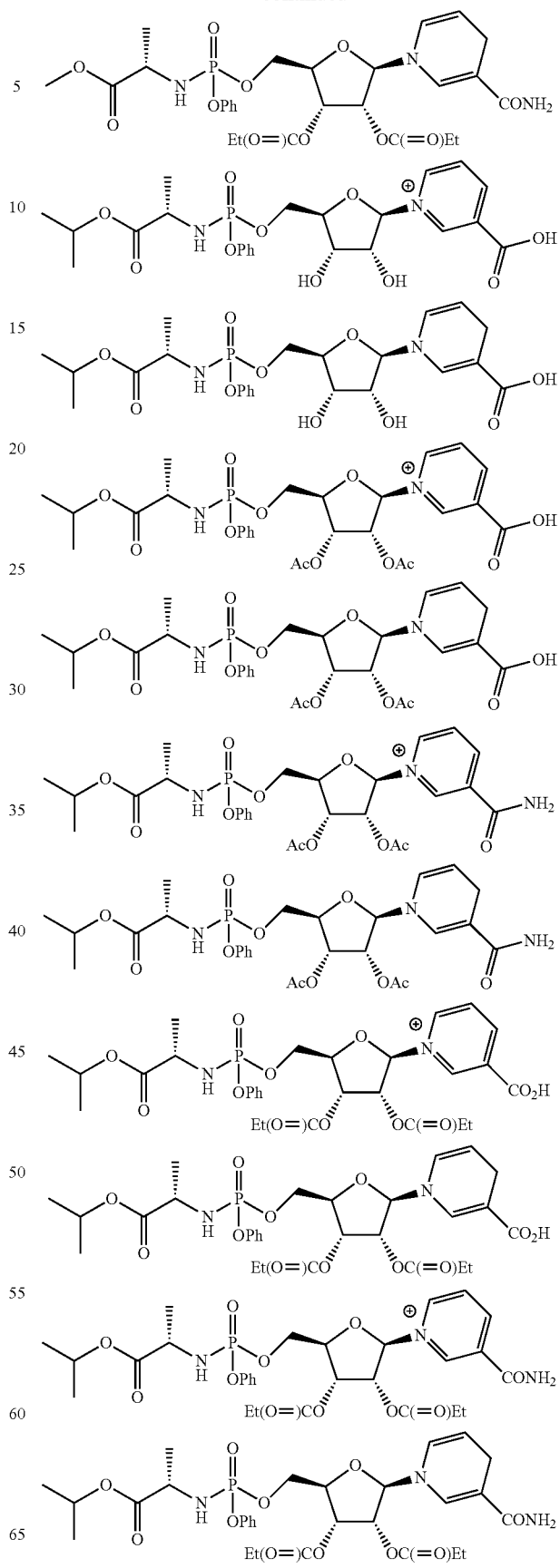

103 -continued

104 -continued

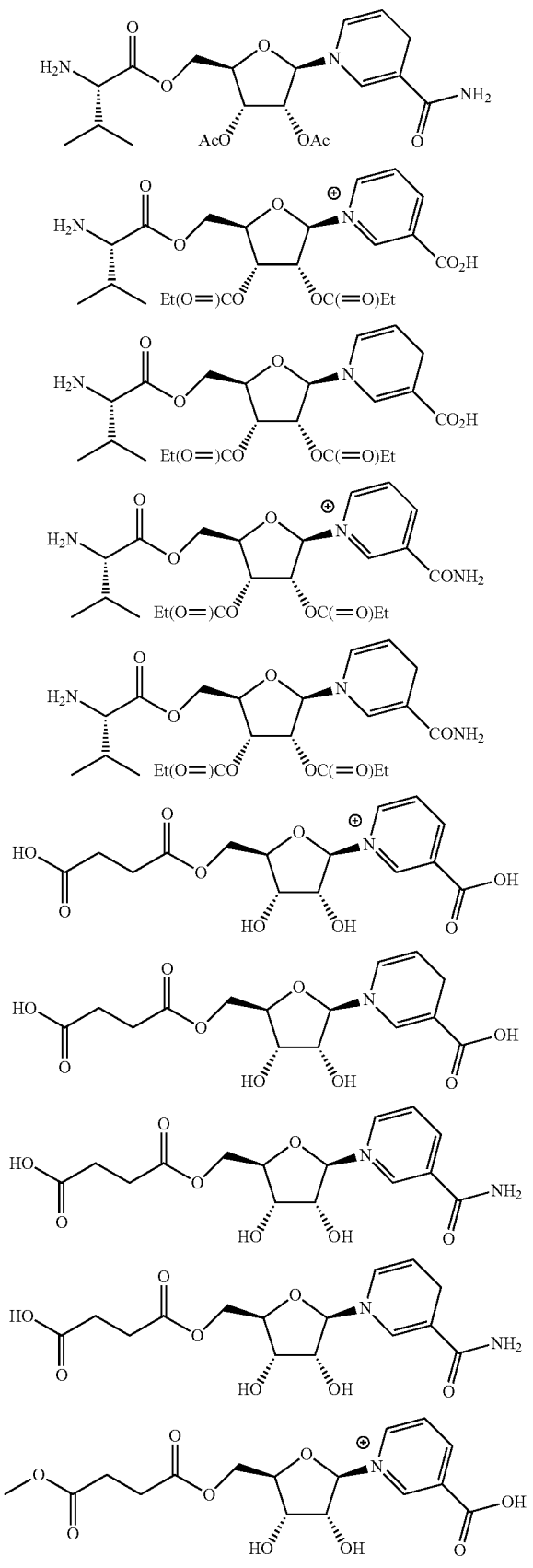
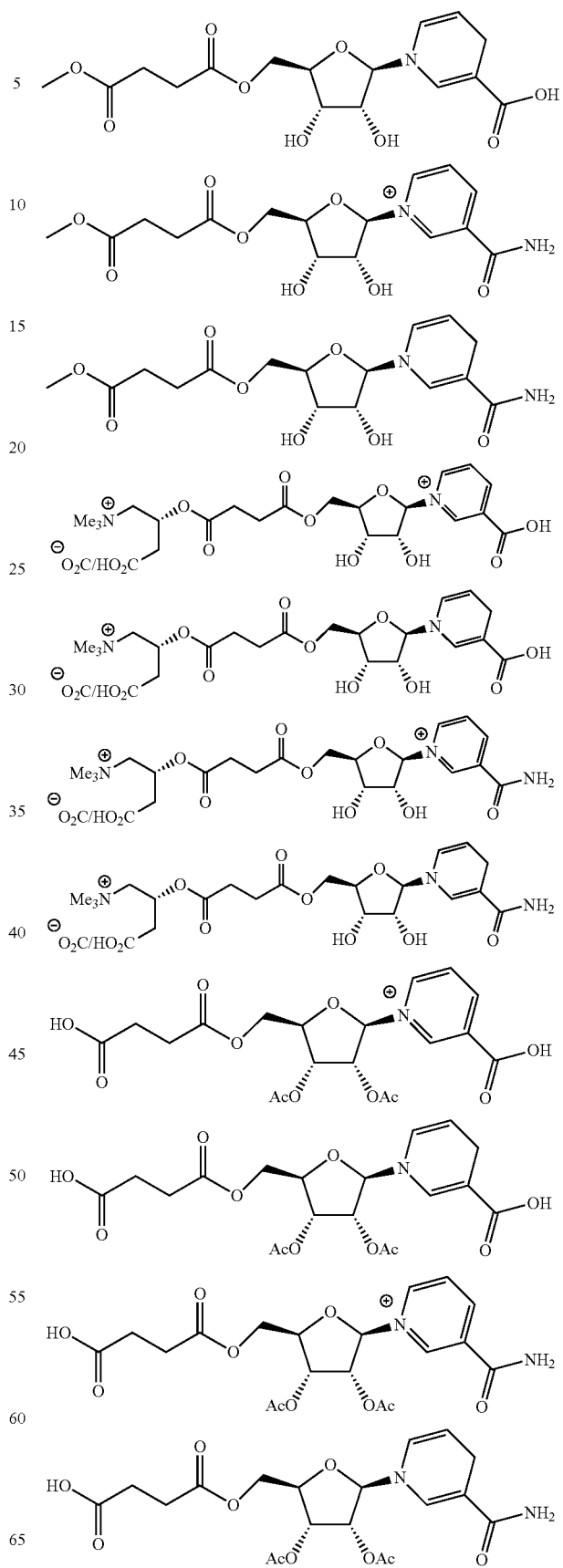

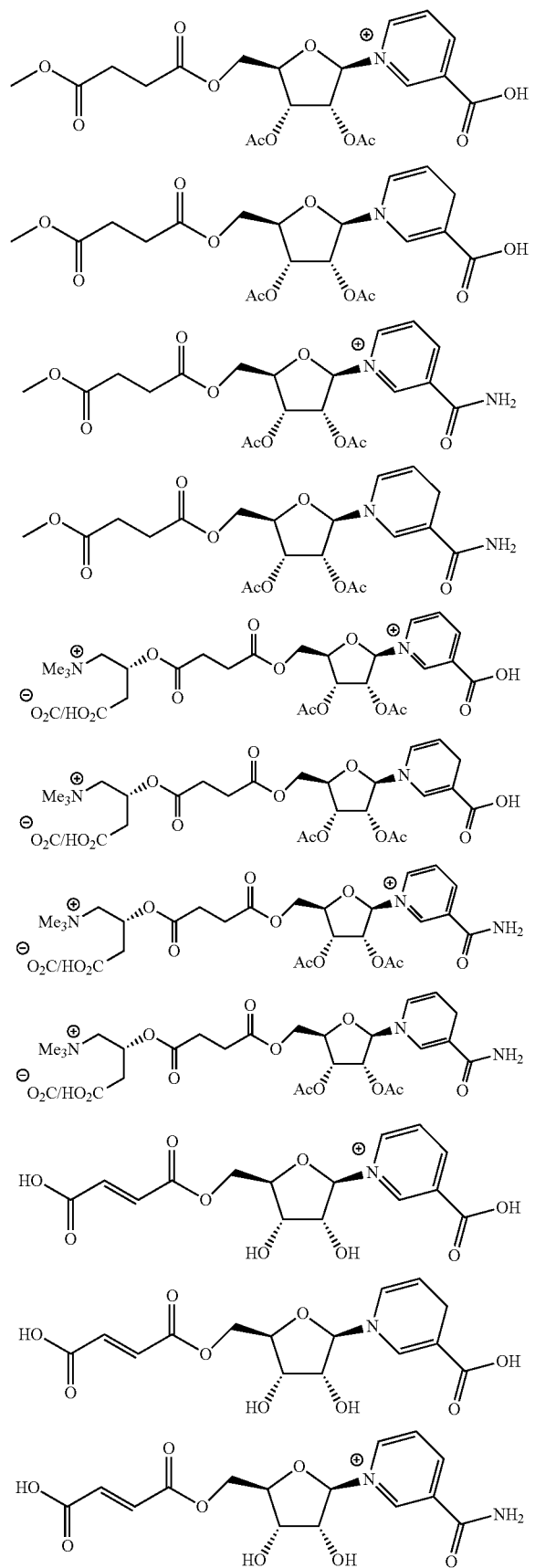
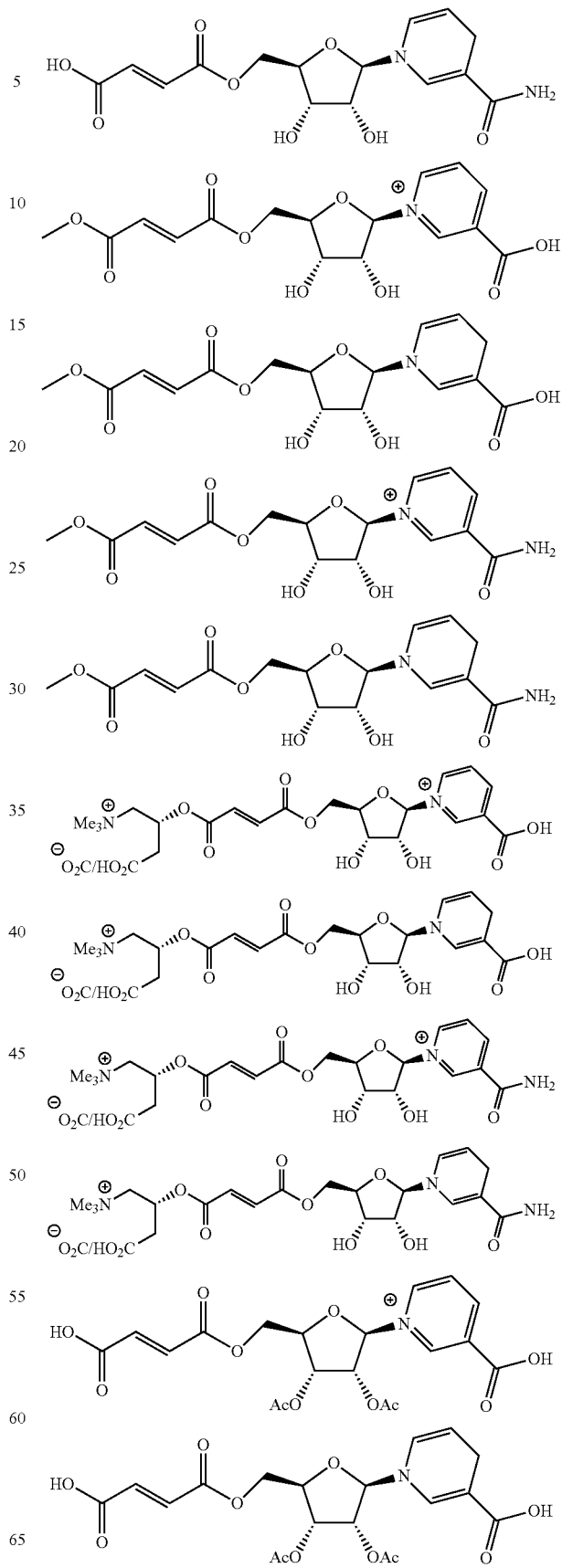

109
-continued
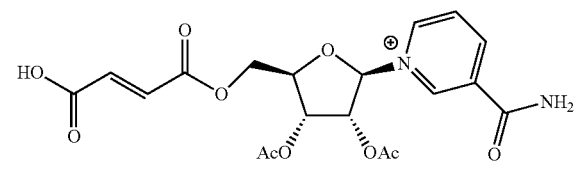
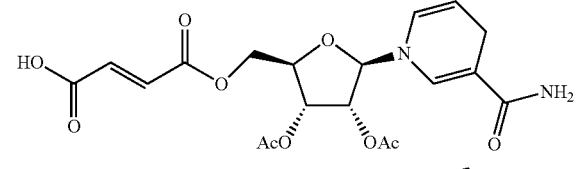
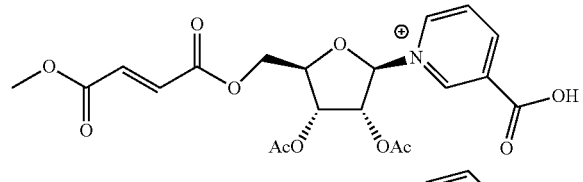
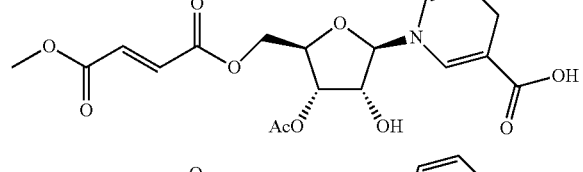
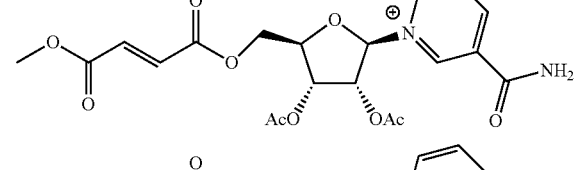
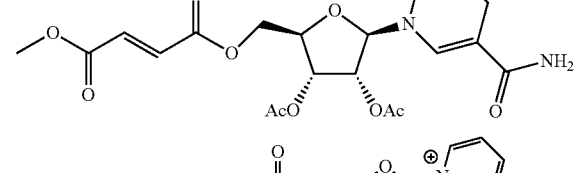
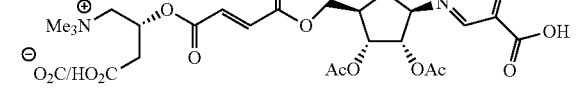
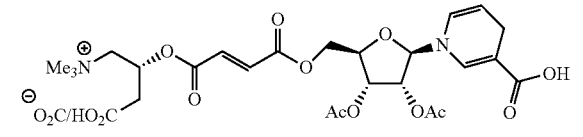
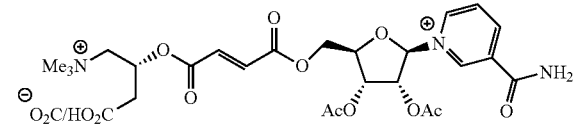
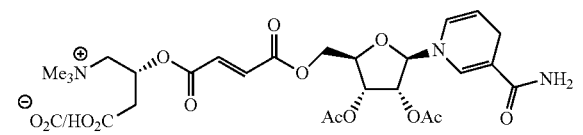
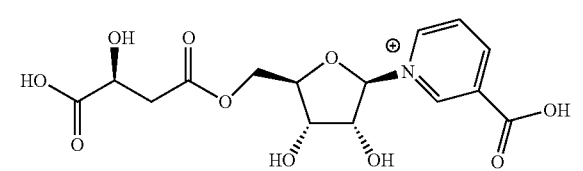
110
-continued
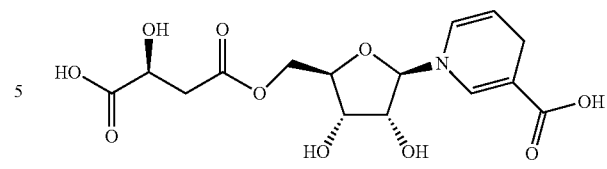
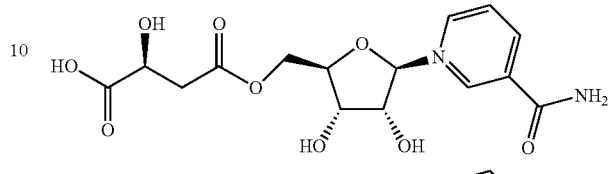
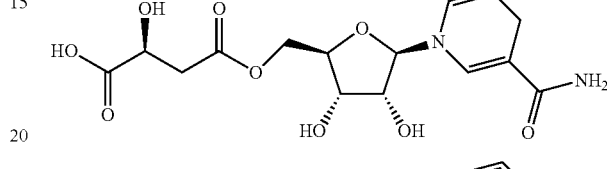
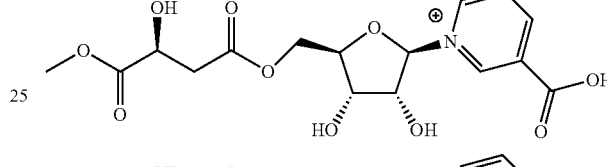
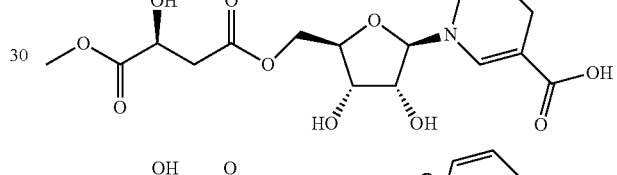
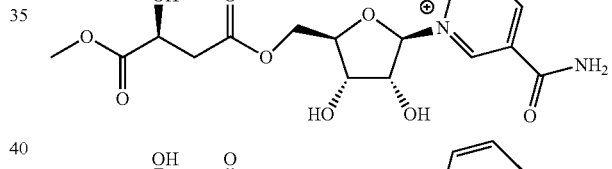
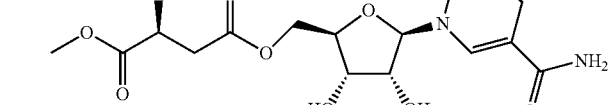
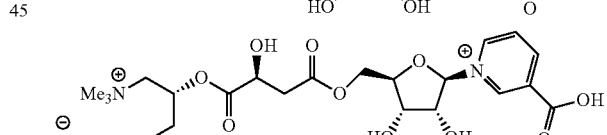
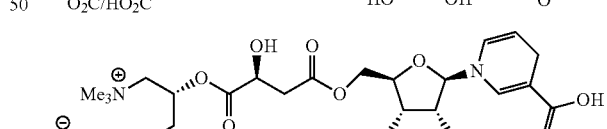
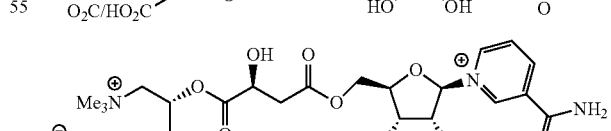
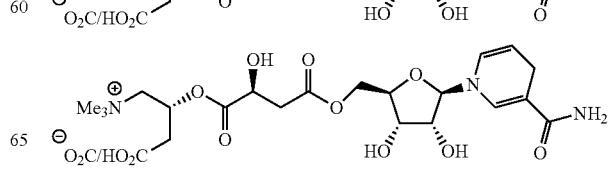

111
-continued
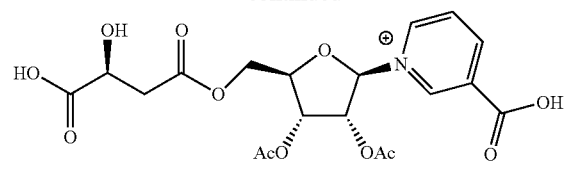
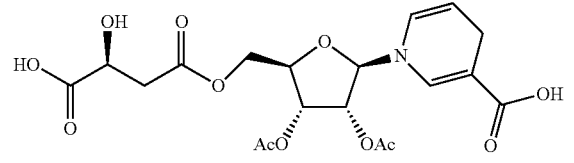
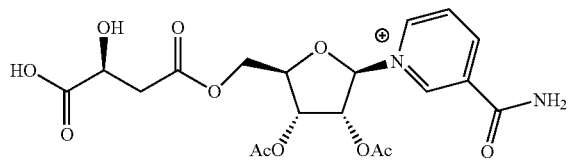
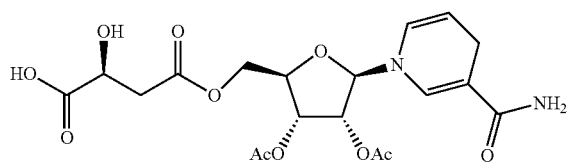
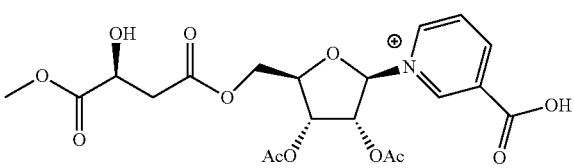
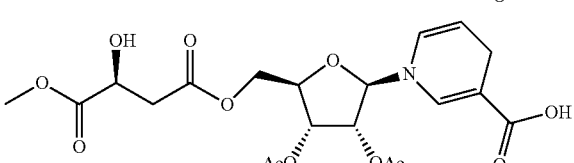
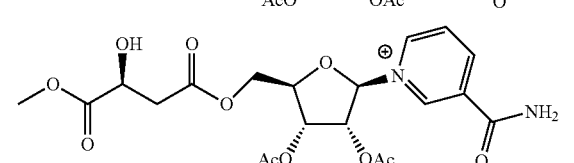
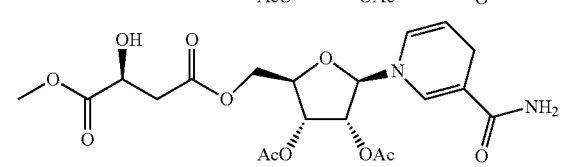
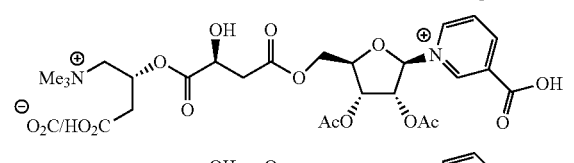
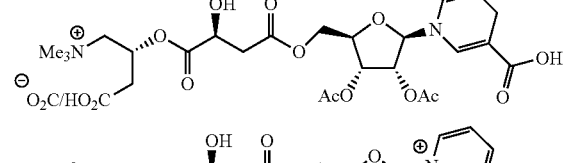
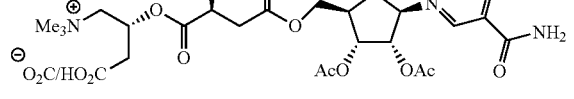
112
-continued
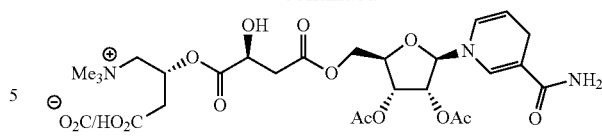
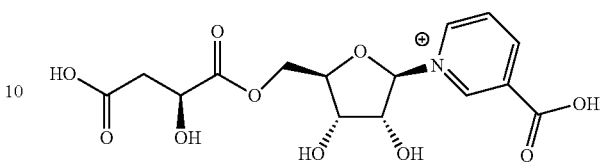
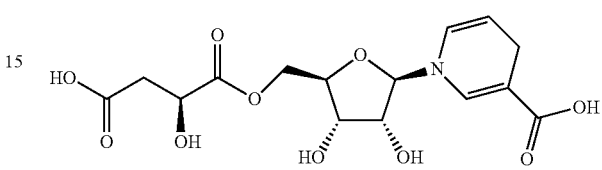
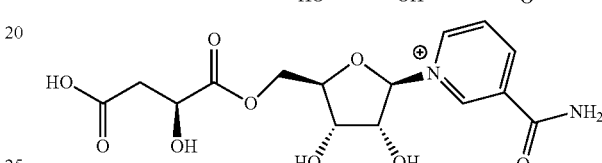
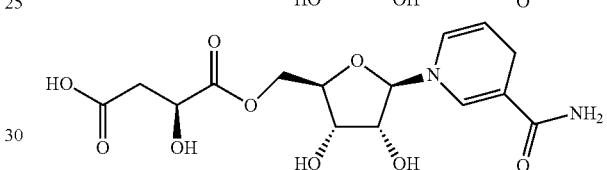
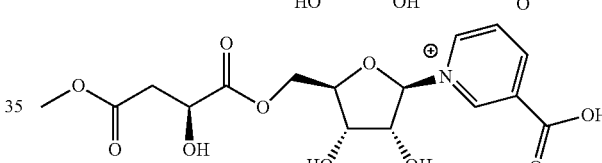
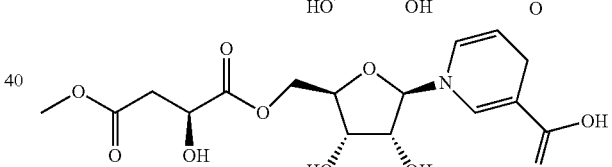
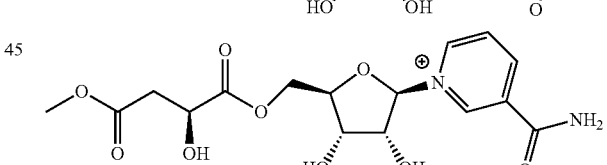
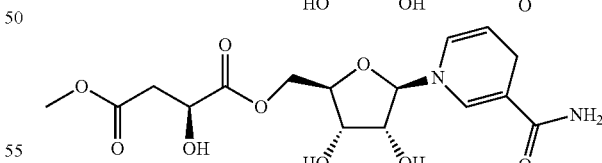
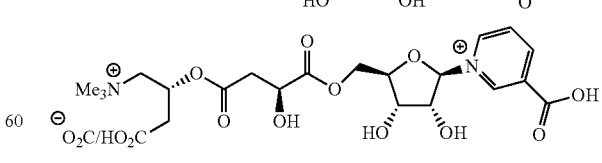
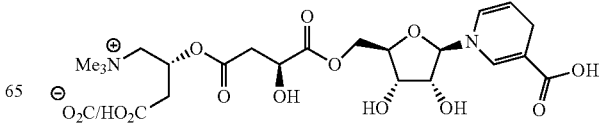

113
-continued

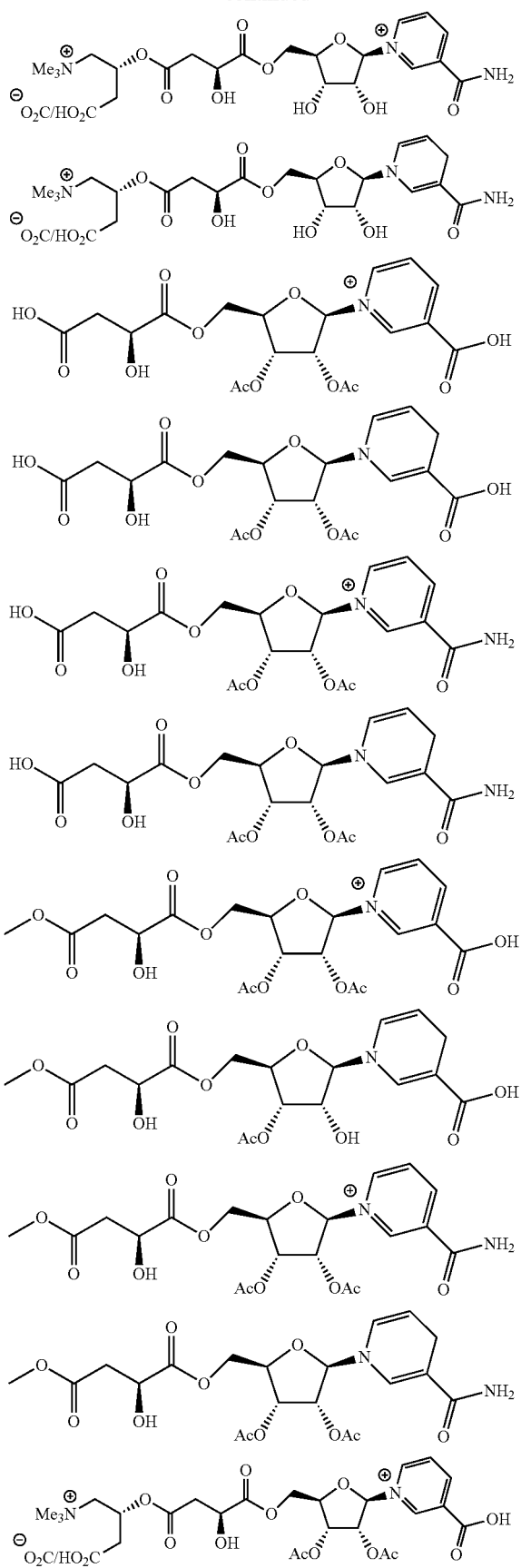

114
-continued

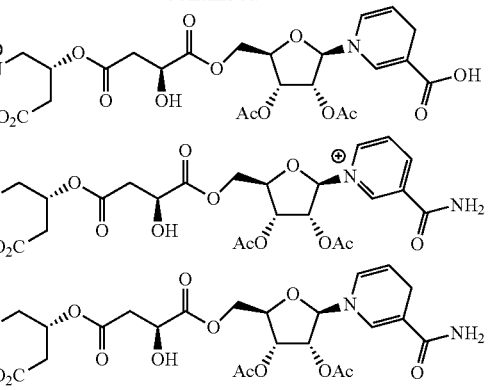

and pharmaceutically acceptable salts, solvates, hydrates, clathrates, polymorphs and stereoisomers thereof.

34. The compound of Formula I or II of any one of the preceding embodiments, which is a compound of Formula II.

35. A compound of Formula III or IV:

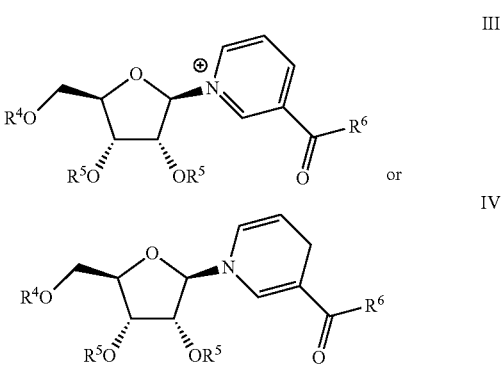

wherein:
R$^4$ is hydrogen or —C(=O)R$^7$, wherein R$^7$ is linear or branched C$_1$-C$_6$ alkyl, C$_3$-C$_6$ cycloalkyl, or phenyl optionally substituted with F, Cl, —NO$_2$, linear or branched C$_1$-C$_4$ alkyl, —CF$_3$ or —O-(linear or branched C$_1$-C$_4$ alkyl);
R$^5$ at each occurrence independently is hydrogen or —C(=O)R$^8$, wherein R$^8$ has the same definition as R$^7$; and
R6 is

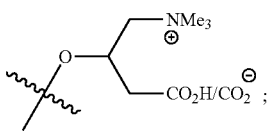

or a pharmaceutically acceptable salt, solvate, hydrate, clathrate, polymorph or stereoisomer thereof.

36. The compound of Formula III or IV of embodiment 35, wherein:
R$^4$ is hydrogen or —C(=O)R$^7$, wherein R$^7$ is linear or branched C$_1$-C$_6$ alkyl; and
R$^5$ at each occurrence independently, or at both occurrences, is hydrogen or —C(=O)R$^8$, wherein R$^8$ is linear or branched C$_1$-C$_6$ alkyl.

37. The compound of Formula III or IV of embodiment 36, wherein:
R[4] is hydrogen, acetyl or propanoyl; and
R[5] at each occurrence independently, or at both occurrences, is hydrogen, acetyl or propanoyl.
38. The compound of Formula III or IV of any one of embodiments 35 to 37, wherein R[6] is
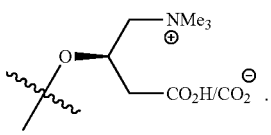
39. The compound of Formula III or IV of any one of embodiments 35 to 38, which is selected from:
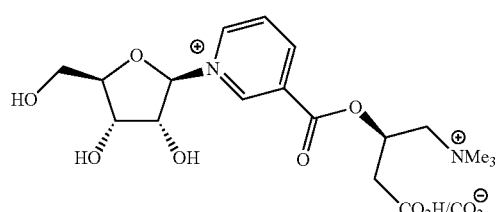
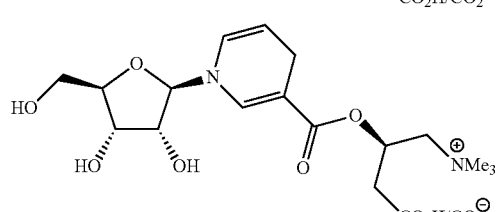
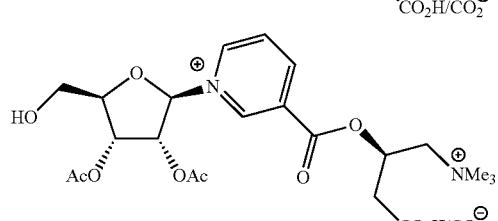
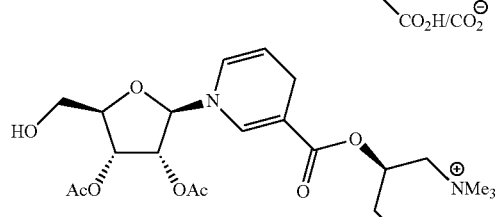
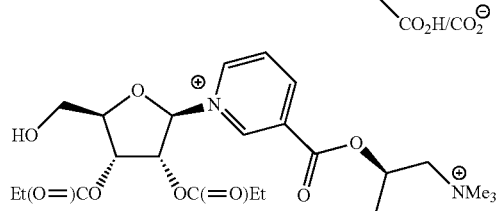
-continued
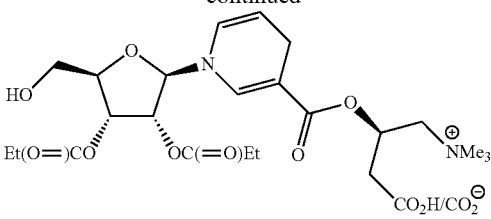
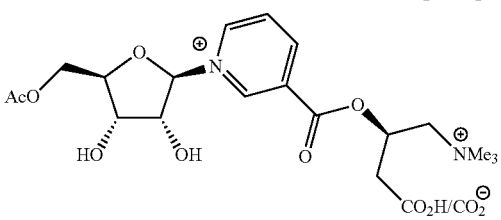
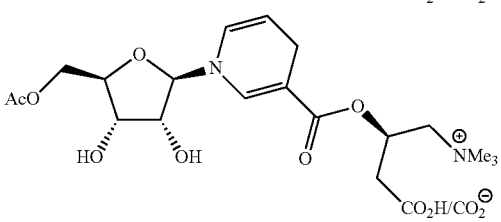
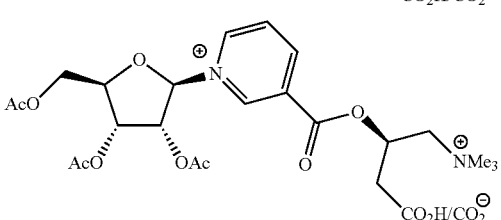
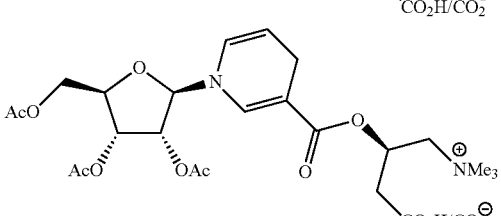
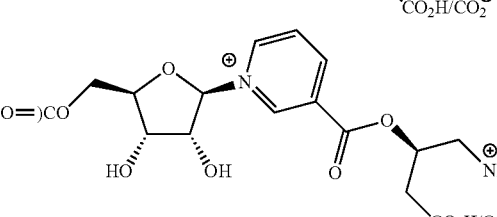
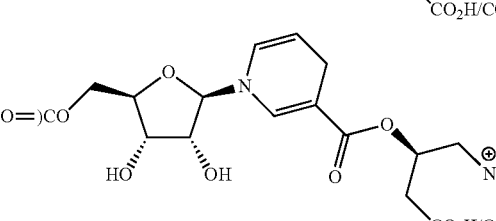
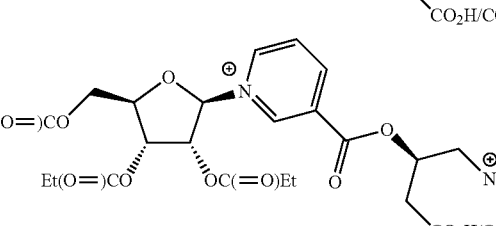

-continued

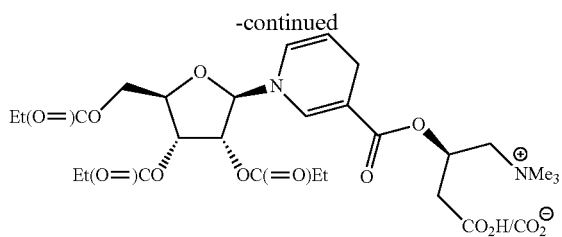

and pharmaceutically acceptable salts, solvates, hydrates, clathrates, polymorphs and stereoisomers thereof.

40. The compound of Formula III or IV of any one of embodiments 35 to 39, which is a compound of Formula IV.

41. The compound of Formula I, II, III or IV of any one of the preceding embodiments, which is a trifluoromethanesulfonate (triflate or $^-$OTf) salt, an acetate ($^-$OAc) salt, a trifluoroacetate ($^-$OTFA) salt, a formate salt or a chloride (Cl$^-$) salt.

42. The compound of Formula I, II, III or IV of any one of the preceding embodiments, which has the beta-D-riboside configuration.

43. The compound of Formula I, II, III or IV of any one of the preceding embodiments, which is stereoisomerically pure (e.g., at least about 90%, 95%, 98% or 99% of the compound is the indicated stereoisomer).

44. The compound of Formula I, II, III or IV of any one of embodiments 1 to 41, which is a racemic mixture.

45. The compound of Formula I, II, III or IV of any one of embodiments 1 to 41, which has the D-riboside configuration and an approximately 1:1 ratio of beta-/alpha-anomers.

46. A pharmaceutical or cosmetic composition comprising one or more compounds of any one of the preceding embodiments or a pharmaceutically acceptable salt, solvate, hydrate, clathrate, polymorph or stereoisomer thereof, and one or more pharmaceutically acceptable carriers or excipients.

47. The pharmaceutical or cosmetic composition of embodiment 46, which comprises a compound of Formula II or IV.

48. The pharmaceutical or cosmetic composition of embodiment 46 or 47, which comprises a compound of Formula I and a compound of Formula II, or a compound of Formula III and a compound of Formula IV.

49. A method of treating a mitochondrial disease, a mitochondria-related disease or condition, or a disease or condition characterized by acute NAD$^+$ depletion due to DNA damage, comprising administering to a subject in need of treatment a therapeutically effective amount of one or more compounds of any one of the preceding embodiments or a pharmaceutically acceptable salt, solvate, hydrate, clathrate, polymorph or stereoisomer thereof, or a pharmaceutical composition comprising the same.

50. The method of embodiment 49, wherein the mitochondrial disease is selected from mitochondrial myopathies; limb-girdle distribution weakness: Kearns-Sayre syndrome (KSS); Pearson syndrome; Leigh syndrome; Barth syndrome; Friedreich's ataxia; neuropathy, ataxia, retinitis pigmentosa and ptosis (NARP); mitochondrial DNA depletion syndrome (Alper's disease); mitochondrial neurogastrointestinal encephalopathy (MNGIE) syndrome; mitochondrial encephalopathy, lactic acidosis and stroke-like episodes (MELAS) syndrome; myoclonic epilepsy with ragged red fibers (MERRF); chronic progressive external ophthalmoplegia (CPEO); Leber's hereditary optic neuropathy (LION); inherited forms of blindness and deafness (e.g., diabetes mellitus and deafness); and acquired forms of reversible or permanent hearing loss (e.g., type 2 diabetes-associated hearing loss and hearing loss induced by ototoxic chemicals (e.g., heavy metals [e.g., lead], solvents [e.g. styrene and toluene] and asphyxiants [e.g., carbon monoxide]) and medications (e.g., loop diuretics [e.g., bumetanide and furosemide], NSAIDs [e.g., aspirin, celecoxib, diclofenac, ibuprofen and naproxen], PDE5 inhibitors, macrolide antibiotics, aminoglycosides [e.g., gentamicin], platinum-based chemotherapeutics [e.g., carboplatin and cisplatin], paracetamol and quinine)}.

51. The method of embodiment 49, wherein the mitochondria-related disease or condition is a neurodegenerative disorder, a neuronal activation disorder, a muscle disorder, a fatty acid/beta oxidation disorder, a metabolic disorder, an inflammatory disorder, a vascular disorder, a kidney disorder, a liver disorder, a tumor or cancer, male or female infertility, or an aging-related disorder.

52. The method of embodiment 49 or 51, wherein the mitochondria-related disease or condition is selected from lipodystrophy, metabolic syndrome, obesity, types 1 and 2 diabetes, non-alcoholic fatty liver disease (NAFLD), non-alcoholic steatohepatitis (NASH), alcoholic liver disease, autoimmune hepatitis, cholestatic liver disease, hemochromatosis and alpha-1 antitrypsin deficiency.

53. The method of embodiment 49, wherein the disease or condition characterized by acute NAD$^+$ depletion due to DNA damage is selected from exposure to radiation (e.g., UV and ionizing radiation such as X-ray), radiation or chemotherapy-induced disorders (e.g., dermatitis, myositis, myocarditis, colitis, prostatitis, hepatitis, pneumonitis, neuropathies and bone marrow failure), burn injuries (including first-degree burns, second-degree burns and third-degree burns), chemical exposure with manifestation of exfoliative dermatitis, exposure to chemical warfare agents, Stevens-Johnson syndrome, acute respiratory distress syndrome, inhalational lung injury due to smoke or chemical toxins, trauma-related crush injuries (including those with bone fractures), peripheral nerve injuries, spinal cord injuries, and contusion to internal organs (such as the heart, lung, liver, and kidneys).

54. The method of any one of embodiments 49 to 53, wherein the one or more compounds are or comprise a compound of Formula II or IV.

55. The method of any one of embodiments 49 to 54, wherein the one or more compounds are or comprise a compound of Formula I and a compound of Formula II, or a compound of Formula III and a compound of Formula IV.

56. The method of any one of embodiments 49 to 55, wherein the one or more compounds or the pharmaceutical composition is/are administered orally, parenterally (e.g., intravenously, intradermally, subcutaneously, intramuscularly or intrathecally), or topically (e.g., transdermally, transmucosally, intranasally, pulmonarily [e.g., by oral inhalation], sublingually or rectally [e.g., by suppository]).

57. The method of any one of embodiments 49 to 55, wherein the one or more compounds or the pharmaceutical composition is/are used in culture medium for preparation of ex vivo therapy.

58. The method of embodiment 57, wherein the ex vivo therapy is a chimeric antigen receptor T-cell (CAR-T) therapy, a stem cell therapy, in vitro fertilization, organ transplantation or for attachment to a carrier molecule such as a dendrimer or an antibody conjugate.

59. The method of any one of embodiments 49 to 58, further comprising administering a therapeutically effective amount of at least one other therapeutic agent selected from sirtuin-activating agents, AMPK-activating agents, CD38 inhibitors, PARP inhibitors, stimulators of cellular oxygen consumption, NMDA receptor antagonists, acetylcholinesterase inhibitors, antidiabetics, anti-obesity agents, antiplatelet agents, anticoagulants, antihypertensive agents, antioxidants, anti-inflammatory agents, analgesics, anesthetics, anticancer agents, antivirals, antibiotics, antifungals, natural compounds, vitamins, vaccines, and combinations thereof.

60. The method of embodiment 59, wherein the at least one other therapeutic agent is or comprises a sirtuin-activating agent, a PARP inhibitor, an antioxidant, a natural compound or a vitamin, or any combination thereof.

61. The method of embodiment 59 or 60, wherein the sirtuin-activating agent is selected from polyphenols (e.g., butein, fisetin, isoliquiritigenin, piceatannol, quercetin and resveratrol), amino acids with a branched side chain (e.g., leucine), methylene blue, SRT-1460, SRT-1720, SRT-2104, SRT-2183 and lamin A.

62. The method of embodiment 59 or 60, wherein the PARP inhibitor is selected from niraparib, olaparib, pamiparib (BGB290), rucaparib, talazoparib, veliparib, 4-amino-1,8-naphthalimide, CEP9722, E7016 and PJ34.

63. The method of embodiment 62, wherein the PARP inhibitor (e.g., olaparib) is administered in a dose significantly lower than its recommended dose as an anticancer agent.

64. The method of embodiment 59 or 60, wherein the antioxidant or/and the natural compound is/are selected from resveratrol, pterostilbene, ellagic acid, urolithin A, quercetin, coenzyme Q, glutathione, N-acetyl-L-cysteine, α-lipoic acid, melatonin, creatine, S-adenosyl methionine, leucine, pyruvic acid/pyruvate, and combinations thereof.

65. The method of embodiment 59 or 60, wherein the vitamin is a member of the vitamin B family selected from thiamine ($B_1$), riboflavin ($B_2$), niacin ($B_3$), pantothenic acid ($B_5$), pyridoxine ($B_6$), biotin ($B_7$), folic acid ($B_9$), cobalamin ($B_{12}$), and combinations thereof, such as $B_1$, $B_2$, $B_3$ or $B_6$ or any combination thereof.

66. The method of embodiment 59, wherein the anti-inflammatory agent is selected from NSAIDs, inhibitors of pro-inflammatory cytokines and receptors therefor and their production, and combinations thereof.

67. The method of embodiment 59, wherein the antidiabetic agent is selected from AMPK agonists (e.g., metformin), PPAR-γ agonists, GLP-1 agonists, SGLT2 inhibitors, and combinations thereof.

68. The method of embodiment 59, wherein the antibiotic comprises ethionamide and optionally SMARt-420.

69. The method of embodiment 59, wherein the anticancer agent comprises radiation therapy, chemotherapy or cancer immunotherapy, or any combination or all thereof.

70. The method of embodiment 69, wherein the chemotherapy comprises a PARP inhibitor (e.g., olaparib), a TGF-β, inhibitor or a cytotoxic agent, or any combination or all thereof.

71. The method of embodiment 69, wherein the cancer immunotherapy comprises an anti-PD1 agent, an anti-PDL1 agent or an anti-CTLA4 agent, or any combination thereof.

72. One or more compounds of any one of embodiments 1 to 45 or a pharmaceutically acceptable salt, solvate, hydrate, clathrate, polymorph or stereoisomer thereof for use as a medicament.

73. A composition comprising one or more compounds of any one of embodiments 1 to 45 or a pharmaceutically acceptable salt, solvate, hydrate, clathrate, polymorph or stereoisomer thereof for use as a medicament.

74. Use of one or more compounds of any one of embodiments 1 to 45 or a pharmaceutically acceptable salt, solvate, hydrate, clathrate, polymorph or stereoisomer thereof in the preparation of a medicament.

75. The compound(s), the composition or the use of embodiment 72, 73 or 74, respectively, wherein the one or more compounds are or comprise a compound of Formula II or IV.

76. The compound(s), the composition or the use of embodiment 72, 73 or 74, respectively, wherein the one or more compounds are or comprise a compound of Formula I and a compound of Formula II, or a compound of Formula III and a compound of Formula IV.

77. The compound(s), the composition or the use of embodiment 72, 73 or 74, respectively, or embodiment 75 or 76, wherein the medicament is for use in treating a mitochondrial disease, a mitochondria-related disease or condition, or a disease or condition characterized by acute $NAD^+$ depletion due to DNA damage.

78. The compound(s), the composition or the use of embodiment 77, which is in combination with the use of at least one other therapeutic agent.

79. A method of elevating nicotinamide adenine dinucleotide ($NAD^+$) level or/and providing cytoprotection in at least one cell type, tissue or organ of a subject, comprising administering to the subject a therapeutically effective amount of, or contacting the at least one cell type, tissue or organ of the subject with, one or more compounds of any one of embodiments 1 to 45 or a pharmaceutically acceptable salt, solvate, hydrate, clathrate, polymorph or stereoisomer thereof, or a pharmaceutical composition comprising the same.

80. The method of embodiment 79, wherein the subject suffers from a disorder or condition characterized by $NAD^+$ depletion or/and cell injury, damage or death.

81. The method of embodiment 80, wherein the $NAD^+$ depletion or/and the cell injury, damage or death are associated with or result from DNA damage.

82. The method of any one of embodiments 79 to 81, wherein the one or more compounds elevate $NAD^+$ level in the mitochondria, the cytoplasm or/and the nucleus of a cell (e.g., total cellular $NAD^+$ level).

83. The method of any one of embodiments 79 to 82, wherein the providing cytoprotection comprises reducing cell injury, damage or death.

84. The method of any one of embodiments 79 to 83, wherein the one or more compounds are or comprise a compound of Formula II or IV.

85. The method of any one of embodiments 79 to 84, wherein the one or more compounds are or comprise a compound of Formula I and a compound of Formula II, or a compound of Formula III and a compound of Formula IV.

86. A method of increasing nicotinamide adenine dinucleotide ($NAD^+$) level or/and providing cytoprotection in at least one cell type, tissue or organ of a subject, or treating a mitochondrial disease, a mitochondria-related disease or condition, or a disease or condition of a subject characterized by acute $NAD^+$ depletion due to DNA damage, comprising administering to the subject a therapeutically effective amount of one or more nicotinyl riboside compounds and a therapeutically effective amount of a poly(ADP-ribose) polymerase (PARP) inhibitor, or contacting the at least one cell type, tissue or organ of the subject with one or more nicotinyl riboside compounds and a PARP inhibitor.

87. The method of embodiment 86, wherein the subject suffers from a disorder or condition characterized by $NAD^+$ depletion or/and cell injury, damage or death.

88. The method of embodiment 87, wherein the NAD+ depletion or/and the cell injury, damage or death are associated with or result from DNA damage.

89. The method of any one of embodiments 86 to 88, wherein the increasing NAD+ level comprises increasing NAD+ level in the mitochondria, the cytoplasm or/and the nucleus of a cell (e.g., total cellular NAD+ level).

90. The method of embodiment 89, wherein the one or more nicotinyl riboside compounds and the PARP inhibitor increase NAD+ level (e.g., total cellular NAD+ level, such as that in target cells) by at least about 50%, 100% (2-fold), 3-fold or 5-fold ex vivo or in vivo.

91. The method of any one of embodiments 86 to 90, wherein the providing cytoprotection comprises reducing cell injury, damage or death.

92. The method of embodiment 91, wherein the one or more nicotinyl riboside compounds and the PARP inhibitor increase the number of viable cells (e.g., target cells) by at least about 20%, 50%, 100% or 200% ex vivo or in vivo.

93. The method of any one of embodiments 86 to 92, wherein the one or more nicotinyl riboside compounds are or comprise one or more of nicotinamide riboside (NR), reduced NR (NRH), nicotinic acid riboside (NAR), reduced NAR (NARH) and pharmaceutically acceptable salts and stereoisomers thereof, or/and one or more derivatives thereof (NR/NAR derivatives).

94. The method of embodiment 93, wherein the one or more nicotinyl riboside compounds are or comprise NR or/and NRH, or a pharmaceutically acceptable salt, solvate, hydrate, clathrate, polymorph or stereoisomer thereof.

95. The method of embodiment 93 or 94, wherein the one or more NR/NAR derivatives are or comprise nicotinamide riboside triacetate (NRTA) or/and reduced NRTA (NRHTA), or a pharmaceutically acceptable salt, solvate, hydrate, clathrate, polymorph or stereoisomer thereof.

96. The method of any one of embodiments 93 to 95, wherein the one or more NR/NAR derivatives are or comprise one or more compounds of any one of embodiments 1 to 45 or a pharmaceutically acceptable salt, solvate, hydrate, clathrate, polymorph or stereoisomer thereof.

97. The method of embodiment 96, wherein the one or more NR/NAR derivatives are or comprise a compound of Formula II or IV.

98. The method of embodiment 96 or 97, wherein the one or more NR/NAR derivatives are or comprise a compound of Formula I and a compound of Formula II, or a compound of Formula III and a compound of Formula IV.

99. The method of any one of embodiments 86 to 98, wherein the therapeutically effective amount of each of the one or more nicotinyl riboside compounds independently is from about 1, 50 or 100 mg to about 500 or 1000 mg per day, or is about 1-100 mg, 100-200 mg, 200-300 mg, 300-400 mg, 400-500 mg or 500-1000 mg per day.

100. The method of any one of embodiments 86 to 99, wherein the PARP inhibitor is selected from niraparib, olaparib, pamiparib (BGB290), rucaparib, talazoparib, veliparib, 4-amino-1,8-naphthalimide, CEP9722, E7016, PJ34, and pharmaceutically acceptable salts thereof.

101. The method of any one of embodiments 86 to 100, wherein the therapeutically effective amount of the PARP inhibitor is significantly lower than its recommended dose as an anticancer agent.

102. The method of embodiment 101, wherein the therapeutically effective amount of the PARP inhibitor is no more than about 10%, 5%, 1%, 0.5% or 0.1% (e.g., no more than about 1%) of its recommended dose as an anticancer agent.

103. The method of any one of embodiments 86 to 102, wherein the PARP inhibitor is olaparib, and the therapeutically effective amount (e.g., per day or per dose) of olaparib is no more than about 10 mg, 5 mg, 1 mg, 0.5 mg or 0.1 mg (e.g., no more than about 1 mg); or is from about 0.01 or 0.1 mg to about 10 mg, from about 0.01 or 0.1 mg to about 1 mg, or from about 1 mg to about 10 mg; or is about 0.01-0.1 mg, 0.1-0.5 mg, 0.5-1 mg, 1-5 mg or 5-10 mg; or is about 10 µg, 50 µg, 0.1 mg, 0.5 mg, 1 mg, 5 mg or 10 mg.

104. The method of any one of embodiments 86 to 103, wherein the one or more nicotinyl riboside compounds and the PARP inhibitor synergistically increase NAD+ level or/and provide cytoprotection (e.g., reduce cytotoxicity), or have a synergistic therapeutic effect.

105. A kit comprising a pharmaceutical or cosmetic composition comprising one or more compounds of any one of embodiments 1 to 45, or one or more nicotinyl riboside compounds and a PARP inhibitor, and one or more pharmaceutically acceptable carriers or excipients.

106. The kit of embodiment 105, wherein the one or more compounds, or the one or more nicotinyl riboside compounds, are or comprise:
   1) a compound of Formula II or IV; or
   2) a compound of Formula I and a compound of Formula II; or
   3) a compound of Formula III and a compound of Formula IV.

107. The kit of embodiment 105 or 106, wherein the one or more nicotinyl riboside compounds are or comprise NR or/and NRH, or a pharmaceutically acceptable salt, solvate, hydrate, clathrate, polymorph or stereoisomer thereof.

108. The kit of any one of embodiments 105 to 107, wherein the one or more nicotinyl riboside compounds are or comprise NRTA or/and NRHTA, or a pharmaceutically acceptable salt, solvate, hydrate, clathrate, polymorph or stereoisomer thereof.

109. The kit of any one of embodiments 105 to 108, wherein the amount of the PARP inhibitor in the pharmaceutical or cosmetic composition is significantly lower than its recommended dose as an anticancer agent.

110. The kit of any one of embodiments 105 to 109, wherein the PARP inhibitor is olaparib.

111. The kit of any one of embodiments 105 to 110, wherein the pharmaceutical or cosmetic composition is a controlled-release, slow-release or sustained-release form.

112. The kit of any one of embodiments 105 to 111, wherein the pharmaceutical or cosmetic composition is an oral dosage form, such as a tablet, capsule or pill.

113. The kit of any one of embodiments 105 to 112, further comprising instructions for using or administering the pharmaceutical or cosmetic composition to treat a mitochondrial disease, a mitochondria-related disease or condition, a disease or condition characterized by acute NAD+ depletion due to DNA damage, or a skin disorder or condition.

114. The kit of embodiment 113, wherein the mitochondria-related disease or condition is a metabolic disorder.

Synthesis of NR and NAR Derivatives

Abbreviations

ACN=acetonitrile
DCC=N,N'-dicyclohexylcarbodiimide
DMAP=4-dimethylaminopyridine
DMF=N,N-dimethylformamide
DMP or 2,2-DMP=2,2-dimethoxypropane
HMDS=hexamethyldisilazide MeOH=methanol
—OAc=acetate
p-TSA=para-toluenesulfonic acid
Py.=pyridine
tBuMgCl=tert-butylmagnesium chloride
TBSCl=tert-butyldimethylsilyl chloride
TEA=triethylamine
TFA=trifluoroacetic acid
THF=tetrahydrofuran
TLC=thin-layer chromatography
TMSOTf=trimethylsilyl trifluromethanesulfonate Compounds of Formulas I and II can be synthesized using the exemplary process shown in FIG. 1. The process in FIG. 1 can be adapted to prepare compounds of Formulas III and IV.

Compounds MP-05, MP-06, MP-07 and MP-08 are synthesized starting from peracetylated β-D-ribofuranose. Standard Vorbrüggen's conditions are employed to obtain common intermediates 3 and 4. Functional group manipulations of intermediate 4 using reported protocols for the respective target compounds result in the synthesis of MP-05, MP-06, MP-07 and MP-08.

Compounds MP-09 and MP-10 are synthesized from intermediate 3 with esterification of the required functional groups toward the end of the synthesis. Compounds MP-12 through MP-24 are synthesized from intermediate 4, with reduction of the nicotinamide ring followed by functional group modifications as shown in FIG. 1, and subsequent regeneration of the aromatic nicotinamide ring.

Figure 2:
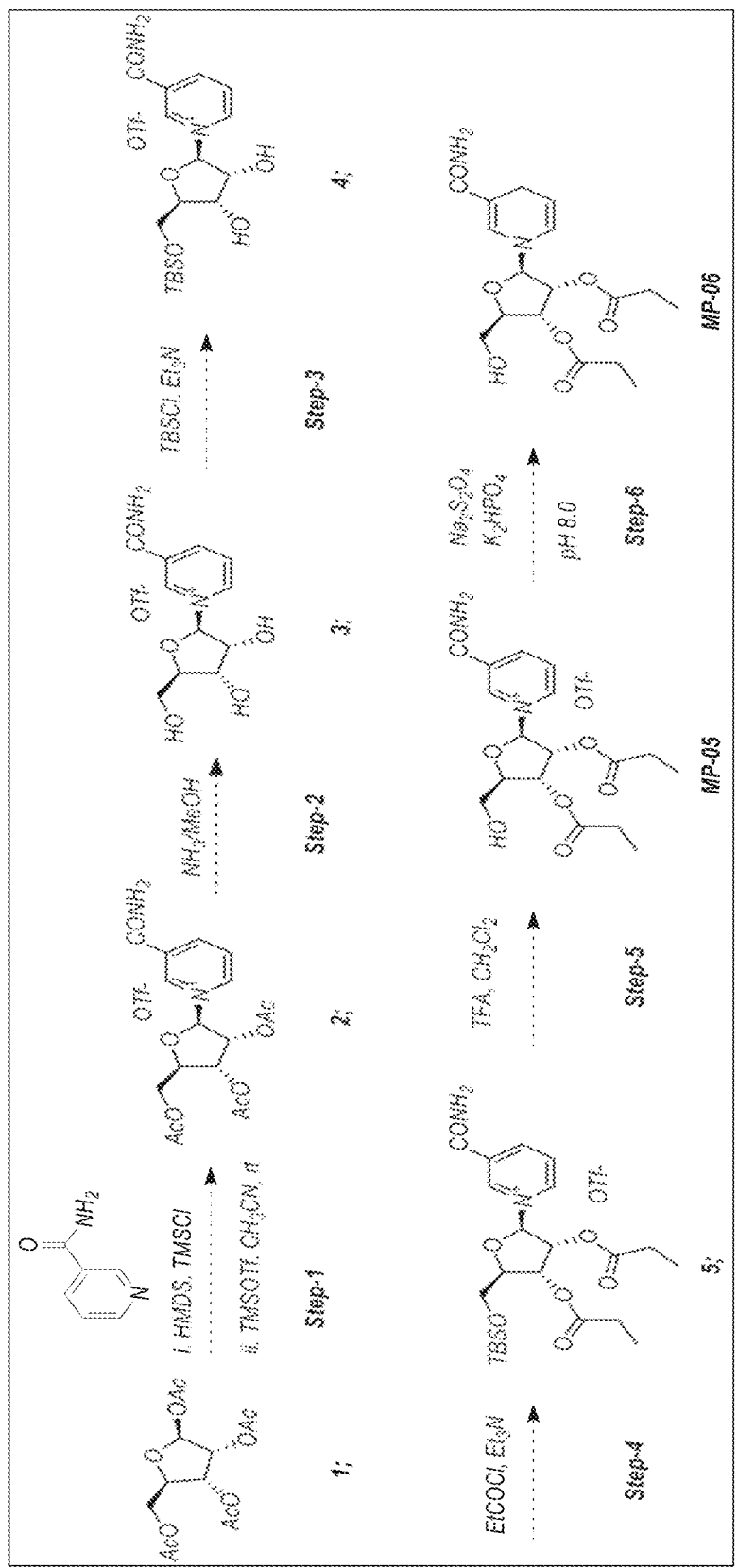
FIG. 2 shows a process for synthesizing MP-05 and MP-06.

Synthesis of MP-05 and MP-06:

FIG. 2 shows an exemplary process for synthesizing compounds MP-05 and MP-06. Their synthesis starts from commercially available peracetylated β-D-ribofuranose 1, the first step being the glycosylation of 1 with nicotinamide using Vorbrüggen's protocol. Selective protection of 5'-hydroxyl with TBSCl followed by bis-acylation using propanoyl chloride (or propionic anhydride) yields advanced intermediate 5. Deprotection of 5'-OTBS yields MP-05, and reduction of the nicotinamide ring with sodium dithionite generates MP-06.

Figure 3:
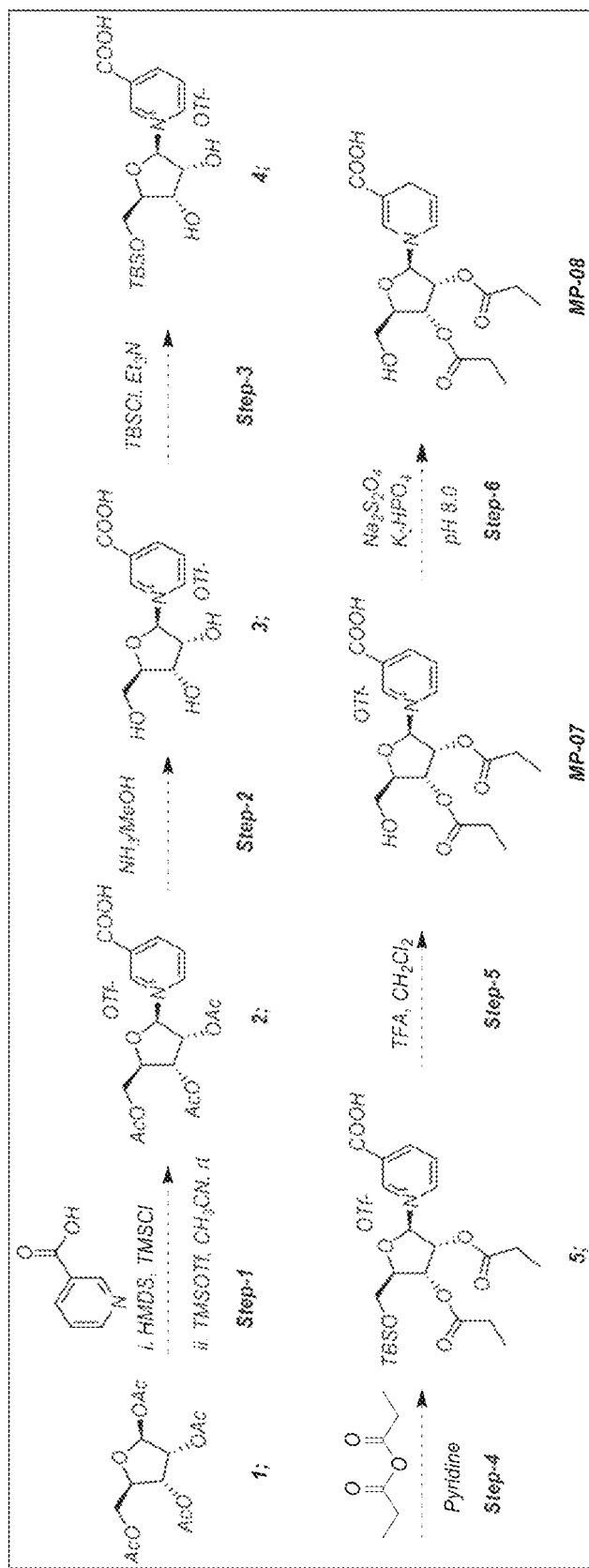
FIG. 3 shows a process for synthesizing MP-07 and MP-08.

Synthesis of MP-07 and MP-08:

FIG. 3 shows an exemplary process for synthesizing NAR derivatives MP-07 and MP-08, which is similar to the process for synthesizing NR derivatives MP-05 and MP-06 in FIG. 2, except that nicotinic acid is used in lieu of nicotinamide in the Vorbrüggen glycosylation reaction.

Figure 4:
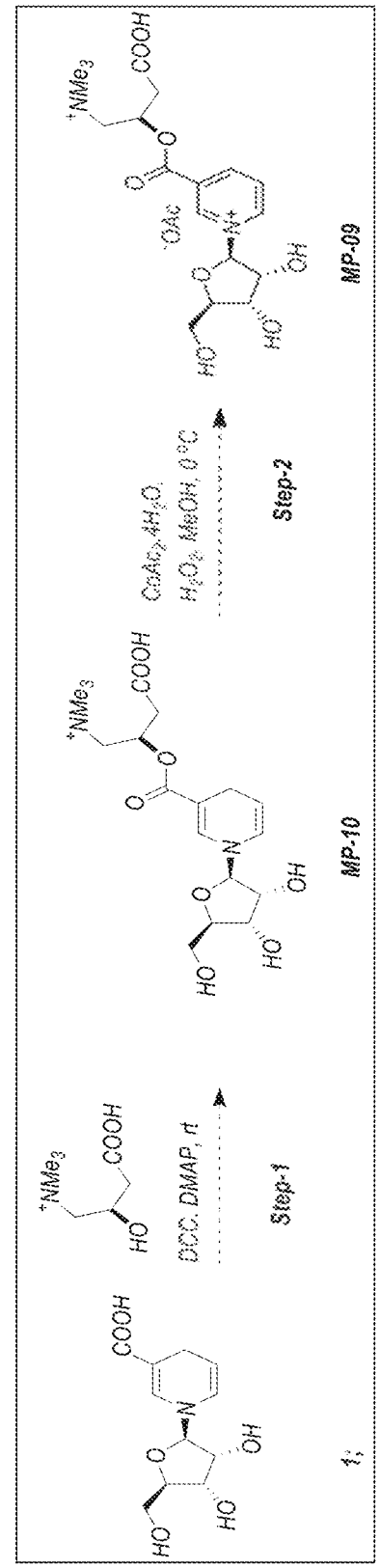
FIG. 4 shows a process for synthesizing MP-09 and MP-10.

Synthesis of MP-09 and MP-10:

FIG. 4 shows an exemplary process for synthesizing compounds MP-09 and MP-10. NARH 1 in FIG. 4 is prepared by sodium dithionite reduction of intermediate 3 in FIG. 3. DCC-mediated coupling of NARH 1 with L-cartinine furnishes MP-10, whose oxidation by cobalt acetate yields MP-09. It is understood that both L-cartinine itself and the L-cartinine moiety of MP-09 and MP-10 can be a zwitterion.

Figure 5:
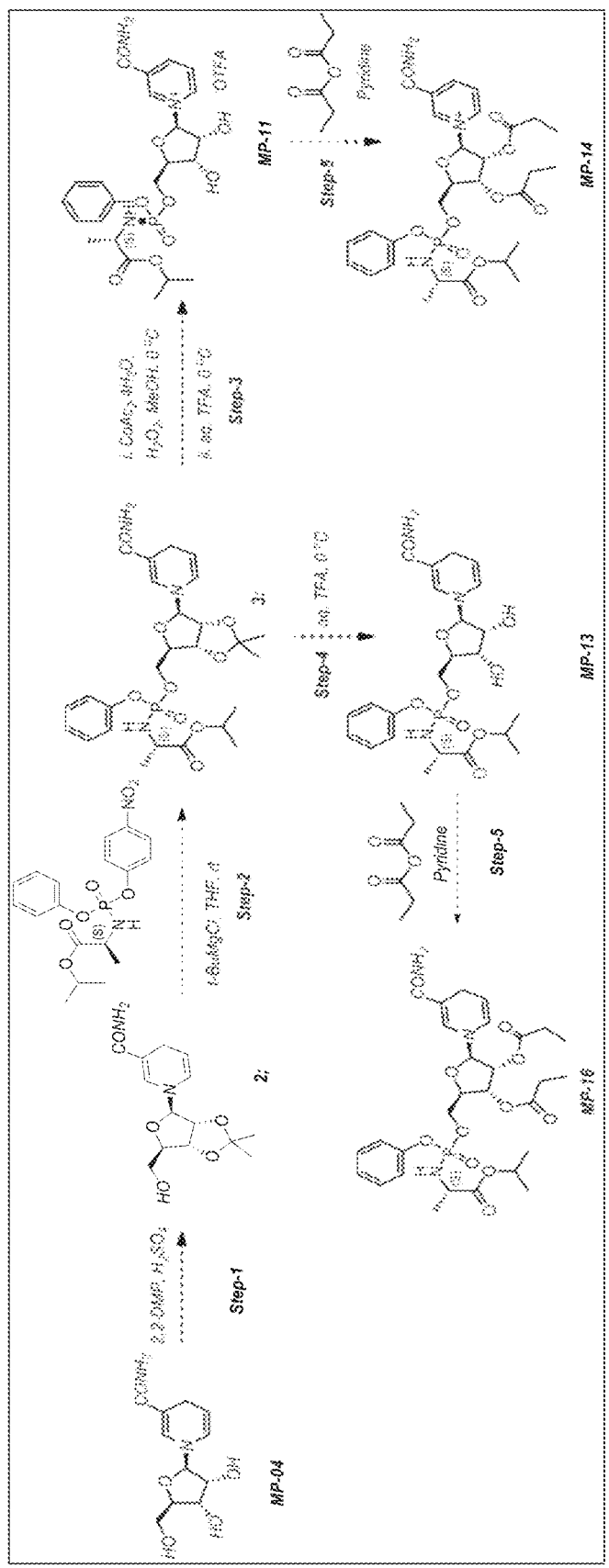
FIG. 5 shows a process for synthesizing MP-14 and MP-16.

Synthesis of MP-14 and MP-16:

FIG. 5 shows an exemplary process for synthesizing compounds MP-14 and MP-16. NRH (MP-04) is prepared by sodium dithionite reduction of NR 3 in FIG. 2. After oxidation and deprotection of the dimethyl ketal group of 5'-phosphoramidate intermediate 3, bis-acylation of the resulting MP-11 generates MP-14. Similarly, deprotection of intermediate 3 without oxidation and bis-acylation of the resulting MP-13 generate MP-16.

Figure 6:
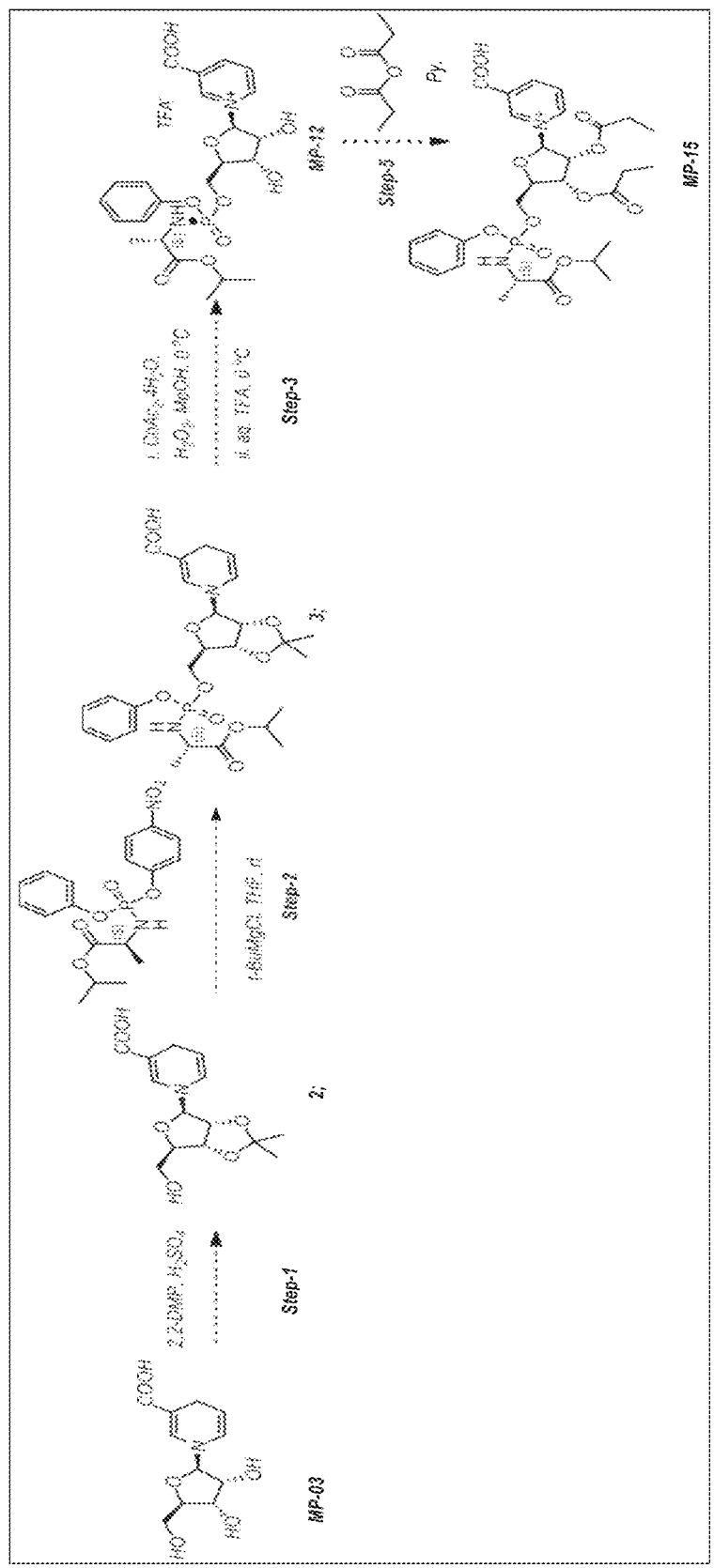
FIG. 6 shows a process for synthesizing MP-12 and MP-15.

Synthesis of MP-12 and MP-15 and their Reduced Forms:

FIG. 6 shows an exemplary process for synthesizing compounds MP-12 and MP-15. Oxidation and deprotection of the dimethyl ketal group of 5'-phosphoramidate intermediate 3 afford MP-12, whose bis-acylation produces MP-15. Deprotection of the dimethyl ketal group of intermediate 3 yields the reduced form of MP-12, and bis-propanoylation of the reduced form of MP-12 generates the reduced form of MP-15.

Figure 7:
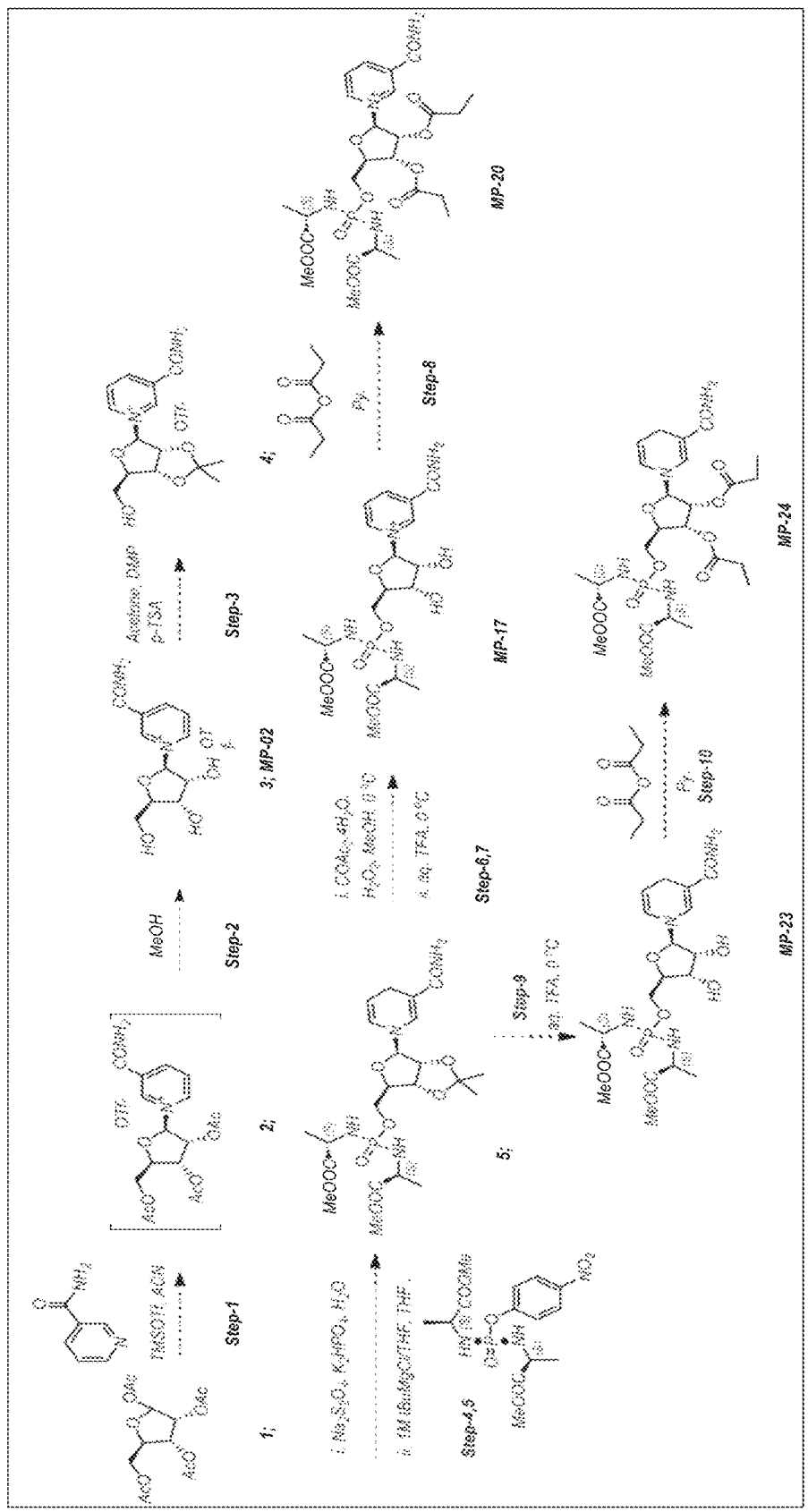
FIG. 7 shows a process for synthesizing MP-17, MP-20, MP-23 and MP-24.

Synthesis of MP-17, MP-20, MP-23 and MP-24:

FIG. 7 shows an exemplary process for synthesizing MP-17, MP-20, MP-23 and MP-24. Reduction of intermediate 4 with sodium dithionite followed by coupling with the indicated phosphorodiamidate reagent affords common intermediate 5. Oxidation and deprotection of the dimethyl ketal group of intermediate 5 produce MP-17, whose bis-acylation yields MP-20. Similarly, deprotection of intermediate 5 without oxidation furnishes MP-23, whose bis-acylation yields MP-24.

Figure 8:
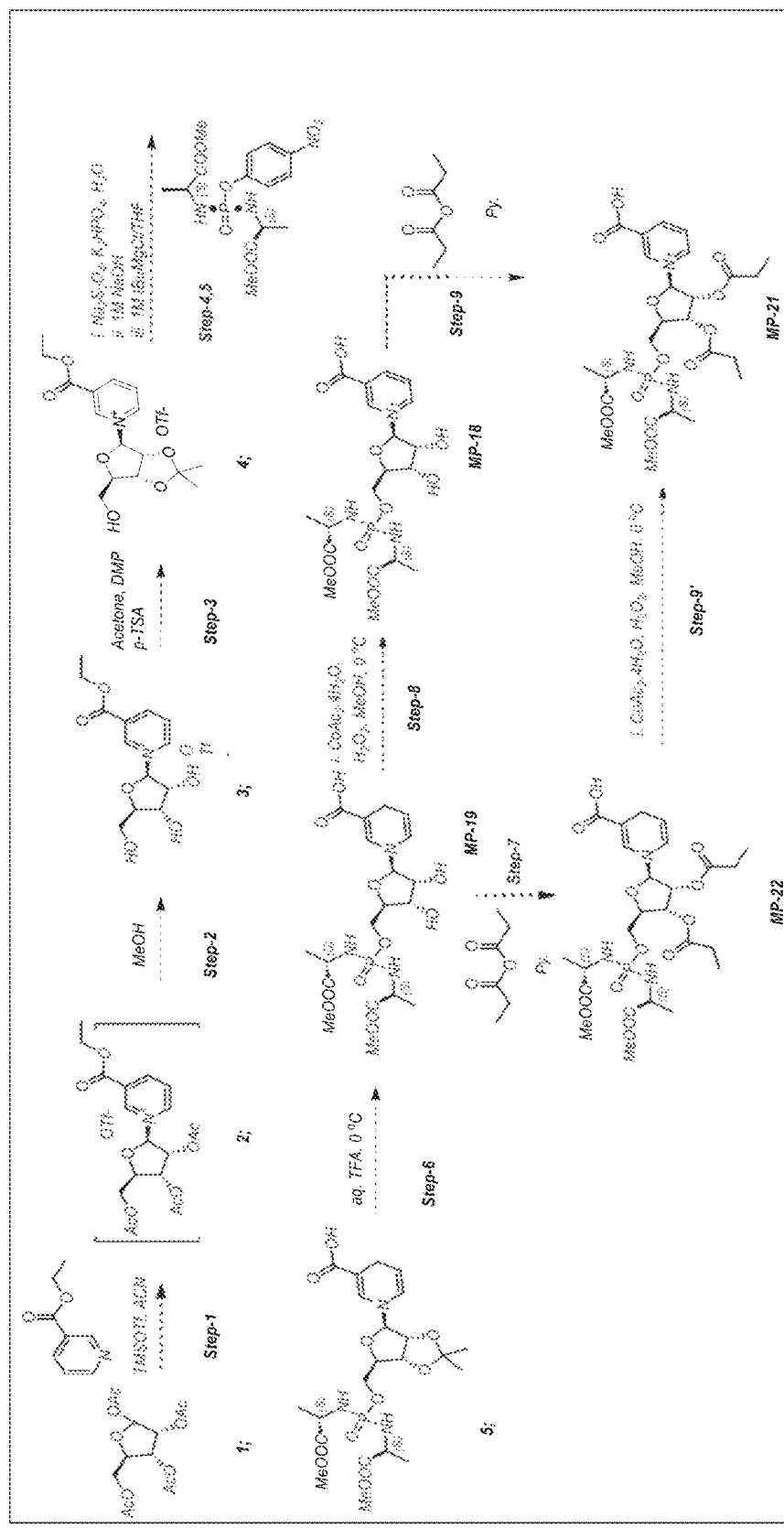
FIG. 8 shows a process for synthesizing MP-18, MP-19, MP-21 and MP-22.

Synthesis of MP-18, MP-19, MP-21 and MP-22:

FIG. 8 shows an exemplary process for synthesizing MP-18, MP-19, MP-21 and MP-22. Intermediate 5 in FIG. 8 is prepared in a similar manner as intermediate 5 in FIG. 7 except that ethylnicotinate is used instead of nicotinamide in the Vorbrüggen glycosylation reaction. Deprotection of the dimethyl ketal group of intermediate 5 furnishes MP-19. Bis-acylation of MP-19 yields MP-22, while oxidation of MP-19 yields MP-18. MP-21 can be made by bis-acylation of MP-18 or oxidation of MP-22.

EXAMPLES

The following examples are intended only to illustrate the disclosure. Other processes, assays, studies, protocols, procedures, methodologies, reagents and conditions may alternatively be used as appropriate.

Example 1. Synthesis of 1-((2R,3R,4S,5R)-5-(((Bis
(((S)-1-methoxy-1-oxopropan-2-yl)amino)phosphoryl)oxy)methyl)-3,4-dihydroxytetrahydrofuran-2-yl)-
3-carboxamidepyridin-1-ium trifluoroacetate (MP-17) and 1-((2R,3R,4R,5R)-5-(((bis(((S)-1-methoxy-
1-oxopropan-2-yl)amino)phosphoryl)oxy)methyl)-3,
4-bis(propionyloxy)tetrahydrofuran-2-yl)-3-
carboxamidepyridin-1-ium trifluoroacetate (MP-20)

Figure 9:
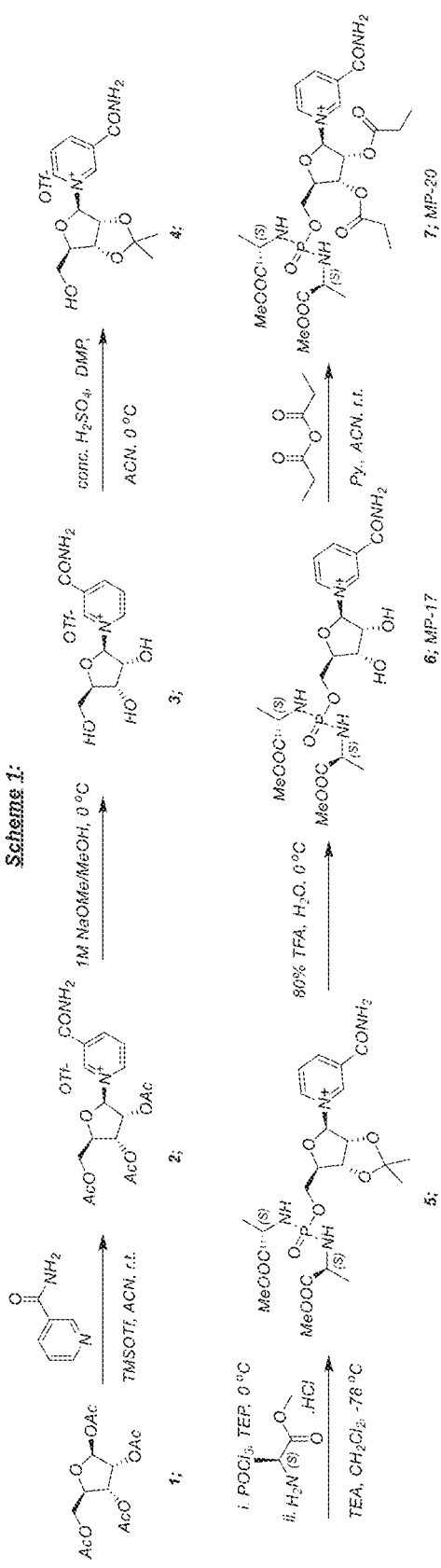
FIG. 9 shows a process for synthesizing MP-17 and MP-20.

FIG. 9 shows the process for the synthesis of MP-17 and MP-20.

3-Carboxamide-1-(2,3,5-tri-O-acetyl-β-D-ribofuranosyl)pyridinium triflate (2)

To a well stirred solution of nicotinamide (115.2 g, 0.942 mol) in dry acetonitrile (1.5 L) was added trimethylsilyl trifluoromethanesulfonate (314 mL, 1.72 mol) in one portion. The nicotinamide was dissolved within 5 min. A solution of 1,2,3,5-tetra-O-acetyl-β-D-ribofuranose 1 (100 g, 0.314 mol) in dry acetonitrile (300 mL) was added all in one portion at room temperature under nitrogen atmosphere. The solution was stirred for 30 min at room temperature. The excess TMSOTf was quenched by the addition of 1.2 M NaHCO$_3$ solution (10 mL) followed by solid NaHCO$_3$ (85 g, 1.01 mol) in small portions. The suspension was stirred for 30 min at room temperature and the solids were filtered and washed with CH$_2$Cl$_2$ (500 mL). Combined filtrates were concentrated under reduced pressure to get a thick yellow residue. The residue was suspended in 2 L of CH$_2$Cl$_2$. The suspension was stirred at room temperature for 15 min, and then solids were filtered and washed with CH$_2$Cl$_2$ (2 L). The filtrate was concentrated under vacuum to obtain compound 2 (120 g crude of which 82% was product by LCMS) as a yellow syrup. $^1$H NMR (400 MHz, DMSO-d$_6$): δ 9.46 (s, 1H), 9.24 (d, J=6.24 Hz, 1H), 9.06 (d, J=8.1 Hz, 1H), 8.67 (s, 1H), 8.40 (t, J=6.5 Hz, 1H), 8.25 (s, 1H), 6.65 (d, J=3.3 Hz, 1H), 5.61-5.62 (m, 1H), 5.44 (t, J=5.92 Hz, 1H), 4.70-4.71 (m, 1H), 4.45 (s, 2H), 2.15 (s, 3H) and 2.11 (s, 3H). LCMS (M$^+$): 381.1.

3-Carboxamide-1-(β-D-ribofuranosyl)pyridinium triflate (3)

To a well-stirred solution of crude compound 2 (120 g) in anhydrous MeOH (1.5 L) was added 1N NaOMe/MeOH (750 mL, 0.75 mol) dropwise over 10 min. The internal temperature was maintained below 5° C. and the reaction mixture was stirred at 0° C. for 0.5 hr, and the progress of the reaction was monitored by LCMS. Then 250 mL of 3 M HCl was added slowly, keeping the internal temperature below 5° C. Excess solvent was removed under reduced pressure below 20° C. to afford crude compound 3 (80 g, 78% pure by LCMS). $^1$H NMR (400 MHz, D$_2$O): δ 9.49 (s, 1H), 9.16 (d, J=5.9 Hz, 1H), 8.88 (t, J=7.2 Hz, 1H), 8.57 (d, J=3.8 Hz, 1H), 6.15 (s, 1H), 4.37-4.38 (m, 2H), 4.25 (t, J=4.7 Hz, 1H), 3.95 (d, J=12.9 Hz, 1H) and 3.78-3.81 (m, 1H). LCMS (M$^+$): 255.1.

3-Carboxamide-1-(2,3-O-isopropylidene-β-D-ribofuranosyl)pyridinium triflate (4)

Into a 50 mL double-neck round-bottom flask containing concentrated sulfuric acid (160 mg, 1.62 mmol) was added dry acetonitrile (8 mL) at 0° C. under inert atmosphere. After stirring for 5 minutes, 2,2-dimethoxypropane (2.5 mL) and a solution of compound 3 (1 g, 2.475 mmol) in dry acetonitrile (2 mL) already cooled at 0° C. were added to the flask, and the resulting reaction mixture was stirred at 0° C. for 30 minutes. After completion of the reaction (monitored by TLC), excess acid was quenched with solid sodium carbonate (202 mg, 0.77 mmol) in the presence of water (0.2 mL) at 0° C. with stirring for 30 minutes, and then the reaction mixture was passed through a pad of Celite and the Celite bed was washed with acetonitrile (2×10 mL). Combined filtrates were concentrated under reduced pressure to afford a crude mass. Purification of the crude mass by silica-gel column chromatography with MeOH/CH$_2$Cl$_2$ (0-10%) yielded compound 4 (400 mg, 34%) as a waxy off-white solid. $^1$H NMR (400 MHz, DMSO-d$_6$): δ 9.43 (s, 1H), 9.30 (d, J=6 Hz, 1H), 9.00 (t, J=7.9 Hz, 1H), 8.65 (s, 1H), 8.29 (t, J=7.8 Hz, 1H), 8.21 (s, 1H), 6.47 (s, 1H), 5.24-5.25 (m, 2H), 4.92 (d, J=5.7 Hz, 1H), 4.74 (s, 1H), 3.74-3.76 (m, 1H), 3.64-3.66 (m, 1H), 1.59 (s, 3H) and 1.36 (s, 3H). LCMS (M$^+$): 295.1.

1-((3aR,4R,6R,6aR)-6-(((Bis(((S)-1-methoxy-1-oxopropan-2-yl)amino)phosphoryl)oxy)methyl)-2,2-dimethyltetrahydrofuro[3,4-d][1,3]dioxol-4-yl)-3-carboxamidepyridin-1-ium ammonium acetate (5)

Method A Using Tert-Butyl Magnesium Chloride and p-Nitrophenyl Bis(Methyl L-Alaninyl)Phosphate:

To a well stirred solution of compound 4 (520 mg, 1.7 mmol) in dry THF (10 mL) was added tert-butyl magnesium chloride (7 mL, 7 mmol, 1 M in THF) under nitrogen atmosphere, and the resulting solution was stirred at room temperature for 10 minutes. To the reaction mixture was added p-nitrophenyl bis(methyl L-alaninyl)phosphate (1 g, 2.6 mmol, prepared using standard literature procedure) in dry THF (5 mL), and the reaction mixture was stirred at ambient temperature for 2 hr. Excess reagent was then quenched with MeOH (5 mL) and saturated ammonium chloride solution (2 mL). The reaction mixture was concentrated under reduced pressure to get a crude residue. The crude residue was purified by reverse-phase prep HPLC (eluting with 10 mM ammonium acetate in acetonitrile as solvent A and water as solvent B), and column fractions containing compound 5 furnished compound 5 (15 mg, 1.5%) as a colorless gum upon lyophilisation. LCMS (M$^+$): 545.2.

Method B Using Phosphorus Oxychloride and Methyl L-Alaninate:

Into a 100 mL single-neck round-bottom flask containing a solution of compound 4 (2 g, 4.9 mmol) in anhydrous triethyl phosphate (TEP, 20 mL) was added phosphoryl chloride (1.67 mL, 18 mmol) at 0° C. under nitrogen atmosphere, and the resulting reaction mixture was stirred at 0° C. for 48 hr. The reaction mixture was cooled to −78° C., and methyl L-alaninate hydrochloride salt (3.14 g, 22 mmol) in anhydrous CH$_2$Cl$_2$ (20 mL) was added to the flask. Triethylamine (6.27 mL, 45 mmol) was added at −78° C. The reaction mixture was allowed to attain ambient temperature with stirring, and stirring continued at ambient temperature for 1 hr. Excess reagent was quenched with saturated sodium carbonate (10 mL), ammonium chloride (10 mL) and water (10 mL). Dichloromethane was removed under reduced pressure. The aqueous layer was washed with 50% diethyl ether/hexane (200 mL) to remove the excess triethyl phosphate, and then the aqueous layer was concentrated under reduced pressure. The residue was treated with 30% MeOH/CH$_2$Cl$_2$ (200 mL), the resulting suspension was filtered through a pad of Celite, and the filtrate was concentrated under reduced pressure to obtain a crude mass. Purification of the crude mass by reverse-phase prep HPLC with 10 mM ammonium acetate in water as solvent A and acetonitrile as solvent B and lyophilisation of the desired column fractions furnished compound 5 (200 mg, 6%) as a white solid. LCMS (M+): 545.2.

1-((2R,3R,4S,5R)-5-(((Bis(((S)-1-methoxy-1-oxopropan-2-yl)amino)phosphoryl)oxy)methyl)-3,4-dihydroxytetrahydrofuran-2-yl)-3-carboxamidepyridin-1-ium trifluoroacetate (MP-17)

The isopropylidene 5 (10 mg) was treated with 80% aqueous trifluoroacetic acid (2 mL) at 0° C. for 0.5 hr, and then the reaction mixture was concentrated under reduced pressure to get a crude residue. The crude residue was purified by reverse-phase prep HPLC with 0.1% trifluoroacetic acid in water as solvent A and acetonitrile as solvent B, and lyophilisation of the desired column fractions yielded MP-17 (4.5 mg, 48%) as a white solid. $^1$H NMR (400 MHz, D$_2$O): δ 9.38 (s, 1H), 9.13 (d, J=6.3 Hz, 1H), 8.92 (d, J=7.4 Hz, 1H), 8.21 (d, J=7.1 Hz, 1H), 6.16 (s, 1H), 4.29-4.35 (m, 3H), 4.19 (s, 1H), 4.06-4.07 (m, 1H), 3.73-3.84 (m, 2H), 3.60 (d, J=7.6 Hz, 6H) and 1.20 (d, J=8 Hz, 6H). LCMS (M$^+$): 505.1.

1-((2R,3R,4R,5R)-5-(((Bis(((S)-1-methoxy-1-oxopropan-2-yl)amino)phosphoryl)oxy)methyl)-3,4-bis(propionyloxy)tetrahydrofuran-2-yl)-3-carboxamidepyridin-1-ium trifluoroacetate (MP-20)

Into a 50 mL single-neck round-bottom flask containing MP-17 (40 mg) in a mixture of anhydrous pyridine (2 mL) and acetonitrile (10 mL) was added propanoic anhydride (0.4 mL) at ambient temperature under nitrogen atmosphere, and the reaction mixture was stirred at ambient temperature for 16 hr. The reaction mixture was concentrated under reduced pressure, and the crude mass was purified by reverse-phase prep HPLC with 0.1% trifluoroacetic acid in water as solvent A and acetonitrile as solvent B. Lyophilisation of the desired column fractions furnished MP-20 (12 mg, 50%) as a white solid. $^1$H NMR (400 MHz, D$_2$O): δ 9.43 (s, 1H), 9.16 (d, J=6.2 Hz, 1H), 8.97 (d, J=8 Hz, 1H), 8.25 (t, J=6.5 Hz, 1H), 6.54 (d, J=4.7 Hz, 1H), 5.43-5.44 (m, 2H), 4.82 (s, 1H), 4.40 (t, J=1.5 Hz, 1H), 4.25-4.25 (m, 1H), 3.87 (t, J=7.4 Hz, 2H), 3.61 (d, J=19.5 Hz, 6H), 2.39-2.41 (m, 4H), 1.28 (d, J=7.04 Hz, 6H) and 1.00-1.02 (m, 6H). LCMS (M$^+$): 617.3.

Example 2. Synthesis of 1-((2R,3R,4S,5R)-5-(((L-Valyl)oxy)methyl)-3,4-dihydroxytetrahydrofuran-2-yl)-3-carboxamidepyridin-1-ium trifluoroacetate (MP-41)

Figure 10:
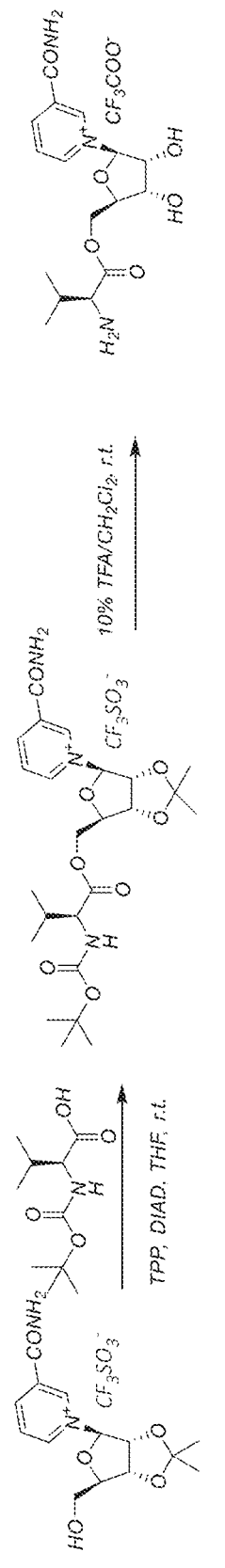
FIG. 10 shows a process for synthesizing MP-41.
Figure 11:
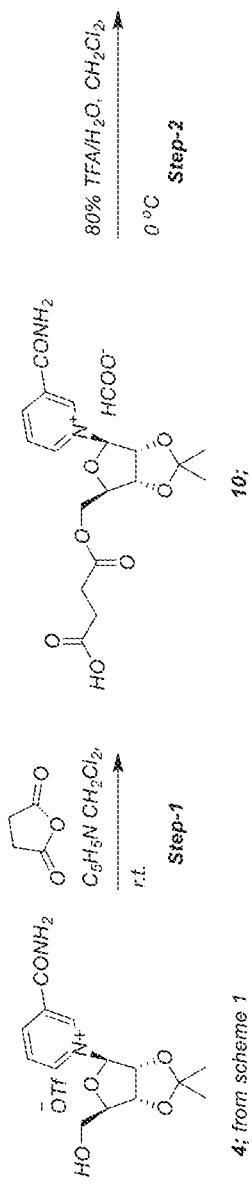
FIG. 11 shows a process for synthesizing MP-42.

FIG. 10 shows the process for the synthesis of MP-41.

1-((3aR,4R,6R,6aR)-6-((((tert-Butoxycarbonyl)-L-valyl)oxy)methyl)-2,2-dimethyltetrahydrofuro[3,4-d][1,3]dioxol-4-yl)-3-carboxamidepyridin-1-ium triflate (8)

To a well stirred solution of compound 4 (700 mg, 1.6 mmol, prepared according to Example 1) in anhydrous THF (10 mL) were added (tert-butoxycarbonyl)-L-valine (618.4 mg, 2.84 mmol) and triphenylphosphine (TPP, 932.9 mg, 3.558 mmol) at ambient temperature under nitrogen atmosphere. The reaction mixture was stirred for 5 min at ambient temperature, and then diisopropyl azodicarboxylate (DIAD, 719.4 mg, 3.558 mmol) was added. The reaction mixture was stirred for 16 hr at room temperature. After completion of the reaction (monitored by LCMS), the reaction mixture was concentrated under reduced pressure to get crude compound 8 (3 g) as a thick viscous orange liquid, which was used in the next step without further purification. LCMS (M$^+$): 494.

1-((2R,3R,4S,5R)-5-(((L-Valyl)oxy)methyl)-3,4-dihydroxytetrahydrofuran-2-yl)-3-carboxamidepyridin-1-ium trifluoroacetate (MP-41)

To a well stirred solution of compound 8 (750 mg, 1.518 mmol) in anhydrous CH$_2$Cl$_2$ (20 mL) was added 2 mL of trifluoroacetic acid under inert atmosphere at 0° C., and the reaction mixture was stirred at ambient temperature for 1 hr. After completion of the reaction (monitored by LCMS), the reaction mixture was concentrated under reduced pressure. The crude residue was purified by reverse-phase HPLC to afford MP-41 (150 mg) as an off-white solid. $^1$H NMR (400 MHz, CD$_3$OD): δ9.52 (s, 1H), 9.20 (d, J=6.2 Hz, 1H), 9.09 (d, J=8.1 Hz, 1H), 8.31-8.34 (m, 1H), 6.25 (d, J=4.1 Hz, 1H), 4.75 (t, J=14 Hz, 1H), 4.63-4.68 (m, 2H), 4.39 (t, J=9 Hz, 1H), 4.27-4.32 (m, 2H), 2.29-3.37 (m, 1H) and 1.08-1.11 (m, 6H). LCMS (M$^+$): 354.

Example 3. Synthesis of 3-Carboxamide-1-((2R,3R,4S,5R)-5-(((3-carboxypropanoyl)oxy)methyl)-3,4-dihydroxytetrahydrofuran-2-yl)pyridin-1-ium trifluoroacetate (MP-42)

3-Carboxamide-1-((3aR,4R,6R,6aR)-6-(((3-carboxypropanoyl)oxy)methyl)-2,2-dimethyltetrahydrofuro[3,4-d][1,3]dioxol-4-yl)pyridin-1-ium formate (10)

Into a 100 mL single-neck round-bottom flask containing a well stirred solution of compound 4 (1 g, 2.25 mmol, prepared according to Example 1) in a mixture of anhydrous pyridine (15 mL) and CH$_2$Cl$_2$ (5 mL) was added succinic anhydride (3.37 g, 33.7 mmol) at ambient temperature under nitrogen atmosphere. The reaction mixture was stirred at room temperature overnight, and then was concentrated under reduced pressure. The crude mass was purified by reverse-phase HPLC with 0.1% formic acid in water as solvent A and acetonitrile as solvent B to yield compound 10 (500 mg, 41%) as a colorless syrupy liquid. $^1$H NMR (400 MHz, D$_2$O): δ 9.33 (s, 1H), 9.14 (d, J=6.4 Hz, 1H), 8.94 (d, J=8 Hz, 1H), 8.25-8.21 (m, 1H), 6.43 (d, J=2 Hz, 1H), 5.26 (t, J=2.4 Hz, 1H), 4.99 (d, J=6 Hz, 2H), 4.41 (s, 2H), 3.61 (s, 4H), 2.46-2.42 (m, 2H), 2.32-2.26 (m, 1H), 2.10-2.03 (m, 1H), 1.59 (s, 3H) and 1.38 (s, 3H). LCMS (M$^+$): 395.1.

3-Carboxamide-1-((2R,3R,4S,5R)-5-(((3-carboxypropanoyl)oxy)methyl)-3,4-dihydroxytetrahydrofuran-2-yl)pyridin-1-ium trifluoroacetate (MP-42)

Into a 25 mL single-neck round-bottom flask containing a well stirred solution of compound 10 (100 mg, 0.18 mmol) in CH$_2$Cl$_2$ (5 mL) was added 80% aqueous trifluoroacetic acid (5 mL) at 0° C. The reaction mixture was stirred at ambient temperature for 2 hr, and then was concentrated under reduced pressure. The crude product was purified by reverse-phase HPLC with 0.1% trifluoroacetic acid in water as solvent A and acetonitrile as solvent B to afford MP-42 (20 mg, 23%) as a colorless syrup. $^1$H NMR (400 MHz, D$_2$O): δ 9.53 (s, 1H), 9.26 (d, J=6.4 Hz, 1H), 9.08-9.05 (m, 1H), 8.34-8.31 (m, 1H), 6.20 (d, J=5.2 Hz, 1H), 4.63-4.61 (m, 1H), 4.53 (t, J=3.6 Hz, 2H), 4.37 (t, J=5.2 Hz, 1H), 4.29-4.27 (m, 1H) and 2.63 (s, 4H). LCMS (M$^+$): 355.1.

Example 4. Synthesis of 3-Carboxamide-1-((2R,3R,4S,5R)-3,4-dihydroxy-5-(((4-methoxy-4-oxobutanoyl)oxy)methyl)tetrahydrofuran-2-yl)pyridin-1-ium trifluoroacetate (MP-43)

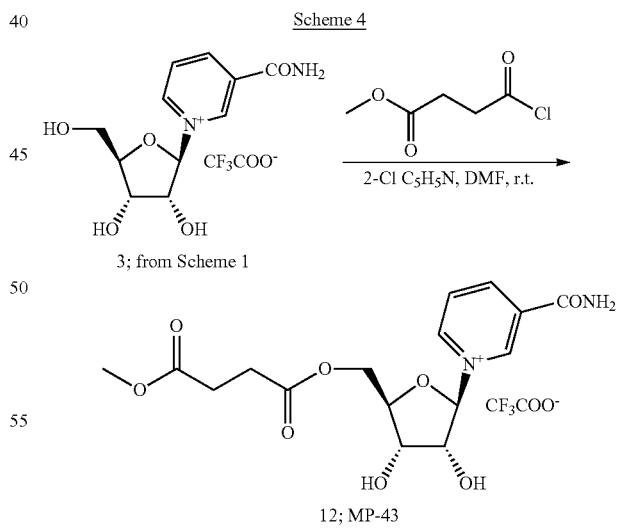

Scheme 4

3-Carboxamide-1-((2R,3R,4S,5R)-3,4-dihydroxy-5-(((4-methoxy-4-oxobutanoyl)oxy)methyl)tetrahydrofuran-2-yl)pyridin-1-ium trifluoroacetate (MP-43)

Into a 25 mL single-neck round-bottom flask containing a well stirred solution of compound 3 (368 mg, 1 mmol, prepared according to Example 1) in anhydrous DMF (5 mL) were added 2-chloropyridine (1.76 g, 15.51 mmol) and methyl 4-chloro-4-oxobutanoate (1.09 g, 7.23 mmol) at ambient temperature under nitrogen atmosphere. The reaction mixture was stirred at ambient temperature for 0.5 hr, the acid chloride was quenched with excess MeOH, and the reaction mixture was concentrated under reduced pressure. The crude product was purified by reverse-phase HPLC with 0.1% trifluoroacetic acid in water as solvent A and acetonitrile as solvent B to yield MP-43 (20 mg, 4%) as a colorless syrup. $^1$HNMR (400 MHz, D$_2$O): δ 9.54 (s, 1H), 9.26 (d, J=6 Hz, 1H), 9.08 (d, J=8 Hz, 1H), 8.35-8.32 (m, 1H), 6.21 (d, J=5.2 Hz, 1H), 4.62-4.61 (m, 1H), 4.54-4.51 (m, 2H), 4.38-4.36 (m, 1H), 4.28-4.26 (m, 1H), 3.65 (s, 3H) and 2.66 (s, 4H). LCMS (M$^+$): 369.1.

Example 5. Elevation of NAD$^+$ Level and Reduction of Cytotoxicity after Acute NAD$^+$ Depletion and Cytotoxicity Induced by DNA Damage Test NR derivatives were evaluated for their ability to increase NAD$^+$ level and reduce cellular toxicity after acute NAD$^+$ depletion and cytotoxicity induced by DNA damage. HEPG2 (liver), HEK (kidney) and Jurkat (T-cells) cell lines were obtained from ATCC. HEPG2 and HEK cells were incubated in Dulbecco's Modified Eagle Medium (DMEM) (Thermo Fischer) with 5% fetal bovine serum (FBS), while Jurkat cells were incubated in RPMI 1640 medium (Gibco). DNA damage in the cells was induced using the DNA-alkylating mutagen N-methyl-N-nitroso-N'-nitroguanidine (MNNG). Dose-response relationships of concentrations of MNNG and the magnitude of NAD$^+$ depletion and cytotoxicity were established in the three different cell lines. Briefly, cells were incubated with varying concentrations of MNNG-containing media for 30 min. The cells were washed, and then were incubated with varying concentrations of a test compound for 3.5 hr. As controls, different combinations of incubation of the cells with or without MNNG for 30 min, washing of the cells, and incubation of the cells with or without a test compound for 3.5 hr were performed. Total cellular NAD$^+$ levels were measured using the NAD/NADH Glo™ Assay (Promega). Cytotoxicity was assessed using the CellTiter-Blue® Cell Viability Assay (Promega). About 80,000 cells per well were utilized for the experiments.

Figure 12:
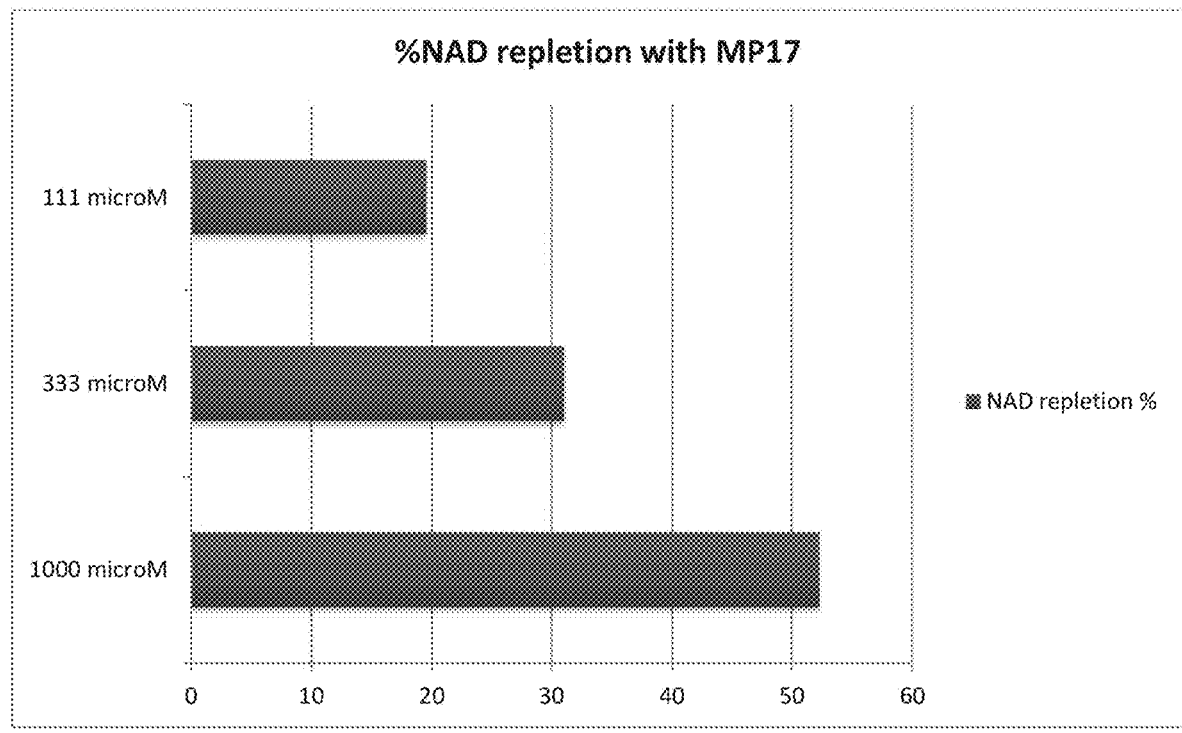
FIG. 12 shows % recovery of NAD⁺ level depleted by the DNA-alkylating mutagen methynitronitrosoguanidine (MNNG) in Jurkat cells with varying concentrations of MP-17.

MP-17 Reduced MNNG-Induced NAD$^+$ Depletion and Cytotoxicity in Jurkat Cells:

Jurkat cells were incubated with or without 100 µM of MMNG for 30 min. The cells were washed, and then were incubated with or without MP-17 (111-1000 µM) for 3.5 hr. MNNG treatment resulted in 76.9% depletion of NAD$^+$ level at 4 hr. Depending on the concentration of MP-17, MP-17 induced 19.5% to 52.3% recovery of NAD$^+$ level (FIG. 12).

Figure 13:
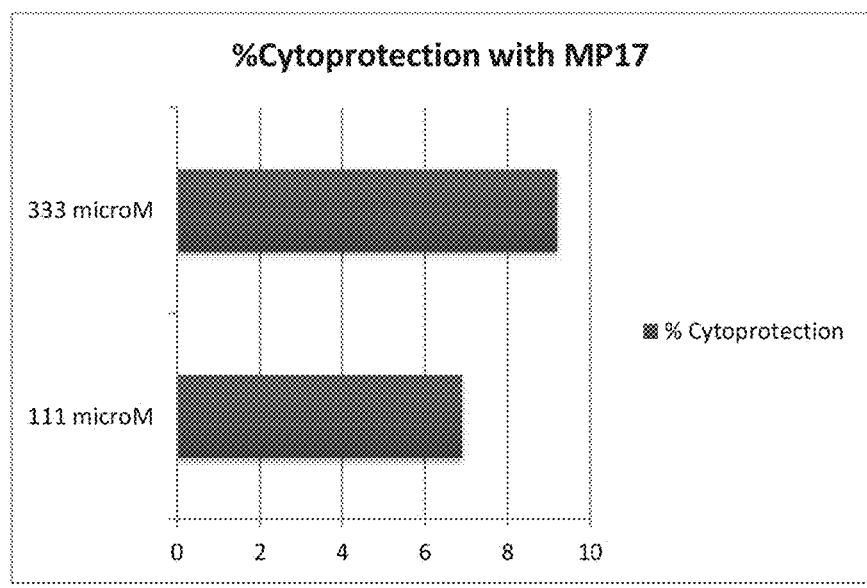
FIG. 13 shows % reduction of MNNG-induced cytotoxicity in Jurkat cells with varying concentrations of MP-17.

Jurkat cells were incubated with or without 150 µM of MMNG for 30 min. The cells were washed, and then were incubated with or without MP-17 (111-1000 µM) for 3.5 hr. MNNG treatment resulted in 63.2% cytotoxicity at 4 hr. MP-17 provided cytoprotection (i.e., reduced cytotoxicity) by 6.9-9.2% (FIG. 13).

Figure 14:
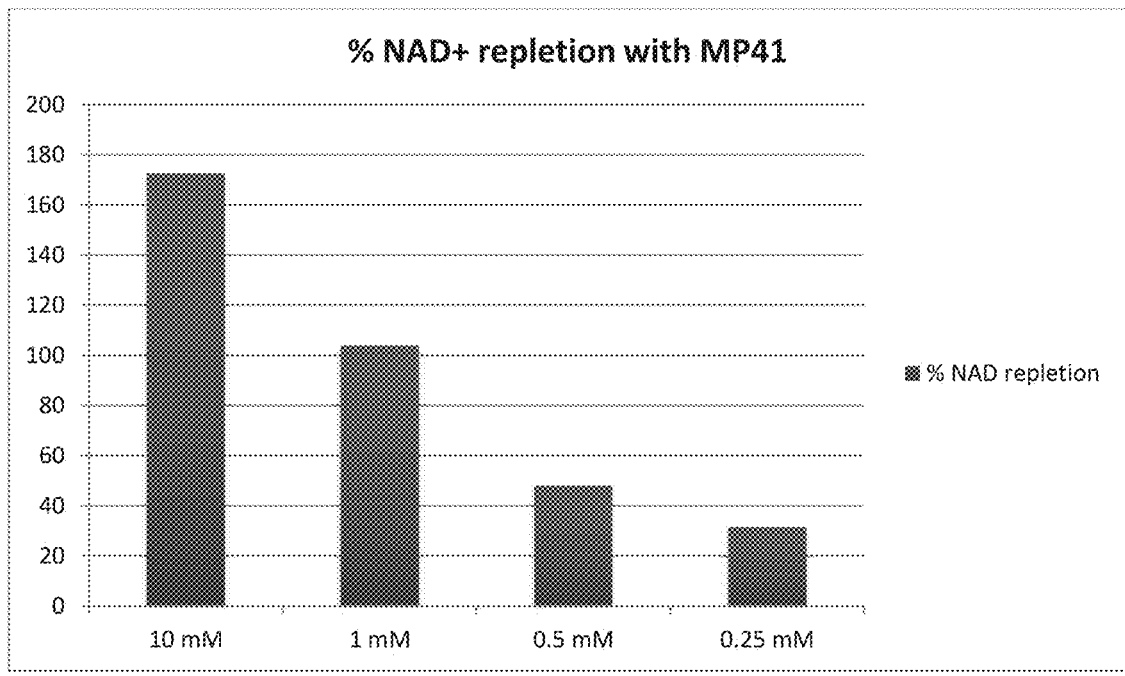
FIG. 14 shows % recovery of NAD⁺ level depleted by MNNG in Jurkat cells with varying concentrations of MP-41.

MP-41 Reduced MNNG-Induced NAD$^+$ depletion and cytotoxicity in Jurkat cells:

Jurkat cells were incubated with or without 75 µM of MMNG for 30 min. The cells were washed, and then were incubated with or without MP-41 (0.25-10 mM) for 3.5 hr. MNNG treatment resulted in 92.1% depletion of NAD$^+$ level at 4 hr. Depending on the concentration of MP-41, MP-41 induced 31% to 172% recovery of NAD$^+$ level (FIG. 14).

Figure 15:
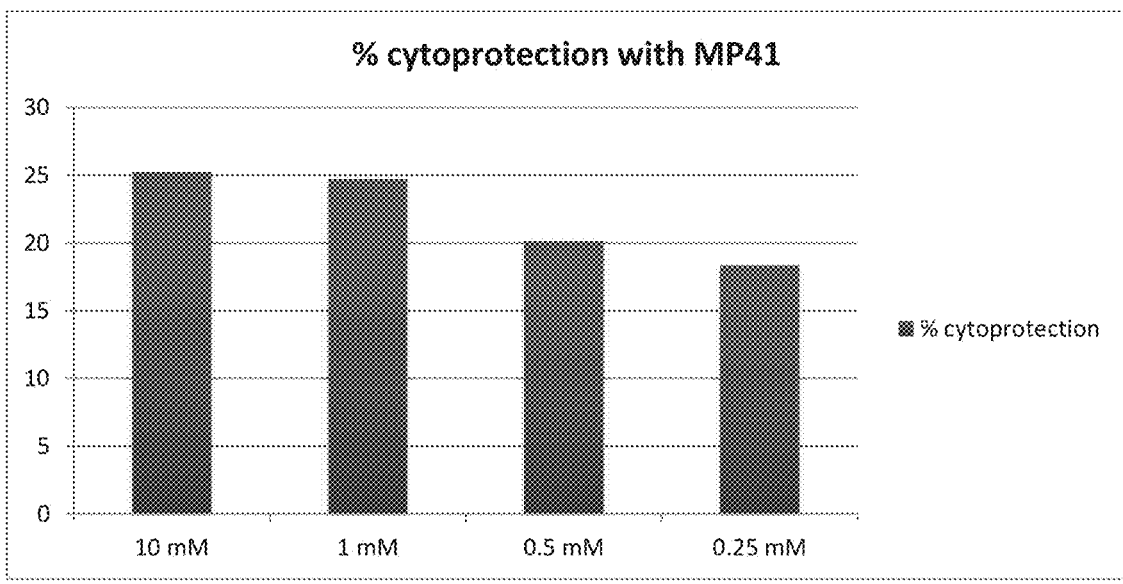
FIG. 15 shows % reduction of MNNG-induced cytotoxicity in Jurkat cells with varying concentrations of MP-41.

Jurkat cells were incubated with or without 75 µM of MMNG for 30 min. The cells were washed, and then were incubated with or without MP-41 (0.25-10 mM) for 3.5 hr. MNNG treatment resulted in 87% cytotoxicity at 4 hr. MP-41 provided cytoprotection (i.e., reduced cytotoxicity) by 18-25% (FIG. 15).

MP-42 and MP-43 Reduced MNNG-Induced NAD$^+$ Depletion and Cytotoxicity in HEPG2 and Jurkat Cells:

Using similar procedures as described above for the assays of MP-17 and MP-41 in Jurkat cells, MP-42 and MP-43 reduced MNNG-induced NAD$^+$ depletion and cytotoxicity in HEPG2 and Jurkat cells, as indicated in Tables 1 and 2. The concentration of MNNG used in the cytotoxicity experiments with HEPG2 cells (Table 2) was higher because these cells are more resistant to cytotoxicity despite a large reduction in NAD$^+$ level.

TABLE 1

| Cell Line | MNNG Conc. (µM) | % NAD$^+$ Repletion | |
|---|---|---|---|
| | | MP-42 (1 mM) | MP-43 (1 mM) |
| HEPG2 | 100 | 23.7 | 31.1 |
| Jurkat | 100 | 8.2 | 12.9 |

TABLE 2

| Cell Line | MNNG Conc. (µM) | % Cytoprotection | |
|---|---|---|---|
| | | MP-42 (1 mM) | MP-43 (1 mM) |
| HEPG2 | 600 | 9.9 | 5.7 |
| Jurkat | 100 | 4.5 | 6.3 |

Figure 16:
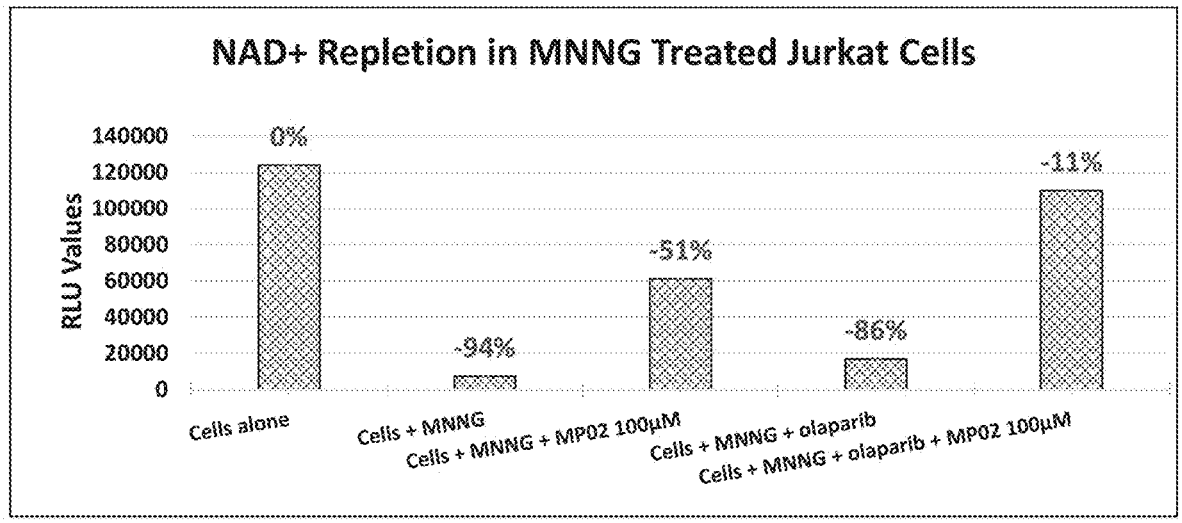
FIG. 16 shows synergistic repletion of NAD⁺ level in MNNG-treated Jurkat cells by a combination of nicotinamide riboside ("MP02" in FIG. 16) and a very low concentration (5 nM) of the PARP inhibitor olaparib.
Figure 17:
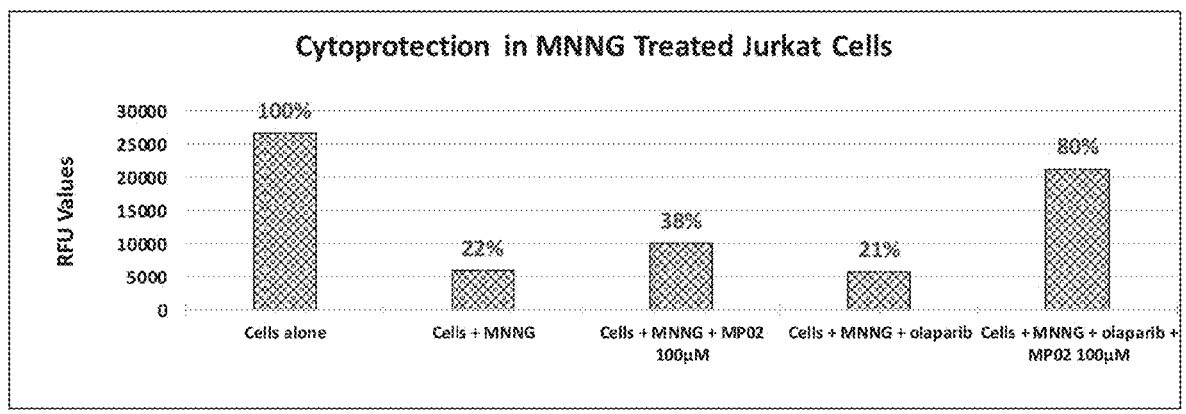
FIG. 17 shows synergistic cytoprotection (reduction of cytotoxicity) in MNNG-treated Jurkat cells by a combination of nicotinamide riboside ("MP02" in FIG. 17) and a very low concentration (5 nM) of olaparib.

Example 6. Synergistic NAD$^+$ Repletion and Cytoprotection by Combination of Nicotinamide Riboside and Very Low-Dose Olaparib DNA damage was induced by MNNG in Jurkat cells, total cellular NAD+ levels were measured, and cytotoxicity was assessed as described in Example 5. Briefly, Jurkat cells were incubated with or without 100 µM of MMNG for 30 min. The cells were washed, and then were incubated with or without 100 µM of nicotinamide riboside (NR) or 5 nM of olaparib, or both NR and olaparib, for 3.5 hr. MNNG treatment resulted in 94% depletion of NAD$^+$ level at 4 hr. NR (100 µM) without olaparib increased NAD$^+$ level by 43%, while olaparib (5 nM) without NR increased NAD$^+$ level by 8%. However, the combination of both NR (100 µM) and olaparib (5 nM) synergistically increased NAD$^+$ level by 75% to a similar level as in cells not treated with MNNG (FIG. 16). MP02 in FIGS. 16 and 17 is NR.

Jurkat cells were incubated with or without 200 µM of MMNG for 30 min. The cells were washed, and then were incubated with or without 100 µM of NR or 5 nM of olaparib, or both NR and olaparib, for 3.5 hr. MNNG treatment resulted in 78% cytotoxicity at 4 hr. NR (100 µM) without olaparib provided cytoprotection (i.e., reduced cytotoxicity) by 16%, while olaparib (5 nM) without NR provided no cytoprotection. However, the combination of both NR (100 µM) and olaparib (5 nM) synergistically enhanced cytoprotection by 58% to a cytotoxicity level of 20% relative to cells not treated with MNNG (FIG. 17).

Example 7. Measurement of Mitochondrial Function in Primary Cells

Mitochondrial function in different cell types (e.g., neural cells, liver cells, kidney cells, lymphoma cells and peripheral blood mononuclear cells) after exposure to NR/NAR derivatives of the disclosure or NR (positive control) is measured. Mitochondrial mass is measured using the Mitotracker assay (ThermoFisher Scientific). Mitochondrial super oxide production is measured using the Mitosox assay (ThermoFisher Scientific) assay. Mitochondrial membrane potential is measured using the JC-1 Dye assay (ThermoFisher Scientific).

Example 8. In Vivo PK and Efficacy of NR and NAR Derivatives

In vivo pharmacokinetic studies and pharmacodynamic studies (e.g., $NAD^+$ levels in the blood and in different cell types, such as neural cells, liver cells and kidney cells) of orally and parenterally (e.g., intravenously and subcutaneously) administered NR and NAR derivatives of the disclosure and NR (positive control) are performed in rats, and $EC_{50}$ values are calculated.

Example 9. Stability of NR and NAR Derivatives

The stability of NR and NAR derivatives of the disclosure and NR (for comparison) in different tyes of media is determined using HPLC-based analytical methods. Examples of such media include: 1) phosphate buffers at pH 2, 4, 6, 7, 7.4, 8 and 9; 2) Cell Culture Media (CCM); 3) Dulbecco's Modified Eagle Medium (DMEM) supplemented with 10% fetal bovine serum (FBS); 4) rat plasma; and 5) human plasma.

REFERENCES

The following citations are incorporated herein by reference in their entirety:
1. Adams and Victor's Principles of Neurology, 10th Ed. (2014)
2. Bieganowski, P. and Brenner, C., Discoveries of nicotinamide riboside as a nutrient and conserved NRK genes establish a Preiss-Handler independent route to $NAD^+$ in fungi and humans, Cell, 117(4):495-502 (2004)
3. Bonkowski, M. and Sinclair, D., Slowing ageing by design: the rise of NAD and sirtuin-activating compounds, Nat. Rev. Mol. Cell Biol., 17(11):679-690 (2016)
4. Camacho-Pereira, J. et al., CD38 Dictates Age-Related NAD Decline and Mitochondrial Dysfunction through an SIRT3-Dependent Mechanism, Cell Metab., 23(6):1127-1139 (2016)
5. Chini, C. et al., NAD and the aging process: Role in life, death and everything in between, Mol. Cell Endocrinol., 455:62-74 (2017)
6. Croteau, D. et al., NAD in DNA repair and mitochondrial maintenance, Cell Cycle, 16(6):491-492 (2017)
7. de Picciotto, N. et al., Nicotinamide mononucleotide supplementation reverses vascular dysfunction and oxidative stress with aging in mice, Aging Cell, 15(3):522-530 (2016)
8. de Vita and Lawrence, Cancer: Principles and Practice of Oncology, 10th Ed. (2015)
9. Fang, E. et al., NAD Replenishment Improves Lifespan and Healthspan in Ataxia Telangiectasia Models via Mitophagy and DNA Repair, Cell Metab., 24(4):566-581 (2016)
10. Fang, E. and Bohr, V., NAD: The convergence of DNA repair and mitophagy, Autophagy, 13(2):442-443 (2017)
11. Frederick, D. et al., Loss of NAD Homeostasis Leads to Progressive and Reversible Degeneration of Skeletal Muscle, Cell Metab., 24(2):269-282 (2016)
12. Imai, S. and Guarente, L., $NAD^+$ and sirtuins in aging and disease, Trends Cell Biol., 24(8):464-471 (2014)
13. López-Otín, C. et al., The Hallmarks of Aging, Cell, 153(6):1194-1217 (2013)
14. Physician's Desk Reference, 70th Ed. (2016)
15. WO 2015/186068 A1
16. WO 2017/079195 A1
17. Mills, K. et al., Long-Term Administration of Nicotinamide Mononucleotide Mitigates Age-Associated Physiological Decline in Mice, Cell Metab., 24(6):795-806 (2016)
18. Ratajczak, J. et al., NRK1 controls nicotinamide mononucleotide and nicotinamide riboside metabolism in mammalian cells, Nat. Commun., 7:13103 (2016)
19. Stein, L. and Imai, S., The dynamic regulation of NAD metabolism in mitochondria, Trends Endocrinol. Metab., 23(9):420-428 (2012)
20. Stunkard and Wadden, Obesity: Theory and Therapy, 2nd Ed. (1993)
21. Trammell, S. et al., Nicotinamide riboside is uniquely and orally bioavailable in mice and humans, Nat. Commun., 7:12948 (2016)
22. U.S. Pat. No. 8,383,086
23. Yang, Y. and Sauve, A., $NAD^+$ metabolism: Bioenergetics, signaling and manipulation for therapy, Biochim. Biophys. Acta, 1864(12):1787-1800 (2016)
24. Zhang, H. et al., $NAD^+$ repletion improves mitochondrial and stem cell function and enhances life span in mice, Science, 352(6292):1436-1443 (2016)

While various embodiments of the present disclosure have been described, such embodiments are provided by way of illustration and example only. Numerous variations thereof and modifications thereto will be apparent to those skilled in the art and are encompassed by the present disclosure. It is understood that various alternatives to the embodiments of the disclosure can be employed in practicing the disclosure and are encompassed by the disclosure.

What is claimed is:

1. A method of increasing cytoprotection in a cell type or tissue at risk of DNA damage in a subject, comprising administering to the subject in need thereof a therapeutically effective amount of a compound of Formula (V) or Formula (VI):

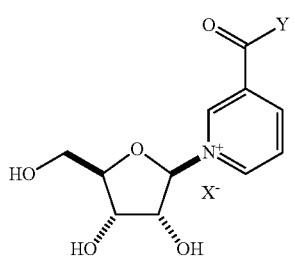

(V)

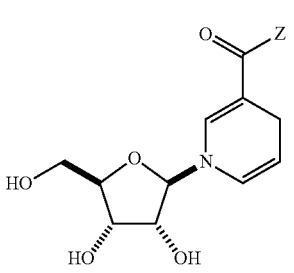

(VI)

or pharmaceutically acceptable salts and a therapeutically effective amount of olaparib or pharmaceutically acceptable salts thereof, wherein:

Y and Z are —OH or —NH$_2$;

X$^-$ is fluoride, chloride, bromide, iodide, nitrate, sulfate, sulfite, phosphate, bicarbonate, carbonate, thiocyanate, formate, acetate, trifluoroacetate, glycolate, lactate, gluconate, ascorbate, benzoate, oxalate, malonate, succinate, citrate, methanesulfonate, ethanesulfonate, propanesulfonate, benzenesulfonate, p-toluenesulfonate or trifluoromethanesulfonate; and the therapeutically effective amount of olaparib is not more than about 10% of the therapeutically effective amount of olaparib used in chemotherapy.

2. The method of claim 1, wherein the therapeutically effective amount of olaparib is no more than about 5%, about 1%, about 0.5% or about 0.1% of the therapeutically effective amount olaparib used in chemotherapy.

3. The method of claim 1, wherein the therapeutically effective amount of olaparib is no more than 10 mg, about 5 mg, about 1 mg, about 0.5 mg or about 0.1 mg.

4. The method of claim 3, wherein the therapeutically effective amount of the compound is about 50 mg, about 100 mg, about 150 mg, about 200 mg, about 250 mg, about 300 mg, about 400 mg, about 500 mg, about 600 mg, about 700 mg, about 900 mg or about 1000 mg.

5. The method of claim 1, wherein the compound is

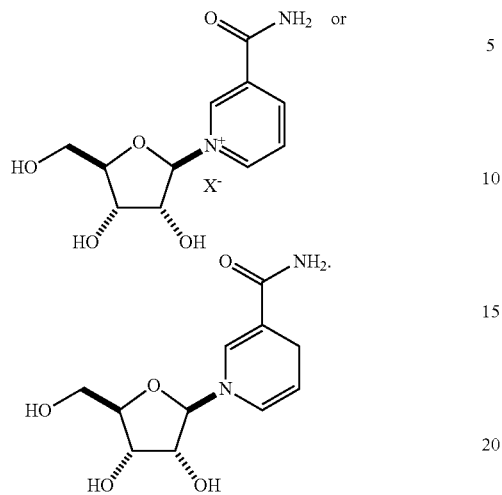

6. The method of claim 5, wherein the therapeutically effective amount of olaparib is no more than about 10 mg, about 5 mg, about 1 mg, about 0.5 mg or about 0.1 mg.

7. The method of claim 6, wherein the therapeutically effective amount of the compound is about 50 mg, about 100 mg, about 150 mg, about 200 mg, about 250 mg, about 300 mg, about 400 mg, about 500 mg, about 600 mg, about 700 mg, about 900 mg or about 1000 mg.

* * * * *

SEQUENCE LISTING

<160> NUMBER OF SEQ ID NOS: 3

<210> SEQ ID NO 1
<211> LENGTH: 4
<212> TYPE: PRT
<213> ORGANISM: Artificial Sequence
<220> FEATURE:

```
<221> NAME/KEY: source
<223> OTHER INFORMATION: /note="Description of Artificial Sequence:
      Synthetic peptide"

<400> SEQUENCE: 1

Gly Phe Leu Gly
1

<210> SEQ ID NO 2
<211> LENGTH: 12
<212> TYPE: PRT
<213> ORGANISM: Unknown
<220> FEATURE:
<221> NAME/KEY: source
<223> OTHER INFORMATION: /note="Description of Unknown:
      MCP1-binding peptide"

<400> SEQUENCE: 2

His Ser Trp Arg His Phe His Thr Leu Gly Gly Gly
1               5                   10

<210> SEQ ID NO 3
<211> LENGTH: 4
<212> TYPE: PRT
<213> ORGANISM: Unknown
<220> FEATURE:
<221> NAME/KEY: source
<223> OTHER INFORMATION: /note="Description of Unknown:
      TGF-beta-1 inhibitor peptide"

<400> SEQUENCE: 3

Leu Ser Lys Leu
1
```